US012700218B2

(12) United States Patent
Aidt et al.

(10) Patent No.: US 12,700,218 B2
(45) Date of Patent: Aug. 4, 2026

(54) TISSUE STAINING AND SEQUENTIAL IMAGING OF BIOLOGICAL SAMPLES FOR DEEP LEARNING IMAGE ANALYSIS AND VIRTUAL STAINING

(71) Applicant: Agilent Technologies, Inc., Santa Clara, CA (US)

(72) Inventors: Frederik Aidt, Santa Clara, CA (US); Jesper Lohse, Santa Clara, CA (US); Elad Arbel, Santa Clara, CA (US); Itay Remer, Santa Clara, CA (US); Amir Ben-Dor, Santa Clara, CA (US); Oded Ben-David, Santa Clara, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 578 days.

(21) Appl. No.: 18/021,779

(22) PCT Filed: Aug. 18, 2021

(86) PCT No.: PCT/IB2021/057583
§ 371 (c)(1),
(2) Date: Feb. 16, 2023

(87) PCT Pub. No.: WO2022/038527
PCT Pub. Date: Feb. 24, 2022

(65) Prior Publication Data
US 2024/0029409 A1 Jan. 25, 2024

Related U.S. Application Data

(60) Provisional application No. 63/067,302, filed on Aug. 18, 2020.

(51) Int. Cl.
*G06V 10/774* (2022.01)
*G06T 7/00* (2017.01)
(Continued)

(52) U.S. Cl.
CPC .......... *G06V 10/774* (2022.01); *G06T 7/0014* (2013.01); *G06T 7/337* (2017.01);
(Continued)

(58) Field of Classification Search
CPC .. G06V 10/774; G06V 20/695; G06V 20/698; G06V 20/70; G06V 10/22;
(Continued)

(56) References Cited

U.S. PATENT DOCUMENTS 10,572,996 B2 * 2/2020 Eurèn .................. G06F 18/214
10,706,535 B2 7/2020 Arar et al.
(Continued)

FOREIGN PATENT DOCUMENTS

CN 109416730 A 3/2019
CN 110023994 A 7/2019
(Continued)

OTHER PUBLICATIONS

Extended European Search Report and Search Opinion received for European Application No. 21857874.8, mailed on Jul. 19, 2024, 10 pages.
(Continued)

*Primary Examiner* — Jennifer Mehmood
*Assistant Examiner* — Pardis Sohraby
(74) *Attorney, Agent, or Firm* — ArentFox Schiff LLP

(57) ABSTRACT

There is provided a method for training a ground truth generator machine learning model, comprising: creating a ground truth multi-record training dataset wherein a record comprises: a first image of a sample of tissue of a subject depicting a first group of biological objects, a second image of the sample depicting a second group of biological objects presenting at least one biomarker, and ground truth labels indicating a respective biological object category of a plurality of biological object categories for biological object
(Continued)

300 members of the first group and the second group; and training the ground truth generator machine learning model on the ground truth multi-record training dataset for automatically generating ground truth labels selected from the plurality of biological object categories for biological objects depicted in an input set of images of a first type corresponding to the first image and a second type corresponding to the second image.

12 Claims, 54 Drawing Sheets
(32 of 54 Drawing Sheet(s) Filed in Color)

(51) Int. Cl.

| | |
|---|---|
| ***G06T 7/33*** | (2017.01) |
| ***G06V 20/69*** | (2022.01) |
| ***G06V 20/70*** | (2022.01) |
| ***G16H 30/40*** | (2018.01) |
| ***G16H 50/20*** | (2018.01) |

(52) U.S. Cl.
CPC .......... *G06V 20/695* (2022.01); *G06V 20/698* (2022.01); *G06V 20/70* (2022.01); *G16H 30/40* (2018.01); *G16H 50/20* (2018.01); *G06T 2207/20021* (2013.01); *G06T 2207/20081* (2013.01); *G06T 2207/20084* (2013.01); *G06T 2207/30096* (2013.01); *G06T 2207/30204* (2013.01); *G06V 2201/03* (2022.01)

(58) Field of Classification Search
CPC .. G06V 10/7792; G06V 10/82; G06T 7/0014; G06T 7/337; G06T 2207/20021; G06T 2207/20081; G06T 2207/20084; G06T 2207/30096; G06T 2207/30204
USPC .......................................................... 382/133
See application file for complete search history.

(56) References Cited

U.S. PATENT DOCUMENTS

| | | | | |
|---|---|---|---|---|
| 11,276,165 | B2 * | 3/2022 | Thagaard | G06T 7/33 |
| 11,783,603 | B2 * | 10/2023 | Stumpe | G06V 20/69 |
| 2019/0266486 | A1 | 8/2019 | Yamada et al. | |
| 2020/0082222 | A1 | 3/2020 | Cohen et al. | |
| 2020/0258223 | A1 | 8/2020 | Yip et al. | |
| 2020/0394825 | A1 | 12/2020 | Stumpe et al. | |
| 2021/0145283 | A1 | 5/2021 | Bryant-Greenwood et al. | |
| 2023/0096719 | A1 * | 3/2023 | Chennubhotla | G06V 10/70 382/128 |
| 2024/0029409 | A1 | 1/2024 | Aidt | |

FOREIGN PATENT DOCUMENTS

| | | | | |
|---|---|---|---|---|
| CN | 110852288 | A | 2/2020 | |
| DE | 102021114290 | A1 | 12/2022 | |
| DE | 102021114291 | A1 | 12/2022 | |
| EP | 3639191 | A1 | 4/2020 | |
| JP | 2019525151 | A | 9/2019 | |
| WO | 2018/229052 | A1 | 12/2018 | |
| WO | 2019154987 | A1 | 8/2019 | |
| WO | 2019/172901 | A1 | 9/2019 | |
| WO | 2020142461 | A1 | 7/2020 | |
| WO | WO-2020198380 | A1 * | 10/2020 | G06V 20/698 |
| WO | 2021133847 | A1 | 7/2021 | |

OTHER PUBLICATIONS

Xu et al., "GAN-based Virtual Re-Staining: A Promising Solution for Whole Slide Image Analysis", arxiv.org, Cornell University Library, 201 Olin Library Cornell University Ithaca, NY 14853, Jan. 13, 2019, 16 pages.
International Search Report and Written Opinion mailed on Dec. 7, 2021 in PCT/IB2021/057583.
https://ieeexplore.ieee.org/stamp/stamp.jsp?tp=&arnumber=7167462 , Interactive Segmentation Relabeling for Classification of Whole-Slide Histopathology Imagery2015 IEEE 28th International Symposium on Computer-Based Systems , IEEE , 2015 , Anoop Haridas; Filiz Bunyak; Kannappan Palaniappan.

* cited by examiner

100

200

500

500

500

500

500

500

500

500

500

500

500

500

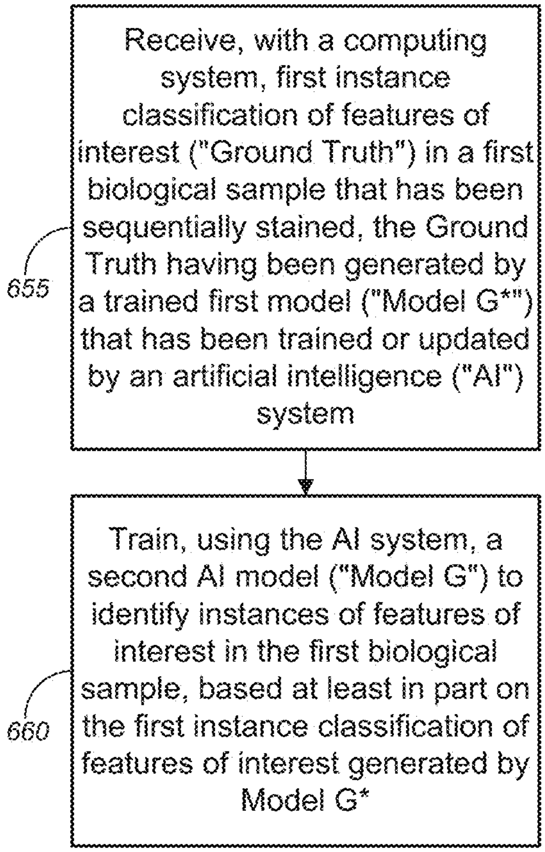
600 Fig. 6D
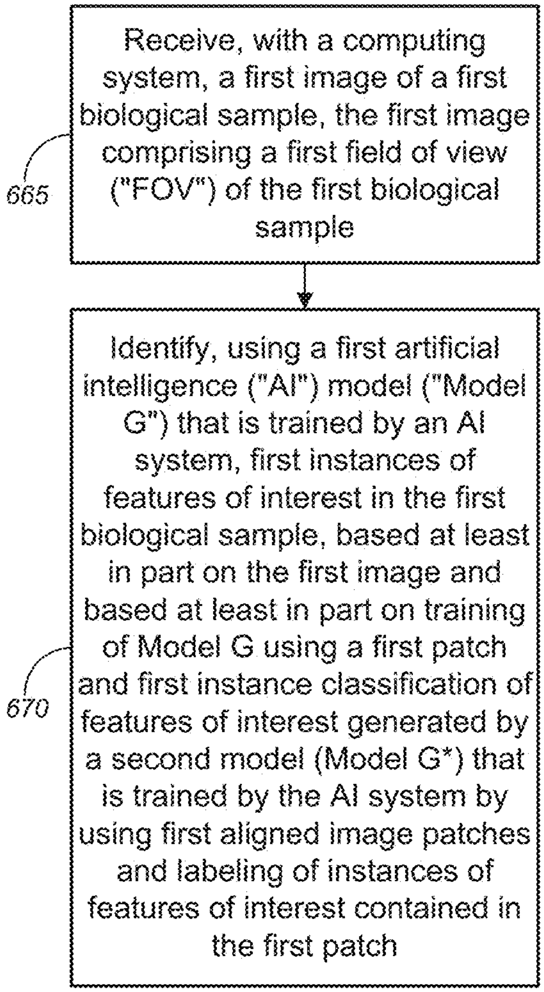
600 Fig. 6E

*Sequentially Stained Input Patch*
H + PD-L1 (DAB)

*Sequentially Stained Ground Truth Patch*
H + PD-L1 (DAB) + CD68 (Magenta)

*Input Patch*
Hematoxylin

*Sequentially Stained Ground Truth Patch*
H + P40 (Magenta)

800

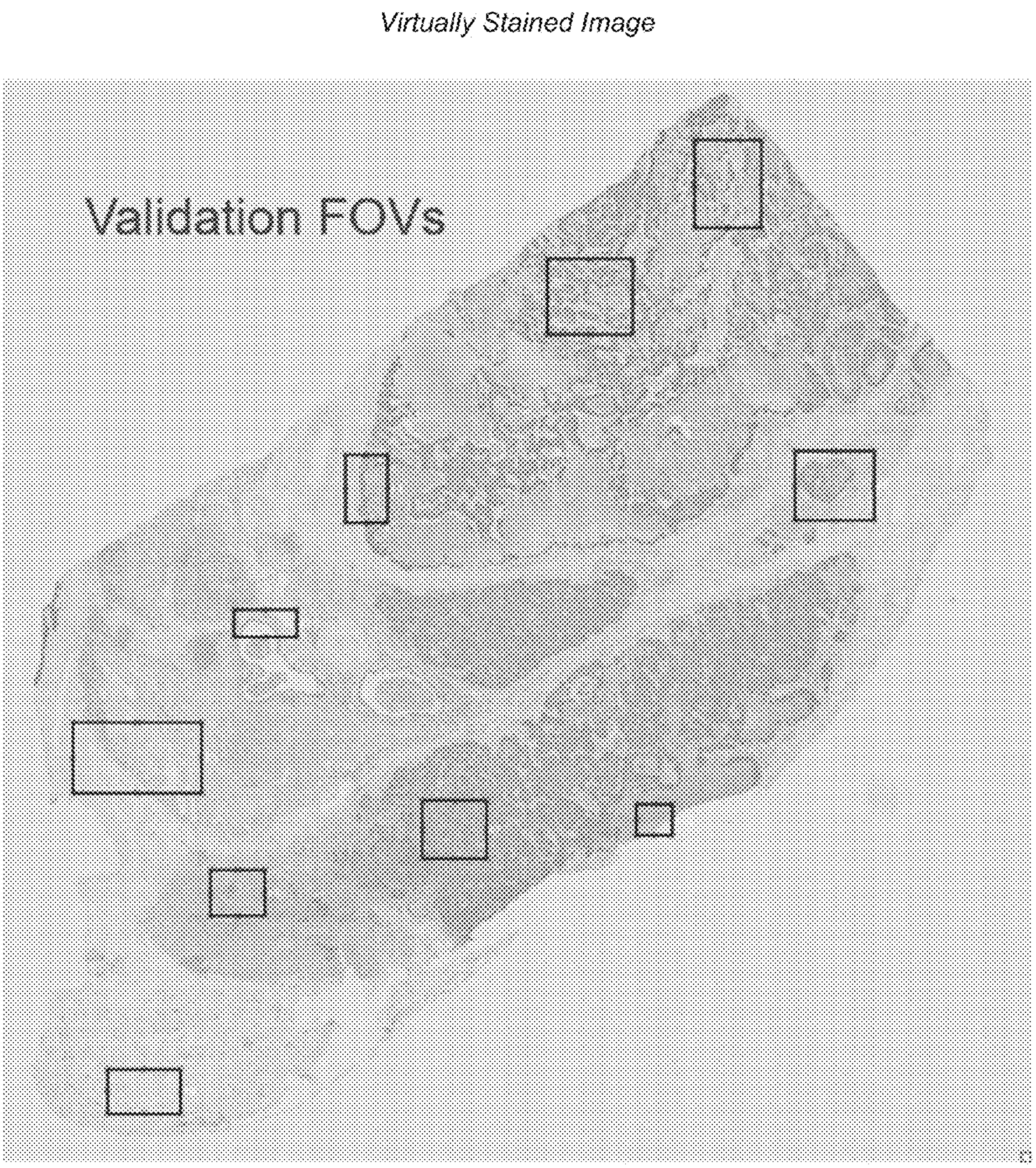
Fig. 8E
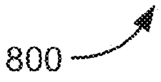

800

Virtual Staining Modelling

Regression

- Target – H + P40 (Magenta)

800

800

800

900

1840

Fer-{Lys{Fer}}3-L150-Lys{Flu}, aka, Fer4Flu, L150 indicating the total number of spacer atoms Fer-4-Flu

TISSUE STAINING AND SEQUENTIAL IMAGING OF BIOLOGICAL SAMPLES FOR DEEP LEARNING IMAGE ANALYSIS AND VIRTUAL STAINING

STATEMENT REGARDING COLOR DRAWINGS

The patent or application file contains at least one drawing executed in color. Copies of this patent or patent application publication with color drawing(s) will be provided by the Office upon request and payment of the necessary fee.

RELATED APPLICATION

This application is a National Stage Entry of PCT/IB2021/057583, filed Aug. 18, 2021, which claims the benefit of priority of U.S. Provisional Application No. 63/067,302, filed Aug. 18, 2020, the contents of which are incorporated herein by reference in their entirety

CROSS-REFERENCES TO RELATED APPLICATIONS

This application may be related to U.S. patent application Ser. No. 16/846,180 (the "'180 application"), filed Apr. 10, 2020 by Elad Arbel et al., entitled, "Deep Learning Based Instance Segmentation via Multiple Regression Layers," and U.S. patent application Ser. No. 16/846,181 (the "'181 Application"), filed Apr. 10, 2020 by Elad Arbel et al., entitled, "User Interface Configured to Facilitate User Annotation for Instance Segmentation Within Biological Samples," each of which claims priority to U.S. Patent Application Ser. No. 62/832,880 (the "'880 Application"), filed Apr. 12, 2019 by Elad Arbel et al., entitled, "DL Based Segmentation via Regression Layers," and U.S. Patent Application Ser. No. 62/832,877 (the "'877 Application"), filed Apr. 11, 2019 by Elad Arbel et al., entitled, "Nuclei Segmentation Using Partial Annotation," the disclosure of each of which is incorporated herein by reference in its entirety for all purposes.

This application may also be related to U.S. Patent Application Ser. No. 63/057,105 (the "'105 Application"), filed Jul. 27, 2020 by Elad Arbel et al., entitled, "Annotation Data Collection Using Gaze-Based Tracking," the disclosure of which is incorporated herein by reference in its entirety for all purposes.

The respective disclosures of these applications/patents (which this document refers to collectively as the "Related Applications") are incorporated herein by reference in their entirety for all purposes.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD

The present disclosure relates generally to methods, devices, reagents, and kits for use in multiplexed assays for detecting target molecules. Such methods have a wide utility in diagnostic applications, in choosing appropriate therapies for individual patients, or in training neural networks or developing algorithms for use in such diagnostic applications or selection of therapies. Further, the present disclosure provides novel compounds for use in detection of target molecules. The present disclosure also relates to methods, systems, and apparatuses for implementing annotation data collection and autonomous annotation, and, more particularly, to methods, systems, and apparatuses for implementing sequential imaging of biological samples for generating training data for developing deep learning based models for image analysis, for cell classification, for feature of interest identification, and/or for virtual staining of biological samples.

BACKGROUND

Histological specimens are frequently disposed upon glass slides as a thin slice of patient tissue fixed to the surface of each of the glass slides. Using a variety of chemical or biochemical processes, one or several colored compounds may be used to stain the tissue to differentiate cellular constituents which can be further evaluated utilizing microscopy. Brightfield slide scanners are conventionally used to digitally analyze these slides.

When analyzing tissue samples on a microscope slide, staining the tissue or certain parts of the tissue with a colored or fluorescent dye can aid the analysis. The ability to visualize or differentially identify microscopic structures is frequently enhanced through the use of histological stains. Hematoxylin and eosin (H&E) stains are the most commonly used stains in light microscopy for histological samples.

In addition to H&E stains, other stains or dyes have been applied to provide more specific staining and provide a more detailed view of tissue morphology. Immunohistochemistry ("IHC") stains have great specificity, as they use a peroxidase substrate or alkaline phosphatase ("AP") substrate for IHC stainings, providing a uniform staining pattern that appears to the viewer as a homogeneous color with intracellular resolution of cellular structures, e.g., membrane, cytoplasm, and nucleus. Formalin Fixed Paraffin Embedded ("FFPE") tissue samples, metaphase spreads or histological smears are typically analyzed by staining on a glass slide, where a particular biomarker, such as a protein or nucleic acid of interest, can be stained with H&E and/or with a colored dye, hereafter "chromogen" or "chromogenic moiety." IHC staining is a common tool in evaluation of tissue samples for the presence of specific biomarkers. IHC stains are precise in the recognition of specific targets in throughout the sample and allow quantification of these targets. IHC staining employs chromogenic and/or fluorescent reporters that mark targets in histological samples. This is carried out by linking the biomarker directly or indirectly with an enzyme, typically either Horse Radish Peroxidase ("HRP") or Alkaline Phosphatase ("AP"), that subsequently catalyzes the formation of an insoluble colored or fluorescent precipitate, at the location of the biomarker from a soluble suitable enzyme substrate, which exhibits a color or fluorescence.

In situ hybridization ("ISH") may be used to detect target nucleic acids in a tissue sample. ISH may employ nucleic acids labeled with a directly detectable moiety, such as a fluorescent moiety, or an indirectly detectable moiety, such as a moiety recognized by an antibody which can then be utilized to generate a detectable signal.

Compared to other detection techniques, such as radioactivity, chemo-luminescence or fluorescence, chromogens generally suffer from much lower sensitivity, but have the advantage of a permanent, plainly visible color which can be visually observed, such as with bright field microscopy. However, the advent of new and useful substrates has alleviated some of these disadvantages. For example, the use of chromogenic peroxidase substrates has been described in U.S. Pat. No. 10,526,646, the disclosure of which is incorporated herein by reference in its entirety. However, more substrates with additional properties which may be useful in various applications, including multiplexed assays, such as IHC or ISH assays, are needed.

With the advent of advanced deep learning methods, additional capabilities for advanced image analysis of histological slides may improve detection and assessment of specific molecular markers, tissue features, and organelles, or the like.

A challenge with such analysis methods (which may be used, for example, in digital pathology) is that they require vast amounts of training data. In some cases, training data may require tens of thousands of manually identified and annotated objects (e.g., tissue features, organelles, molecular markers, etc.) and can be an extremely time-consuming process. In addition, even experienced professionals may encounter difficulties evaluating tissue specimens microscopically to provide accurate interpretation of patient specimens. For example, detecting lymphocytes within a tumor stained for PD-L1 antigen can be difficult or impossible to do with an acceptably low error rate. One option is to use serial sections of tissue, where different biological markers are stained for in each of the two slides, which are then digitalized and aligned, and the staining pattern on one slide is used to annotate the other slide. One problem with this approach is that the discrete digitized layers or sections may be spatially different (e.g., in terms of orientation, focus, signal strength, and/or the like) from one another (e.g., with differences among annotation layers and training layers, or the like). Consequently, image alignment may be broadly correct or accurate for larger or more distinct objects (such as bulk tumor detection) but may not have cell-level or organelle-level precision, or the like, since the same cells are not necessarily present on the two slides or images. This can create challenges in developing suitable training data, which may not be well suited for identifying single cells, organelles, and/or molecular markers, or the like.

SUMMARY

According to a first aspect, there is provided a computer implemented method for training a ground truth generator machine learning model, the method comprises: creating a ground truth multi-record training dataset wherein a record comprises: a first image of a sample of a tissue of a subject depicting a first group of biological objects, a second image of the sample of tissue depicting a second group of biological objects presenting at least one biomarker, and ground truth labels indicating a respective biological object category of a plurality of biological object categories for biological object members of the first group and the second group, and training the ground truth generator machine learning model on the ground truth multi-record training dataset for automatically generating ground truth labels selected from the plurality of biological object categories for biological objects depicted in an input set of images of the first type and the second type.

In a further implementation form of the first aspect, the first image depicts the first group of biological objects presenting at least one first biomarker, and the second image depicts the second group of biological objects presenting at least one second biomarker different than the at least one first biomarker.

In a further implementation form of the first aspect, the first image comprises a brightfield image, and the second images comprises at least one of: (i) a fluorescent image with fluorescent markers indicating the at least one biomarker, (ii) spectral imaging image indicating the at least one biomarker, and (iii) non-labelled image depicting the at least one biomarker.

In a further implementation form of the first aspect, the first image depicts tissue stained with a first stain designed to stain the first group of biological objects depicting the at least one first biomarker, wherein the second image depicts the tissue stained with the first stain further stained with a second sequential stain designed to stain the second group of biological objects depicting at least one second biomarker, wherein the second group includes a first sub-group of the first group, and wherein a second sub-group of the first group is unstained by the second stain and excluded from the second group.

In a further implementation form of the first aspect, the method further comprising: feeding unlabeled sets of images of samples of tissue of a plurality of sample individuals into the ground truth generator machine learning model to obtain automatically generated ground truth labels, wherein the unlabeled sets of images depict biological objects respectively presenting the at least one first biomarker and at least one second biomarker, and creating a synthetic multi-record training dataset, wherein a synthetic record comprises images depicting the at least one first biomarker and excludes images depicting the at least one second biomarker, labelled with the automatically generated ground truth labels obtained from the ground truth generator machine learning model.

In a further implementation form of the first aspect, the method further comprising: training a biological object machine learning model on the synthetic multi-record training dataset for generating an outcome of at least one of the plurality of biological object categories for respective target biological objects depicted in a target image depicting biological objects presenting at least one first biomarker.

In a further implementation form of the first aspect, the method further comprising: training a diagnosis machine learning model on a biological object category multi-record training dataset comprising images depicting biological objects presenting at least one first biomarker, wherein biological objects depicted in the images are labelled with at least one of the plurality of biological object categories obtained as an outcome of the biological object machine learning model in response to input of the images, wherein images are labelled with ground truth labels indicative of a diagnosis.

In a further implementation form of the first aspect, ground truth labels of biological objects presenting the at least one second biomarker depicted in one respective image of a respective set are mapped to corresponding non-labeled biological objects presenting the at least one first biomarker depicted in another respective image of the set, wherein synthetic records of biological objects depicting the at least one first biomarker are labelled with ground truth labels mapped from biological objects depicting the at least one second biomarker.

In a further implementation form of the first aspect, the method further comprising: creating an imaging multi-record training dataset, wherein a record comprises a first image of a sample of tissue of a subject depicting a first group of biological objects presenting the at the least one first biomarker, and a ground truth indicated by a corresponding second image of the sample of tissue depicting a second group of biological objects presenting at least one second biomarker, and training a virtual stainer machine learning model on the imaging multi-record training dataset for generating a virtual image depicting biological objects presenting the at least one second biomarker in response to an input image depicting biological objects presenting the at the least one first biomarker.

In a further implementation form of the first aspect, the method further comprising: for each respective record: identifying a first plurality of biological features depicted in the first image, identifying a second plurality of biological features depicted in the second image that correspond to the identified first plurality of biological features, applying an optical flow process and/or non-rigid registration process to the respective second image to compute a respective aligned image, the optical flow process and/or non-rigid registration process aligns pixels locations of the second image to corresponding pixel locations of the first image using optical flow computed between the second plurality of biological features and the first plurality of biological features, wherein the ground truth comprises the aligned image.

In a further implementation form of the first aspect, the second image of the same sample included in the ground truth training dataset is obtained as an outcome of the virtual stainer machine learning model fed the corresponding first image.

In a further implementation form of the first aspect, second images fed into the ground truth generator machine learning model to generate a synthetic multi-record training dataset for training a biological object machine learning model, are obtained as outcomes of the virtual stainer machine learning model fed respective first images.

In a further implementation form of the first aspect, a biological object machine learning model is trained on a synthetic multi-record training dataset including sets of first and second images labelled with ground truth labels selected from a plurality of biological object categories, wherein the biological object machine learning model is fed a first target image depicting biological objects presenting the at least one first biomarker and a second target image depicting biological objects presenting at least one second biomarker obtained as an outcome of the virtual stainer machine learning model fed the first target image.

In a further implementation form of the first aspect, the first image is captured with a first imaging modality selected to label the first group of biological objects, wherein the second image is captured with a second imaging modality different from the first imaging modality selected to visually highlight the second group of biological objects depicting the at least one biomarker without labelling the second group of biological objects.

In a further implementation form of the first aspect, the method further comprising: segmenting biological visual features of the first image using an automated segmentation process to obtain a plurality of segmentations, mapping the plurality of segmentation of the first image to the second image, for respective segmentations of the second image: computing intensity values of pixels within and/or in proximity to a surrounding of the respective segmentation indicating visual depiction of at least one second biomarker, and classifying the respective segmentation by mapping the computed intensity value using a set of rules to a classification category indicating a respective biological object type.

According to a second aspect, there is provided a computer implemented method of automatically generating ground truth labels for biological objects, the method comprises: feeding unlabeled sets of images of samples of tissue of a plurality of sample individuals into a ground truth generator machine learning model, wherein the unlabeled sets of images depict biological objects respectively presenting at least one first biomarker and at least one second biomarker different than the at least one first biomarker, and obtaining automatically generated ground truth labels as an outcome of the ground truth generator machine learning model, wherein the ground truth generator machine learning model is trained on a ground truth multi-record training dataset wherein a record comprises: a first image of a sample of tissue of a subject depicting a first group of biological objects presenting the at least one first biomarker, a second image of the sample of tissue depicting a second group of biological objects presenting the at least one second biomarker different than the at least one first biomarker, and ground truth labels indicating a respective biological object category of a plurality of biological object categories for biological object members of the first group and the second group.

In a further implementation form of the second aspect, in response to receiving a respective image of a respective sample of tissue of a respective sample individual depicting the first group of biological objects presenting the at least one first biomarker, the respective image is fed into a virtual stainer machine learning model, and obtaining as an outcome of the virtual stainer machine learning model at least one of: (i) a synthetic image used as a second image of the unlabeled sets of images, and (ii) a synthetic image used as the second image of the sample of the record of the ground truth multi-record training dataset, wherein the virtual stainer machine learning model is trained on a virtual imaging multi-record, wherein a record comprises a first image of a sample of tissue of a subject depicting a first group of biological objects presenting the at the least one first biomarker, and a ground truth indicated by a corresponding second image of the sample of tissue depicting a second group of biological objects presenting the at least one second biomarker.

In a further implementation form of the second aspect, the further comprising feeding a target image depicting a plurality of biological objects presenting the at least one first biomarker into a biological object machine learning model, and obtaining at least one of the plurality of biological object categories for respective target biological objects depicted in the target image as an outcome of the biological object machine learning model, wherein the biological object machine learning model is trained on a synthetic multi-record training dataset, wherein a synthetic record comprises images depicting the at least one first biomarker and excludes images depicting the at least one second biomarker, labelled with the automatically generated ground truth labels obtained from the ground truth generator machine learning model.

According to a third aspect, there is provided a computer implemented method for generating virtual images, the method comprises: feeding a target image of a sample of tissue of a subject depicting a first group of biological objects presenting at least one first biomarker into a virtual stainer machine learning model, and obtaining a synthetic image of the sample depicting a second group of biological objects presenting at least one second biomarker different than the at least one first biomarker as an outcome of the virtual stainer machine learning model, wherein the virtual stainer machine learning model is trained on a virtual imaging multi-record, wherein a record comprises a first image of a sample of tissue of a subject depicting a first group of biological objects presenting the at the least one first biomarker, and a ground truth indicated by a corresponding second image of the sample of tissue depicting a second group of biological objects presenting the at least one second biomarker.

According to an aspect of some embodiments of the present invention there is provided a method for detecting multiple target molecules in a biological sample comprising cells, which comprises:

contacting the biological sample with one or more first reagents which generate a detectable signal in cells comprising a first target molecule;

contacting the biological sample with one or more second reagents which are capable of generating a detectable signal in cells comprising a second target molecule under conditions in which the one or more second reagents do not generate a detectable signal;

detecting the signal generated by the one or more first reagents;

creating conditions in which the one or more second reagents generate a signal in cells comprising the second molecule; and detecting the signal generated by the one or more second reagents.

According to some of any of the embodiments described herein, the method further comprises:

obtaining a first digital image of the signal generated by the one or more first reagents;

obtaining a second digital image of the signal generated by the one or more first reagents and the signal generated by the one or more second reagents; and copying a mask of the second digital image to the first digital image.

According to some of any of the embodiments described herein, the biological sample comprises one of a human tissue sample, an animal tissue sample, or a plant tissue sample.

According to some of any of the embodiments described herein, the target molecules are indicative of at least one of normal cells, cell type, abnormal cells, damaged cells, cancer cells, tumors, subcellular structures, a marker indicative of or associated with a disease, disorder or health condition, or organ structures.

According to some of any of the embodiments described herein, the target molecules are selected from the group consisting of nuclear proteins, cytoplasmic proteins, membrane proteins, nuclear antigens, cytoplasmic antigens, membrane antigens and nucleic acids.

According to exemplary embodiments, the target molecules are nucleic acids.

According to exemplary embodiments described herein, the target molecules are polypeptides.

According to some of any of the embodiments described herein, the first reagents comprise a first primary antibody against a first target polypeptide, an HRP coupled polymer that binds to the first primary antibody and a chromogen which is an HRP substrate.

According to some of these embodiments, the second reagents comprise a second primary antibody against a second target polypeptide, an HRP coupled polymer that binds to the second primary antibody, a fluorescein-coupled long single chained polymer, an antibody against FITC that binds to the fluorescein-coupled long single chained polymer and is coupled to HRP and a chromogen which is an HRP substrate.

According to some of any of the embodiments described herein, the method further comprises using a digital image of the signals detected in the biological sample to train a neural network, in accordance with some of any of the respective embodiments as described herein.

According to some embodiments, there is provided a neural network trained using the method as described herein. According to another aspect of some of any of the embodiments described herein, there is provided a method for generating cell-level annotations from a biological sample comprising cells, which comprises:

a) exposing the biological sample to a first ligand that recognizes a first antigen thereby forming a first ligand antigen complex;

b) exposing the first ligand antigen complex to a first labeling reagent binding to the first ligand, the first labeling reagent forming a first detectable reagent, whereby the first detectable reagent is precipitated around the first antigen and visible in brightfield;

c) exposing the biological sample to a second ligand that recognizes a second antigen thereby forming a second ligand antigen complex;

d) exposing the second ligand antigen complex to a second labeling reagent binding to the second ligand, the second labeling reagent comprising a substrate not visible in brightfield, whereby the substrate is precipitated around the second antigen;

e) obtaining a first image of the biological sample in brightfield to visualize the first chromogen precipitated in the biological sample;

f) exposing the biological sample to a third labeling reagent that recognizes the substrate, thereby forming a third ligand antigen complex, the third labeling reagent forming a second detectable reagent, whereby the second detectable reagent is precipitated around the second antigen;

g) obtaining a second image of the biological sample in brightfield with the second detectable reagent precipitated in the biological sample;

h) creating a mask from the second image; and i) applying the mask to the first image so as to obtain an image of the biological sample annotated with the second antigen.

According to some of any of the embodiments of this aspect of the present invention, the biological sample comprises one of a human tissue sample, an animal tissue sample, or a plant tissue sample.

According to some of any of the embodiments of this aspect of the present invention, the target molecules are indicative of at least one of normal cells, cell type, abnormal cells, damaged cells, cancer cells, tumors, subcellular structures, a marker indicative of or associated with a disease, disorder or health condition, or organ structures.

According to some of any of the embodiments of this aspect of the present invention, the method further comprises, prior to step a), applying a target retrieval buffer and protein blocking solution to the biological sample, whereby the first and second antigens are exposed for the subsequent steps and endogenous peroxidases are inactivated.

According to some of any of the embodiments of this aspect of the present invention, the first and third labeling reagents comprise an enzyme that acts on a detectable reagent substrate to form the first and second detectable reagents, respectively.

According to some of any of the embodiments of this aspect of the present invention, the first and second antigens are non-nuclear proteins.

According to some of any of the embodiments of this aspect of the present invention, the method further comprises, following step b), denaturing the first ligands to retrieve the first antigens available.

According to some of any of the embodiments of this aspect of the present invention, the method further comprises, following step d), i) counterstaining cell nuclei of the biological sample, and ii) dehydrating and mounting the sample on a slide.

According to some of any of the embodiments of this aspect of the present invention, the method further comprises following step e), i) removing mounting medium from the slide, and ii) rehydrating the biological sample.

According to some of any of the embodiments of this aspect of the present invention, the method further comprises following step f), i) counterstaining cell nuclei of the biological sample, and ii) dehydrating and mounting the sample on a slide.

According to exemplary embodiments of this aspect of the present invention, the first ligand comprises an anti-lymphocyte-specific antigen antibody ("primary antibody"), the first labeling reagent comprises a horseradish peroxidase (HRP)-coupled polymer capable of binding to the primary antibody, the first detectable reagent comprises a chromogen comprising an HRP substrate comprising HRP Magenta or 3,3'-diaminobenzidine tetrahydrochloride (DAB), the second antigen comprises PD-L1, the second ligand comprises anti-PD-L1 antibodies, the second labeling reagent comprises an HRP-coupled polymer capable of binding to anti-PD-L1 antibodies, the substrate comprises fluorescein-coupled long single-chained polymer (fer-4-flu linker), a third labeling reagent comprises an anti-FITC antibody coupled to HRP, and the second detectable reagent comprises a chromogen comprising HRP Magenta or DAB.

According to exemplary embodiments of this aspect of the present invention, the first antigen comprises PD-L1, the first ligand comprises anti-PD-L1 antibodies, the first labeling reagent comprises an HRP-coupled polymer capable of binding to anti-PD-L1 antibodies, the substrate comprises fluorescein-coupled long single-chained polymer (fer-4– flu linker), the second ligand comprises an anti-lymphocyte-specific antigen antibody ("primary antibody"), the second labeling reagent comprises a horseradish peroxidase (HRP)-coupled polymer capable of binding to the primary antibody, the second detectable reagent comprises a chromogen comprising an HRP substrate comprising HRP Magenta or 3,3'-diaminobenzidine tetrahydrochloride (DAB), a third labeling reagent comprises an anti-FITC antibody coupled to HRP, and the second detectable reagent comprises a chromogen comprising HRP Magenta or DAB.

According to exemplary embodiments of this aspect of the present invention, the first labeling reagent comprises a horseradish peroxidase (HRP)-coupled polymer capable of binding to the primary antibody, the first detectable reagent comprises a chromogen comprising an HRP substrate comprising HRP Magenta or 3,3'-diaminobenzidine tetrahydrochloride (DAB), the second antigen comprises p40, the second ligand comprises anti-p40 antibodies, the second labeling reagent comprises an HRP-coupled polymer capable of binding to anti-p40 antibodies, the substrate comprises fluorescein-coupled long single-chained polymer (fer-4–flu linker), the third labeling reagent is an anti-FITC antibody coupled to HRP, and the second detectable reagent comprises a chromogen comprising HRP Magenta or DAB.

According to exemplary embodiments of this aspect of the present invention, the first antigen comprises p40, the first ligand comprises anti-p40 antibodies, the first labeling reagent comprises an HRP-coupled polymer capable of binding to anti-p40 antibodies, the substrate comprises fluorescein-coupled long single-chained polymer (fer-4–flu linker), the second labeling reagent comprises a horseradish peroxidase (HRP)-coupled polymer capable of binding to the primary antibody, the second detectable reagent comprises a chromogen comprising an HRP substrate comprising HRP Magenta or 3,3'-diaminobenzidine tetrahydrochloride (DAB), a third labeling reagent an anti-FITC antibody coupled to HRP, and the second detectable reagent comprises a chromogen comprising HRP Magenta or DAB.

According to some of these embodiments, a counterstaining agent is hematoxylin.

According to some of any of the embodiments of this aspect of the present invention, the method further comprises using a digital image of the signals detected in the biological sample to train a neural network, as described herein in any of the respective embodiments, and according to some embodiments, there is provided a neural network trained using this method.

According to some embodiments, there is provided an annotated image obtained by the method as described herein in any of the respective embodiments and any combination thereof.

According to yet another aspect of some embodiments of the present invention there is provided a method for detecting multiple target molecules in a biological sample comprising cells, which comprises:

contacting the biological sample with one or more first reagents which generate a detectable signal in cells comprising a first target molecule;

contacting the biological sample with one or more second reagents which generate a detectable signal in cells comprising a second target molecule, wherein the detectable signal generated by the one or more second reagents is removable;

detecting the signal generated by the one or more first reagents and the signal generated by the one or more second reagents;

creating conditions in which the signal generated by the one or more second reagents is removed; and detecting the signal generated by the one or more first reagents.

According to some of any of the embodiments of this aspect of the present invention, the method further comprises: obtaining a first digital image of the signal generated by the one or more first reagents and the signal generated by the one or more second reagents; obtaining a second digital image of the signal generated by the one or more first reagents; and copying a mask of the first digital image to the second digital image.

According to some of any of the embodiments of this aspect of the present invention, the biological sample comprises one of a human tissue sample, an animal tissue sample, or a plant tissue sample.

According to some of any of the embodiments of this aspect of the present invention, the target molecules are indicative of at least one of normal cells, cell type, abnormal cells, damaged cells, cancer cells, tumors, subcellular structures, a marker indicative of or associated with a disease, disorder or health condition, or organ structures.

According to some of any of the embodiments of this aspect of the present invention, the target molecules are selected from the group consisting of nuclear proteins, cytoplasmic proteins, membrane proteins, nuclear antigens, cytoplasmic antigens, membrane antigens and nucleic acids.

According to exemplary embodiments, the target molecules are nucleic acids.

According to exemplary embodiments, the target molecules are polypeptides.

According to some of any of the embodiments of this aspect of the present invention, the first reagents comprise a first primary antibody against a first target polypeptide, an HRP coupled polymer that binds to the first primary antibody and a chromogen which is an HRP substrate.

According to some of any of the embodiments of this aspect of the present invention, the second reagents comprise a second primary antibody against a second target polypeptide, an HRP coupled polymer that binds to the second primary antibody, and amino ethyl carbazole.

According to some of any of the embodiments of this aspect of the present invention, the method further comprises using a digital image of the signals detected in the biological sample to train a neural network, as described herein in any of the respective embodiments, and according to some embodiments, there is provided a neural network trained using the method.

According to still another aspect of some embodiments of the present invention there is provided a method for generating cell-level annotations from a biological sample comprising cells, which comprises:

a) exposing the biological sample to a first ligand that recognizes a first antigen thereby forming a first ligand antigen complex;

b) exposing the first ligand antigen complex to a first labeling reagent binding to the first ligand, the first labeling reagent forming a first detectable reagent, whereby the first detectable reagent is precipitated around the first antigen;

c) exposing the biological sample to a second ligand that recognizes a second antigen thereby forming a second ligand antigen complex;

d) exposing the second ligand antigen complex to a second labeling reagent binding to the second ligand, the second labeling reagent forming a second detectable reagent, whereby the second detectable reagent is precipitated around the second antigen;

e) obtaining a first image of the biological sample with the first and second detectable reagents precipitated in the biological sample;

f) incubating the tissue sample with an agent which dissolves the second detectable reagent;

g) obtaining a second image of the biological sample with the first detectable reagent precipitated in the biological sample;

h) creating a mask from the first image; and i) applying the mask to the second image so as to obtain an annotated image of the biological sample with the second antigen.

According to some of any of the embodiments of this aspect of the present invention, the first biological sample comprises one of a human tissue sample, an animal tissue sample, or a plant tissue sample, wherein the objects of interest comprise at least one of normal cells, abnormal cells, damaged cells, cancer cells, tumors, subcellular structures, or organ structures.

According to some of any of the embodiments of this aspect of the present invention, the method further comprises, prior to step a), applying a target retrieval buffer and protein blocking solution to the biological sample, whereby the first and second antigens are exposed for the subsequent steps and endogenous peroxidases are inactivated.

According to some of any of the embodiments of this aspect of the present invention, the first and second labeling reagents comprise an enzyme that acts on a detectable reagent substrate to form the first and second detectable reagents, respectively.

According to some of any of the embodiments of this aspect of the present invention, the first and second antigens are non-nuclear proteins.

According to some of any of the embodiments of this aspect of the present invention, the method further comprises, following step b), denaturing the first ligands to retrieve the first antigens available.

According to some of any of the embodiments of this aspect of the present invention, the method further comprises, following step d), i) counterstaining cell nuclei of the biological sample, and ii) dehydrating and mounting the sample on a slide.

According to some of any of the embodiments of this aspect of the present invention, the method further comprises, following step e), i) removing mounting medium from the slide, and ii) rehydrating the biological sample.

According to some of any of the embodiments of this aspect of the present invention, the method further comprises, following step f), dehydrating and mounting the sample on a slide.

According to some of any of the embodiments of this aspect of the present invention, the first antigen comprises a lymphocyte-specific antigen, the first ligand comprises an anti-lymphocyte-specific antigen antibody ("primary antibody"), the first labeling reagent comprises a horseradish peroxidase (HRP)-coupled polymer capable of binding to the primary antibody, the first detectable reagent comprises an HRP substrate comprising HRP Magenta or 3,3'-diaminobenzidine tetrahydrochloride (DAB), the second antigen comprises PD-L1, the second ligand comprises anti-PD-L1 antibodies, the second labeling reagent comprises an HRP-coupled polymer capable of binding to anti-PD-L1 antibodies, the second detectable reagent comprises amino ethyl carbazole (AEC), and the agent which dissolves the second detectable reagent is alcohol or acetone.

According to some of any of the embodiments of this aspect of the present invention, the first labeling reagent comprises a horseradish peroxidase (HRP)-coupled polymer capable of binding to the primary antibody, the first detectable reagent comprises an HRP substrate comprising HRP Magenta or 3,3'-diaminobenzidine tetrahydrochloride (DAB), the second antigen comprises p40, the second ligand comprises anti-p40 antibodies, the second labeling reagent comprises an HRP-coupled polymer capable of binding to anti-p40 antibodies, the second detectable reagent comprises amino ethyl carbazole (AEC), and the agent which dissolves the second detectable reagent is alcohol or acetone.

According to some of any of the embodiments of this aspect of the present invention, a counterstaining agent is hematoxylin.

According to some of any of the embodiments of this aspect of the present invention, the method further comprises using a digital image of the signals detected in the biological sample to train a neural network, as described herein in any of the respective embodiments, and according to some embodiments, there is provided a neural network trained using the method.

According to some embodiments, there is provided an annotated image obtained by the method as described herein.

According to another aspect of some embodiments of the present invention there is provided a method for detecting multiple target molecules in a biological sample comprising cells, which comprises:

contacting the biological sample with one or more first reagents which generate a first detectable signal in cells comprising a first target molecule, wherein the first detectable signal is detectable using a first detection method;

contacting the biological sample with one or more second reagents which generate a second detectable signal in cells comprising a second target molecule, wherein the second detectable signal is detectable using a second detection method and is substantially undetectable using the first detection method and wherein the first detectable signal is substantially undetectable using the second detection method;

detecting the signal generated by the one or more first reagents using the first detection method; and detecting the signal generated by the one or more second reagents using the second detection method.

According to some of any of the embodiments of this aspect of the present invention, the biological sample comprises one of a human tissue sample, an animal tissue sample, or a plant tissue sample.

According to some of any of the embodiments of this aspect of the present invention, the target molecules are indicative of at least one of normal cells, cell type, abnormal cells, damaged cells, cancer cells, tumors, subcellular structures, a marker indicative of or associated with a disease, disorder or health condition, or organ structures.

According to some of any of the embodiments of this aspect of the present invention, the target molecules are selected from the group consisting of nuclear proteins, cytoplasmic proteins, membrane proteins, nuclear antigens, cytoplasmic antigens, membrane antigens and nucleic acids.

According to exemplary embodiments, the target molecules are nucleic acids.

According to exemplary embodiments, the target molecules are polypeptides.

According to some of any of the embodiments of this aspect of the present invention, the first reagents comprise a first primary antibody against a first target polypeptide, an HRP coupled polymer that binds to the first primary antibody and a chromogen which is an HRP substrate.

According to some of any of the embodiments of this aspect of the present invention, the second reagents comprise a second primary antibody against a second target polypeptide, an HRP coupled polymer that binds to the second primary antibody, and a rhodamine based fluorescent compound coupled to a long single chained polymer.

According to some of any of the embodiments of this aspect of the present invention, the method further comprises using a digital image of the signals detected in the biological sample to train a neural network, as described herein in any of the respective embodiments, and according to some embodiments, there is provided a neural network trained using this method.

According to yet another aspect of some embodiments of the present invention there is provided a method for generating cell-level annotations from a biological sample comprising cells, which comprises:

a) exposing the biological sample to a first ligand that recognizes a first antigen thereby forming a first ligand antigen complex;

b) exposing the first ligand antigen complex to a first labeling reagent binding to the first ligand, the first labeling reagent forming a first detectable reagent, wherein the first detectable reagent is visible in brightfield; whereby the first detectable reagent is precipitated around the first antigen;

c) exposing the biological sample to a second ligand that recognizes a second antigen thereby forming a second ligand antigen complex;

d) exposing the second ligand antigen complex to a second labeling reagent binding to the second ligand, the second labeling reagent forming a second detectable reagent, wherein the second detectable reagent is visible in fluorescence; whereby the second detectable reagent is precipitated around the second antigen;

e) obtaining a first brightfield image of the biological sample with the first detectable reagent precipitated in the biological sample;

f) obtaining a second fluorescent image of the biological sample with the second detectable reagent precipitated in the biological sample;

g) creating a mask from the second image; and h) applying the mask to the first image so as to obtain an annotated image of the tissue sample with the second marker.

According to some of any of the embodiments of this aspect of the present invention, the method further comprises, prior to step a), applying a target retrieval buffer and protein blocking solution to the biological sample, whereby the first and second antigens are exposed for the subsequent steps and endogenous peroxidases are inactivated.

According to some of any of the embodiments of this aspect of the present invention, the first biological sample comprises one of a human tissue sample, an animal tissue sample, or a plant tissue sample.

According to some of any of the embodiments of this aspect of the present invention, the target molecules are indicative of at least one of normal cells, cell type, abnormal cells, damaged cells, cancer cells, tumors, subcellular structures, a marker indicative of or associated with a disease, disorder or health condition, or organ structures.

According to some of any of the embodiments of this aspect of the present invention, the first and second labeling reagents comprise an enzyme that acts on a detectable reagent substrate to form the first and second detectable reagents, respectively.

According to some of any of the embodiments of this aspect of the present invention, the first and second antigens are non-nuclear proteins.

According to some of any of the embodiments of this aspect of the present invention, the method further comprises, following step b), denaturing the first ligands to retrieve the first antigens available.

According to some of any of the embodiments of this aspect of the present invention, the method further comprises, following step d), i) counterstaining cell nuclei of the biological sample, and ii) dehydrating and mounting the sample on a slide.

According to exemplary embodiments, the first labeling reagent comprises a horseradish peroxidase (HRP)-coupled polymer capable of binding to the primary antibody, the first detectable reagent comprises an HRP substrate comprising HRP Magenta or 3,3'-diaminobenzidine tetrahydrochloride (DAB), the second antigen comprises PD-L1, the second ligand comprises anti-PD-L1 antibodies, the second labeling reagent comprises an HRP-coupled polymer capable of binding to anti-PD-L1 antibodies, and the second detectable reagent comprises a rhodamine-based fluorescent compound coupled to a long single-chain polymer.

According to exemplary embodiments, the first antigen comprises PD-L1, the first ligand comprises anti-PD-L1 antibodies, the first labeling reagent comprises a horseradish peroxidase (HRP)-coupled polymer capable of binding to anti-PD-L1 antibodies, the first detectable reagent comprises a rhodamine-based fluorescent compound coupled to a long single-chain polymer, the second labeling reagent comprises an HRP-coupled polymer capable of binding to the primary antibody, and the second detectable reagent comprises an HRP substrate comprising HRP Magenta or 3,3'-diaminobenzidine tetrahydrochloride (DAB).

According to exemplary embodiments, the first antigen comprises a lymphocyte-specific antigen, the first ligand comprises an anti-lymphocyte-specific antigen antibody ("primary antibody"), the first labeling reagent comprises a horseradish peroxidase (HRP)-coupled polymer capable of binding to the primary antibody, the first detectable reagent comprises an HRP substrate comprising HRP Magenta or 3,3'-diaminobenzidine tetrahydrochloride (DAB), the second antigen comprises p40, the second ligand comprises anti-p40 antibodies, the second labeling reagent comprises an HRP-coupled polymer capable of binding to anti-p40 antibodies, and the second detectable reagent comprises rhodamine-based fluorescent compound coupled to a long single-chain polymer.

According to some of any of the embodiments of this aspect of the present invention, the first antigen comprises p40, the first ligand comprises anti-p40 antibodies, the first labeling reagent comprises a horseradish peroxidase (HRP)-coupled polymer capable of binding to anti-p40 antibodies, the first detectable reagent comprises rhodamine-based fluorescent compound coupled to a long single-chain polymer, the second antigen comprises a lymphocyte-specific antigen, the second ligand comprises an anti-lymphocyte-specific antigen antibody ("primary antibody"), the second labeling reagent comprises HRP-coupled polymer capable of binding to the primary antibody, and the second detectable reagent comprises an HRP substrate comprising HRP Magenta or 3,3'-diaminobenzidine tetrahydrochloride (DAB).

According to some of any of the embodiments described herein, a counterstaining agent is hematoxylin.

According to some of any of the embodiments of this aspect of the present invention, there is provided an annotated image obtained by the described method.

According to an aspect of some embodiments of the present invention, there is provided a compound of Formula I (CM):

Formula I

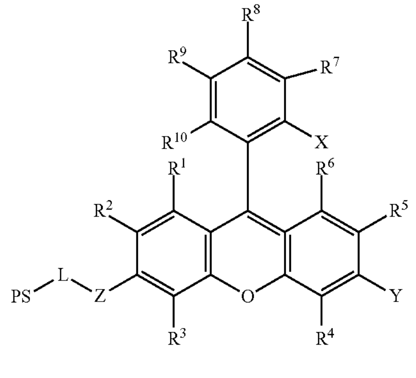

wherein:

X is —COOR$^X$, —CH2COOR$^X$, —CONR$^X$R$^{XX}$, —CH$_2$CONR$^X$R$^{XX}$, which includes the corresponding spirolactones or spirolactams of Formula I, where the spiro-ring is formed between X and the carbon on the middle ring of the tricyclic structure.

wherein:

Y is =O, =NR$^y$, or =N$^+$R$^y$R$^{yy}$;

Z is O or NR$^z$,

Wherein:

R$^1$, R$^2$, R$^3$, R$^4$, R$^5$, R$^6$, R$^7$, R$^8$, R$^9$, R$^{10}$, R$^x$, R$^{xx}$, R$^z$, R$^y$, and R$^{yy}$ are each independently selected from hydrogen and a substituent having less than 40 atoms;

L is a linker comprising a linear chain of 5 to 29 consecutively connected atoms; and PS is a peroxidase substrate moiety.

According to some of any of the embodiments that relate to this aspect of the present invention, R$^1$ is selected from hydrogen, R$^{11}$, (C1-C20) alkyl or heteroalkyl optionally substituted with one or more of the same or different R$^{14}$ groups, (C5-C20) aryl or heteroaryl optionally substituted with one or more of the same or different R$^{13}$ or suitable R$^{14}$ groups and (C6-C40) arylalkyl or heteroaryl alkyl optionally substituted with one or more of the same or different R$^{13}$ or suitable R$^{14}$ groups, or alternatively, R$^1$ may be taken together with R$^2$ to form part of a benzo, naphtho or polycyclic aryleno group which is optionally substituted with one or more of the same or different R$^{13}$ or suitable R$^{14}$ groups;

R$^2$ is selected from hydrogen, R$^{11}$, (C1-C20) alkyl or heteroalkyl optionally substituted with one or more of the same or different R$^{14}$ groups, (C5-C20) aryl or heteroaryl optionally substituted with one or more of the same or different R$^{13}$ or suitable R$^{14}$ groups and (C6-C40) arylalkyl or heteroaryl alkyl optionally substituted with one or more of the same or different R$^{13}$ or suitable R$^{14}$ groups, or alternatively, R$^2$ may be taken together with R$^1$, to form part of a benzo, naptho or polycyclic aryleno group which is optionally substituted with one or more of the same or different R$^{13}$ or suitable R$^{14}$ groups;

R$^X$, when present, is selected from hydrogen, (C1-C20) alkyl or heteroalkyl optionally substituted with one or more of the same or different R$^{14}$ groups, (C5-C20) aryl or heteroaryl optionally substituted with one or more of the same or different R$^{13}$ or suitable R$^{14}$ groups and (C6-C40) arylalkyl or heteroaryl alkyl optionally substituted with one or more of the same or different $R^{13}$ or suitable $R^{14}$ groups;

$R^{xx}$, when present, is selected from (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups;

$R^3$ is selected from hydrogen, $R^{11}$, (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups;

$R^4$ is selected from hydrogen, $R^{11}$, (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups, or, alternatively, when Y is $—N^{+}R^{Y}R^{YY}$, $R^4$ may be taken together with Ryy to form a 5- or 6-membered ring which is optionally substituted with one or more of the same or different $R^{13}$ or suitable $R^{14}$ groups;

$R^{yy}$, when present, is selected from (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups, or, alternatively $R^{y}$ may be taken together with $R^4$ to form a 5- or 6-membered ring which is optionally substituted with one or more of the same or different $R^{13}$ or suitable $R^{14}$ groups;

$R^{y}$, when present, is selected from hydrogen, (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups, or, alternatively, $R^{y}$ may be taken together with $R^5$ to form a 5- or 6-membered ring optionally substituted with one or more of the same or different $R^{13}$ or suitable $R^{14}$ groups;

$R^{z}$, when present, is selected from hydrogen, (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups;

$R^5$ is selected from hydrogen, $R^{11}$, (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups, or, alternatively, $R^5$ may be taken together with $R^6$ to form part of a benzo, naptho or polycyclic aryleno group which is optionally substituted with one or more of the same or different $R^{13}$ or suitable $R^{14}$ groups, or alternatively, when Y is $—N^{+}R^{Y}R^{Y}Y$, $R^5$ may be taken together with Ry to form a 5- or 6-membered ring optionally substituted with one or more of the same or different $R^{13}$ or suitable $R^{14}$ groups;

$R^6$ is selected from hydrogen, $R^{11}$, (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups, or, alternatively, $R^6$ together with $R^5$ may form part of a benzo, naptho or polycyclic aryleno group which is optionally substituted with one or more of the same or different $R^{13}$ or suitable $R^{14}$ groups;

$R^7$, $R^8$ and $R^9$ are each, independently of one another, selected from hydrogen, $R^{11}$, (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups;

$R^{10}$ is selected from selected from hydrogen, $R^{11}$, (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups, halo, haloalkyl, $—OR^{12}$, $—SR^{12}$, $—SOR^{12}$, $—SO_2R^{12}$, and nitrile;

$R^{11}$ is selected from $—NR^{15}R^{15}$, $—OR^{16}$, $—SR^{16}$, halo, haloalkyl, —CN, —NC, —OCN, —SCN, —NO, $—NO_2$, $—N_3$, $—S(O)R^{16}$, $—S(O)_2R^{16}$, $—S(O)_2OR^{16}$, $—S(O)NR^{15}R^{15}$, $—S(O)_2NR^{15}R^{15}$, $—OS(O)R^{16}$, $—OS(O)_2R^{16}$, $—OS(O)_2NR^{15}R^{15}$, $—OP(O)_2R^{16}$, $—OP(O)_3R^{16}R^{16}$, $—P(O)_3R^{16}R^{16}$, $—C(O)R^{16}$, $—C(O)OR^{16}$, $—C(O)NR^{15}R^{15}$, $—C(NH)NR^{15}R^{15}$, $—OC(O)R^{16}$, $—OC(O)OR^{16}$, $—OC(O)NR^{15}R^{15}$ and $—OC(NH)NR^{15}R^{15}$;

$R^{12}$ is selected from (C1-C20) alkyls or heteroalkyls optionally substituted with lipophilic substituents, (C5-C20) aryls or heteroaryls optionally substituted with lipophilic substituents and (C2-C26) arylalkyl or heteroarylalkyls optionally substituted with lipophilic substituents;

$R^{13}$ is selected from hydrogen, (C1-C8) alkyl or heteroalkyl, (C5-C20) aryl or heteroaryl and (C6-C28) arylalkyl or heteroarylalkyl;

$R^{14}$ is selected from $—NR^{15}R^{15}$, =O, $—OR^{16}$, =S, $—SR^{16}$, $=NR^{16}$, $=NOR^{16}$, halo, haloalkyl, —CN, —NC, —OCN, —SCN, —NO, $—NO_2$, $=N_2$, $—N_3$, $—S(O)R^{16}$, $—S(O)_2R^{16}$, $—S(O)_2OR^{16}$, $—S(O)NR^{15}R^{15}$, $—S(O)_2NR^{15}R^{15}$, $—OS(O)R^{16}$, $—OS(O)_2R^{16}$, $—OS(O)_2NR^{15}R^{15}$, $—OS(O)_2OR^{16}$, $—OS(O)_2NR^{15}R^{15}$, $—C(O)R^{16}$, $—C(O)OR^{16}$, $—C(O)NR^{15}R^{15}$, $—C(NH)NR^{15}R^{15}$, $—OC(O)R^{16}$, $—OC(O)OR^{16}$, $—OC(O)NR^{15}R^{15}$ and $—OC(NH)NR^{15}R^{15}$;

each $R^{15}$ is independently hydrogen or $R^{16}$, or alternatively, each $R^{15}$ is taken together with the nitrogen atom to which it is bonded to form a 5- to 8-membered saturated or unsaturated ring which may optionally include one or more of the same or different additional heteroatoms and which may optionally be substituted with one or more of the same or different $R^{13}$ or $R^{16}$ groups;

each $R^{16}$ is independently $R^{13}$ or $R^{13}$ substituted with one or more of the same or different $R^{13}$ or $R^{17}$ groups; and each $R^{17}$ is selected from $-NR^{13}R^{13}$, $-OR^{13}$, $=S$, $-SR^{13}$, $=NR^{13}$, $=NOR^{13}$, halo, haloalkyl, $-CN$, $-NC$, $-OCN$, $-SCN$, $-NO$, $-NO_2$, $=N_2$, $-N_3$, $-S(O)R^{13}$, $-S(O)_2R^{13}$, $-S(O)_2OR^{13}$, $-S(O)NR^{13}R^{13}$, $-S(O)_2NR^{13}R^{13}$, $-OS(O)R^{13}$, $-OS(O)_2R^{13}$, $-OS(O)_2NR^{13}R^{13}$, $-OS(O)_2OR^{16}$, $-OS(O)_2NR^{13}R^{13}$, $-C(O)R^{13}$, $-C(O)OR^{13}$, $-C(O)NR^{13}R^{13}$, $-C(NH)NR^{15}R^{13}$, $-OC(O)R^{13}$, $-OC(O)OR^{13}$, $-OC(O)NR^{13}R^{13}$ and $-OC(NH)NR^{13}R^{13}$.

According to some of any of the embodiments of this aspect of the present invention, the compound comprises a chromogenic moiety selected from the group consisting of rhodamine, rhodamine derivatives, fluorescein, fluorescein derivatives in which X is $-COOH$, $-CH_2COOH$, $-CONH_2$, $-CH_2CONH_2$ and salts of the foregoing.

According to some of any of the embodiments of this aspect of the present invention, the compound comprises a chromogenic moiety selected from the group consisting of rhodamine, rhodamine 6G, tetramethylrhodamine, rhodamine B, rhodamine 101, rhodamine 110, fluorescein, O-carboxymethyl fluorescein, derivatives of the foregoing in which X is $-COOH$, $-CH_2COOH$, $-CONH_2$, $-CH_2CONH_2$ and salts of the foregoing.

According to some of any of the embodiments of this aspect of the present invention, the peroxidase substrate moiety has the following formula:

Formula II

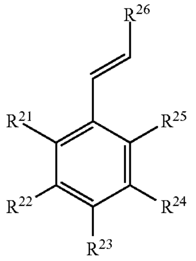

wherein:

$R^{21}$ is $-H$, $R^{22}$ is $-H$, $-O-Y$, or $-N(Y)_2$; $R^{23}$ is $-OH$ or $NH_2$;

$R^{24}$ is $-H$, $-O-Y$, or $-N(Y)_2$;

$R^{25}$ is $-H$, $-O-Y$, or $-N(Y)_2$;

$R^{26}$ is CO;

Y is H, alkyl or aryl;

wherein PS is linked to L through $R^{26}$.

According to some of any of the embodiments of this aspect of the present invention, $R^{23}$ is $-OH$, and $R^{24}$ is $-H$.

According to some of any of the embodiments of this aspect of the present invention, either $R^{21}$ or $R^{25}$ is $-OH$, $R^{22}$ and $R^{24}$ are $-H$, and $R^{23}$ is $-OH$.

According to some of any of the embodiments of this aspect of the present invention, the peroxidase substrate moiety is a residue of ferulic acid, cinnamic acid, caffeic acid, sinapinic acid, 2,4-dihydroxycinnamic acid or 4-hydroxycinnamic acid (coumaric acid).

According to some of any of the embodiments of this aspect of the present invention, the peroxidase substrate moiety is a residue of 4-hydroxycinnamic acid.

According to some of any of the embodiments of this aspect of the present invention, the linker is a compound ($R^{35}$) that comprises:

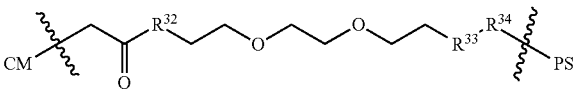

wherein the curved lines denote attachment points to the compound (CM) and to the peroxidase substrate (PS), and wherein $R^{34}$ is optional and can be omitted or used as an extension of linker, wherein $R^{34}$ is:

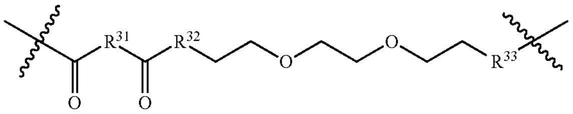

wherein the curved lines denote attachment point to $R^{33}$ and PS, wherein $R^{31}$ is selected from methyl, ethyl, propyl, $OCH_2$, $CH_2OCH_2$, $(CH_2OCH_2)_2$, $NHCH_2$, $NH(CH_2)_2$, $CH_2NHCH_2$, cycloalkyl, alkyl-cycloalkyl, alkyl-cycloalkyl-alkyl, heterocyclyl (such as nitrogen-containing rings of 4 to 8 atoms), alkyl-heterocyclyl, alkyl-heterocyclyl-alkyl, and wherein no more than three consecutively repeating ethyloxy groups, and $R^{32}$ and $R^{33}$ are independently in each formula is selected from NH and O.

According to some of any of the embodiments of this aspect of the present invention, the linker is selected from one or two repeat of a moiety of Formula IIIa, IIb, or IIc:

Formula IIIa

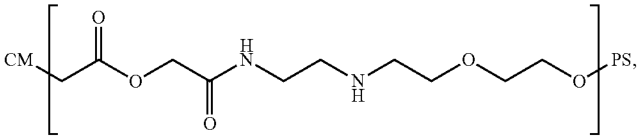

-continued

Formula IIIb

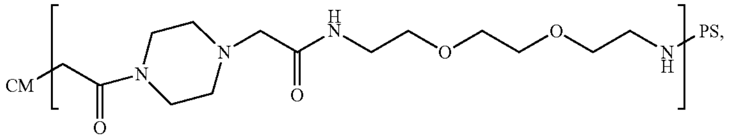

Formula IIIc

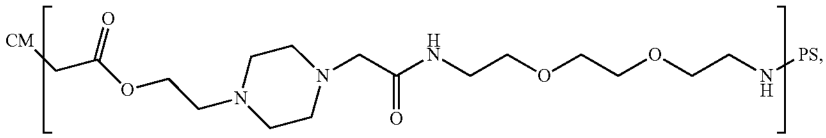

with an optional extension:

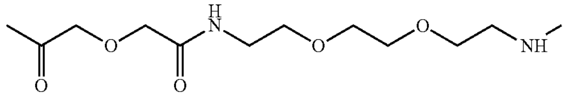 [SMILES: CNCCOCCOCCNC(=O)COCC(C)=O]

which would be inserted between the respective atom N in the compound (CM) and PS bond.

According to some of any of the embodiments of this aspect of the present invention, Z-L-PS together comprises:

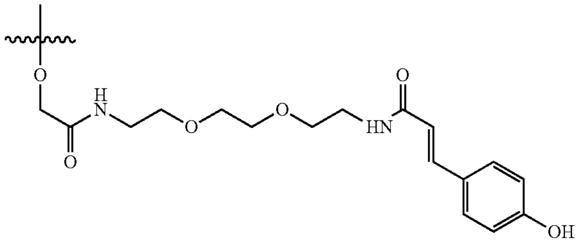 [SMILES: *OCC(=O)NCCOCCOCCNC(=O)/C=C/c1ccc(O)cc1]

wherein the curved line denotes the attachment point.

According to some of any of the embodiments of this aspect of the present invention, the compound has the formula:

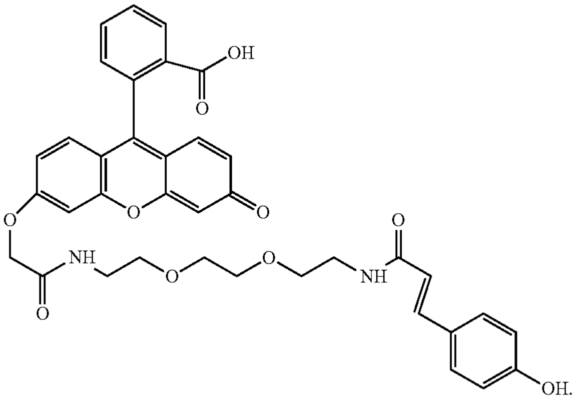 [SMILES: O=C(/C=C/c1ccc(O)cc1)NCCOCCOCCNC(=O)COc1ccc2c(-c3ccccc3C(=O)O)c3ccc(=O)cc-3oc2c1]

According to some of any of the embodiments of this aspect of the present invention, the compound has a formula selected from the group consisting of:

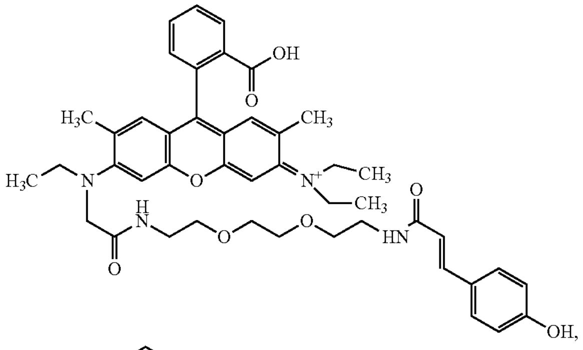

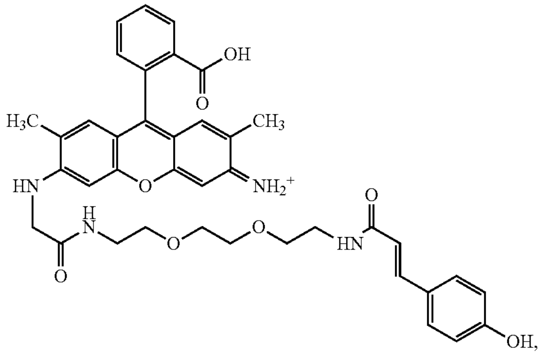

and

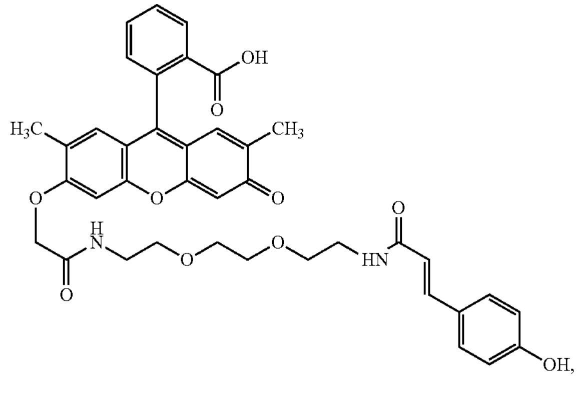

and their corresponding spiro-derivates, or salts thereof.

According to some of any of the embodiments of this aspect of the present invention, the compound has the formula:

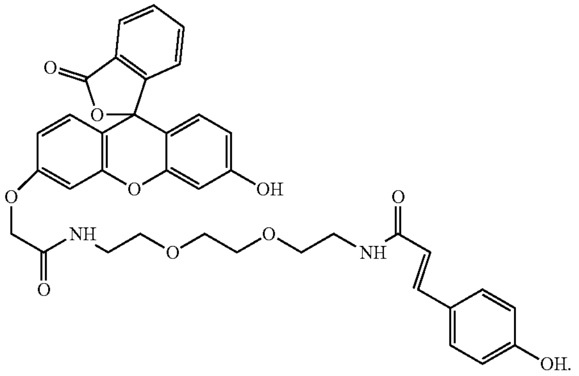 [SMILES: O=C(/C=C/c1ccc(O)cc1)NCCOCCOCCNC(=O)COc1ccc2c(c1)Oc1cc(O)ccc1C21OC(=O)c2ccccc21]

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

A further understanding of the nature and advantages of particular embodiments may be realized by reference to the remaining portions of the specification and the drawings, in which like reference numerals are used to refer to similar components. In some instances, a sub-label is associated with a reference numeral to denote one of multiple similar components. When reference is made to a reference numeral without specification to an existing sub-label, it is intended to refer to all such multiple similar components.

FIGS. 6A-6E are flow diagrams illustrating a method for implementing sequential imaging of biological samples for generating training data for developing deep learning based models for image analysis, for cell classification, and/or for features of interest identification of biological samples, in accordance with various embodiments.

DETAILED DESCRIPTION

Figure 1B:
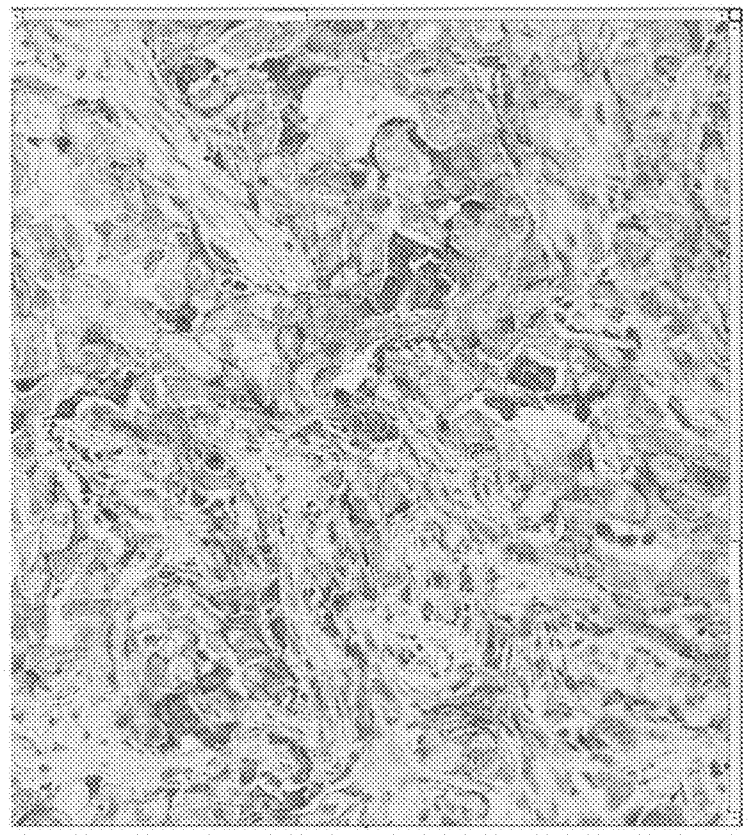
FIGS. 1A and 1B illustrate PD-L1 sequential staining, in accordance with various embodiments.

An aspect of some embodiments of the present disclosure relates to systems, methods, a computing device, and/or code instructions (stored on a memory and executable by one or more hardware processors) for automatically creating a ground truth training dataset for training a ground truth generating machine learning model (sometimes referred to herein as "Model G*"). The ground truth training dataset includes multiple records, where each record includes a first image, a second image, and ground truth labels (e.g., manually entered by a user, and/or automatically determined such as by a set of rules). The first and second images are of a same sample of tissue of a subject. The first image depicts a first group of biological objects (e.g., cells, nucleoli). The first image may be stained with a stain and/or illuminated with an illumination, designed to visually distinguish a first biomarker. Alternatively, the first image may not be stained and/or illuminated with a specific illumination, for example, a brightfield image. The second image may be stained with a sequential stain over the first stain (when the first image depicts tissue stained with the first stain), stained with the first stain (when the first image depicts unstained tissue) and/or illuminated with an illumination, designed to visually distinguish a second biomarker(s) (when the first image depicts the first biomarker) and/or distinguish a biomarker(s) (when the first image does not necessarily depict a specific biomarker(s). The ground truth labels indicate respective biological object categories. The ground truth labels may be manually provided by a user and/or automatically determined such as by a set of rules. The ground truth generating machine learning model is trained on the ground truth training dataset.

As used herein, the term "unlabeled" with reference to the images refers to no annotations, which may be manually inputted by a user and/or automatically generated (e.g., by the ground truth generator and/or rule based approach, as described herein). The term "unlabeled" is not meant to exclude some staining approaches (e.g., fluorescence stain) which in some fields of biology may be referred to as "labels". For example, in live-cell image analysis. As such, images stained with stains such as fluorescence stains that are unannotated as referred to herein as "unlabeled".

The ground truth generating machine learning model is used to generate ground truth labels in response to an input of unlabeled first and/or second images. A synthetic training dataset may be created, where each record of the synthetic training dataset includes the unlabeled first and/or second images, labeled with the ground truth labels automatically generated by the ground truth generating machine learning model. Records of the synthetic training dataset may be further labeled with a ground truth indication of a diagnosis for the sample of tissue depicted in the unlabeled first and/or second images. The diagnosis may be obtained, for example, using a set of rules (e.g., compute percentage of tumor cells relative to all cells), extracted from a pathology report, and/or manually provided by a user (e.g., pathologist). The synthetic training dataset may be used to train a diagnosis machine learning model and/or biological object machine learning model (sometimes referred to herein as "Model G").

In different implementations, to obtain a diagnosis, once the diagnosis and/or biological object machine learning model (Model G) is trained, the ground truth generating machine learning model (Model G*) is not necessarily used for inference. A target unlabeled first and/or second image may be fed into the diagnosis and/or biological object machine learning model to obtain the diagnosis. It is noted that alternatively or additionally, a deterministic approach (i.e., non-ML model that is based on a predefined process and not learned from the data) may be used for the biological object implementation.

In another implementation, during inference, a target unlabeled first and/or second image is fed into the ground truth generating machine learning model to obtain automatically generated labels. The labelled target first and/or second images may be analyzed to obtain a diagnosis, by feeding into the diagnosis machine learning model and/or applying the set of rules.

Virtual second images corresponding to the first image may be synthesized by a virtual stainer machine learning model (sometimes referred to herein as "Model F"), and used as the second images described herein. This enables using only first images without requiring physical capturing second images which may require special sequential staining procedures and/or special illumination.

In another implementation, during inference, a combination of the first image and a second virtually stained image obtained from the virtual stainer in response to an input of the first image, may be fed into the ground truth generating machine learning model to obtain annotations. The automatically annotated first and second images (i.e., first image and virtual second image) may be fed in combination into the diagnosis and/or biological object machine learning model to obtain the diagnosis. Alternatively, in yet another implementation, the combination of the first image and a second virtually stained image are fed into the diagnosis and/or biological object machine learning model to obtain the diagnosis, i.e., the step of feeding into the ground truth generator may be omitted.

Examples of biological objects (sometimes referred to herein as "target molecules") include cells, for example, immune cells, red blood cells, malignant cells, non-malignant tumor cells, fibroblasts, epithelial cells, connective tissue cells, muscle cells, and neurite cells), and internal/or part of cell structures, such as nucleus, DNA, mitochondria, and cell organelles. Biological objects may be a complex of multiple cells, for example, a gland, a duct, an organ or portion thereof such as liver tissue, lung tissue, and skin. Biological objects may include non-human cells, for example, pathogens, bacteria, protozoa, and worms. Biological objects may sometimes be referred to herein as "target", and may include examples of targets described herein.

Examples of samples that are depicted in images include slides of tissues (e.g., created by slicing a frozen section, Formalin-Fixed Paraffin-Embedded (FFPE)) which may be pathological tissue, and live cell images. Other examples of the sample (sometimes referred to herein as "biological sample") are described herein.

The sample of tissue may be obtained intra-operatively, during for example, a biopsy procedure, a FNA procedure, a core biopsy procedure, colonoscopy for removal of colon polyps, surgery for removal of an unknown mass, surgery for removal of a benign cancer, and/or surgery for removal of a malignant cancer, surgery for treatment of the medical condition. Tissue may be obtained from fluid, for example, urine, synovial fluid, blood, and cerebral spinal fluid. Tissue may be in the form of a connected group of cells, for example, a histological slide. Tissue may be in the form of individual or clumps of cells suspended within a fluid, for example, a cytological sample.

Other exemplary cellular biological samples include, but are not limited to, blood (e.g., peripheral blood leukocytes, peripheral blood mononuclear cells, whole blood, cord blood), a solid tissue biopsy, cerebrospinal fluid, urine, lymph fluids, and various external secretions of the respiratory, intestinal and genitourinary tracts, synovial fluid, amniotic fluid and chorionic villi.

Biopsies include, but are not limited to, surgical biopsies including incisional or excisional biopsy, fine needle aspirates and the like, complete resections or body fluids. Methods of biopsy retrieval are well known in the art.

The biomarker(s) may refer to a physical and/or chemical and/or biological feature of the biological object that is enhanced with the stain and/or illumination, for example, surface proteins. In some embodiments, the biomarker may be indicative of a particular cell type, for example a tumor cell or a mononuclear inflammatory cell.

Alternatively or additionally, the term "biomarker" may describe a chemical or biological species which is indicative of a presence and/or severity of a disease or disorder in a subject. Exemplary biomarkers include small molecules such as metabolites, and biomolecules such as antigens, hormones, receptors, and any other proteins, as well as polynucleotides. Any other species indicative of a presence and/or severity of medical conditions are contemplated.

The terms first image, image of a first type, image depicting one or more first biomarkers (or biomarkers of a first type), are used herein interchangeably. The first image depicts a sample of tissue of a subject depicting a first group of biological objects. The first image may be unstained and/or without application of special light, i.e., not necessarily depicting a specific biomarker, for example, a brightfield image. Alternatively or additionally, the first image may be stained with a stain designed to depict a specific biomarker expressed by the first group, also sometimes referred to herein as a first biomarker. Exemplary stains include: immunohistochemistry (IHC), fluorescence, Fluorescence In Situ Hybridization (FISH) which may be made by Agilent® (e.g., see https://www(dot)agilent(dot)com/en/products/dako-omnis-solution-for-ihc-ish/define-your-fish, Hematoxylin and Eosin (H&E), PD-L1, Multiplex Ion Beam Imaging (MIBI), special stains manufactured by Agilent® (e.g., see https://www(dot)agilent(dot)com/en/product/special-stains), and the like. Alternatively or additionally, the first image is captured by applying a selected illumination, that does not necessarily physically stain the sample (although physical staining may be performed), for example, a color image (e.g., RGB), a black and white image, multispectral (e.g., Raman spectroscopy, Brillouin spectroscopy, second/third harmonic generation spectroscopy (SHG/THG)), confocal, fluorescent, near infrared, short wave infrared, and the like. Alternatively or additionally, the first image is captured by a label modality such as chromatin stained bright field image and/or fluorescence stained image. Alternatively or additionally, the first image is captured by a non-label process such as auto-fluorescence and/or a spectral approach that emphasize naturally the biomarker without the need of an external tagging stain. Alternatively or additionally, the first image is captured by another non-label modality, for example, cross-polarization microscopy. It is noted that processes described with reference to the first image are not necessarily limited to the first image, and may be used for the second image or additional images, in different combinations. For example, the first image is processed using a non-label process and the second image is processed using a label process.

The terms second image, image of a second type, image depicting one or more biomarkers (used when the first image does not necessarily depict any specific biomarkers, such as for brightfield images), and image depicting one or more second biomarkers (or biomarkers of a second type), are used herein interchangeably. The second image depicts the same tissue depicted in the first image, and visually distinguishes a second group of biological objects. The second image may be stained with a stain designed to depict a specific biomarker expressed by the second group. The second image may be stained with a sequential stain designed to depict the second biomarker(s), where the first image is stained with a first stain designed to depict the first biomarker(s), and the second sequential stain is further applied to the sample stained with the first stain to generate a second image with both the first stain and the second sequential stain. Alternatively or additionally, the first image is captured by applying a selected illumination, that does not necessarily physically stain the sample (although physical staining may be performed), for example, autofluorescence, and the second image depicts staining and/or another illumination.

The images may be obtained, for example, from an image sensor that captures the images, from a scanner that captures images, from a server that stores the images (e.g., PACS server, EMR server, pathology server). For example, tissue images are automatically sent to analysis after capture by the imager and/or once the images are stored after being scanned by the imager.

The images may be whole slide images (WSI), and/or patches extracted from the WSI, and/or portions of the sample. The images may be of the sample obtained at high magnification, for example, for an objective lens—between about 20×-40×, or other values. Such high magnification imaging may create very large images, for example, on the order of Giga Pixel sizes. Each large image may be divided into smaller sized patches, which are then analyzed. Alternatively, the large image is analyzed as a whole. Images may be scanned along different x-y planes at different axial (i.e., z axis) depth.

In some implementations, the first image may be stained with a first stain depicting a first type of biomarker(s), and the second image may be further stained with a second stain depicting a second type of biomarker(s) which is different than the first type of biomarker(s), also referred to herein as a sequential stain. The second sequential stain is a further stain of the tissue specimen after the first stain has been applied. Alternatively or additionally, the second image may be captured by a second imaging modality, which is different than a first imaging modality used to capture the first image.

The second imaging modality may be designed to depict a second type of physical characteristic(s) (e.g., biomarkers) of the tissue specimen that is different than a first type of physical characteristic(s) of the tissue specimens depicted by the first imaging modality. For example, different imaging sensors that capture images at different wavelengths.

The first image and the second image may be selected as a set. The second image and the first image are of the same sample of tissue. The second image depicts biomarkers or second biomarkers when the first image does not explicitly depict the biomarkers (e.g., brightfield). The second image may depict second biomarkers when the first image depicts first biomarkers. The second group of biological objects may be different than the first group of biological objects, for example, the first group is immune cells, and the second group is tumor cells. The second group of biological objects may be in the environment of the first group, for example, in near proximity, such as within a tumor environment. For example, immune cells located in proximity to the tumor cells. The second group of biological objects depicted in the second image may include a first sub-group of the first group of biological objects of the first image, for example, the first group in the first image includes white blood cells, and the second group is macrophages, which are a sub-group of white blood cells. The second image may depict a second sub-group of the first group that is not expressing the second biomarkers, for example, in the case of sequential staining the second sub-group is unstained by the second stain (but may be stained by the first stain of the first image). The second sub-group is excluded from the second group of biological structures. For example, in the example of the first image stained with a first stain that depicts white blood cells, and the second image is stained with a sequential stain that depicts macrophages, other white blood cells that are non-macrophages (e.g., T cells, B cells) are not stained with the sequential stain.

It is noted that the first and second biomarkers may be expressed in different regions and/or compartments of the same object. For example, the first biomarker is expressed in the cell membrane and the second biomarker is expressed in the cell cytoplasm. In another example, the first biomarker and/or second biomarker may be expressed in a nucleus (e.g., compartment) of the cell.

Figure 1A:
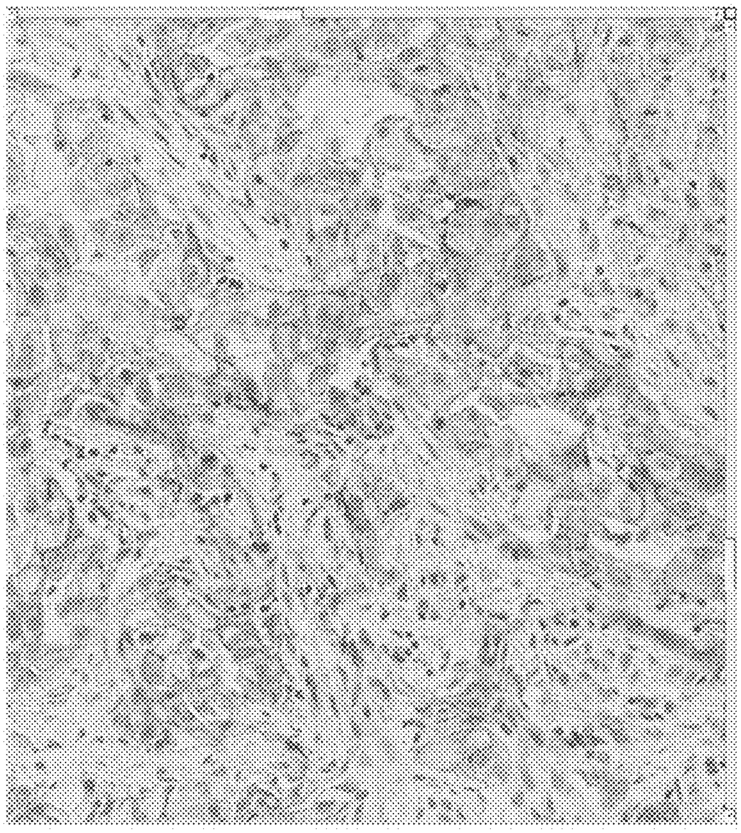
Figure 2B:
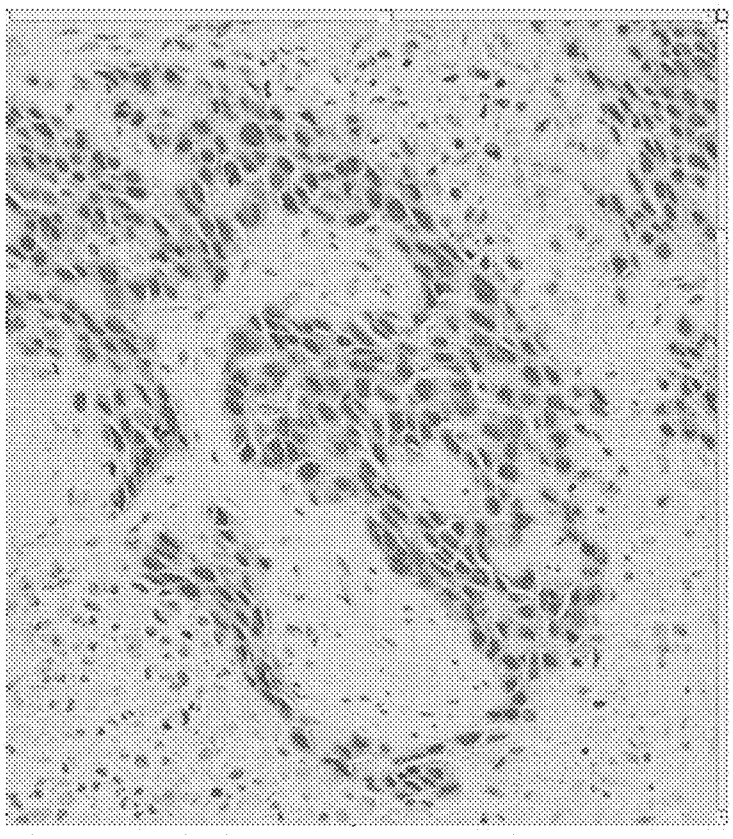
FIGS. 2A and 2B illustrate p40 sequential staining, in accordance with various embodiments.
Figure 2A:
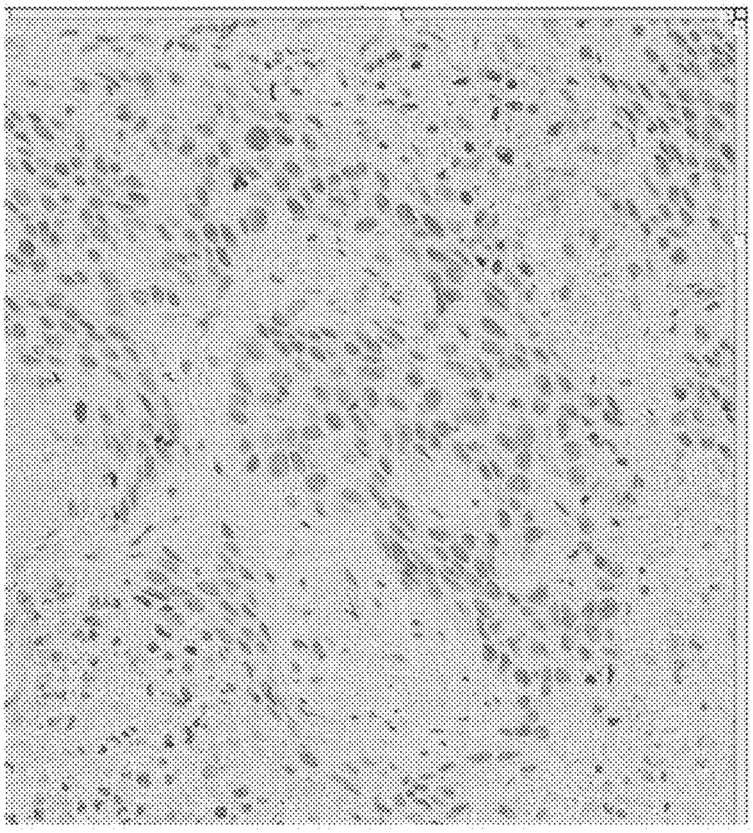

Examples of first images are shown with respect to FIGS. 1A and 2A, and corresponding second images depicting sequential staining are shown with respect to FIGS. 1B and 2B.

In some implementations, the first image depicts the first group of biological objects presenting the first biomarker, and the second image depicts the second group of biological objects presenting the second biomarker. The second biomarker may be different than the first biomarker. The first image may depict tissue stained with a first stain designed to stain the first group of biological objects depicting the first biomarker. The second image may depict a sequential stain, where the tissue stained with the first stain is further stained with a second sequential stain designed to stain the second group of biological objects depicting the second biomarker in addition to the first group of biological objects depicting the first biomarker (e.g., stained with the first stain).

In some implementations, the first image is captured with a first imaging modality that applies a first specific illumination selected to visually highlight the first group of biological objects depicting the first biomarker, for example, an auto-fluorescence imager, and a spectral imager. In another example, the first image is a brightfield image, i.e., not necessarily depicting a specific first biomarker. The second image is captured with a second imaging modality that applies a second specific illumination selected to visually highlight the second group of biological objects depicting the second biomarker (or a biomarker in the case of the first image not necessarily depicting the first biomarker).

In some implementations, the first image is captured by a first imaging modality, and the second image is captured by a second imaging modality that is different than the first imaging modality. Examples of the first and second imaging modalities include a label modality and a non-label modality (or process). The label modality may be, for example, chromatin stained bright field image and/or fluorescence stained image. The non-label may be, for example, auto-fluorescence and/or a spectral approach that emphasize naturally the biomarker without the need of an external tagging stain. Another example of the non-label modality is cross-polarization microscopy. In other examples, the first image comprises a brightfield image, and the second images comprises one or both of: (i) spectral imaging image indicating the at least one biomarker, and (ii) non-labelled image depicting the at least one biomarker (e.g., auto-fluorescence, spectral approach, and cross-polarization microscopy). Alternatively or additionally, the first image is captured by applying a selected illumination, that does not necessarily physically stain the sample (although physical staining may be performed), for example, a color image (e.g., RGB), a black and white image, multispectral (e.g., Raman spectroscopy, Brillouin spectroscopy, second/third harmonic generation spectroscopy (SHG/THG)), confocal, fluorescent, near infrared, short wave infrared, and the like. Alternatively or additionally, the first image is captured by a label modality such as chromatin stained bright field image and/or fluorescence stained image. Alternatively or additionally, the first image is captured by a non-label process such as auto-fluorescence and/or a spectral approach that emphasize naturally the biomarker without the need of an external tagging stain. Alternatively or additionally, the first image is captured by another non-label modality, for example, cross-polarization microscopy.

As used herein, the term first and second images, or sequential image and/or the term sequential stain is not necessarily limited to two. It is to be understood that the approaches described herein with respect to the first and second images may be expanded to apply to three or more images, which may be sequential images (e.g., sequential stains) and/or other images (e.g., different illuminations which are not necessarily sequentially applied in addition to previous illuminations). In a non-limiting example, the first image is a PD-L1 stain, the second image is a sequential stain further applied to the sample stained with PD-L1, and the third image is a fluorescence image, which may be obtained of one or more of: bright field image of the sample, of the first image, of the second image. Implementations described herein are described for clarity and simplicity with reference to the first and second images, but it is to be understood that the implementations are not necessarily limited to the first and second images, and may be adapted to three or more images.

An alignment process may be performed to align the first image and the second image with each other. The physical staining of the second image may physically distort the second image, causing a misalignment with respect to the first image, even though the first image and second image are of the same sample. The distortion may of the sample and therefore of the image itself may occur, for example, from uncovering of a slide to perform an additional staining procedure (e.g., sequential staining). It is noted that only the image itself may be distorted due to multiple scanning operations, and the sample itself may remain undistorted. The alignment may be performed with respect to identified biological objects. In the aligned images, pixels of a certain biological object in one image map to the same biological object depicted in the other image. The alignment may be, for example, a rough alignment (e.g., where large features are aligned) and/or a fine alignment (e.g., where fine features are aligned). The rough alignment may include an automated global affine alignment process that accounts for translation, rotation, and/or uniform deformation between the first and second images. The fine alignment may be performed on rough aligned images. The fine alignment may be performed to account for local non-uniform deformations. The fine alignment may be performed, for example, using optical flow and/or non-rigid registration. The rough alignment may be sufficient for creating annotated datasets, as described herein, however fine alignment may be used for the annotated datasets. The fine alignment may be used for creating a training dataset for training the virtual stainer described herein. Examples of alignment approaches are described herein.

At least some implementations of the systems, methods, apparatus, and/or code instructions described herein generate outcomes of ML models which are used for biomarker and/or co-developed or companion diagnosis (CDx) discovery and/or development processes.

At least some implementations of the systems, methods, apparatus, and/or code instructions described herein address the technical problem of obtaining sufficient amount of ground truth labels for biological objects depicted in images of samples of tissue for training a machine learning model, for example, for identifying target biological objects in target image(s) and/or generating a diagnosis for the target image(s) (e.g., treat subject with chemotherapy, medical condition diagnosis). At least some implementations of the systems, methods, apparatus, and/or code instructions described herein improve the technical field of machine learning, by providing an automated approach for obtaining sufficient amount of ground truth labels for biological objects depicted in images of samples of tissue for training a machine learning model, for example, for identifying target biological objects in target image(s) and/or generating a diagnosis for the target image(s).

Training a machine learning model requires a large number of labelled images. Traditionally, the labelling is performed manually. The difficulty is that the person qualified to perform the manual labor is generally a trained pathologist, which are in short supply and difficult to find to generate the large number of labelled images. Even when such trained pathologists are identified, the manual labelling is time consuming, since each image may contain thousands of biological objects (e.g., cells) of different types and/or at different states (e.g., dividing, apoptosis, actively moving). Some types of biological objects (e.g., cells) are difficult to differentiate using the image, which requires even more time to evaluate. Moreover, the manual labelling is prone to error, for example, error in differentiating the different types of biological objects.

In at least some implementations, a solution provided for the technical problem, and/or an improvement over the existing standard manual approaches, is to provide a second (or more) image in addition to the first image, where the second image and the first image depict the same sample, and may be aligned with each other, such that specific biological objects in one tissue are directly mapped to the same specific biological objects depicted in the other image. In some implementations, the solution is based on a sequential second image of a second type (e.g., using a second sequential stain in addition to a first stain) in addition to the original first image of a first type (e.g., the first stain without the second sequential stain), for presentation on a display to the manual annotator. The manual annotation performed using the first and second images increases accuracy of differentiating between the different types of biological objects. The number of biological objects that are manually annotated is significantly smaller than would otherwise be required for generating a ground truth data for a desired target performance level. A ground truth generator machine learning model is trained on a training dataset of sets (e.g., pairs or greater number) of images (i.e., the first image and the second image) labelled with the manual annotations as ground truth and/or labelled with ground truth annotations that are automatically obtained such as by a set of rules. In some implementations, the training data includes one of the images and exclude the other (e.g., only first images excluding second images), where the included images are labelled with annotations generated using both the first and second images. The ground truth generator is fed unlabeled sets of images (which may be new images, or patches of the images used in the training dataset which have not been manually annotated) and/or fed single images such as of the first type (e.g., according to the structure of records of the training dataset) and automatically generates an outcome of annotations for the biological objects depicted in the input sets of images and/or input single image such as the first image. The ground truth generator automatically generates labelled sample images, in an amount that is sufficient for training a machine learning model, such as to perform at a target performance metric. The sample imaged labeled with the automatically generated labels may be referred to herein as synthetic records. The synthetic records may further be labelled, for example, with an indication of diagnosis, and used to train a diagnosis machine learning model that generates an outcome of a diagnosis for an input of an automatically labelled target image (e.g., labelled by the ground truth generator).

At least some implementations of the systems, methods, apparatus, and/or code instructions described herein address the technical problem of providing additional sequential images depicting additional biomarkers, in addition to first images of a first type depicting first type of biomarker(s). At least some implementations of the systems, methods, apparatus, and/or code instructions described herein improve the technology of analysis of image of samples of tissue by providing sequential images. The sequential image is of the same physical tissue slice depicted in the first image. The additional images depicting additional biomarkers may assist pathologists in making a diagnosis, and/or classifying biological objects (e.g., cells) which may be difficult to make using the first images alone. Traditionally, pathologists do not have access to sequential images depicting additional biomarkers, and are required to make a diagnosis and/or classify biological objects on the basis of the first image alone. Once a sample of tissue is stained the first time, in many cases another stain cannot be applied using traditional methods, as applying a second stain over the first stain may destroy the tissue sample, and/or render the tissue sample illegible for reading by a pathologist. Using the first image alone is more difficult, more prone to error, and/or requires higher levels of training. Using sequential images increases the amount of data available, including increased accuracy of assigning specific classification categories to objects depicted in the images. The additional data and/or increased classification categories may be used to train a machine learning model.

As described herein, sequential images may be prepared and presented on a display. However, some facilities may be unable to generate their own sequential images, such as due to lack of availability of equipment and/or lack of know-how. In at least some implementations, the technical solution to the technical problem is to train a virtual image machine learning model (sometimes referred to herein as a virtual stainer), which generates a virtual second sequential image in response to an input of a first image. The virtual second sequential image is similar to a second image that would otherwise be prepared by physically adding the second sequential stain, and/or by capturing the second image using a second sequential imaging modality. The virtual second sequential image is generated by the virtual stainer model without requiring physically performing the second sequential stain and/or without capturing the second image with the second imaging modality.

At least some implementations of the systems, methods, apparatus, and/or code instructions described herein improve the technology of machine learning, by training and providing the virtual stainer machine learning model.

The virtually created second sequential images may be used as-is, by presenting the virtually created second sequential image on a display optionally beside the first image, to assist the pathologist in making the diagnosis and/or labelling the biological objects depicted therein. Moreover, the virtually created second sequential images may be used in other processes described herein, for example, for creating the second images of the set that is fed into the ground truth generator. In another example, the diagnosis machine learning model training might require sets of labelled patches, rather than only labelled first images. In those cases, when a target first image is obtained, the target second image may be automatically created by feeding the target first image into the virtual stainer. The set of the target first image and the target second image created by the virtual stainer may then be fed into the ground truth generator to obtain labels, and then fed as a set into the diagnosis machine learning model to obtain a diagnosis. This enables using the diagnosis machine learning model trained on sets of ground truth images without requiring physically generating the second image by staining and/or by capturing using a second imaging modality that applies a specific illumination.

Another technical challenge lies in the inability to obtain a second sequential image of the first image, where the second image and the first image are of the same physical tissue slice specimen, and where the second image depicts a second type of biomarker(s) that are different than the first type of biomarker(s). Using standard approaches, images of neighboring slices may be used to help make the diagnosis and/or classify biological objects in a main image. The images of the neighboring slices are usually of the same first type of image, such as stained with the same stain as the first image. The neighboring slices are created by taking the tissue sample, physically slicing the sample into parallel physical slices, and creates slides of each slice. However, since the distance between the different slices is usually larger than size of cells, most cells will appear only in one slice, and not in neighboring slices. The amount of information available from neighboring slices is therefore limited. Once the slice is stained using a standard staining approach, no additional information may be extracted using standard approaches, i.e., there are no standard approaches for staining with another stain over the first stained slide that depicts biomarkers that are different than the biomarkers depicted in the first stained slide, and/or there are no standard approaches for imaging the first stained slide with another imaging modality that depicts different biomarkers. The virtually created second sequential image provides additional visual data for the pathologist, depicting additional biomarkers in the same physical slice of tissue, in addition to the first biomarkers in the first stained same physical slice of tissue. Therefore allowing the pathologist to view information about two (or more) bio-marker for each cell.

At least some implementations of the systems, methods, apparatus, and/or code instructions described herein address the technical problem of classifying biological objects depicted in images of tissue slices without relying on manual annotated data for training a machine learning model. Traditionally, a trained pathologist is required to manually label biological objects. The trained pathologist may not be available, and/or may be limited in the amount of data that they can annotate. At least some implementations of the systems, methods, apparatus, and/or code instructions described herein improve the technology of image analysis, by automatically classifying biological objects depicted in images of tissue slices without relying on manual annotated data for training a machine learning model.

The second sequential image, which may be the virtually created second sequential images, is used for classification of segmented biological objects. In some implementations, the virtually created second sequential image is created by the virtual stainer from an input first image. Target biological objects of the second sequential image, optionally the virtually created second sequential image, are segmented by a segmentation process, for example nuclei are segmented. A set of rules is applied to pixel values of colors specific to the second sequential image, optionally the virtually created second sequential image, for mapping the pixel values using a set of rules or other mapping function to classification categories indicative of labels for the segmented biological objects. The set of rules and/or other mapping function may be used instead of a machine learning model trained on manually labelled images. The set of rules may be used, for example, when the segmented biological objects are stained with colors specific to the virtually created second sequential image, which may or may not also include colors specific to the first type of image optionally stained with a first stain. For example, when the first stain is brown, and the second sequential stain is magenta (e.g., as described herein), the set of rules may map for example pixel intensity values indicating magenta to a specific classification category. The set of rules may be set, for example, based on observation by Inventors that the specific classification category has pixel values indicating presence of the second sequential stain.

At least some implementations described herein provide for robust and/or scalable solutions for tissue staining, for detectable reagents capable of serving as substrates of an enzyme with peroxidase activity, and/or for detecting multiple target molecules in biological samples comprising cells. There is also a need for robust and scalable solutions implementing annotation data collection and autonomous annotation. According to the present In at least some implementations described herein, teachings, methods, systems, and apparatuses are disclosed for implementing sequential imaging of biological samples for generating training data for developing deep learning based models for image analysis, for cell classification, for feature of interest identification, and/or for virtual staining of biological samples Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 11:
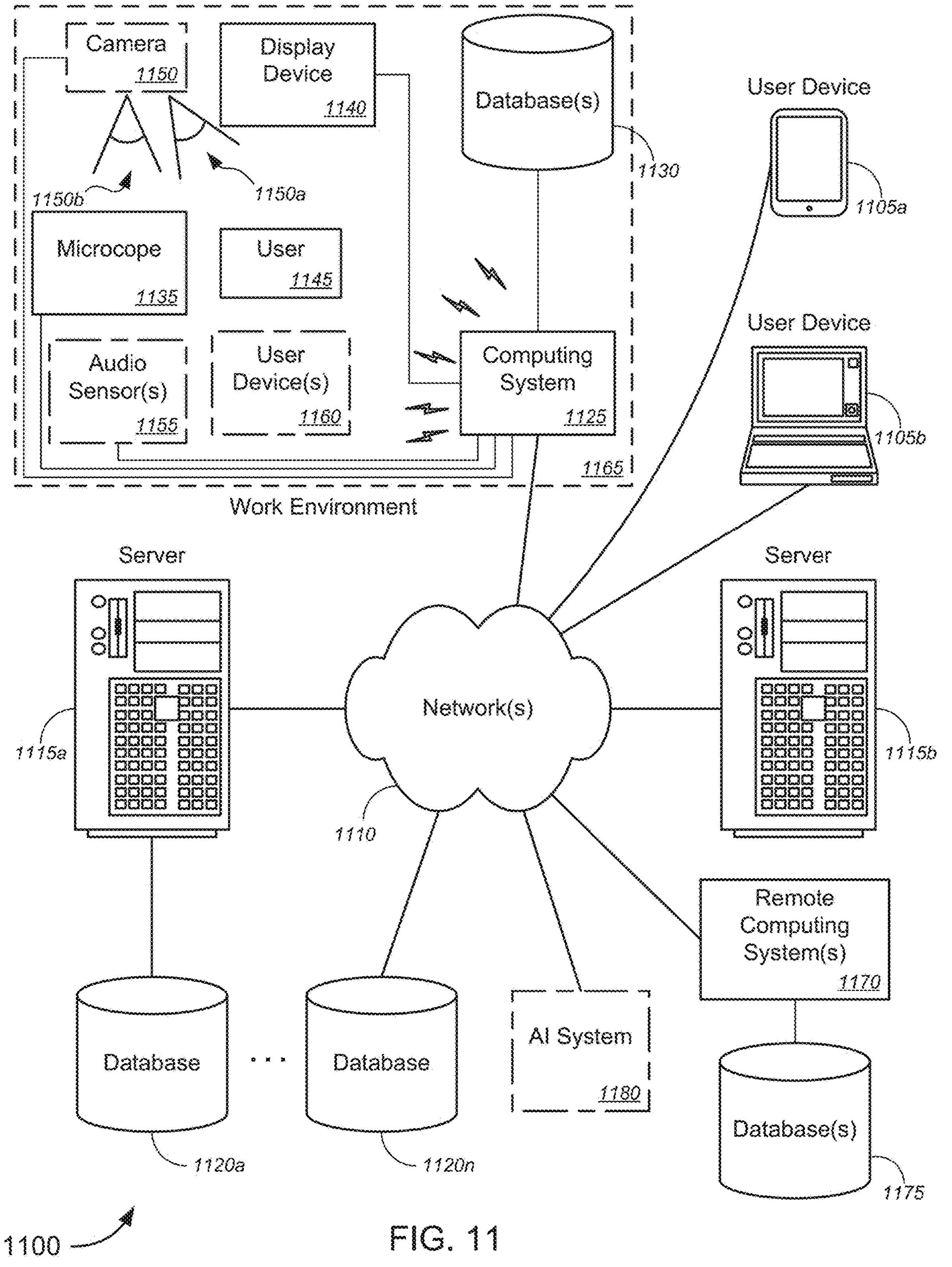
FIG. 11 is a block diagram illustrating a networked system of computers, computing systems, or system hardware architecture, which can be used in accordance with various embodiments.
Figure 12:
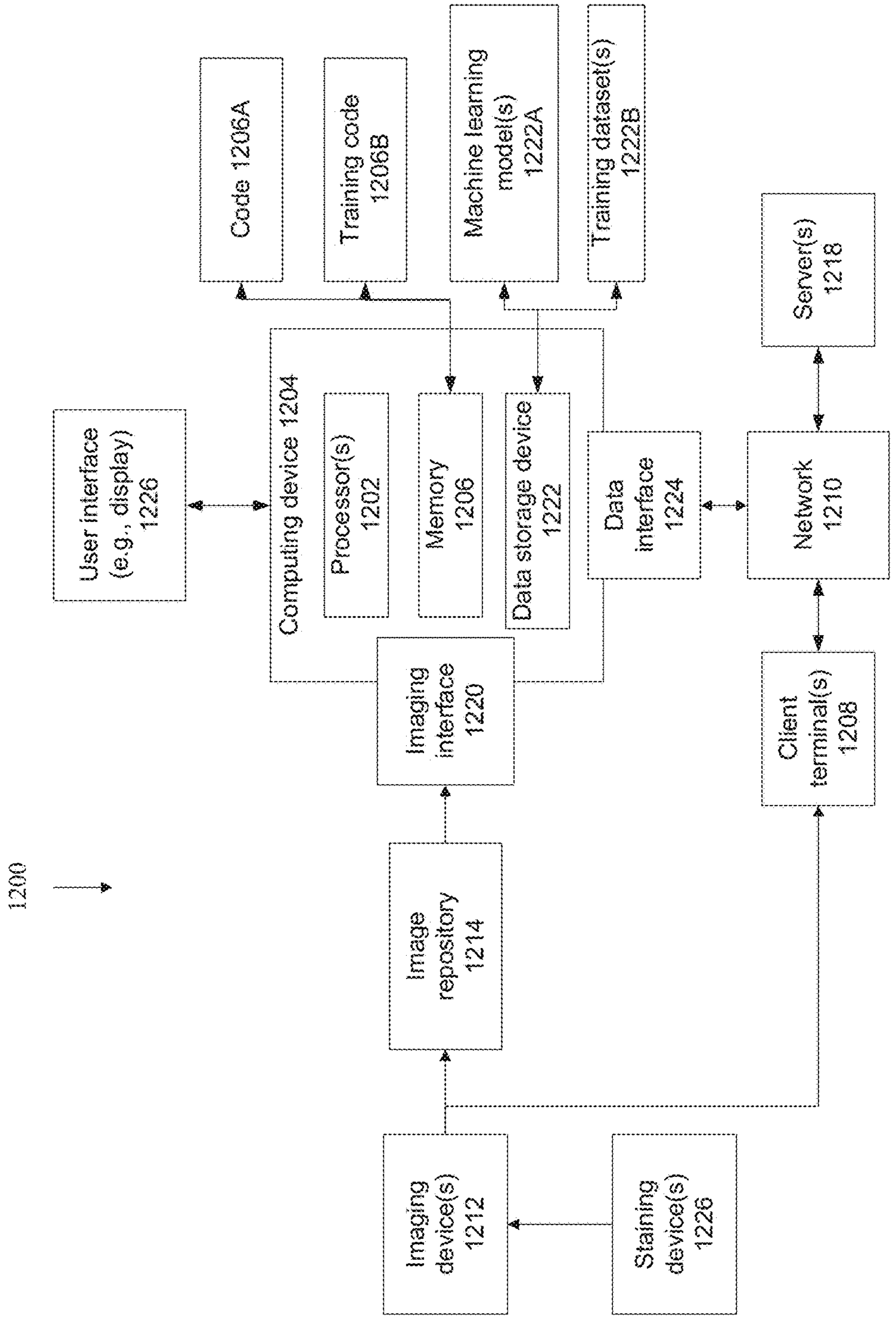
FIG. 12 is a block diagram of components of a system for training ML models that analyze first and second images of a sample of tissue and/or for inference of first and second images of a sample of tissue using the ML models, in accordance with various embodiments.

Reference is now made to FIG. 12, which is a block diagram of components of a system 1200 for training ML models that analyze first and second images of a sample of tissue and/or for inference of first and second images of a sample of tissue using the ML models, in accordance with some embodiments of the present disclosure. System 1200 may be an alternative to, and/or combined with (e.g., using one or more components) the system described with reference to FIG. 3, FIG. 10, and/or FIG. 11.

System 1200 may implement the acts of the method described with reference to FIGS. 13-17 and/or FIGS. 4A-4C, 5A-5O, 6A-6E, 7A-7D, 9A-9E, optionally by a hardware processor(s) 1202 of a computing device 1204 executing code instructions 1206A and/or 1206B stored in a memory 1206.

Computing device 1204 may be implemented as, for example, a client terminal, a server, a virtual server, a laboratory workstation (e.g., pathology workstation), a procedure (e.g., operating) room computer and/or server, a virtual machine, a computing cloud, a mobile device, a desktop computer, a thin client, a Smartphone, a Tablet computer, a laptop computer, a wearable computer, glasses computer, and a watch computer. Computing 1204 may include an advanced visualization workstation that sometimes is implemented as an add-on to a laboratory workstation and/or other devices for presenting images of samples of tissues to a user (e.g., pathologist).

Different architectures of system 1200 based on computing device 1204 may be implemented, for example, central server based implementations, and/or localized based implementation.

In an example of a central server based implementation, computing device 1204 may include locally stored software that performs one or more of the acts described with reference to FIGS. 13-17 and/or FIGS. 4A-4C, 5A-5O, 6A-6E, 7A-7D, 9A-9E, and/or may act as one or more servers (e.g., network server, web server, a computing cloud, virtual server) that provides services (e.g., one or more of the acts described with reference to FIGS. 13-17 and/or FIGS. 4A-4C, 5A-5O, 6A-6E, 7A-7D, 9A-9E) to one or more client terminals 1208 (e.g., remotely located laboratory workstations, remote picture archiving and communication system (PACS) server, remote electronic medical record (EMR) server, remote image storage server, remotely located pathology computing device, client terminal of a user such as a desktop computer) over a network 1210, for example, providing software as a service (SaaS) to the client terminal(s) 1208, providing an application for local download to the client terminal(s) 1208, as an add-on to a web browser and/or a tissue sample imaging viewer application, and/or providing functions using a remote access session to the client terminals 1208, such as through a web browser. In one implementation, multiple client terminals 1208 each obtain images of the samples from different imaging device(s) 1212. Each of the multiple client terminals 1208 provides the images to computing device 1204. The images may be of a first image type (e.g., stained with the first stain depicting a first biomarker, imaged with a specific illumination, and/or bright field) and/or second image type (e.g., sequential image stained with the sequential stain depicting the second biomarker, stained with a non-sequential stain, and/or imaged with a different specific illumination). The images may be unlabeled, or may include patches with labelled biological objects, for example, for training a ground truth annotator machine learning model, as described herein. Computing device may feed the sample image(s) into one or more machine learning model(s) 1222A to obtain an outcome, for example, a virtual image, automatic labels assigned to biological objects depicted in the image(s), and/or other data such as metrics and/or other clinical scores (e.g., computed percentage of specific cells relative to total number of cells), which may be used for diagnosis and/or treatment (e.g., selecting subjects for treatment with chemotherapy). The outcome obtained from computing device 1204 may be provided to each respective client terminal 1208, for example, for presentation on a display and/or storage in a local storage and/or feeding into another process such as a diagnosis application. Training of machine learning model(s) 1222A may be centrally performed by computing device 1204 based on images of samples and/or annotation of data obtained from one or more client terminal(s) 1208, optionally multiple different client terminals 1208, and/or performed by another device (e.g., server(s) 1218) and provided to computing device 1204 for use.

In a local based implementation, each respective computing device 1204 is used by a specific user, for example, a specific pathologist, and/or a group of users in a facility, such as a hospital and/or pathology lab. Computing device 1204 receives sample images from imaging device 1212, for example, directly, and/or via an image repository 1214 (e.g., PACS server, cloud storage, hard disk). Received images may be of the first image type and/or second image type. The raw images may be presented on a display 1226 associated with computing device 1204, for example, for manual annotation by a user, for training the ground truth generator machine learning model, as described herein. Images may be locally fed into one or more machine learning model(s) 1222A to obtain an outcome. The outcome may be, for example, presented on display 1226, locally stored in a data storage device 1222 of computing device 1204, and/or fed into another application which may be locally stored on data storage device 1222. Training of machine learning model(s) 1222A may be locally performed by each respective computing device 1204 based on images of samples and/or annotation of data obtained from respective imaging devices 1212, for example, different users may each train their own set of machine learning models 1222A using the samples used by the user, and/or different pathological labs may each train their own set of machine learning models using their own images. For example, a pathologist specializing in analyzing bone marrow biopsy trains ML models designed to annotated and/or infer bone marrow images. Another lab specializing in blood smears trains ML models designed to annotated and/or infer blood smear images. In another example, trained machine learning model(s) 1222A are obtained from another device, such as a central server.

Computing device 1204 receives images of samples, captured by one or more imaging device(s) 1212. Exemplary imaging device(s) 1212 include: a scanner scanning in standard color channels (e.g., red, green blue), a multispectral imager acquiring images in four or more channels, a confocal microscope, a black and white imaging device, and an imaging sensor. Imaging device 1212 captures at least the first image described herein. The second image described herein may be captured by imaging device 1212, another imaging device, and/or synthesized by feeding the first image into the virtual stainer, as described herein.

Optionally, one or more staining devices 1226 apply stains to the sample which is then imaged by imaging device 1212. Staining device 1226 may apply the first stain, and optionally the second stain, which may be the sequential stain, as described herein.

Imaging device(s) 1212 may create two dimensional (2D) images of the samples, optionally whole slide images.

Images captured by imaging machine 1212 may be stored in an image repository 1214, for example, a storage server (e.g., PACS, EHR server), a computing cloud, virtual memory, and a hard disk.

Training dataset(s) 1222B may be created based on the captured images, as described herein.

Machine learning model(s) 1222A may be trained on training dataset(s) 1222B, as described herein.

Exemplary architectures of the machine learning models described herein include, for example, statistical classifiers and/or other statistical models, neural networks of various architectures (e.g., convolutional, fully connected, deep, encoder-decoder, recurrent, graph), support vector machines (SVM), logistic regression, other regressors, k-nearest neighbor, decision trees, boosting, random forest, a regressor, and/or any other commercial or open source package allowing regression, classification, dimensional reduction, supervised, unsupervised, semi-supervised or reinforcement learning. Machine learning models may be trained using supervised approaches and/or unsupervised approaches.

Machine learning models described herein may be fine turned and/or updated. Existing trained ML models trained for certain types of tissue, such as bone marrow biopsy, may be used as a basis for training other ML models using transfer learning approaches for other types of tissue, such as blood smear. The transfer learning approach of using an existing ML model may increase the accuracy of the newly trained ML model and/or reduce the size of the training dataset for training the new ML model, and/or reduce the time and/or reduce the computational resources for training the new ML model, over standard approaches of training the new ML model 'from scratch'.

Computing device 1204 may receive the images for analysis from imaging device 1212 and/or image repository 1214 using one or more imaging interfaces 1220, for example, a wire connection (e.g., physical port), a wireless connection (e.g., antenna), a local bus, a port for connection of a data storage device, a network interface card, other physical interface implementations, and/or virtual interfaces (e.g., software interface, virtual private network (VPN) connection, application programming interface (API), software development kit (SDK)). Alternatively or additionally, Computing device 1204 may receive the slide images from client terminal(s) 1208 and/or server(s) 1218.

Hardware processor(s) 1202 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 1202 may include one or more processors (homogenous or heterogeneous), which may be arranged for parallel processing, as clusters and/or as one or more multi core processing units.

Memory 1206 (also referred to herein as a program store, and/or data storage device) stores code instruction for execution by hardware processor(s) 1202, for example, a random access memory (RAM), read-only memory (ROM), and/or a storage device, for example, non-volatile memory, magnetic media, semiconductor memory devices, hard drive, removable storage, and optical media (e.g., DVD, CD-ROM). Memory 1206 stores code 1206A and/or training code 1206B that implements one or more acts and/or features of the method described with reference to FIGS. 13-17 and/or FIGS. 4A-4C, 5A-5O, 6A-6E, 7A-7D, 9A-9E.

Computing device 1204 may include a data storage device 1222 for storing data, for example, machine learning model(s) 1222A as described herein (e.g., ground truth generator, virtual stainer, biological object machine learning model, and/or diagnosis machine learning model) and/or training dataset 1222B for training machine learning model(s) 1222A (e.g., ground truth training dataset, synthetic training dataset, biological object category training dataset, and/or imaging dataset), as described herein. Data storage device 1222 may be implemented as, for example, a memory, a local hard-drive, a removable storage device, an optical disk, a storage device, and/or as a remote server and/or computing cloud (e.g., accessed over network 1210). It is noted that execution code portions of the data stored in data storage device 1222 may be loaded into memory 1206 for execution by processor(s) 1202. Computing device 1204 may include data interface 1224, optionally a network interface, for connecting to network 1210, for example, one or more of, a network interface card, a wireless interface to connect to a wireless network, a physical interface for connecting to a cable for network connectivity, a virtual interface implemented in software, network communication software providing higher layers of network connectivity, and/or other implementations. Computing device 1204 may access one or more remote servers 1218 using network 1210, for example, to download updated versions of machine learning model(s) 1222A, code 1206A, training code 1206B, and/or the training dataset(s) 1222B.

Computing device 1204 may communicate using network 1210 (or another communication channel, such as through a direct link (e.g., cable, wireless) and/or indirect link (e.g., via an intermediary computing device such as a server, and/or via a storage device) with one or more of:

Client terminal(s) 1208, for example, when computing device 1204 acts as a server providing image analysis services (e.g., SaaS) to remote laboratory terminals, as described herein.

Server 1218, for example, implemented in association with a PACS and/or electronic medical record, which may store images of samples from different individuals (e.g., patients) for processing, as described herein.

Image repository 1214 that stores images of samples captured by imaging device 1212.

It is noted that imaging interface 1220 and data interface 1224 may exist as two independent interfaces (e.g., two network ports), as two virtual interfaces on a common physical interface (e.g., virtual networks on a common network port), and/or integrated into a single interface (e.g., network interface).

Computing device 1204 includes or is in communication with a user interface 1226 that includes a mechanism designed for a user to enter data (e.g., provide manual annotation of biological objects) and/or view data (e.g., virtual images, captured images). Exemplary user interfaces 1226 include, for example, one or more of, a touchscreen, a display, a keyboard, a mouse, and voice activated software using speakers and microphone.

Figure 13:
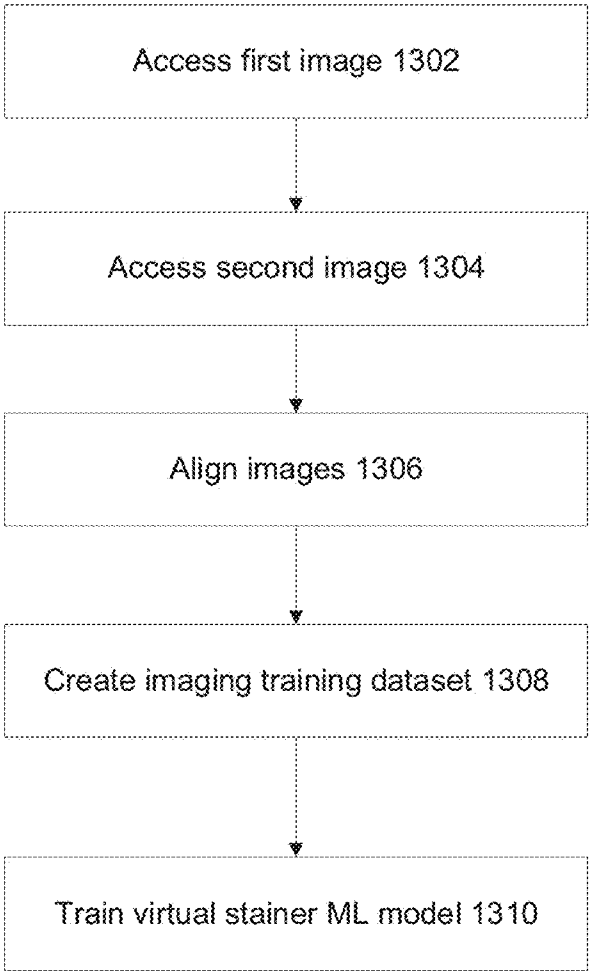
FIG. 13 is a flowchart of a method of automatically generating a virtual stainer machine learning model (also referred to herein as virtual stainer) that generates an outcome of a second image in response to an input of a first image, in accordance with various embodiments.

Reference is now made to FIG. 13, which is a flowchart of a method of automatically generating a virtual stainer machine learning model (also referred to herein as virtual stainer) that generates an outcome of a second image in response to an input of a first image, in accordance with some embodiments of the present disclosure. The virtual stainer creates a virtual second image from a target first image, making it unnecessary to physically create the second image, for example, the sequential stain does not need to be applied to the sample stained with the first sample, and/or the illumination does not need to be applied. The virtual second image may be presented on a display, for example, alongside the first image. A user (e.g., pathologist) may use the first image and/or the virtual second image during the manual process of viewing and/or reading the sample, such as for creating the pathological report. The presentation of the virtual second image may be a standalone process, and/or in combination with other processes described herein. Other exemplary approaches for training the virtual stainer are described with reference to FIGS. 7A, 7C, and/or 7D. Examples of input first images and virtual second images created by the virtual stainer are described with reference to FIGS. 8A-8O

Referring now back to FIG. 13, at 1302, a first image of a sample of tissue of a subject depicting a first group of biological objects, is accessed.

At 1304, a second image of the sample of tissue depicting a second group of biological objects, is accessed.

At 1306, the first image and second image, which depict the same tissue, may be aligned. Alignment may be performed when the second image is not directly correlated with the first image. For example, physically applying the sequential stain to the sample of tissue already stained with the first stain may physical distort the tissue, creating the misalignment between the first and second images. The second image may include local non-uniform deformations. For example, the alignment may align pixels depicting cells and/or pixels depicting nucleoli of the second image with the corresponding pixels depicting the same cells and/or the same nucleoli of the first image.

An exemplary alignment process is now described. Biological features depicted in the first image are identified, for example, by a segmentation process that segments target feature (e.g., cells, nucleoli), such as a trained neural network (or other ML model implementation) and/or using other approaches such as edge detection, histograms, and the like. The biological features may be selected as the biological objects which are used for example, for annotating the image and/or for determining a diagnosis for the sample. Biological features depicted in the second image that correspond to the identified biological features of the first image are identified, for example, using the approach used for the first image. An alignment process, for example, an optical flow process and/or non-rigid registration process, is applied to the second image to compute an aligned image. The alignment process (e.g., optical flow process and/or non-rigid registration process) aligns pixels of the second image to corresponding pixels of the first image, for example, using optical flow and/or non-rigid registration computed between the biological features of the second image and the biological features of the first image. In some implementations, the alignment is a two stage process. A first course alignment brings the two images to a cell-based alignment, and the second stage, which uses non-rigid registration, provides pixel-perfect alignment.

The first stage may be implemented using affine transform and/or scale transform (to compensate for different magnifications) followed Euclidian/rigid transform At 1308, an imaging training dataset is created. The imaging training dataset may be multi-record, where a specific record includes the first image, and a ground truth is indicated by the corresponding second image, optionally the aligned image.

At 1310, a virtual stainer machine learning model is trained on the imaging training dataset. The virtual stainer ML model may be implemented, for example, using a generative adversarial network (GAN) implementation where a generative network is trained to generate candidate virtual images that cannot be distinguished from real images by a discriminative network, and/or based on the approaches described herein, for example, with reference to FIGS. 7C and/or 7D.

Figure 14:
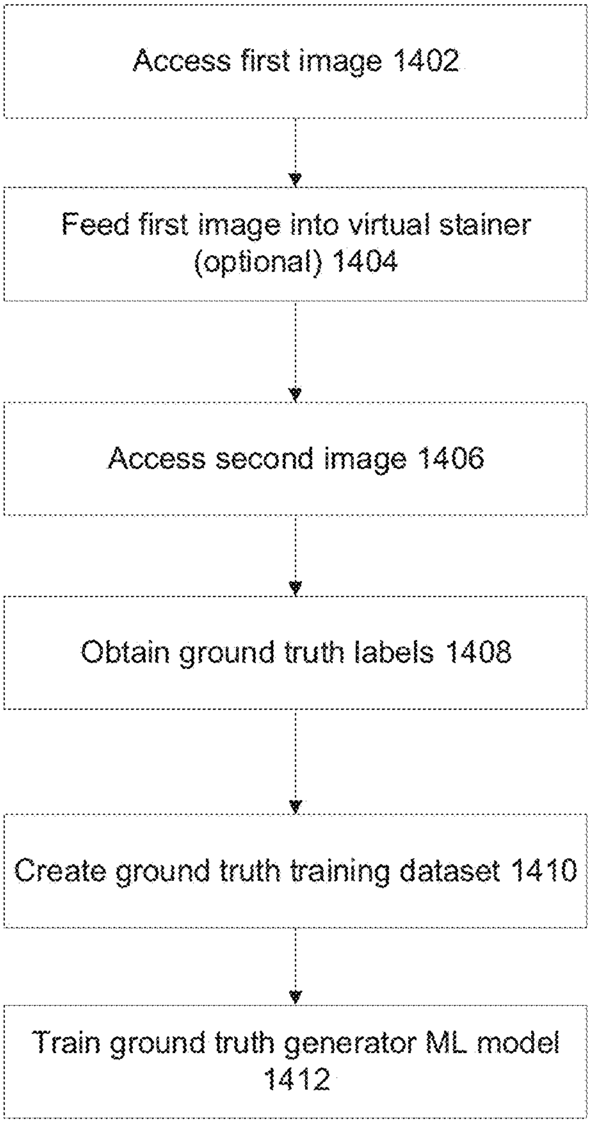
FIG. 14 is a flowchart of a method of automatically generating an annotated dataset of an image of a sample of tissue, in accordance with various embodiments.

Reference is now made to FIG. 14, which is a flowchart of a method of automatically generating an annotated dataset of an image of a sample of tissue, in accordance with some embodiments of the present disclosure. The annotated dataset may be used to train a machine learning model, as described herein.

Referring now back to FIG. 14, at 1402, a first image of a sample of tissue of a subject depicting a first group of biological objects, is accessed. The first image is unlabeled.

At 1404, the first image may be fed into the virtual stainer (e.g., as described herein, for example, trained as described with reference to FIG. 13) to obtain the second image. The virtual stainer may be used, for example, when second images are not available, for example, in facilities where sequential staining cannot be performed, and/or by individual pathologists that do not have the equipment to generate second images.

Alternatively, second images are available, in which case the virtual stainer is not necessarily used.

At 1406, the second image of the sample of tissue depicting a second group of biological objects, is accessed. The second image may be the virtual image created by the virtual stainer, and/or a captured image of the sample (e.g., sequentially stained sample, specific illumination pattern applied). The second image is unlabeled.

At 1408, ground truth labels are manually provided by a user. For example, the user uses a graphical user interface (GUI) to manually label biological objects, such as with a dot, line, outline, segmentation, and the like. Each indication represents a respective biological object category, which may be selected from one or more biological object categories. For example, the user may mark macrophages with blue dots, and mark tumor cells with red dots. Users may mark biological object members of the first group of the first and/or the second group of the second image.

Alternatively or additionally, as discussed herein, ground truth labels may be obtained directly from the second image by applying an image manipulation process. For example, segmenting the second stain on the second image and mapping the segmentation results to the biological object. In such case, 1408 and 1410 might be considered as a single step generating ground truth using a rule-based approach applied on the set of images.

Presenting the user with both the first image and second image may aid the user to distinguish between biological objects. For example, biological objects stained with the first stain but not with the sequential stain are of one category, and biological objects stained with the sequential stain (in addition to the first stain) are of another category.

The ground truth labels may be applied to biological objects of the first image and/or second image. The labelling may be mapped to the biological objects themselves, rather to the specific image, since the same biological objects are depicted in both the first and second images. Alternatively or additionally, the labelling is mapped to one or both images, where a label applied to one image is mapped to the same biological object in the other image. Ground truth labels of biological objects in the second image (e.g., presenting the second biomarker) may be mapped to corresponding non-labeled biological objects of the first image (e.g., presenting the first biomarker).

It is noted that the user may apply ground truth labels to a portion of the biological objects depicted in the image(s). For example, when the image(s) is a whole slide image, a portion of the biological objects may be marked, and another portion remains unlabeled. The image may be divided into patches. Annotations of ground truth labels may be applied to objects in some patches, while other patches remain unlabeled.

At 1410, a ground truth training dataset is created. The ground truth training dataset may be multi-record. Different implementations of the training dataset may be created for example:

Each record includes a set of images, optionally a pair (or more) of the first type and second type, annotated with the ground truth labels. Each label may be for individual biological objects, which appear in both the first and second images.

Each record includes only the first images, annotated with the ground truth labels. Second images are excluded.

Each record includes only the second images, annotated with the ground truth labels. First images are excluded.

At 1412, a ground truth generator machine learning model (also referred to herein as ground truth generator) is trained on the ground truth training dataset. The ground truth generator automatically generates ground truth labels selected from the biological object categories for biological objects depicted in an input image corresponding to the structure of the records used for training, for example, pair (or other set) of images of the first type and the second type, only first images, and only second images.

Figure 15:
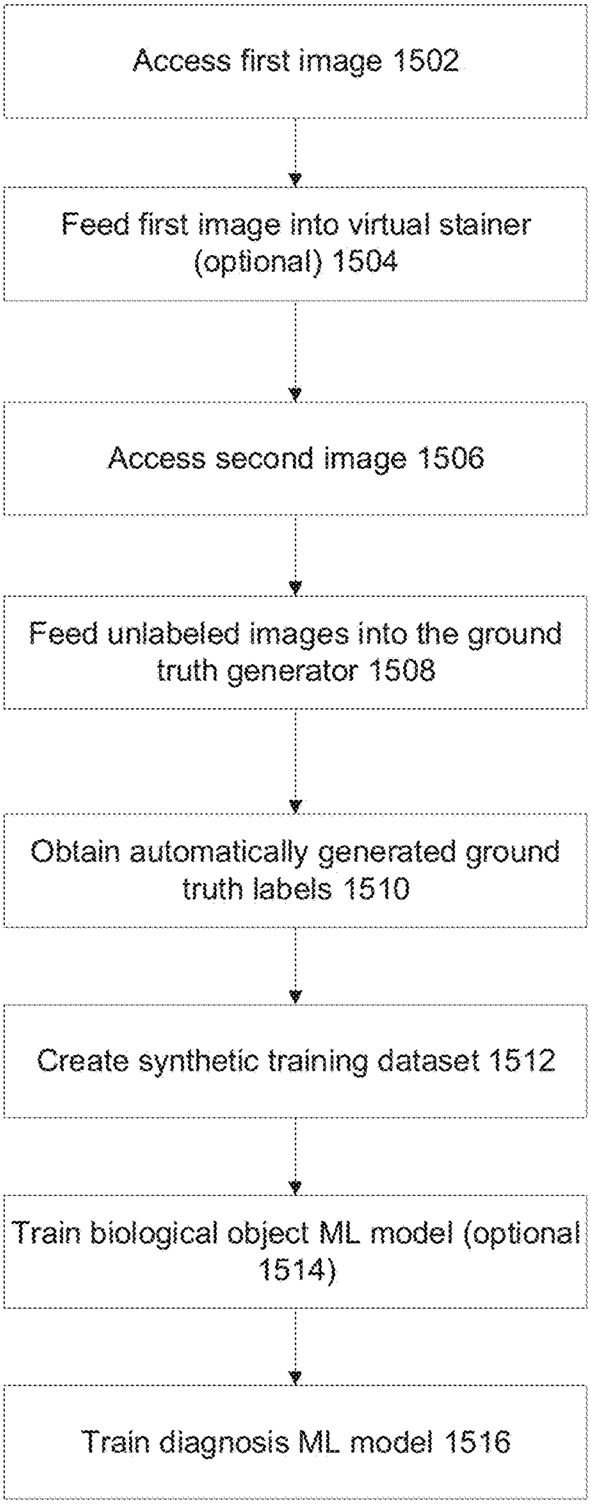
FIG. 15 is a flowchart of a method of training a biological object machine learning model and/or a diagnosis machine learning model using unlabeled images of samples of tissue, in accordance with various embodiments.

Reference is now made to FIG. 15, which is a flowchart of a method of training a biological object machine learning model and/or a diagnosis machine learning model using unlabeled images of samples of tissue, in accordance with some embodiments of the present disclosure. The object machine learning model and/or a diagnosis machine learning model are trained on ground truth annotations automatically generated for the input unlabeled images by the ground truth generator.

Referring now back to FIG. 15, at 1502, a first image of a sample of tissue of a subject depicting a first group of biological objects, is accessed. The first image is unlabeled.

At 1504, the first image may be fed into the virtual stainer (e.g., as described herein, for example, trained as described with reference to FIG. 13) to obtain the second image. The virtual stainer may be used, for example, when second images are not available, for example, in facilities where sequential staining cannot be performed, and/or by individual pathologists that do not have the equipment to generate second images.

Alternatively, second images are available, in which case the virtual stainer is not necessarily used.

At 1506, the second image of the sample of tissue depicting a second group of biological objects, may be accessed. The second image may be the virtual image created by the virtual stainer, and/or a captured image of the sample (e.g., sequentially stained sample, specific illumination pattern applied). The second image is unlabeled.

At 1508, the unlabeled images(s) are fed into the ground truth generator machine learning model. The ground truth generator may be trained as described herein, for example, as described with reference to FIG. 14.

The unlabeled images(s) fed into the ground truth generator correspond to the structure of the records of the ground truth training dataset used to train the ground truth generator. For example, the unlabeled images(s) fed into the ground truth generator may include: a set of unlabeled first and second images (where the second image may be an actual image and/or a virtual image created by the virtual stainer from an input of the first image), only first images (i.e., excluding second images), and only second images (i.e., excluding first images, where the second image may be an actual image and/or a virtual image created by the virtual stainer from an input of the first image.

At 1510, automatically generated ground truth labels for the unlabeled first and/or second images are obtained from the ground truth generator. The labels may be for specific biological objects, without necessarily being associated with the first and/or second images in particular, since the same biological objects appear in both images and directly correspond to each other. It is noted that labels may be associated with first and/or second images in particular, where The generated ground truth labels correspond to the ground truth labels of the training dataset used to train the ground truth generator. The labels may be of object categories selected from multiple candidate categories (e.g., different cell types are labelled) and/or of a specific category (e.g., only cells types of the specific category are labelled). Labels may be for biological objects depicting the first biomarker, and/or biological objects depicting the second biomarker where the second biomarker is different than the first biomarker. Labels may be for any biological objects not necessarily depicting any biomarker (e.g., brightfield images).

The generated ground truth labels may be implemented as, for example, segmentation of the respective biological objects, color coding of the respective biological objects, markers on the input images (e.g., different colored dots marking the biological objects of different categories), a separate overlay image that maps to the input image (e.g., overlay of colored dots and/or colored segmentation region that when placed on the input images corresponds to the locations of the biological objects), metadata tags mapped to specific locations in the input image, and/or a table of locations in the input image (e.g., x-y pixel coordinates) and corresponding label, and the like.

The ground truth labels may be of a regression type, for example, on a scale, which may be continuous and/or discrete. For example, a numerical score on a scale of 1-5, or 1-10, or 0-1, or 1-100, or other values. A regressor and/or other ML model architectures may be trained on such ground truth labels.

At 1512, a synthetic training dataset may be created from the automatically generated ground truth labels. The synthetic training dataset may be multi-record. Different implementations of the synthetic training dataset may be created for example:

Each synthetic record includes a set (e.g. pair) of the input images of the first type and second type, annotated with the automatically generated ground truth labels. Each label may be for individual biological objects, which appear in both the first and second images. Such implementation may be used, for example, for the ground truth generator bootstrapping itself, generating more ground truth from which a ML model similar to the ground truth generator itself is trained.

Each synthetic record includes only the first input images, annotated with the automatically generated ground truth labels generated for the first and/or second images. Labels generated for the second images may be mapped to corresponding biological objects on the first images. Second images are excluded.

Each synthetic record includes only the second input images, annotated with the automatically generated ground truth labels for the first and/or second images. Labels generated for the first images may be mapped to corresponding biological objects on the second images. First images are excluded.

At 1514, a biological object machine learning model may be trained on the synthetic training dataset. The biological object machine learning model may generate an outcome of one or more biological object categories assigned to respective target biological objects depicted in a target image(s), for example, labels such as metadata tags and/or color coded dots assigned to individual biological objects. The target input image may correspond to the structure of the synthetic record used to train the biological object machine learning model, for example, only the first image, only the second image, and a set (e.g., pair) of first image or second image where the second image may be a virtual image created by the virtual stainer in response to an input of the first mage and/or the second image may be an actual captured image.

At 1516, alternatively or additionally to 1514, a diagnosis machine learning model may be trained. The diagnosis machine learning model generates an outcome indicating a diagnosis in response to an input of image(s).

Alternatively or additionally to a machine learning model, a deterministic (i.e., non-ML model that is based on a predefined process and not learned from the data) diagnosis based approach may be used.

The diagnosis machine learning model and/or the deterministic diagnosis approach may, for example, count tumor cells classified as positive and tumor cells classified as negative and providing, for example, the ratio between the number of cells classified as positive and the number of cells classified as negative, and/or the ratio of positive classified cells to the whole number of cells. Such diagnosis may be done, for example, on top of the object machine learning model, for example, in the context of PD-L1 scoring.

The diagnosis machine learning model may be trained on a biological object category training dataset, which may include multiple records. Different implementations of the biological object category training dataset may be created for example:

The synthetic records of the synthetic training dataset are used to represent the target input, labeled with a ground truth label of a diagnosis. The synthetic records may include: sets (e.g., pairs) of first and second images, only first images, and only second images, as described with reference to the structure of the synthetic records. The diagnosis may be obtained, for example, manually from the user, extracted from a pathological report generated by a pathologist, and/or computed using a set of rules from the respective annotations, for example, counting the number of total cells and computing a percentage of cells of a specific cell type.

Records may include images labelled with biological object categories obtained as an outcome of the biological object machine learning model in response to input of the images (e.g., sets (e.g., pairs), only first images, only second images), labeled with a ground truth label of a diagnosis.

Figure 16:
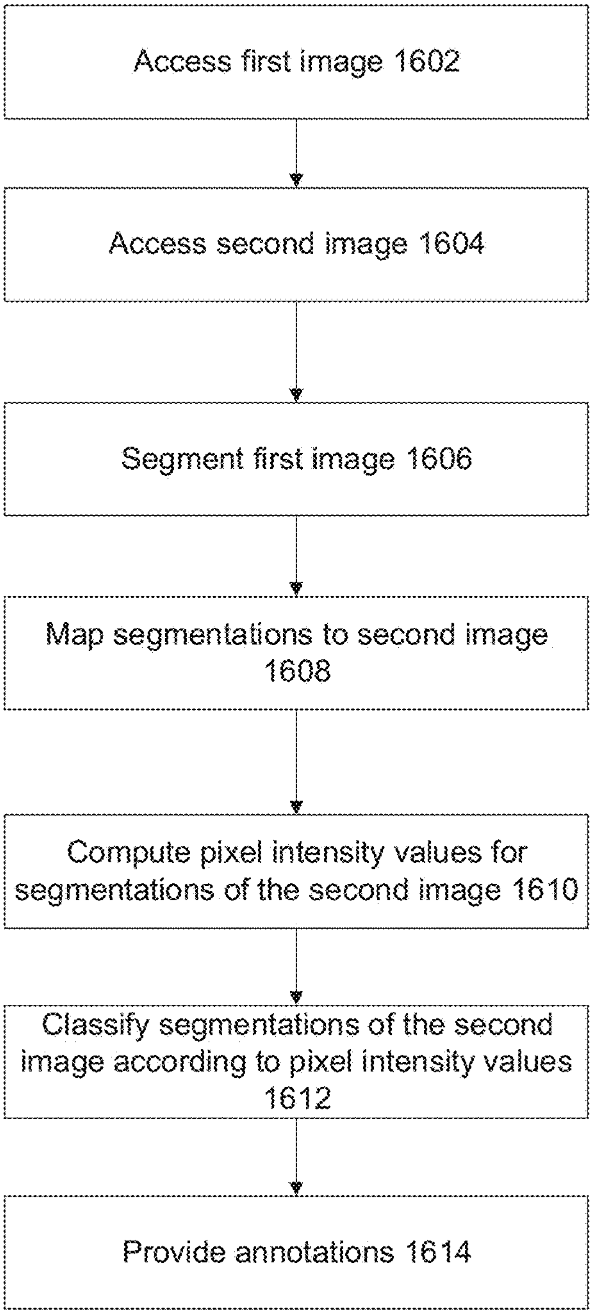
FIG. 16 is a flowchart of an alternative deterministic based approach for automatically annotating biological objects in images of samples of tissue, in accordance with various embodiments.

Reference is now made to FIG. 16, which is a flowchart of an alternative deterministic based approach for automatically annotating biological objects in images of samples of tissue, in accordance with some embodiments of the present disclosure. The process described with reference to FIG. 16 may be an alternative to, and/or combined with, the nuclei detection system described herein. The approach described with reference to FIG. 16 may be an alternative to, and/or combined with one or more features of the process described with reference to FIGS. 5A-5N.

Referring now back to FIG. 16, at 1602, first images are accessed.

At 1604, second images are accessed. The second images may be actual images, or virtual images obtained as an outcome of the virtual stainer (e.g., as described herein, such as trained as described with reference to FIG. 13) fed an input of the first images.

The second image may be aligned to the first image, for example, using optical flow, non-rigid registration, and/or other approaches, as described herein, for example, with reference to feature 1306 of FIG. 13.

At 1606, biological visual features of the first image are segmented. The segmented regions may correspond to biological objects that are for annotating, and/or used for determining a diagnosis, for example, cells and/or nucleoli. The segmentation is performed using an automated segmentation process, for example, a trained segmentation neural network (or other ML model implementation), using edge detection approaches, using histogram computations, and the like.

At 1608, the segmentation computed for the first image are mapped to the second image. When the images are aligned, the segmentations of the first image may directly correspond to create segmentation on the second image.

At 1610, pixel values within and/or in proximity to a surrounding of the respective segmentation of the second image are computed. The pixel values indicate visual depiction of the second biomarker.

For example, when the first image is stained with a standard stain that appears brown, and the second image is stained with a sequential stain that appears to have a magenta color, pixel values within and/or in proximity to a surrounding of the respective segmentation of the second image indicating the magenta color are identified.

At 1612, the respective segmentation of the second image is classified by mapping the computed intensity value using a set of rules to a classification category indicating a respective biological object type. For example, segmentations for which the magenta color is identified are labelled with a certain cell type indicating cells that express the second biomarker.

At 1614, an annotation of the first and/or second images using the classification categories is provided. Classification categories determined for segmentations of the second image may be used to label corresponding segmentations of the first image.

Figure 17:
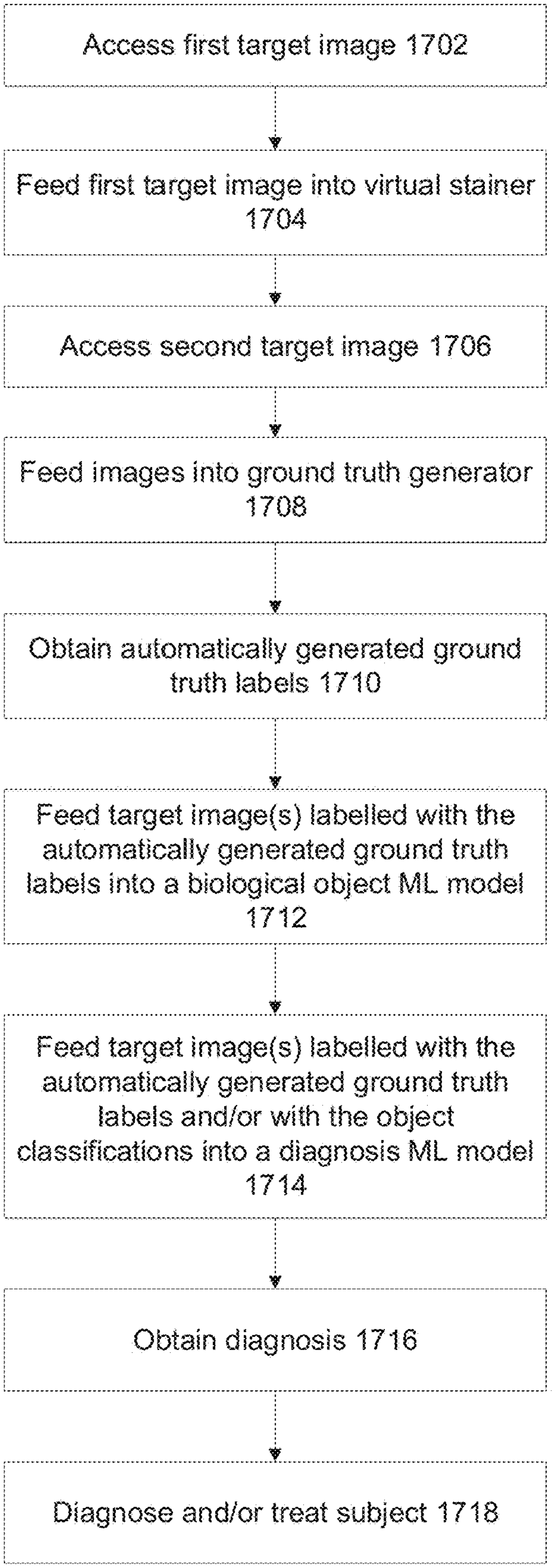
FIG. 17 is a flowchart of a method of obtaining a diagnosis for a sample of tissue of a subject, in accordance with various embodiments.

Reference is now made to FIG. 17, which is a flowchart of a method of obtaining a diagnosis for a sample of tissue of a subject, in accordance with some embodiments of the present disclosure. The diagnosis may be obtained using a first image, without necessarily obtaining a second image by applying a sequential stain and/or specific illumination.

Referring now back to FIG. 17, at 1702, a first target image of a sample of tissue of a subject is accessed. The first target image is unlabeled. Additional exemplary details are described, for example, with reference to 1502 of FIG. 15.

At 1704, the first target image may be fed into the virtual stainer (e.g., as described herein, for example, trained as described with reference to FIG. 13) to obtain the second target image. Alternatively, second target images are available, in which case the virtual stainer is not necessarily used.

Additional exemplary details are described, for example, with reference to 1504 of FIG. 15.

At 1706, the second target image of the sample of tissue may be accessed. The second target image is unlabeled. Additional exemplary details are described, for example, with reference to 1506 of FIG. 15.

At 1708, the target images(s), i.e., the first target image and/or second target images, are fed into the ground truth generator machine learning model. The ground truth generator may be trained as described herein, for example, as described with reference to FIG. 14.

Additional exemplary details are described, for example, with reference to 1508 of FIG. 15.

At 1710, automatically generated ground truth labels for the unlabeled first target image and/or second target image are obtained from the ground truth generator. Additional exemplary details are described, for example, with reference to 1510 of FIG. 15.

At 1712, the target image(s) (i.e., the first and/or second images) may be labelled with the automatically generated ground truth labels obtained from the ground truth generator. The labelled target image(s) may be fed into a biological object machine learning model (e.g., created as described herein, for example, with reference to 1514 of FIG. 15). An outcome of respective biological object categories for respective target biological objects depicted in the target image(s) is obtained from the biological object machine learning model. Alternatively, the target image(s) when non-labelled are fed into the biological object machine learning model, to obtain an object classification outcome. The target image may be labelled with the object classification.

It is noted that the step of feeding into the biological object machine learning model may be omitted in some implementations.

At 1714, the target image(s) may be labelled with the automatically generated ground truth labels obtained from the ground truth generator, and/or labelled with the biological object classifications obtained from the biological object machine learning model.

The labelled target image(s) may be fed into a diagnosis machine learning model (e.g., created as described herein, for example, with reference to 1516 of FIG. 15. It is noted that the step of feeding into the diagnosis machine learning model may be omitted in some implementations.

Alternatively or additionally, one or more metrics (sometimes referred to herein as "clinical score") are computed for the sample, using a set of rules, and/or using the diagnosis machine learning model. Metrics may be computed, for example, per specific biological object category, and/or for multiple biological object categories. Metrics may be computed, for example, for the sample as a whole, for the whole image (e.g., WSI), and/or for a patch of the image, and/or for a region(s) of interest. Examples of metrics include: Tumor Proportion Score (e.g., as described herein), Combined Positive Score (e.g., as described herein), number of specific cells (e.g., tumor cells), percentage of certain cells (e.g., percent of macrophages out of depicted immune cells, percentage of viable tumor cells that express a specific biomarker relative to all viable tumor cells present in the sample, percentage of cells expressing a specific biomarker, ratio between tumor and non-tumor cells), and other scores described herein.

It is noted that alternatively, rather than using the diagnosis machine learning model, a set of rules may be used, and/or other deterministic code, such as code that counts the number of biological objects in specific categories and computes the percentage and/or other metrics.

At 1716, a diagnosis for the sample may be obtained as an outcome of the diagnosis machine learning model.

At 1718, the subject (whose sample is depicted in the target image(s)) may be diagnosed and/or treated according to the obtained diagnosis and/or metric. For example, the subject may be administered chemotherapy, may undergo surgery, may be instructed to watch-and-wait, and/or may be instructed to undergo additional testing.

Alternatively or additionally, new drugs and/or companion diagnostics for drugs may be developed using the diagnosis and/or computed metric.

Figure 18A:
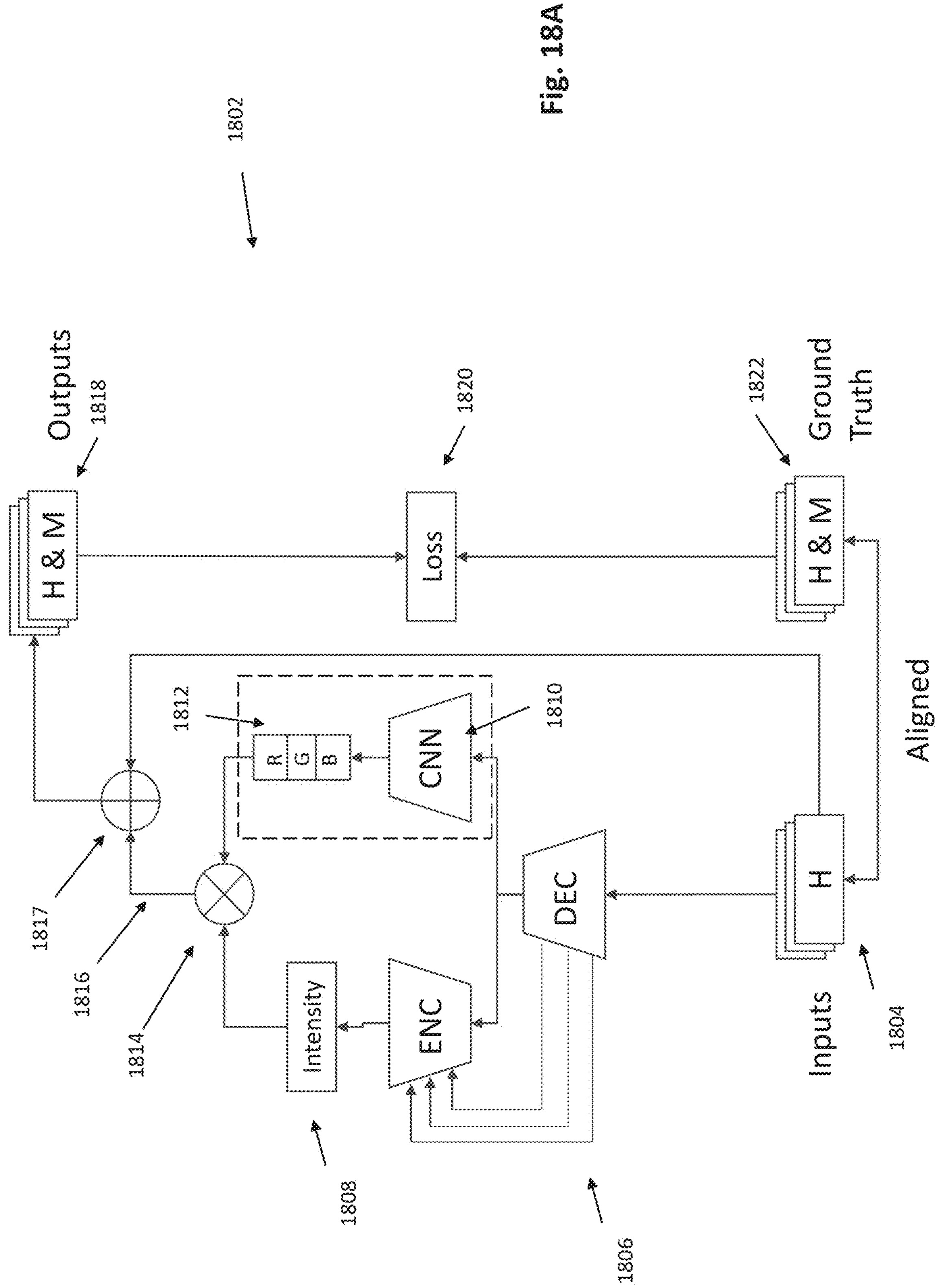
FIGS. 18A-C are schematics of exemplary architectures of the virtual stainer machine learning model (sometimes referred to herein as "Model F"), in accordance with various embodiments.
Figure 18B:
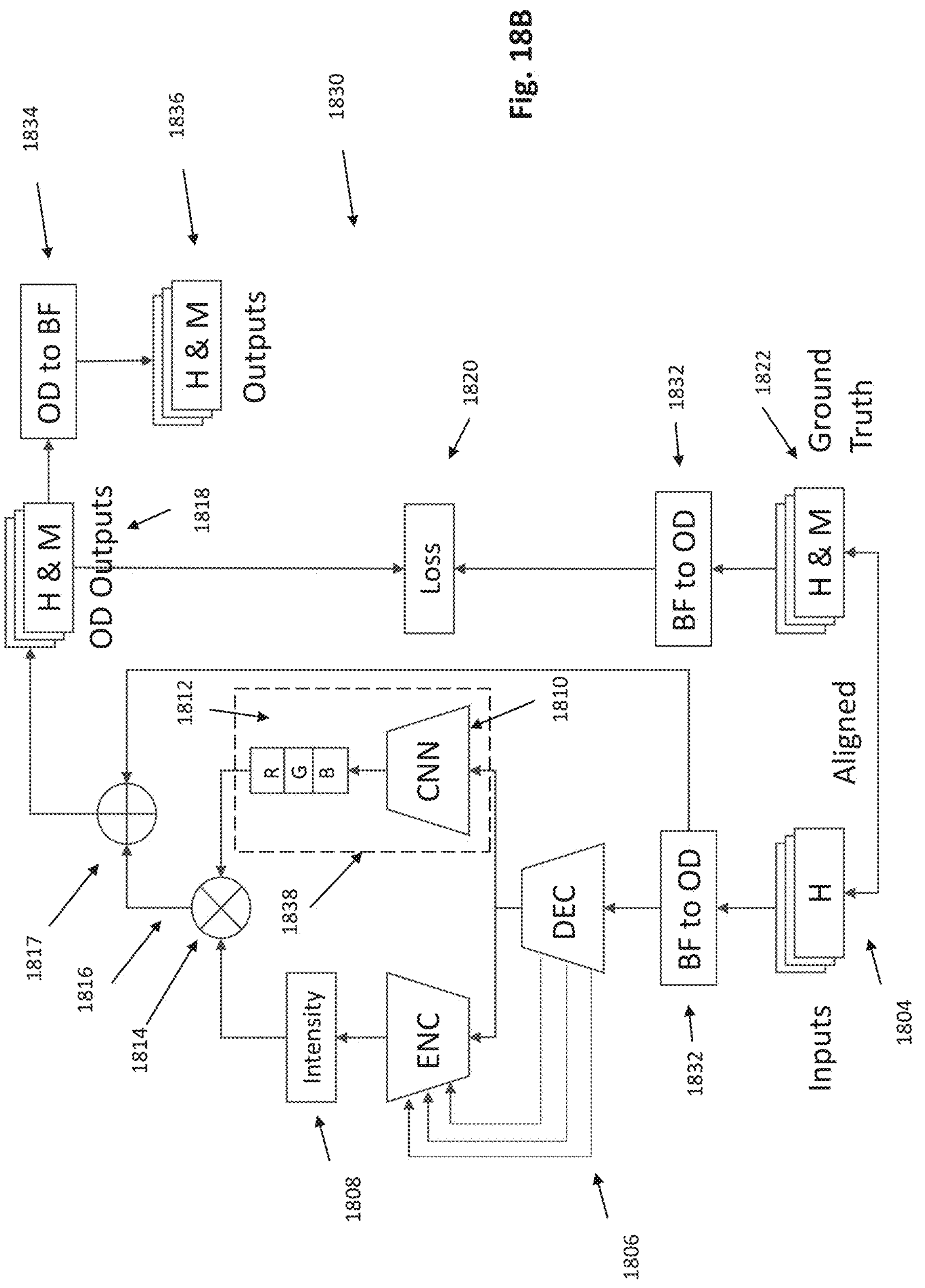
Figure 18C:
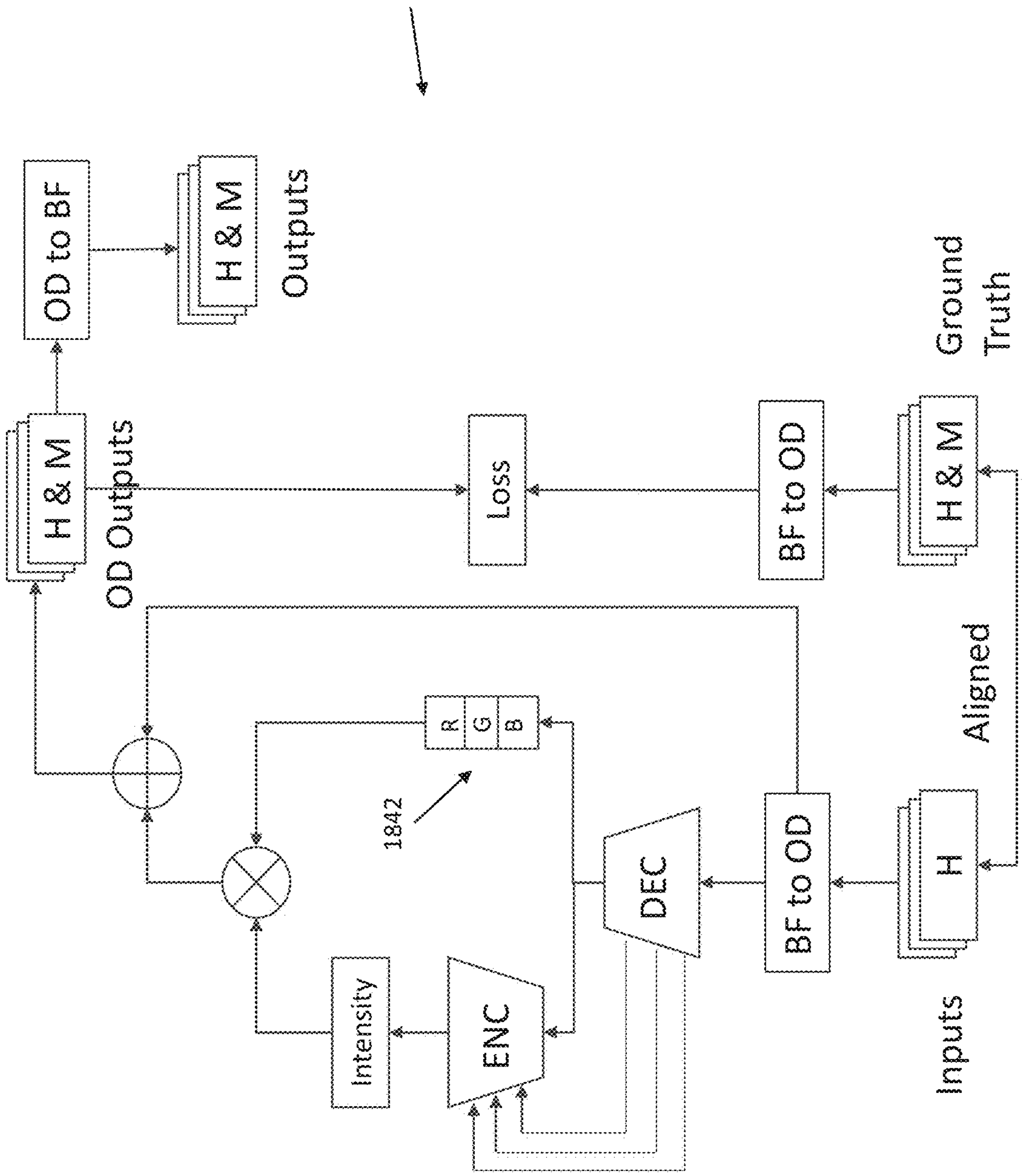

Reference is now made to FIG. 18A-C, which are schematics of exemplary architectures of the virtual stainer machine learning model (sometimes referred to herein as "Model F"), in accordance with some embodiments of the present disclosure. For example, an image of a slide stained with Hematoxylin is fed into the virtual stainer, and an outcome of a sequential stain (e.g., magenta appearance, as described herein) that is further applied over the Hematoxylin stain is generated.

Referring now to FIG. 18A, a first exemplary architecture 1802 of the virtual stainer machine learning model is depicted. An input image 1804 of spatial dimensions H×W is inputted into architecture 1802. Image 1804 is fed into an encoder/decoder (ENC/DEC) network 1806, for example, based on a Unet architecture with a single channel output of the same spatial size as the input image, Intensity Map 1808. A Convolutional Neural Network (CNN) 1810 operates on the output of the encoder with a color vector output, RGB vector 1812. Intensity map 1808 and color vector 1812 are combined 1814 to produce a 3-channel image of the virtual stain (virtual magenta) 1816. Predicted virtual stain 1816 is added 1817 to input image 1804 to produce the output, a predicted virtually stained image 1818. Architecture 1802 is trained with a loss 1820, for example, MSE loss, between the virtually stained image 1818 and its paired sequentially stained ground truth image 1822.

Referring now to FIG. 18B, a second exemplary architecture 1830 of the virtual stainer machine learning model is depicted. Architecture 1830 is similar to architecture 1802 described with reference to FIG. 18A, with the adaptation of an added transformation of input images 1804 and ground truth images 1822 to Optical Density (OD), by logarithmic transformation, using a bright-field (BF) to OD process 1832. The transformation to OD improves training of architecture 1830. When using trained model 1830 for inference, the inverse transformation, from OD space ("log space") to the regular image space ("linear space"), denoted OD to BF 1834 is applied to the output of model 1830 to generate output 1836.

Referring now to FIG. 18C, a third exemplary architecture 1840 of the virtual stainer machine learning model is depicted. Architecture 1834 is similar to architecture 1830 described with reference to FIG. 18B, with the adaptation of RGB color prediction network 1838 of FIG. 18B being replaced by a parameter vector of length three 1842, The (globally) optimal values for the virtual Magenta hue (R,G, B) 1842 are learnt during training and are kept fixed during inference.

In at least some implementations, the present disclosure provides detectable reagents capable of serving as substrates of an enzyme with peroxidase activity, and describes their utility for detecting molecular targets in samples. The present disclosure also provides methods for detecting multiple target molecules in biological samples comprising cells. Various embodiments also provide for implementing annotation data collection and autonomous annotation, and, more particularly, to methods, systems, and apparatuses for implementing sequential imaging of biological samples for generating training data for developing deep learning based models for image analysis, for cell classification, for feature of interest identification, and/or for virtual staining of biological samples.

A. Tissue Staining Methodology

A "moiety" is a portion of a molecule that retains chemical and/or physical and/or functional features of the entire molecule, that are relevant for performance of the chromogenic conjugates; e.g., "peroxidase substrate moiety" is a portion of a molecule capable of serving as substrate of an enzyme with peroxidase activity; "peroxidase moiety" is a portion of a molecule that has inherent peroxidase activity, e.g., an enzyme.

A "target" is an object in a test sample to be detected by use of the present chromogenic conjugates and methods; Exemplary targets include, but are not limited to, chemical and biological molecules and structures such as cellular components. A target molecule includes, but is not limited to: nuclear proteins, cytoplasmic proteins, membrane proteins, nuclear antigens, cytoplasmic antigens, polypeptides and membrane antigens, nucleic acid targets, DNA, RNA, nucleic acids inherent to the examined biological material, and/or nucleic acids acquired in the form of viral, parasitic or bacterial nucleic acids. Embodiments of present targets are discussed herein.

The linker compound L comprises a chain of 5-29 interconnected atoms (correspondingly abbreviated "L5-L29"); wherein, in some preferred embodiments, the linker compound comprises two consecutive carbons followed by an oxygen or nitrogen atom.

The term "detection method" can refer to immunohistochemistry (IHC), in situ hybridization (ISH), ELISA, Southern, Northern and Western blotting.

The term, "Spectral characteristics" are characteristics of electromagnetic radiation emitted or absorbed due to a molecule or moiety making a transition from one energy state to another energy state, for example from a higher energy state to a lower energy state. Only certain colors appear in a molecule's or moiety's emission spectrum, since certain frequencies of light are emitted and certain frequencies are absorbed. Spectral characteristics may be summarized or referred to as the color of the molecule or moiety.

The term "CM" refers to the portion of the compound of Formula I as described below other than the L-PS moieties.

The term "colorless" can refer to the characteristic where the absorbance and emission characteristics of the compound changes, making the compound invisible to the naked eye, but not invisible to the camera, or other methods of detection. It is known in the art that various compounds can change their spectrum depending on conditions. In some embodiments, changing the pH of the mounting medium can change the absorbance and emission characteristics wherein a compound can go from visible in a basic aqueous mounting medium to invisible in an acidic mounting medium. This change is useful with regard to the detectable reagents as defined herein. Additionally, the chromogen as defined as Formula IV below (visible as yellow in aqueous mounting media), changes to Formula VII (invisible or colorless) when placed in organic mounting media.

Further, some embodiments use florescent compounds, which change their absorbance and emission characteristics through changing the pH of the mounting medium, wherein, changing to a basic aqueous mounting medium wherein the compound fluoresces, to an acidic mounting medium wherein the compound does not. An example of such is Rhodamine spirolactam (non-fluorescent, acidic conditions) to spirolactone (highly fluorescent basic conditions). Compounds include: fluorescein spirolactone, fluorescein spirolactams, Rhodamine Spirolactams and Rhodamine spirolactones. This includes Rhodamines and Fluoresceins that are modified (derivatives). At acidic pH it is the less colored spiroform and at basic pH it is the "open form."

Other colorless compounds that can be used in one embodiment of the invention includes biotin as the CM, which is invisible to the naked eye, but can be visualized at the appropriate time using streptavidin/HRP or an antibody/HRP (anti-biotin) and a peroxidase substrate that is either colored or fluorescent when precipitated.

The phrase, "visible in brightfield" means visible in parts of or the whole brightfield spectra.

The phrase, "obtaining an image" includes obtaining an image from a digital scanner.

The term "detectable reagents" includes labels including chromogens.

B. Sequential Imaging of Biological Samples for Generating Training Data for Developing Deep Learning Based Models for Image Analysis, for Cell Classification, for Feature Of Interest Identification, and/or for Virtual Staining of the Biological Sample In various embodiments, a computing system may receive a first image of a first biological sample, the first image comprising a first field of view ("FOV") of the first biological sample that has been processed with a first biological marker (which may include, without limitation, a first stain, a first chromogen, or other suitable compound that is useful for characterizing the first biological sample, or the like); and may receive a second image of the first biological sample, the second image comprising a second FOV of the first biological sample that has been processed with a second biological marker (which may include, but is not limited to, a second stain, a second chromogen, or other suitable compound, or the like). The computing system may be configured to create a first set of image patches using the first image and the second image, wherein each image patch among the first set of image patches may further correspond to a portion of the first image and a corresponding portion of the second image. The first set of image patches may comprise a first patch corresponding to the extracted portion of the first image and a second patch corresponding to the extracted portion of the second image. In such cases, the first set of image patches may comprise labeling of instances of features of interest in the first biological sample that is based at least in part upon information contained in the first patch, information contained in the second patch, and/or information contained in one or more external labeling sources.

The computing system may utilize an AI system to train a first model ("Model G*") to generate first instance classification of features of interest ("Ground Truth") in the first biological sample, based at least in part on the first set of image patches and the labeling of instances of features of interest contained in the first set of image patches; and may utilize the AI system to train a second AI model ("Model G") to identify instances of features of interest in the first biological sample, based at least in part on the first patch and the first instance classification of features of interest generated by Model G*.

According to some embodiments, the first biological sample may include, without limitation, any tissue or cellular sample derived from a living organism (including, but not limited to, a human tissue or cellular sample, an animal tissue or cellular sample, or a plant tissue or cellular sample, and/or the like) or an artificially produced tissue sample, and/or the like. In some instances, the features of interest may include, but are not limited to, at least one of normal cells, abnormal cells, diseased cells, damaged cells, cancer cells, tumors, subcellular structures, organs, organelles, cellular structures, pathogens, antigens, or biological markers, and/or the like.

In some embodiments, the first image may comprise highlighting or identification of first features of interest in the first biological sample by the first biological marker that had been applied to the first biological sample. Similarly, the second image may comprise one of highlighting or identification of second features of interest in the first biological sample by the second biological marker that had been applied to the first biological sample in addition to highlighting or identification of the first features of interest by the first biological marker or highlighting of the second features of interest by the second biological marker without highlighting of the first features of interest by the first biological marker, the second features of interest being different from the first features of interest. In some cases, the second biological marker may be similar or identical to the first biological marker but used to process the second features of interest or different from the first biological marker, or the like.

Merely by way of example, in some cases, the first biological marker may include, without limitation, at least one of Hematoxylin, Acridine orange, Bismarck brown, Carmine, Coomassie blue, Cresyl violet, Crystal violet, 4',6-diamidino-2-phenylindole ("DAPI"), Eosin, Ethidium bromide intercalates, Acid fuchsine, Hoechst stain, Iodine, Malachite green, Methyl green, Methylene blue, Neutral red, Nile blue, Nile red, Osmium tetroxide, Propidium Iodide, Rhodamine, Safranine, programmed death-ligand 1 ("PD-L1") stain, 3,3'-Diaminobenzidine ("DAB") chromogen, Magenta chromogen, cyanine chromogen, cluster of differentiation ("CD") 3 stain, CD20 stain, CD68 stain, 40S ribosomal protein SA ("p40") stain, antibody-based stain, or label-free imaging marker (which may result from the use of imaging techniques including, but not limited to, Raman spectroscopy, near infrared ("NIR") spectroscopy, autofluorescence imaging, or phase imaging, and/or the like, and which may be used to highlight features of interest without an external dye or the like), and/or the like. In some cases, the contrast when using label-free imaging techniques may be generated without additional markers such as fluorescent dyes or chromogen dyes, or the like.

Likewise, the second biological marker may include, but is not limited to, at least one of Hematoxylin, Acridine orange, Bismarck brown, Carmine, Coomassie blue, Cresyl violet, Crystal violet, DAPI, Eosin, Ethidium bromide intercalates, Acid fuchsine, Hoechst stain, Iodine, Malachite green, Methyl green, Methylene blue, Neutral red, Nile blue, Nile red, Osmium tetroxide, Propidium Iodide, Rhodamine, Safranine, PD-L1 stain, DAB chromogen, Magenta chromogen, cyanine chromogen, CD3 stain, CD20 stain, CD68 stain, p40 stain, antibody-based stain, or label-free imaging marker, and/or the like.

According to some embodiments, the first image may include, without limitation, one of a first set of color or brightfield images, a first fluorescence image, a first phase image, or a first spectral image, and/or the like, where the first set of color or brightfield images may include, but is not limited to, a first red-filtered ("R") image, a first green-filtered ("G") image, and a first blue-filtered ("B") image, and/or the like. The first fluorescence image may include, but is not limited to, at least one of a first autofluorescence image or a first labelled fluorescence image having one or more channels with different excitation or emission characteristics, and/or the like. The first spectral image may include, but is not limited to, at least one of a first Raman spectroscopy image, a first near infrared ("NIR") spectroscopy image, a first multispectral image, a first hyperspectral image, or a first full spectral image, and/or the like. Similarly, the second image may include, without limitation, one of a second set of color or brightfield images, a second fluorescence image, a second phase image, or a second spectral image, and/or the like, where the second set of color or brightfield images may include, but is not limited to, a second R image, a second G image, and a second B image, and/or the like. The second fluorescence image may include, but is not limited to, at least one of a second autofluorescence image or a second labelled fluorescence image having one or more channels with different excitation or emission characteristics, and/or the like. The second spectral image may include, but is not limited to, at least one of a second Raman spectroscopy image, a second NIR spectroscopy image, a second multispectral image, a second hyperspectral image, or a second full spectral image, and/or the like.

Alternatively, or additionally, the computing system may receive a first image of a first biological sample, the first image comprising a first field of view ("FOV") of the first biological sample; and may identify, using a first AI model ("Model G") that is generated or updated by a trained AI system, first instances of features of interest in the first biological sample, based at least in part on the first image and based at least in part on training of Model G using a first patch and first instance classification of features of interest generated by a second model (Model G*) that is generated or updated by the trained AI system by using first aligned image patches and labeling of instances of features of interest contained in the first patch. In some cases, the first aligned image patches may comprise an extracted portion of first aligned images, which may comprise a second image and a third image that have been aligned. The second image may comprise a second FOV of a second biological sample that has been processed with a first biological marker (which may include, without limitation, a first stain, a first chromogen, or other suitable compound that is useful for characterizing the first biological sample, or the like), the second biological sample being different from the first biological sample. The third image may comprise a third FOV of the second biological sample that has been processed with a second biological marker (which may include, without limitation, a second stain, a second chromogen, or other suitable compound that is useful for characterizing the second biological sample, or the like). The second patch may comprise labeling of instances of features of interest as shown in the extracted portion of the second image of the first aligned images. The first image may comprise highlighting of first features of interest in the second biological sample by the first biological marker that had been applied to the second biological sample. The second patch may comprise one of highlighting of second features of interest in the second biological sample by the second biological marker that had been applied to the second biological sample in addition to highlighting of the first features of interest by the first biological marker or highlighting of the second features of interest by the second biological marker without highlighting of the first features of interest by the first biological marker.

Alternatively, or additionally, the computing system may receive first instance classification of features of interest ("Ground Truth") in a first biological sample that has been sequentially stained or processed, the Ground Truth having been generated by a trained first model ("Model G*") that has been trained or updated by an AI system, wherein the Ground Truth is generated by using first aligned image patches and labeling of instances of features of interest contained in the first aligned image patches, wherein the first aligned image patches comprise an extracted portion of first aligned images, wherein the first aligned images comprise a first image and a second image that have been aligned, wherein the first image comprises a first FOV of the first biological sample that has been stained or processed with a first biological marker (which may include, without limitation, a first stain, a first chromogen, or other suitable compound that is useful for characterizing the first biological sample, or the like), wherein the second image comprises a second FOV of the first biological sample that has been stained or processed with a second biological marker (which may include, without limitation, a second stain, a second chromogen, or other suitable compound that is useful for characterizing the first biological sample, or the like), wherein the first aligned image patches comprise labeling of instances of features of interest as shown in the extracted portion of the first aligned images; and may utilize the AI system to train a second AI model ("Model G") to identify instances of features of interest in the first biological sample, based at least in part on the first instance classification of features of interest generated by Model G*.

Alternatively, or additionally, the computing system may generate ground truth for developing accurate AI models for biological image interpretation, based at least in part on images of a first biological sample depicting sequential staining or processing of the first biological sample.

In another aspect, the computing system may receive a first image of a first biological sample, the first image comprising a first field of view ("FOV") of the first biological sample that has been stained or processed with a first biological marker (which may include, without limitation, a first stain, a first chromogen, or other suitable compound that is useful for characterizing the first biological sample, or the like); may receive a second image of the first biological sample, the second image comprising a second FOV of the first biological sample that has been stained or processed with at least a second biological marker (which may include, without limitation, a second stain, a second chromogen, or other suitable compound that is useful for characterizing the first biological sample, or the like); and may align the first image with the second image to create first aligned images, by aligning one or more features of interest in the first biological sample as depicted in the first image with the same one or more features of interest in the first biological sample as depicted in the second image.

The computing system may create first aligned image patches from the first aligned images, by extracting a portion of the first aligned images, the portion of the first aligned images comprising a first patch corresponding to the extracted portion of the first image and a second patch corresponding to the extracted portion of the second image; may utilize an AI system to train a first AI model ("Model F") to generate a third patch comprising a virtual stain of the first aligned image patches, based at least in part on the first patch and the second patch, the virtual stain simulating staining or processing by at least the second biological marker of features of interest in the first biological sample as shown in the second patch; and may utilize the AI system to train a second model ("Model G*") to identify or classify first instances of features of interest in the first biological sample, based at least in part on the third patch and based at least in part on results from an external instance classification process or a region of interest detection process.

According to some embodiments, the first image may comprise highlighting or identification of first features of interest in the first biological sample by the first biological marker that had been applied to the first biological sample. In some cases, the third patch may comprise one of highlighting or identification of the first features of interest by the first biological marker and highlighting of second features of interest in the first biological sample by the virtual stain that simulates the second biological marker having been applied to the first biological sample or highlighting or identification of the first features of interest by the first biological marker and highlighting or identification of first features of interest by the virtual stain, the second features of interest being different from the first features of interest. In some instances, the second biological marker may be one of the same as the first biological marker but used to stain or process the second features of interest or different from the first biological marker.

In some embodiments, utilizing the AI system to train Model F may comprise: receiving, with an encoder, the first patch; receiving the second patch; encoding, with the encoder, the received first patch; decoding, with the decoder, the encoded first patch; generating an intensity map based on the decoded first patch; simultaneously operating on the encoded first patch to generate a color vector; combining the generated intensity map with the generated color vector to generate an image of the virtual stain; adding the generated image of the virtual stain to the received first patch to produce a predicted virtually stained image patch; determining a first loss value between the predicted virtually stained image patch and the second patch; calculating a loss value using a loss function, based on the first loss value between the predicted virtually stained image patch and the second patch; and updating, using the AI system, Model F to generate the third patch, by updating one or more parameters of Model F based on the calculated loss value. In some instances, the loss function may include, but is not limited to, one of a mean squared error loss function, a mean squared logarithmic error loss function, a mean absolute error loss function, a Huber loss function, or a weighted sum of squared differences loss function, and/or the like.

Alternatively, utilizing the AI system to train Model F may comprise: receiving, with the AI system, the first patch; receiving, with the AI system, the second patch; generating, with a second model of the AI system, an image of the virtual stain; adding the generated image of the virtual stain to the received first patch to produce a predicted virtually stained image patch; determining a first loss value between the predicted virtually stained image patch and the second patch; calculating a loss value using a loss function, based on the first loss value between the predicted virtually stained image patch and the second patch; and updating, using the AI system, Model F to generate the third patch, by updating one or more parameters of Model F based on the calculated loss value. In some embodiments, the second model may include, without limitation, at least one of a convolutional neural network ("CNN"), a U-Net, an artificial neural network ("ANN"), a residual neural network ("ResNet"), an encode/decode CNN, an encode/decode U-Net, an encode/decode ANN, or an encode/decode ResNet, and/or the like.

Alternatively, or additionally, the computing system may receive a first image of a first biological sample, the first image comprising a first field of view ("FOV") of the first biological sample; and may identify, using a first model ("Model G*") that is generated or updated by a trained AI system, first instances of features of interest in the first biological sample, based at least in part on the first image and based at least in part on training of Model G* using at least a first patch comprising a virtual stain of first aligned image patches, the first patch being generated by a second AI model (Model F) that is generated or updated by the trained AI system by using a second patch. In some cases, the first aligned image patches may comprise an extracted portion of first aligned images. The first aligned images may comprise a second image and a third image that have been aligned. The second image may comprise a second FOV of a second biological sample that is different from the first biological sample that has been stained or processed with a first biological marker (which may include, without limitation, a first stain, a first chromogen, or other suitable compound that is useful for characterizing the first biological sample, or the like). The second patch may comprise the extracted portion of the second image. The third image may comprise a third FOV of the second biological sample that has been stained or processed with at least a second biological marker (which may include, without limitation, a second stain, a second chromogen, or other suitable compound that is useful for characterizing the second biological sample, or the like).

In order to overcome the problems and limitations with conventional techniques (as noted above), the present teachings provide for improved annotation analysis and for generating cell-perfect annotations as an input for training of an automated image analysis architecture. This can be accomplished by leveraging differential tissue imagings such as comparing a baseline, control, or uncontaminated image of a tissue followed by a second image of the same tissue, but now with the objects of interest stained or processed to be visible or identifiable. With good image alignment, such processes can generate tens of thousands (or more) of accurate and informative cell-level annotations, without requiring the intervention of a human observer, such as a technician or pathologist, or the like. Hence, the potential to generate high quality and comprehensive training data for a deep learning or other computational methods is immense and may greatly improve the performance of automated and semi-automated image analysis where the ground truth may be established directly from biological data and reduces or removes human observer-based errors and limitations. In addition, the speed of annotation may be vastly improved compared to the time it would take a pathologist to annotate similar datasets.

There are many commercial applications for this technology, such as developing image analysis techniques suitable for use with PharmDx kits. PD-L1 is a non-limiting example where a computational image analysis method may be used to identify and/or designate lymphocytes complimenting and extending the assay. For instance, AI models developed based on the methods described herein can be used to develop digital scoring of PD-L1 immunohistochemistry ("IHC") products (including, but not limited to, Agilent PD-L1 IHC 22C3 family of products, or other PD-L1 IHC family of products, or the like). For example, PD-L1 IHC 22C3 pharmDx interpretation manual for NSCLC may require calculation of a Tumor Proportion Score ("TPS"), which may be calculated as the percentage of viable tumor cells showing partial or complete membrane staining relative to all viable tumor cells present in the sample (positive and negative) of the number of PD-L1 staining cells (including tumor cells, lymphocytes, macrophages, and/or the like) divided by the total number of viable tumor cells, multiplied by 100. Infiltrating immune cells, normal cells, and necrotic cells may be excluded from the TPS calculation. AI models trained by the methods presented herein enable exclusion of various immune cell types such as T-cells, B-cells, and macrophages, or the like. Following this exclusion, cells may be further classified as PD-L1 positive, PD-L1 negative cells, viable tumor cells, or non-tumor cells, or the like, and accurate TPS scores may be calculated. Methods described herein may also be relevant for the calculation of a Combined Positive Score ("CPS"), or the like. Another non-limiting example is identification of p40-positive tumor cells to differentiate squamous cell carcinomas and adenocarcinomas for non-small cell lung cancer ("NSCLC") specimens.

Various embodiments of the present teachings provide a two-step IHC staining or processing with different biological markers (which may include, without limitation, stains, chromogens, or other suitable compounds that are useful for characterizing biological samples, or the like). Biological markers may be visualized using brightfield or fluorescent imaging. In various embodiments described herein, two sets of methods—namely, (a) sequential imaging of (sequentially stained or processed) biological samples for generating training data for developing deep learning based models for image analysis, for cell classification, and/or for features of interest identification of biological samples and (b) sequential imaging of (sequentially stained or processed) biological samples for generating training data for virtual staining of biological samples—may be used to generate the necessary data.

These and other aspects of the sequential imaging of biological sample for generating training data for developing deep learning based models for image analysis, for cell classification, for feature of interest identification, and/or for virtual staining of biological samples are described in greater detail with respect to the figures. Although the various embodiments are described in terms of digital pathology implementations, the various embodiments are not so limited, and may be applicable to live cell imaging, or the like.

Various embodiments described herein, while embodying (in some cases) software products, computer-performed methods, and/or computer systems, represent tangible, concrete improvements to existing technological areas, including, without limitation, annotation collection technology, annotation data collection technology, autonomous annotation technology, deep learning technology for autonomous annotation, and/or the like. In other aspects, certain embodiments, can improve the functioning of user equipment or systems themselves (e.g., annotation collection system, annotation data collection system, autonomous annotation system, deep learning system for autonomous annotation, etc.), for example, by receiving, with a computing system, a first image of a first biological sample, the first image comprising a first field of view ("FOV") of the first biological sample that has been stained with a first stain; receiving, with the computing system, a second image of the first biological sample, the second image comprising a second FOV of the first biological sample that has been stained with a second stain; autonomously creating, with the computing system, a first set of image patches based on the first image and the second image, by extracting a portion of the first image and extracting a corresponding portion of the second image, the first set of image patches comprising a first patch corresponding to the extracted portion of the first image and a second patch corresponding to the extracted portion of the second image; training, using an artificial intelligence ("AI") system, a first model ("Model G*") to generate first instance classification of features of interest ("Ground Truth") in the first biological sample, based at least in part on the first aligned image patches and the labeling of instances of features of interest contained in the first patch; training, using the AI system, a second AI model ("Model G") to identify instances of features of interest in the first biological sample, based at least in part on the first patch and the first instance classification of features of interest generated by Model G*; and/or the like.

In particular, to the extent any abstract concepts are present in the various embodiments, those concepts can be implemented as described herein by devices, software, systems, and methods that involve specific novel functionality (e.g., steps or operations), such as, training, using an AI system, a (AI) model (referred to herein as "Model G*") based on sequentially stained biological samples to generate Ground Truth, which can be used to train another AI model (referred to herein as "Model G") to identify instances of features of interest in biological samples (i.e., to score images of biological samples, or the like); and, in some cases, to train, using the AI system, an AI model (referred to herein as "Model F") to generate virtual staining of biological samples, which can be used to train Model G* to identify instances of features of interest in biological samples (i.e., to score images of biological samples, or the like); and/or the like, to name a few examples, that extend beyond mere conventional computer processing operations. These functionalities can produce tangible results outside of the implementing computer system, including, merely by way of example, optimize sample annotation techniques and systems to improve precision and accuracy in identifying features of interest in biological samples (that in some instances are difficult or impossible for humans to distinguish or identify) that, in some cases, obviates the need to apply one or more additional stains for sequential staining (by implementing virtual staining, as described according to the various embodiments), and/or the like, at least some of which may be observed or measured by users and/or service providers.

A. Summary for Tissue Staining Methodology

The present disclosure provides detectable reagents capable of serving as substrates of an enzyme with peroxidase activity, and describes their utility for detecting molecular targets in samples. The present disclosure also provides methods for detecting multiple target molecules in biological samples comprising cells.

One general aspect includes a method for detecting multiple target molecules in a biological sample comprising cells. The method includes contacting the biological sample with one or more first reagents which generate a detectable signal in cells may include a first target molecule, contacting the biological sample with one or more second reagents which are capable of generating a detectable signal in cells, comprising a second target molecule under conditions in which the one or more second reagents do not generate a detectable signal. The method may also include detecting the signal generated by the one or more first reagents. The method may also include creating conditions in which the one or more second reagents generate a signal in cells comprising the second molecule. The method also includes detecting the signal generated by the one or more second reagents.

The method may include: obtaining a first digital image of the signal generated by the one or more first reagents, obtaining a second digital image of the signal generated by the one or more first reagents and the signal generated by the one or more second reagents, and copying a mask of the second digital image to the first digital image.

The biological sample may include one of a human tissue sample, an animal tissue sample, or a plant tissue sample. The target molecules may be indicative of at least one of normal cells, cell type, abnormal cells, damaged cells, cancer cells, tumors, subcellular structures, a marker indicative of or associated with a disease, disorder or health condition, or organ structures. The target molecules may be selected from the group consisting of nuclear proteins, cytoplasmic proteins, membrane proteins, nuclear antigens, cytoplasmic antigens, membrane antigens and nucleic acids. The target molecules may be nucleic acids or polypeptides.

The first reagents may include a first primary antibody against a first target molecule, an HRP coupled polymer that binds to the first primary antibody and a chromogen which is an HRP substrate.

The second reagents may include a second primary antibody against a second target molecule, an HRP coupled polymer that binds to the second primary antibody, a fluorescein-coupled long single chained polymer, an antibody against FITC that binds to the fluorescein-coupled long single chained polymer and is coupled to HRP and a chromogen which is an HRP substrate.

The method may include using a digital image of the signals detected in the biological sample to train a neural network.

A neural network trained using the methods is also contemplated.

Another aspect includes a method for generating cell-level annotations from a biological sample comprising cells. The method includes a) exposing the biological sample to a first ligand that recognizes a first antigen thereby forming a first ligand antigen complex; b) exposing the first ligand antigen complex to a first labeling reagent binding to the first ligand, the first labeling reagent forming a first detectable reagent, where the first detectable reagent is precipitated around the first antigen and visible in brightfield; c) exposing the biological sample to a second ligand that recognizes a second antigen thereby forming a second ligand antigen complex; d) exposing the second ligand antigen complex to a second labeling reagent binding to the second ligand, the second labeling reagent may include a substrate not visible in brightfield, where the substrate is precipitated around the second antigen; e) obtaining a first image of the biological sample in brightfield to visualize the first chromogen precipitated in the biological sample; f) exposing the biological sample to a third labeling reagent that recognizes the substrate, thereby forming a third ligand antigen complex, the third labeling reagent forming a second detectable reagent, where the second detectable reagent is precipitated around the second antigen; g) obtaining a second image of the biological sample in brightfield with the second detectable reagent precipitated in the biological sample; h) creating a mask from the second image; i) applying the mask to the first image so as to obtain an image of the biological sample annotated with the second antigen.

The biological sample may include one of a human tissue sample, an animal tissue sample, or a plant tissue sample, where the objects of interest may include at least one of normal cells, abnormal cells, damaged cells, cancer cells, tumors, subcellular structures, or organ structures.

In this aspect, the method may include, prior to step a), applying a target retrieval buffer and protein blocking solution to the biological sample, where the first and second antigens are exposed for the subsequent steps and endogenous peroxidases are inactivated.

The first and third labeling reagents may include an enzyme that acts on a detectable reagent substrate to form the first and second detectable reagents, respectively.

The first and second antigens may be non-nuclear proteins.

The method may include, following step b), denaturing the first ligands to retrieve the first antigens available.

The method may include, following step d), i) counter-staining cell nuclei of the biological sample, and ii) dehydrating and mounting the sample on a slide.

The method may include, following step e), i) removing mounting medium from the slide, and ii) rehydrating the biological sample.

The method may include, following step f), i) counter-staining cell nuclei of the biological sample, and ii) dehydrating and mounting the sample on a slide.

In some aspects, the first ligand may include an anti-lymphocyte-specific antigen antibody (primary antibody), the first labeling reagent may include a horseradish peroxidase (HRP)-coupled polymer capable of binding to the primary antibody, the first detectable reagent may include a chromogen may include an HRP substrate may include HRP magenta or 3,3'-diaminobenzidine tetrahydrochloride (DAB), the second antigen may include PD-L1 the second ligand may include anti-PD-L1 antibodies, the second labeling reagent may include an HRP-coupled polymer capable of binding to anti-PD-L1 antibodies, the substrate may include fluorescein-coupled long single-chained polymer (fer-4-flu linker; see U.S. Patent Application Publication No. 2016/0122800, incorporated by reference in its entirety), third labeling reagent may include an anti-FITC antibody coupled to HRP, and the second detectable reagent may include a chromogen may include HRP magenta or DAB.

Figure 22:
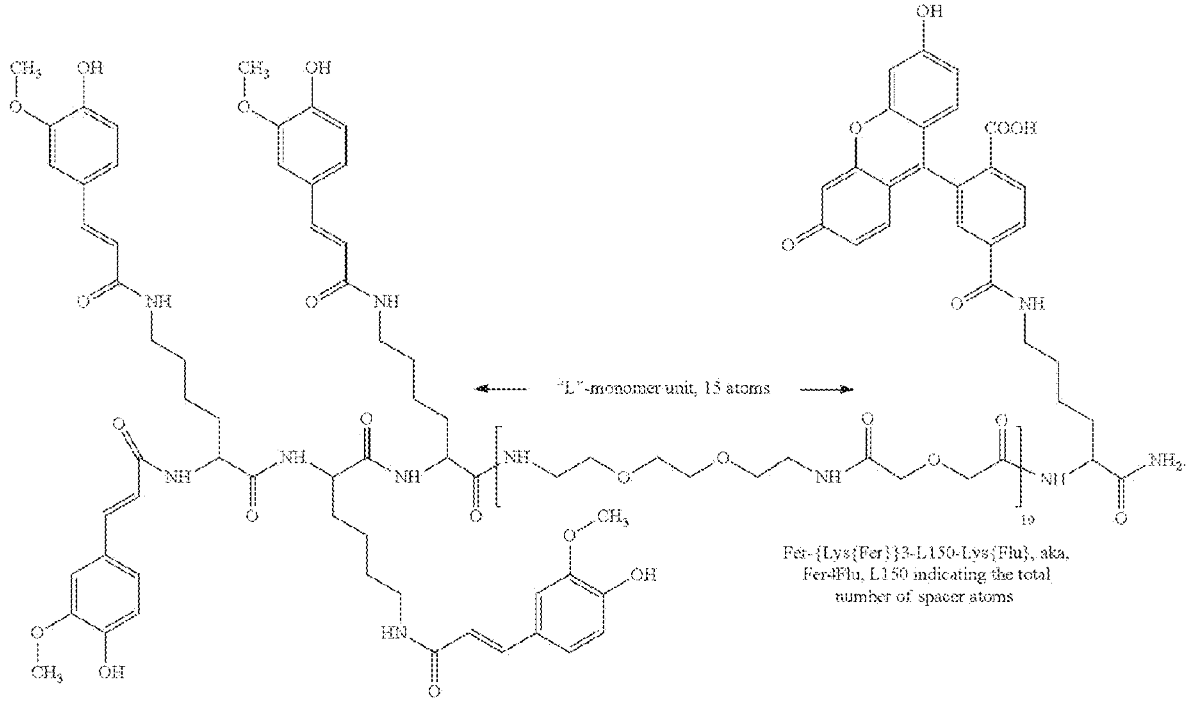
FIG. 22 presents the chemical structure of a fer-4-flu linker, as described in U.S. Patent Application Publication No. 2016/0122800.

Fer-4-flu from U.S. Patent Application Publication No. 2016/0122800 is shown in FIG. 22.

In some aspects, the first labeling reagent may include a horseradish peroxidase (HRP)-coupled polymer capable of binding to the primary antibody, the first detectable reagent may include a chromogen may include an HRP substrate may include HRP magenta or 3,3'-diaminobenzidine tetrahydrochloride (DAB), the second antigen may include p40 the second ligand may include anti-p40 antibodies, the second labeling reagent may include an HRP-coupled polymer capable of binding to anti-p40 antibodies, the substrate may include fluorescein-coupled long single-chained polymer (fer-4-flu linker), third labeling reagent an anti-FITC antibody coupled to HRP, and the second detectable reagent may include a chromogen may include HRP magenta or dab. It will be appreciated that the antigens may be stained in any order. For example, the p40 antigen may be stained first, followed by the lymphocyte-specific antigen. Alternatively, the lymphocyte-specific antigen may be stained first, followed by the p40 antigen.

A counterstaining agent may be hematoxylin.

In some aspects, the method further includes using a digital image of the signals detected in the biological sample to train a neural network.

A neural network trained using the methods is also contemplated.

An annotated image obtained by the methods is also contemplated.

A further aspect includes a method for detecting multiple target molecules in a biological sample comprising cells. The method also includes contacting the biological sample with one or more first reagents which generate a detectable signal in cells may include a first target molecule. The method also includes contacting the biological sample with one or more second reagents which generate a detectable signal in cells; it may include a second target molecule, where the detectable signal generated by the one or more second reagents is removable. The method also includes detecting the signal generated by the one or more first reagents and the signal generated by the one or more second reagents. The method also includes creating conditions in which the signal generated by the one or more second reagents is removed. The method also includes detecting the signal generated by the one or more first reagents.

Implementations may include one or more of the following features. The method may include: obtaining a first digital image of the signal generated by the one or more first reagents and the signal generated by the one or more second reagents, obtaining a second digital image of the signal generated by the one or more first reagents, and copying a mask of the first digital image to the second digital image.

The biological sample may comprise one of a human tissue sample, an animal tissue sample, or a plant tissue sample, wherein the objects of interest comprise at least one of normal cells, abnormal cells, damaged cells, cancer cells, tumors, subcellular structures, or organ structures.

The target molecules are indicative of at least one of normal cells, cell type, abnormal cells, damaged cells, cancer cells, tumors, subcellular structures, a marker indicative of or associated with a disease, disorder or health condition, or organ structures.

The target molecules may include nuclear proteins, cytoplasmic proteins, membrane proteins, nuclear antigens, cytoplasmic antigens, membrane antigens and nucleic acids. The target molecules may be nucleic acids or polypeptides.

The first reagents may include a first primary antibody against a first target molecule, an HRP coupled polymer that binds to the first primary antibody and a chromogen which is an HRP substrate.

The second reagents may include a second primary antibody against a second target molecule, an HRP coupled polymer that binds to the second primary antibody, and amino ethyl carbazole.

The method may include using a digital image of the signals detected in the biological sample to train a neural network. A neural network trained using the method is also contemplated.

Another aspect includes a method for generating cell-level annotations from a biological sample comprising cells. The method includes a) exposing the biological sample to a first ligand that recognizes a first antigen thereby forming a first ligand antigen complex. The method also includes b) exposing the first ligand antigen complex to a first labeling reagent binding to the first ligand, the first labeling reagent forming a first detectable reagent, where the first detectable reagent is precipitated around the first antigen. The method also includes c) exposing the biological sample to a second ligand that recognizes a second antigen thereby forming a second ligand antigen complex. The method also includes d) exposing the second ligand antigen complex to a second labeling reagent binding to the second ligand, the second labeling reagent forming a second detectable reagent, where the second detectable reagent is precipitated around the second antigen. The method also includes e) obtaining a first image of the biological sample with the first and second detectable reagents precipitated in the biological sample. The method also includes f) incubating the tissue sample with an agent which dissolves the second detectable reagent. The method also includes g) obtaining a second image of the biological sample with the first detectable reagent precipitated in the biological sample. The method also includes h) creating a mask from the first image. The method also includes i) applying the mask to the second image so as to obtain an annotated image of the biological sample with the second antigen.

Implementations may include one or more of the following features. The first biological sample may include one of a human tissue sample, an animal tissue sample, or a plant tissue sample, where the objects of interest may include at least one of normal cells, abnormal cells, damaged cells, cancer cells, tumors, subcellular structures, or organ structures.

The method may include, prior to step a), applying a target retrieval buffer and protein blocking solution to the biological sample, where the first and second antigens are exposed for the subsequent steps and endogenous peroxidases are inactivated.

The first and second labeling reagents may include an enzyme that acts on a detectable reagent substrate to form the first and second detectable reagents, respectively.

The first and second antigens may be non-nuclear proteins.

The method may include, following step b), denaturing the first ligands to retrieve the first antigens available.

The method may include, following step d), i) counterstaining cell nuclei of the biological sample, and ii) dehydrating and mounting the sample on a slide.

The method may include, following step e), i) removing mounting medium from the slide, and ii) rehydrating the biological sample.

The method may include, following step f), dehydrating and mounting the sample on a slide.

The first antigen may include a lymphocyte-specific antigen, the first ligand may include an anti-lymphocyte-specific antigen antibody (primary antibody), the first labeling reagent may include a horseradish peroxidase (HRP)-coupled polymer capable of binding to the primary antibody, the first detectable reagent may include an HRP substrate may include HRP magenta or 3,3'-diaminobenzidine tetrahydrochloride (DAB), the second antigen may include PD-L1 the second ligand may include anti-PD-L1 antibodies, the second labeling reagent may include an HRP-coupled polymer capable of binding to anti-PD-L1 antibodies, the second detectable reagent may include amino ethyl carbazole (AEC), and the agent which dissolves the second detectable reagent is alcohol or acetone.

The first labeling reagent may include a horseradish peroxidase (HRP)-coupled polymer capable of binding to the primary antibody, the first detectable reagent may include an HRP substrate may include HRP magenta or 3,3'-diaminobenzidine tetrahydrochloride (dab), the second antigen may include p40 the second ligand may include anti-p40 antibodies, the second labeling reagent may include an HRP-coupled polymer capable of binding to anti-p40 antibodies, the second detectable reagent may include amino ethyl carbazole (AEC), and the agent which dissolves the second detectable reagent is alcohol or acetone. It will be appreciated that the antigens may be stained in any order. For example, the p40 antigen may be stained first, followed by the lymphocyte-specific antigen. Alternatively, the lymphocyte-specific antigen may be stained first, followed by the p40 antigen.

A counterstaining agent can be hematoxylin.

The method may include using a digital image of the signals detected in the biological sample to train a neural network.

An annotated image obtained by the method is also contemplated. A neural network trained using the method is also contemplated.

Another aspect includes a method for detecting multiple target molecules in a biological sample comprising cells. The method includes contacting the biological sample with one or more first reagents which generate a first detectable signal in cells may include a first target molecule, where said first detectable signal is detectable using a first detection method. The method also includes contacting the biological sample with one or more second reagents which generate a second detectable signal and may include a second target molecule, where the second detectable signal is detectable using a second detection method and is substantially undetectable using the first detection method and where the first detectable signal is substantially undetectable using the second detection method. The method also includes detecting the signal generated by the one or more first reagents using the first detection method. The method also includes detecting the signal generated by the one or more second reagents using the second detection method.

Implementations may include one or more of the following features. The biological sample may include one of a human tissue sample, an animal tissue sample, or a plant tissue sample, where the objects of interest may include at least one of normal cells, abnormal cells, damaged cells, cancer cells, tumors, subcellular structures, or organ structures.

The target molecules may be indicative of at least one of normal cells, cell type, abnormal cells, damaged cells, cancer cells, tumors, subcellular structures, a marker indicative of or associated with a disease, disorder or health condition, or organ structures.

The target molecules are selected from the group consisting of nuclear proteins, cytoplasmic proteins, membrane proteins, nuclear antigens, cytoplasmic antigens, membrane antigens and nucleic acids. The target molecules may include nucleic acids or polypeptides.

The first reagents may include a first primary antibody against a first target molecule, an HRP coupled polymer that binds to the first primary antibody and a chromogen which is an HRP substrate.

The second reagents may include a second primary antibody against a second target molecule, an HRP coupled polymer that binds to the second primary antibody, and a rhodamine based fluorescent compound coupled to a long single chained polymer.

The method may include using a digital image of the signals detected in the biological sample to train a neural network. A neural network trained using the method is also contemplated.

A further aspect includes a method for generating cell-level annotations from a biological sample. The method includes a) exposing the biological sample to a first ligand that recognizes a first antigen thereby forming a first ligand antigen complex. The method also includes b) exposing the first ligand antigen complex to a first labeling reagent binding to the first ligand, the first labeling reagent forming a first detectable reagent, where the first detectable reagent is visible in brightfield; where the first detectable reagent is precipitated around the first antigen. The method also includes c) exposing the biological sample to a second ligand that recognizes a second antigen thereby forming a second ligand antigen complex. The method also includes d) exposing the second ligand antigen complex to a second labeling reagent binding to the second ligand, the second labeling reagent forming a second detectable reagent, where the second detectable reagent is visible in fluorescence; where the second detectable reagent is precipitated around the second antigen. The method also includes e) obtaining a first brightfield image of the biological sample with the first detectable reagent precipitated in the biological sample. The method also includes f) obtaining a second fluorescent image of the biological sample with the second detectable reagent precipitated in the biological sample. The method also includes g) creating a mask from the second image. The method also includes h) applying the mask to the first image so as to obtain an annotated image of the tissue sample with the second marker.

Implementations may include one or more of the following features. The first biological sample may include one of a human tissue sample, an animal tissue sample, or a plant tissue sample, where the objects of interest may include at least one of normal cells, abnormal cells, damaged cells, cancer cells, tumors, subcellular structures, or organ structures.

The method may include, prior to step a), applying a target retrieval buffer and protein blocking solution to the biological sample, where the first and second antigens are exposed for the subsequent steps and endogenous peroxidases are inactivated.

The first and second labeling reagents may include an enzyme that acts on a detectable reagent substrate to form the first and second detectable reagents, respectively.

The first and second antigens may be non-nuclear proteins.

The method may include, following step b), denaturing the first ligands to retrieve the first antigens available.

The method may include, following step d), i) counterstaining cell nuclei of the biological sample, and ii) dehydrating and mounting the sample on a slide.

The first labeling reagent may include a horseradish peroxidase (HRP)-coupled polymer capable of binding to the primary antibody, the first detectable reagent may include an HRP substrate may include HRP magenta or 3,3'-diaminobenzidine tetrahydrochloride (dab), the second antigen may include PD-L1 the second ligand may include anti-PD-L1 antibodies, the second labeling reagent may include an HRP-coupled polymer capable of binding to anti-PD-L1 antibodies, and the second detectable reagent may include a rhodamine-based fluorescent compound coupled to a long single-chain polymer.

The first antigen may include a lymphocyte-specific antigen, the first ligand may include an anti-lymphocyte-specific antigen antibody (primary antibody), the first labeling reagent may include a horseradish peroxidase (HRP)-coupled polymer capable of binding to the primary antibody, the first detectable reagent may include an HRP substrate may include HRP magenta or 3,3'-diaminobenzidine tetrahydrochloride (DAB), the second antigen may include p40 the second ligand may include anti-p40 antibodies, the second labeling reagent may include an HRP-coupled polymer capable of binding to anti-p40 antibodies, and the second detectable reagent may include rhodamine-based fluorescent compound coupled to a long single-chain polymer. It will be appreciated that the antigens may be stained in any order. For example, the p40 antigen may be stained first, followed by the lymphocyte-specific antigen. Alternatively, the lymphocyte-specific antigen may be stained first, followed by the p40 antigen.

A counterstaining agent may be hematoxylin. An annotated image obtained by the methods is also contemplated. A neural network trained using the method is also contemplated.

One aspect includes a compound of Formula I:

Formula I

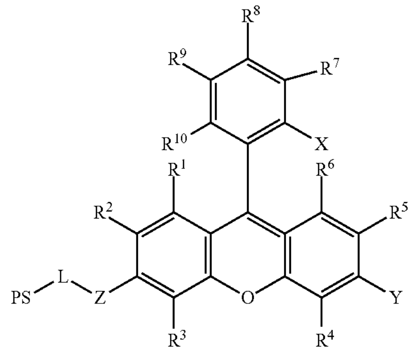

where X is —$COOR^X$, or —$CH_2COOR^X$, or —$CONR^XR^{XX}$, or —$CH_2CONR^XR^{XX}$;

where Y is =O, =$NR^Y$, or =$N^+R^YR^{YY}$;

wherein $R^1$, $R^2$, $R^3$, $R^4$, $R^5$, $R^6$, $R^7$, $R^8$, $R^9$, $R^{10}$, $R^X$, $R^{XX}$, $R^Z$, $R^Y$, and $R^{YY}$ are independently selected from hydrogen and a substituent having less than 40 atoms;

L is a linker comprising a linear chain of 5 to 29 consecutively connected atoms; and PS is a peroxidase substrate moiety.

In some aspects, $R^1$ is selected from hydrogen, $R^{11}$, (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups, or alternatively, $R^1$ may be taken together with $R^2$ to form part of a benzo, naptho or polycyclic aryleno group which is optionally substituted with one or more of the same or different $R^{13}$ or suitable $R^{14}$ groups;

$R^2$ is selected from hydrogen, $R^{11}$, (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups, or alternatively, $R^2$ may be taken together with $R^1$, to form part of a benzo, naptho or polycyclic aryleno group which is optionally substituted with one or more of the same or different $R^{13}$ or suitable $R^{14}$ groups;

$R^X$, when present, is selected from hydrogen, (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups;

$R^{XX}$, when present, is selected from (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups;

$R^3$ is selected from hydrogen, $R^{11}$, (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups;

$R^4$ is selected from hydrogen, $R^{11}$, (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups, or, alternatively, when Y is —$N^+R^YR^{YY}$, $R^4$ may be taken together with $R^{yy}$ to form a 5- or 6-membered ring which is optionally substituted with one or more of the same or different $R^{13}$ or suitable $R^{14}$ groups;

$R^{yy}$, when present, is selected from (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups, or, alternatively $R^{yy}$ may be taken together with $R^4$ to form a 5- or 6-membered ring which is optionally substituted with one or more of the same or different $R^{13}$ or suitable $R^{14}$ groups;

$R^Y$, when present, is selected from hydrogen, (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups, or, alternatively, $R_Y$ may be taken together with $R^5$ to form a 5- or 6-membered ring optionally substituted with one or more of the same or different $R^{13}$ or suitable $R^{14}$ groups;

$R^Z$, when present, is selected from hydrogen, (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups;

$R^5$ is selected from hydrogen, $R^{11}$, (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups, or, alternatively, $R^5$ may be taken together with $R^6$ to form part of a benzo, naptho or polycyclic aryleno group which is optionally substituted with one or more of the same or different $R^{13}$ or suitable $R^{14}$ groups, or alternatively, when Y is —$N^+R^YR^{YY}$, $R^5$ may be taken together with $R^y$ to form a 5- or 6-membered ring optionally substituted with one or more of the same or different $R^{13}$ or suitable $R^{14}$ groups;

$R^6$ is selected from hydrogen, $R^{11}$, (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups, or, alternatively, $R^6$ together with $R^5$ may form part of a benzo, naptho or polycyclic aryleno group which is optionally substituted with one or more of the same or different $R^{13}$ or suitable $R^{14}$ groups;

$R^7$, $R^8$ and $R^9$ are each, independently of one another, selected from hydrogen, $R^{11}$, (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups;

$R^{10}$ is selected from selected from hydrogen, $R^{11}$, (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups, halo, haloalkyl, —$OR^{12}$, —$SR^{12}$, —$SOR^{12}$, —$SO_2R^{12}$, and nitrile;

$R^{11}$ is selected from —$NR^{15}R^{15}$, —$OR^{16}$, —$SR^{16}$, halo, haloalkyl, —CN, —NC, —OCN, —SCN, —NO, —$NO_2$, —$N_3$, —$S(O)R^{16}$, —$S(O)_2R^{16}$, —$S(O)_2OR^{16}$, —$S(O)NR^{15}R^{15}$, —$S(O)_2NR^{15}R^{15}$—$OS(O)R^{16}$, —$OS(O)_2R^{16}$, —$OS(O)_2NR^{15}R^{15}$, —$OP(O)_2R^{16}$, —$OP(O)_3R^{16}R^{16}$, —$P(O)_3R^{16}R^{16}$, —$C(O)R^{16}$, —$C(O)OR^{16}$, —$C(O)NR^{15}R^{15}$, —$C(NH)NR^{15}R^{15}$, —$OC(O)R^{16}$, —$OC(O)OR^{16}$, —$OC(O)NR^{15}R^{15}$ and —$OC(NH)NR^{15}R^{15}$;

$R^{12}$ is selected from (C1-C20) alkyls or heteroalkyls optionally substituted with lipophilic substituents, (C5-C20) aryls or heteroaryls optionally substituted with lipophilic substituents and (C2-C26) arylalkyl or heteroarylalkyls optionally substituted with lipophilic substituents;

$R^{13}$ is selected from hydrogen, (C1-C8) alkyl or heteroalkyl, (C5-C20) aryl or heteroaryl and (C6-C28) arylalkyl or heteroarylalkyl;

$R^{14}$ is selected from —$NR^{15}R^{15}$, =O, —$OR^{16}$, =S, —$SR^{16}$, =$NR^{16}$, =$NOR^{16}$, halo, haloalkyl, —CN, —NC, —OCN, —SCN, —NO, —$NO_2$, =$N_2$, —$N_3$, —$S(O)R^{16}$, —$S(O)_2R^{16}$, —$S(O)_2OR^{16}$, —$S(O)NR^{15}R^{15}$, —$S(O)_2NR^{15}R^{15}$, —$OS(O)R^{16}$, —$OS(O)_2R^{16}$, —$OS(O)_2NR^{15}R^{15}$, —$OS(O)_2OR^{16}$, —$OS(O)_2NR^{15}R^{15}$, —$C(O)R^{16}$, —$C(O)OR^{16}$, —$C(O)NR^{15}R^{15}$, —$C(NH)NR^{15}R^{15}$, —$OC(O)R^{16}$, —$OC(O)OR^{16}$, —$OC(O)NR^{15}R^{15}$ and —$OC(NH)NR^{15}R^{15}$;

each $R^{15}$ is independently hydrogen or $R^{16}$, or alternatively, each $R^{15}$ is taken together with the nitrogen atom to which it is bonded to form a 5- to 8-membered saturated or unsaturated ring which may optionally include one or more of the same or different additional heteroatoms and which may optionally be substituted with one or more of the same or different $R^{13}$ or $R^{16}$ groups;

each $R^{16}$ is independently $R^{13}$ or $R^{13}$ substituted with one or more of the same or different $R^{13}$ or $R^{17}$ groups; and each $R^{17}$ is selected from —$NR^{13}R^{13}$, —$OR^{13}$, =S, —$SR^{13}$, =$NR^{13}$, =$NOR^{13}$, halo, haloalkyl, —CN, —NC, —OCN, —SCN, —NO, —$NO_2$, =$N_2$, —$N_3$, —S(O)$R^{13}$, —S(O)$_2R^{13}$, —S(O)$_2OR^{13}$, —S(O)$NR^{13}R^{13}$, —S(O)$_2NR^{13}R^{13}$, —OS(O)$R^{13}$, —OS(O)$_2R^{13}$, —OS(O)$_2NR^{13}R^{13}$, —OS(O)$_2OR^{16}$, —OS(O)$_2NR^{13}R^{13}$, —C(O)$R^{13}$, —C(O)$OR^{13}$, —C(O)$NR^{13}R^{13}$, —C(NH)$NR^{15}R^{13}$, —OC(O)$R^{13}$, —OC(O)$OR^{13}$, —OC(O)$NR^{13}R^{13}$ and —OC(NH)$NR^{13}R^{13}$.

In some aspects, the compound comprises a chromogenic moiety selected from the group consisting of rhodamine, rhodamine derivatives, fluorescein, fluorescein derivatives in which X is COOH, $CH_2COOH$, —$CONH_2$, —$CH_2CONH_2$, and salts of the foregoing.

In some aspects, the compound comprises a chromogenic moiety selected from the group consisting of rhodamine, rhodamine 6G, tetramethylrhodamine, rhodamine B, rhodamine 101, rhodamine 110, fluorescein, O-carboxymethyl fluorescein, derivatives of the foregoing in which X is —COOH, —$CH_2COOH$, —$CONH_2$, —$CH_2CONH_2$, and salts of the foregoing.

In some aspects, the peroxidase substrate moiety has the following formula:

Formula II

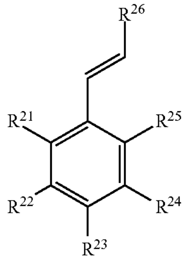

wherein $R^{21}$ is —H, $R^{22}$ is —H, —O—X, or —N(X)$_2$; $R^{23}$ is —OH; $R^{24}$ is —H, —O—X, or —N(X)$_2$; $R^{25}$ is —H, —O—X, or —N(X)$_2$; $R^{26}$ is CO, X is H, alkyl or aryl; wherein PS is linked to L through $R^{26}$. In some aspects, $R^{23}$ is —OH, and $R^{24}$ is —H. In some aspects, either $R^{21}$ or $R^{25}$ is —OH, $R^{22}$ and $R^{24}$ are —H, and $R^{23}$ is —OH or —$NH_2$.

In some aspects, the peroxidase substrate moiety is a residue of ferulic acid, cinnamic acid, caffeic acid, sinapinic acid, 2,4-dihydroxycinnamic acid or 4-hydroxycinnamic acid (coumaric acid).

In some aspects, the peroxidase substrate moiety is a residue of 4-hydroxycinnamic acid.

In some aspects, the linker is a compound that comprises (Formula $R^{35}$):

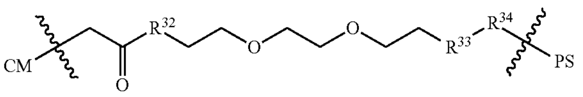

wherein the curved lines denote attachment points to the compound (CM) and to the peroxidase substrate (PS), and wherein $R^{34}$ is optional and can be omitted or used as an extension of linker, wherein $R^{34}$ is:

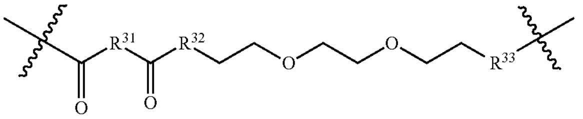

wherein the curved lines denote attachment point to $R^{33}$ and PS, wherein $R^{31}$ is selected from methyl, ethyl, propyl, $OCH_2$, $CH_2OCH_2$, $(CH_2OCH_2)_2$, $NHCH_2$, $NH(CH_2)_2$, $CH_2NHCH_2$, cycloalkyl, alkyl-cycloalkyl, alkyl-cycloalkyl-alkyl, heterocyclyl (such as nitrogen-containing rings of 4 to 8 atoms), alkyl-heterocyclyl, alkyl-heterocyclyl-alkyl, and wherein no more than three consecutively repeating ethyloxy groups, and $R^{32}$ and $R^{33}$ are independently in each formula elected from NH and O.

In some aspects, the linker is selected from one or two repeat of a moiety of Formula IIIa, IIb, or IIc:

Formula IIIa

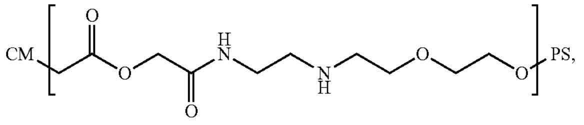

Formula IIIb

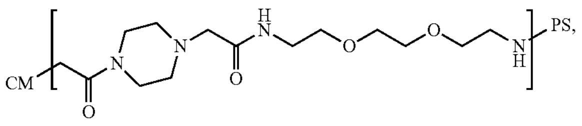

Formula IIIc

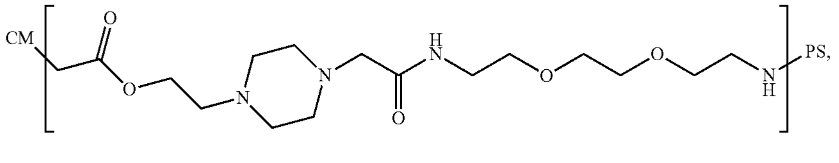

with an optional extension:
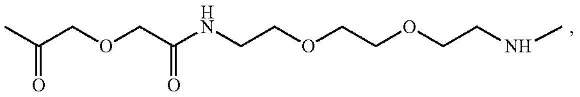
which may be inserted between N and PS bond.
In some aspects, Z-L-PS together comprises:
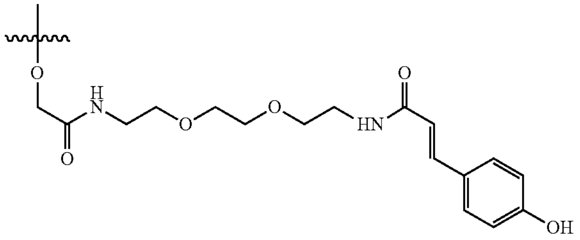 [SMILES: *OCC(=O)NCCOCCOCCNC(=O)/C=C/c1ccc(O)cc1]
wherein the curved line denotes the attachment point.
In some aspects, the compound has the formula (Formula IV):
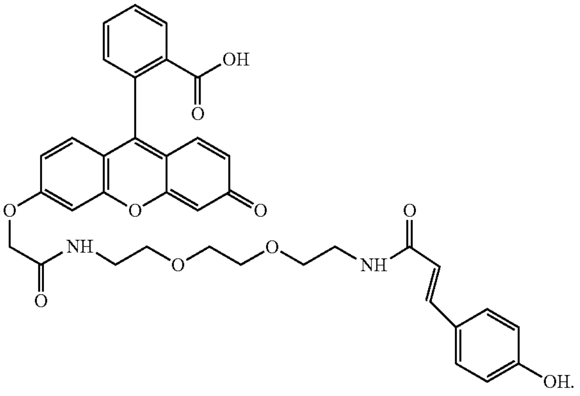 [SMILES: O=C(/C=C/c1ccc(O)cc1)NCCOCCOCCNC(=O)COc1ccc2c(-c3ccccc3C(=O)O)c3ccc(=O)cc-3oc2c1]
In some aspects, the compound has the formula (Formula V):
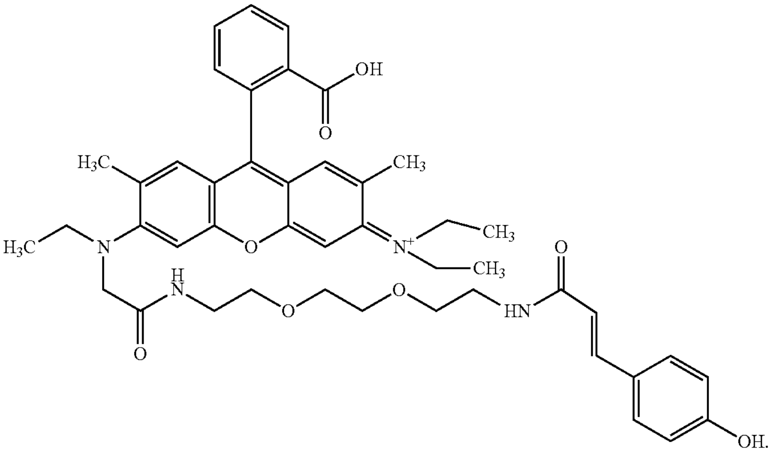 [SMILES: CCN(CC(=O)NCCOCCOCCNC(=O)/C=C/c1ccc(O)cc1)c1cc2oc3cc(=[N+](CC)CC)c(C)cc-3c(-c3ccccc3C(=O)O)c2cc1C]

In some aspects, the compound has the formula (Formula VI):

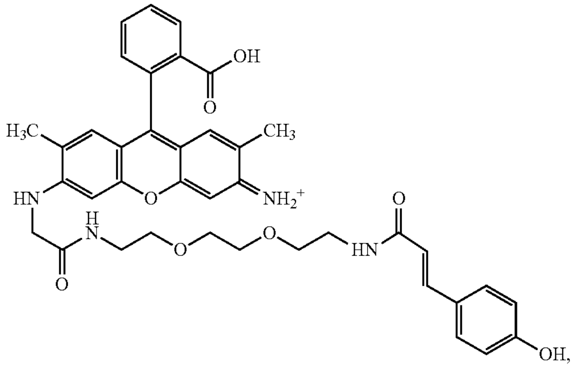 [SMILES: Cc1cc2c(-c3ccccc3C(=O)O)c3cc(C)c(=[NH2+])cc-3oc2cc1NCC(=O)NCCOCCOCCNC(=O)/C=C/c1ccc(O)cc1]

and their corresponding spiro-derivatives, or salts thereof.

In some aspects, the compound has the formula (formula VII):

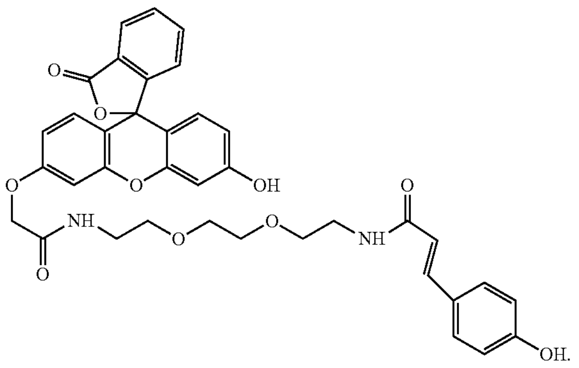 [SMILES: O=C(/C=C/c1ccc(O)cc1)NCCOCCOCCNC(=O)COc1ccc2c(c1)Oc1cc(O)ccc1C21OC(=O)c2ccccc21]

B. Summary for Sequential Imaging of Biological Samples for Generating Training Data for Developing Deep Learning Based Models for Image Analysis, for Cell Classification, for Feature of Interest Identification, and/or for Virtual Staining of the Biological Sample In an aspect, a method may comprise receiving, with a computing system, a first image of a first biological sample, the first image comprising a first field of view ("FOV") of the first biological sample that has been stained with a first stain; and receiving, with the computing system, a second image of the first biological sample, the second image comprising a second FOV of the first biological sample that has been stained with a second stain. The method may also comprise autonomously creating, with the computing system, a first set of image patches based on the first image and the second image, by extracting a portion of the first image and extracting a corresponding portion of the second image, the first set of image patches comprising a first patch corresponding to the extracted portion of the first image and a second patch corresponding to the extracted portion of the second image, wherein the first set of image patches comprises labeling of instances of features of interest in the first biological sample that is based at least in part on at least one of information contained in the first patch, information contained in the second patch, or information contained in one or more external labeling sources.

The method may further comprise training, using an artificial intelligence ("AI") system, a first model ("Model G*") to generate first instance classification of features of interest ("Ground Truth") in the first biological sample, based at least in part on the first set of image patches and the labeling of instances of features of interest contained in the first set of image patches; and training, using the AI system, a second AI model ("Model G") to identify instances of features of interest in the first biological sample, based at least in part on the first patch and the first instance classification of features of interest generated by Model G*.

In some embodiments, the computing system may comprise one of a computing system disposed in a work environment, a remote computing system disposed external to the work environment and accessible over a network, a web server, a web browser, or a cloud computing system, and/or the like. In some instances, the work environment may comprise at least one of a laboratory, a clinic, a medical facility, a research facility, a healthcare facility, or a room.

According to some embodiments, the AI system may comprise at least one of a machine learning system, a deep learning system, a model architecture, a statistical model-based system, or a deterministic analysis system, and/or the like. In some instances, the model architecture may comprise at least one of a neural network, a convolutional neural network ("CNN"), or a fully convolutional network ("FCN"), and/or the like. In some cases, the first biological sample may comprise one of a human tissue sample, an animal tissue sample, a plant tissue sample, or an artificially produced tissue sample, and/or the like, wherein the features of interest may comprise at least one of normal cells, abnormal cells, damaged cells, cancer cells, tumors, subcellular structures, or organ structures, and/or the like.

In some embodiments, the first image may comprise highlighting of first features of interest in the first biological sample by the first stain that had been applied to the first biological sample. Similarly, the second image may comprise one of highlighting of second features of interest in the first biological sample by the second stain that had been applied to the first biological sample in addition to highlighting of the first features of interest by the first stain or highlighting of the second features of interest by the second stain without highlighting of the first features of interest by the first stain, the second features of interest being different from the first features of interest. In some cases, the second stain may be one of the same as the first stain but used to stain the second features of interest or different from the first stain, or the like.

Merely by way of example, in some cases, the first stain may comprise at least one of Hematoxylin, Acridine orange, Bismarck brown, Carmine, Coomassie blue, Cresyl violet, Crystal violet, 4',6-diamidino-2-phenylindole ("DAPI"), Eosin, Ethidium bromide intercalates, Acid fuchsine, Hoechst stain, Iodine, Malachite green, Methyl green, Methylene blue, Neutral red, Nile blue, Nile red, Osmium tetroxide, Propidium Iodide, Rhodamine, Safranine, programmed death-ligand 1 ("PD-L1") stain, 3,3'-Diaminobenzidine ("DAB") chromogen, Magenta chromogen, cyanine chromogen, cluster of differentiation ("CD") 3 stain, CD20 stain, CD68 stain, 40S ribosomal protein SA ("p40") stain, antibody-based stain, or label-free imaging marker, and/or the like. Likewise, the second stain may comprise at least one of Hematoxylin, Acridine orange, Bismarck brown, Carmine, Coomassie blue, Cresyl violet, Crystal violet, DAPI, Eosin, Ethidium bromide intercalates, Acid fuchsine, Hoechst stain, Iodine, Malachite green, Methyl green, Methylene blue, Neutral red, Nile blue, Nile red, Osmium tetroxide, Propidium Iodide, Rhodamine, Safranine, PD-L1 stain, DAB chromogen, Magenta chromogen, cyanine chromogen, CD3 stain, CD20 stain, CD68 stain, p40 stain, antibody-based stain, or label-free imaging marker, and/or the like.

According to some embodiments, the first image may comprise one of a first set of color or brightfield images, a first fluorescence image, a first phase image, or a first spectral image, and/or the like, wherein the first set of color or brightfield images may comprise a first red-filtered ("R") image, a first green-filtered ("G") image, and a first blue-filtered ("B") image, and/or the like. The first fluorescence image may comprise at least one of a first autofluorescence image or a first labelled fluorescence image having one or more channels with different excitation or emission characteristics, and/or the like. The first spectral image may comprise at least one of a first Raman spectroscopy image, a first near infrared ("NIR") spectroscopy image, a first multispectral image, a first hyperspectral image, or a first full spectral image, and/or the like. Similarly, the second image may comprise one of a second set of color or brightfield images, a second fluorescence image, a second phase image, or a second spectral image, and/or the like, wherein the second set of color or brightfield images may comprise a second R image, a second G image, and a second B image, and/or the like. The second fluorescence image may comprise at least one of a second autofluorescence image or a second labelled fluorescence image having one or more channels with different excitation or emission characteristics, and/or the like. The second spectral image may comprise at least one of a second Raman spectroscopy image, a second NIR spectroscopy image, a second multispectral image, a second hyperspectral image, or a second full spectral image, and/or the like.

In some embodiments, the method may further comprise aligning, with the computing system, the first image with the second image to create first set of aligned images, by aligning one or more features of interest in the first biological sample as depicted in the first image with the same one or more features of interest in the first biological sample as depicted in the second image. In some instances, aligning the first image with the second image may be one of performed manually using manual inputs to the computing system or performed autonomously, wherein autonomous alignment may comprise alignment using at least one of automated global alignment techniques or optical flow alignment techniques, or the like.

According to some embodiments, the method may further comprise receiving, with the computing system, a third image of the first biological sample, the third image comprising a third FOV of the first biological sample that has been stained with a third stain different from each of the first stain and the second stain; and autonomously performing, with the computing system, one of: aligning the third image with each of the first image and the second image to create second aligned images, by aligning one or more features of interest in the first biological sample as depicted in the third image with the same one or more features of interest in the first biological sample as depicted in each of the first image and the second image; or aligning the third image with the first aligned images to create second aligned images, by aligning one or more features of interest in the first biological sample as depicted in the third image with the same one or more features of interest in the first biological sample as depicted in the first aligned images.

The method may further comprise autonomously creating, with the computing system, second aligned image patches from the second aligned images, by extracting a portion of the second aligned images, the portion of the second aligned images comprising a first patch corresponding to the extracted portion of the first image, a second patch corresponding to the extracted portion of the second image, and a third patch corresponding to the extracted portion of the third image; training the AI system to update Model G* to generate second instance classification of features of interest in the first biological sample, based at least in part on the second aligned image patches and the labeling of instances of features of interest contained in the first set of image patches; and training the AI system to update Model G to identify instances of features of interest in the first biological sample, based at least in part on the first patch and the second instance classification of features of interest generated by Model G*.

In some embodiments, the first image may comprise highlighting of first features of interest in the first biological sample by the first stain that had been applied to the first biological sample. In some cases, the second image may comprise one of highlighting of second features of interest in the first biological sample by the second stain that had been applied to the first biological sample in addition to highlighting of the first features of interest by the first stain or highlighting of the second features of interest by the second stain without highlighting of the first features of interest by the first stain, the second features of interest being different from the first features of interest. In some instances, the third image may comprise one of highlighting of third features of interest in the first biological sample by the third stain that had been applied to the first biological sample in addition to highlighting of the first features of interest by the first stain and highlighting of the second features of interest by the second stain, highlighting of the third features of interest by the third stain in addition to only one of highlighting of the first features of interest by the first stain or highlighting of the second features of interest by the second stain, or highlighting of the third features of interest by the third stain without any of highlighting of the first features of interest by the first stain or highlighting of the second features of interest by the second stain, and/or the like, the third features of interest being different from each of the first features of interest and the second features of interest.

According to some embodiments, the first image may comprise one of a first set of color or brightfield images, a first fluorescence image, a first phase image, or a first spectral image, and/or the like, wherein the first set of color or brightfield images may comprise a first red-filtered ("R") image, a first green-filtered ("G") image, and a first blue-filtered ("B") image, and/or the like. The first fluorescence image may comprise at least one of a first autofluorescence image or a first labelled fluorescence image having one or more channels with different excitation or emission characteristics, and/or the like. The first spectral image may comprise at least one of a first Raman spectroscopy image, a first near infrared ("NIR") spectroscopy image, a first multispectral image, a first hyperspectral image, or a first full spectral image, and/or the like. Likewise, the second image may comprise one of a second set of color or brightfield images, a second fluorescence image, a second phase image, or a second spectral image, and/or the like, wherein the second set of color or brightfield images may comprise a second R image, a second G image, and a second B image, and/or the like. The second fluorescence image may comprise at least one of a second autofluorescence image or a second labelled fluorescence image having one or more channels with different excitation or emission characteristics, and/or the like. The second spectral image may comprise at least one of a second Raman spectroscopy image, a second NIR spectroscopy image, a second multispectral image, a second hyperspectral image, or a second full spectral image, and/or the like. Similarly, the third image may comprise one of a third set of color or brightfield images, a third fluorescence image, a third phase image, or a third spectral image, and/or the like, wherein the third set of color or brightfield images may comprise a third R image, a third G image, and a third B image, and/or the like. The third fluorescence image may comprise at least one of a third autofluorescence image or a third labelled fluorescence image having one or more channels with different excitation or emission characteristics, and/or the like. The third spectral image may comprise at least one of a third Raman spectroscopy image, a third NIR spectroscopy image, a third multispectral image, a third hyperspectral image, or a third full spectral image, and/or the like.

In some embodiments, the method may further comprise receiving, with the computing system, a fourth image, the fourth image comprising one of a fourth FOV of the first biological sample different from the first FOV and the second FOV or a fifth FOV of a second biological sample, wherein the second biological sample is different from the first biological sample; and identifying, using Model G, second instances of features of interest in the second biological sample, based at least in part on the fourth image and based at least in part on training of Model G using the first patch and the first instance classification of features of interest generated by Model G*. In some cases, the fourth image may comprise the fifth FOV and may further comprise only highlighting of first features of interest in the second biological sample by the first stain that had been applied to the second biological sample. According to some embodiments, the method may further comprise generating, using Model G, a clinical score, based at least in part on the identified second instances of features of interest.

In another aspect, a system may comprise a computing system, which may comprise at least one first processor and a first non-transitory computer readable medium communicatively coupled to the at least one first processor. The first non-transitory computer readable medium may have stored thereon computer software comprising a first set of instructions that, when executed by the at least one first processor, causes the computing system to: receive a first image of a first biological sample, the first image comprising a first field of view ("FOV") of the first biological sample that has been stained with a first stain; receive a second image of the first biological sample, the second image comprising a second FOV of the first biological sample that has been stained with a second stain; autonomously create a first set of image patches based on the first image and the second image, by extracting a portion of the first image and extracting a corresponding portion of the second image, the first set of image patches comprising a first patch corresponding to the extracted portion of the first image and a second patch corresponding to the extracted portion of the second image, wherein the first set of image patches may comprise labeling of instances of features of interest in the first biological sample that is based at least in part on at least one of information contained in the first patch, information contained in the second patch, or information contained in one or more external labeling sources; train, using an artificial intelligence ("AI") system, a first model ("Model G*") to generate first instance classification of features of interest ("Ground Truth") in the first biological sample, based at least in part on the first set of image patches and the labeling of instances of features of interest contained in the first set of image patches; and train, using the AI system, a second AI model ("Model G") to identify instances of features of interest in the first biological sample, based at least in part on the first patch and the first instance classification of features of interest generated by Model G*.

In some embodiments, the computing system may comprise one of a computing system disposed in a work environment, a remote computing system disposed external to the work environment and accessible over a network, a web server, a web browser, or a cloud computing system, and/or the like. In some cases, the work environment may comprise at least one of a laboratory, a clinic, a medical facility, a research facility, a healthcare facility, or a room, and/or the like. In some instances, the AI system may comprise at least one of a machine learning system, a deep learning system, a model architecture, a statistical model-based system, or a deterministic analysis system, and/or the like. In some instances, the model architecture may comprise at least one of a neural network, a convolutional neural network ("CNN"), or a fully convolutional network ("FCN"), and/or the like.

According to some embodiments, the first biological sample may comprise one of a human tissue sample, an animal tissue sample, a plant tissue sample, or an artificially produced tissue sample, and/or the like. In some instances, the features of interest may comprise at least one of normal cells, abnormal cells, damaged cells, cancer cells, tumors, subcellular structures, or organ structures, and/or the like.

In some embodiments, the first image may comprise highlighting of first features of interest in the first biological sample by the first stain that had been applied to the first biological sample. In some cases, the second image may comprise one of highlighting of second features of interest in the first biological sample by the second stain that had been applied to the first biological sample in addition to highlighting of the first features of interest by the first stain or highlighting of the second features of interest by the second stain without highlighting of the first features of interest by the first stain, the second features of interest being different from the first features of interest. In some instances, the second stain may be one of the same as the first stain but used to stain the second features of interest or different from the first stain.

According to some embodiments, the first image may comprise one of a first set of color or brightfield images, a first fluorescence image, a first phase image, or a first spectral image, and/or the like, wherein the first set of color or brightfield images may comprise a first red-filtered ("R") image, a first green-filtered ("G") image, and a first blue-filtered ("B") image, and/or the like. The first fluorescence image may comprise at least one of a first autofluorescence image or a first labelled fluorescence image having one or more channels with different excitation or emission characteristics, and/or the like. The first spectral image may comprise at least one of a first Raman spectroscopy image, a first near infrared ("NIR") spectroscopy image, a first multispectral image, a first hyperspectral image, or a first full spectral image, and/or the like. Similarly, the second image may comprise one of a second set of color or brightfield images, a second fluorescence image, a second phase image, or a second spectral image, and/or the like, wherein the second set of color or brightfield images may comprise a second R image, a second G image, and a second B image, and/or the like. The second fluorescence image may comprise at least one of a second autofluorescence image or a second labelled fluorescence image having one or more channels with different excitation or emission characteristics, and/or the like. The second spectral image may comprise at least one of a second Raman spectroscopy image, a second NIR spectroscopy image, a second multispectral image, a second hyperspectral image, or a second full spectral image, and/or the like.

In some embodiments, the first set of instructions, when executed by the at least one first processor, may further cause the computing system to: receive a third image of the first biological sample, the third image comprising a third FOV of the first biological sample that has been stained with a third stain different from each of the first stain and the second stain; and autonomously perform one of: aligning the third image with each of the first image and the second image images to create second aligned images, by aligning one or more features of interest in the first biological sample as depicted in the third image with the same one or more features of interest in the first biological sample as depicted in each of the first image and the second image; or aligning the third image with the first aligned images to create second aligned images, by aligning one or more features of interest in the first biological sample as depicted in the third image with the same one or more features of interest in the first biological sample as depicted in the first aligned images. The first set of instructions, when executed by the at least one first processor, may further cause the computing system to: autonomously create second aligned image patches from the second aligned images, by extracting a portion of the second aligned images, the portion of the second aligned images comprising a first patch corresponding to the extracted portion of the first image, a second patch corresponding to the extracted portion of the second image, and a third patch corresponding to the extracted portion of the third image; train the AI system to update Model G* to generate second instance classification of features of interest in the first biological sample, based at least in part on the second aligned image patches and the labeling of instances of features of interest contained in the first set of image patches; and train the AI system to update Model G to identify instances of features of interest in the first biological sample, based at least in part on the first patch and the second instance classification of features of interest generated by Model G*.

According to some embodiments, the first set of instructions, when executed by the at least one first processor, may further cause the computing system to: receive a fourth image, the fourth image comprising one of a fourth FOV of the first biological sample different from the first FOV and the second FOV or a fifth FOV of a second biological sample, wherein the second biological sample is different from the first biological sample; and identify, using Model G, second instances of features of interest in the second biological sample, based at least in part on the fourth image and based at least in part on training of Model G using the first patch and the first instance classification of features of interest generated by Model G*. According to some embodiments, the first set of instructions, when executed by the at least one first processor, may further cause the computing system to: generate, using Model G*, a clinical score, based at least in part on the identified second instances of features of interest.

In yet another aspect, a method may comprise receiving, with a computing system, a first image of a first biological sample, the first image comprising a first field of view ("FOV") of the first biological sample; and identifying, using a first artificial intelligence ("AI") model ("Model G") that is generated or updated by a trained AI system, first instances of features of interest in the first biological sample, based at least in part on the first image and based at least in part on training of Model G using a first patch and first instance classification of features of interest generated by a second model (Model G*) that is generated or updated by the trained AI system by using first aligned image patches and labeling of instances of features of interest contained in the first patch. In some cases, the first aligned image patches may comprise an extracted portion of first aligned images. The first aligned images may comprise a second image and a third image that have been aligned. The second image may comprise a second FOV of a second biological sample that has been stained with a first stain, the second biological sample being different from the first biological sample. The third image may comprise a third FOV of the second biological sample that has been stained with a second stain. The second patch may comprise labeling of instances of features of interest as shown in the extracted portion of the second image of the first aligned images. The first image may comprise highlighting of first features of interest in the second biological sample by the first stain that had been applied to the second biological sample. The second patch may comprise one of highlighting of second features of interest in the second biological sample by the second stain that had been applied to the second biological sample in addition to highlighting of the first features of interest by the first stain or highlighting of the second features of interest by the second stain without highlighting of the first features of interest by the first stain.

In still another aspect, a system may comprise a computing system, which may comprise at least one first processor and a first non-transitory computer readable medium communicatively coupled to the at least one first processor. The first non-transitory computer readable medium may have stored thereon computer software comprising a first set of instructions that, when executed by the at least one first processor, causes the computing system to: receive a first image of a first biological sample, the first image comprising a first field of view ("FOV") of the first biological sample; and identify, using a first artificial intelligence ("AI") model ("Model G") that is generated or updated by a trained AI system, first instances of features of interest in the first biological sample, based at least in part on the first image and based at least in part on training of Model G using a first patch and first instance classification of features of interest generated by a second model (Model G*) that is generated or updated by the trained AI system by using first aligned image patches and labeling of instances of features of interest contained in the first patch, wherein the first aligned image patches may comprise an extracted portion of first aligned images, wherein the first aligned images may comprise a second image and a third image that have been aligned, wherein the second image may comprise a second FOV of a second biological sample that has been stained with a first stain, the second biological sample being different from the first biological sample, wherein the third image may comprise a third FOV of the second biological sample that has been stained with a second stain, wherein the second patch may comprise labeling of instances of features of interest as shown in the extracted portion of the second image of the first aligned images, wherein the first image may comprise highlighting of first features of interest in the second biological sample by the first stain that had been applied to the second biological sample wherein the second patch may comprise one of highlighting of second features of interest in the second biological sample by the second stain that had been applied to the second biological sample in addition to highlighting of the first features of interest by the first stain or highlighting of the second features of interest by the second stain without highlighting of the first features of interest by the first stain.

In yet another aspect, a method may comprise receiving, with a computing system, first instance classification of features of interest ("Ground Truth") in a first biological sample that has been sequentially stained, the Ground Truth having been generated by a trained first model ("Model G*") that has been trained or updated by an artificial intelligence ("AI") system, wherein the Ground Truth is generated by using first aligned image patches and labeling of instances of features of interest contained in the first aligned image patches, wherein the first aligned image patches comprise an extracted portion of first aligned images, wherein the first aligned images comprise a first image and a second image that have been aligned, wherein the first image comprises a first FOV of the first biological sample that has been stained with a first stain, wherein the second image comprises a second FOV of the first biological sample that has been stained with a second stain, wherein the first aligned image patches comprise labeling of instances of features of interest as shown in the extracted portion of the first aligned images; and training, using the AI system, a second AI model ("Model G") to identify instances of features of interest in the first biological sample, based at least in part on the first instance classification of features of interest generated by Model G*.

In still another aspect, a system may comprise a computing system, which may comprise at least one first processor and a first non-transitory computer readable medium communicatively coupled to the at least one first processor. The first non-transitory computer readable medium may have stored thereon computer software comprising a first set of instructions that, when executed by the at least one first processor, causes the computing system to: receive first instance classification of features of interest ("Ground Truth") in a first biological sample that has been sequentially stained, the Ground Truth having been generated by a trained first model ("Model G*") that has been trained or updated by an artificial intelligence ("AI") system, wherein the Ground Truth is generated by using first aligned image patches and labeling of instances of features of interest contained in the first aligned image patches, wherein the first aligned image patches comprise an extracted portion of first aligned images, wherein the first aligned images comprise a first image and a second image that have been aligned, wherein the first image comprises a first FOV of the first biological sample that has been stained with a first stain, wherein the second image comprises a second FOV of the first biological sample that has been stained with a second stain, wherein the first aligned image patches comprise labeling of instances of features of interest as shown in the extracted portion of the first aligned images; and train, using the AI system, a second artificial intelligence ("AI") model ("Model G") to identify instances of features of interest in the first biological sample, based at least in part on the first. instance classification of features of interest generated by Model G*.

In yet another aspect, a method may comprise generating, using a computing system, ground truth for developing accurate artificial intelligence ("AI") models for biological image interpretation, based at least in part on images of a first biological sample depicting sequential staining of the first biological sample.

In an aspect, a method may comprise receiving, with a computing system, a first image of a first biological sample, the first image comprising a first field of view ("FOV") of the first biological sample that has been stained with a first stain; receiving, with the computing system, a second image of the first biological sample, the second image comprising a second FOV of the first biological sample that has been stained with at least a second stain; and aligning, with the computing system, the first image with the second image to create first aligned images, by aligning one or more features of interest in the first biological sample as depicted in the first image with the same one or more features of interest in the first biological sample as depicted in the second image.

The method may further comprise autonomously creating, with the computing system, first aligned image patches from the first aligned images, by extracting a portion of the first aligned images, the portion of the first aligned images comprising a first patch corresponding to the extracted portion of the first image and a second patch corresponding to the extracted portion of the second image; training, using an artificial intelligence ("AI") system, a first AI model ("Model F") to generate a third patch comprising a virtual stain of the first aligned image patches, based at least in part on the first patch and the second patch, the virtual stain simulating staining by at least the second stain of features of interest in the first biological sample as shown in the second patch; and training, using the AI system, a second model ("Model G*") to identify or classify first instances of features of interest in the first biological sample, based at least in part on the third patch and based at least in part on results from an external instance classification process or a region of interest detection process.

According to some embodiments, the computing system may comprise one of a computing system disposed in a work environment, a remote computing system disposed external to the work environment and accessible over a network, a web server, a web browser, or a cloud computing system, and/or the like. In some cases, the work environment may comprise at least one of a laboratory, a clinic, a medical facility, a research facility, a healthcare facility, or a room, and/or the like. In some instances, the AI system may comprise at least one of a machine learning system, a deep learning system, a model architecture, a statistical model-based system, or a deterministic analysis system, and/or the like. In some instances, the model architecture may comprise at least one of a neural network, a convolutional neural network ("CNN"), or a fully convolutional network ("FCN"), and/or the like.

In some embodiments, the first biological sample may comprise one of a human tissue sample, an animal tissue sample, a plant tissue sample, or an artificially produced tissue sample, and/or the like. In some instances, the features of interest may comprise at least one of normal cells, abnormal cells, damaged cells, cancer cells, tumors, subcellular structures, or organ structures, and/or the like.

According to some embodiments, the first image may comprise highlighting of first features of interest in the first biological sample by the first stain that had been applied to the first biological sample. In some cases, the third patch may comprise one of highlighting of the first features of interest by the first stain and highlighting of second features of interest in the first biological sample by the virtual stain that simulates the second stain having been applied to the first biological sample or highlighting of the first features of interest by the first stain and highlighting of first features of interest by the virtual stain, the second features of interest being different from the first features of interest. In some instances, the second stain may be one of the same as the first stain but used to stain the second features of interest or different from the first stain.

Merely by way of example, in some cases, the first stain may comprise at least one of Hematoxylin, Acridine orange, Bismarck brown, Carmine, Coomassie blue, Cresyl violet, Crystal violet, 4',6-diamidino-2-phenylindole ("DAPI"), Eosin, Ethidium bromide intercalates, Acid fuchsine, Hoechst stain, Iodine, Malachite green, Methyl green, Methylene blue, Neutral red, Nile blue, Nile red, Osmium tetroxide, Propidium Iodide, Rhodamine, Safranine, programmed death-ligand 1 ("PD-L1") stain, 3,3'-Diaminobenzidine ("DAB") chromogen, Magenta chromogen, cyanine chromogen, cluster of differentiation ("CD") 3 stain, CD20 stain, CD68 stain, 40S ribosomal protein SA ("p40") stain, antibody-based stain, or label-free imaging marker, and/or the like. Similarly, the second stain may comprise at least one of Hematoxylin, Acridine orange, Bismarck brown, Carmine, Coomassie blue, Cresyl violet, Crystal violet, DAPI, Eosin, Ethidium bromide intercalates, Acid fuchsine, Hoechst stain, Iodine, Malachite green, Methyl green, Methylene blue, Neutral red, Nile blue, Nile red, Osmium tetroxide, Propidium Iodide, Rhodamine, Safranine, PD-L1 stain, DAB chromogen, Magenta chromogen, cyanine chromogen, CD3 stain, CD20 stain, CD68 stain, p40 stain, antibody-based stain, or label-free imaging marker, and/or the like.

In some embodiments, the first image may comprise one of a first set of color or brightfield images, a first fluorescence image, a first phase image, or a first spectral image, and/or the like, wherein the first set of color or brightfield images may comprise a first red-filtered ("R") image, a first green-filtered ("G") image, and a first blue-filtered ("B") image, and/or the like. The first fluorescence image may comprise at least one of a first autofluorescence image or a first labelled fluorescence image having one or more channels with different excitation or emission characteristics, and/or the like. The first spectral image may comprise at least one of a first Raman spectroscopy image, a first near infrared ("NIR") spectroscopy image, a first multispectral image, a first hyperspectral image, or a first full spectral image, and/or the like. In some instances, the second image may comprise one of a second set of color or brightfield images, a second fluorescence image, a second phase image, or a second spectral image, and/or the like, wherein the second set of color or brightfield images may comprise a second R image, a second G image, and a second B image, and/or the like. The second fluorescence image may comprise at least one of a second autofluorescence image or a second labelled fluorescence image having one or more channels with different excitation or emission characteristics, and/or the like. The second spectral image may comprise at least one of a second Raman spectroscopy image, a second NIR spectroscopy image, a second multispectral image, a second hyperspectral image, or a second full spectral image, and/or the like. In some cases, the third patch may comprise one of a third set of color or brightfield images, a third fluorescence image, a third phase image, or a third spectral image, and/or the like, wherein the third set of color or brightfield images may comprise a third R image, a third G image, and a third B image, and/or the like. The third fluorescence image may comprise at least one of a third autofluorescence image or a third labelled fluorescence image having one or more channels with different excitation or emission characteristics, and/or the like. The third spectral image may comprise at least one of a third Raman spectroscopy image, a third NIR spectroscopy image, a third multispectral image, a third hyperspectral image, or a third full spectral image, and/or the like.

According to some embodiments, aligning the first image with the second image may be one of performed manually using manual inputs to the computing system or performed autonomously, wherein autonomous alignment may comprise alignment using at least one of automated global alignment techniques or optical flow alignment techniques.

In some embodiments, training, using the AI system, Model G* to identify or classify instances of features of interest in the first biological sample may comprise training, using the AI system, Model G* to identify or classify instances of features of interest in the first biological sample, based at least in part on one or more of the first patch, the second patch, or the third patch and based at least in part on the results from the external instance classification process or the region of interest detection process. In some cases, the external instance classification process or the region of interest detection process may each comprise at least one of detection of nuclei in the first image or the first patch by a nuclei detection method, identification of nuclei in the first image or the first patch by a user (e.g., a pathologist, or other domain expert, or the like), detection of features of interest in the first image or the first patch by a feature detection method, or identification of features of interest in the first image or the first patch by the pathologist, and/or the like.

According to some embodiments, training the AI system to update Model F may comprise: receiving, with an encoder, the first patch; receiving the second patch; encoding, with the encoder, the received first patch; decoding, with the decoder, the encoded first patch; generating an intensity map based on the decoded first patch; simultaneously operating on the encoded first patch to generate a color vector; combining the generated intensity map with the generated color vector to generate an image of the virtual stain; adding the generated image of the virtual stain to the received first patch to produce a predicted virtually stained image patch; determining a first loss value between the predicted virtually stained image patch and the second patch; calculating a loss value using a loss function, based on the first loss value between the predicted virtually stained image patch and the second patch; and updating, with the AI system, Model F to generate the third patch, by updating one or more parameters of Model F based on the calculated loss value. In some instances, the loss function may comprise one of a mean squared error loss function, a mean squared logarithmic error loss function, a mean absolute error loss function, a Huber loss function, or a weighted sum of squared differences loss function, and/or the like.

In some embodiments, the first patch may comprise one of a first set of color or brightfield images, a first fluorescence image, a first phase image, or a first spectral image, and/or the like, wherein the first set of color or brightfield images may comprise a first red-filtered ("R") image, a first green-filtered ("G") image, and a first blue-filtered ("B") image, and/or the like. The first fluorescence image may comprise at least one of a first autofluorescence image or a first labelled fluorescence image having one or more channels with different excitation or emission characteristics, and/or the like. The first spectral image may comprise at least one of a first Raman spectroscopy image, a first near infrared ("NIR") spectroscopy image, a first multispectral image, a first hyperspectral image, or a first full spectral image, and/or the like. In some cases, the second image may comprise one of a second set of color or brightfield images, a second fluorescence image, a second phase image, or a second spectral image, and/or the like, wherein the second set of color or brightfield images may comprise a second R image, a second G image, and a second B image, and/or the like. The second fluorescence image may comprise at least one of a second autofluorescence image or a second labelled fluorescence image having one or more channels with different excitation or emission characteristics, and/or the like. The second spectral image may comprise at least one of a second Raman spectroscopy image, a second NIR spectroscopy image, a second multispectral image, a second hyperspectral image, or a second full spectral image, and/or the like. In some instances, the predicted virtually stained image patch may comprise one of a third set of color or brightfield images, a third fluorescence image, a third phase image, or a third spectral image, and/or the like, wherein the third set of color or brightfield images may comprise a third R image, a third G image, and a third B image, and/or the like. The third fluorescence image may comprise at least one of third autofluorescence image or a third labelled fluorescence image having one or more channels with different excitation or emission characteristics, and/or the like. The third spectral image may comprise at least one of a third Raman spectroscopy image, a third NIR spectroscopy image, a third multispectral image, a third hyperspectral image, or a third full spectral image, and/or the like.

According to some embodiments, operating on the encoded first patch to generate the color vector may comprise operating on the encoded first patch to generate a color vector, using a color vector output and one of a model architecture, a statistical model-based system, or a deterministic analysis system, and/or the like, wherein the model architecture may comprise at least one of a neural network, a convolutional neural network ("CNN"), or a fully convolutional network ("FCN"), and/or the like, wherein the color vector may be one of a fixed color vector or a learned color vector that is not based on the encoded first patch, and/or the like.

In some embodiments, the image of the virtual stain may comprise one of a 3-channel image of the virtual stain, a RGB-transform image of the virtual stain, or a logarithmic transform image of the virtual stain, and/or the like. In some instances, generating the predicted virtually stained image patch may comprise adding the generated image of the virtual stain to the received first patch to produce the predicted virtually stained image patch.

According to some embodiments, the first loss value may comprise one of a pixel loss value between each pixel in the predicted virtually stained image patch and a corresponding pixel in the second patch or a generative adversarial network ("GAN") loss value between the predicted virtually stained image patch and the second patch, and/or the like, wherein the GAN loss value may be generated based on one of a minimax GAN loss function, a non-saturating GAN loss function, a least squares GAN loss function, or a Wasserstein GAN loss function, and/or the like.

Alternatively, training the AI system to update Model F may comprise: receiving, with the AI system, the first patch; receiving, with the AI system, the second patch; generating, with a second model of the AI system, an image of the virtual stain; adding the generated image of the virtual stain to the received first patch to produce a predicted virtually stained image patch; determining a first loss value between the predicted virtually stained image patch and the second patch; calculating a loss value using a loss function, based on the first loss value between the predicted virtually stained image patch and the second patch; and updating, with the AI system, Model F to generate the third patch, by updating one or more parameters of Model F based on the calculated loss value.

In some embodiments, the second model may comprise at least one of a convolutional neural network ("CNN"), a U-Net, an artificial neural network ("ANN"), a residual neural network ("ResNet"), an encode/decode CNN, an encode/decode U-Net, an encode/decode ANN, or an encode/decode ResNet, and/or the like.

According to some embodiments, the method may further comprise receiving, with the computing system, a fourth image, the fourth image comprising one of a fourth FOV of the first biological sample different from the first FOV and the second FOV or a fifth FOV of a second biological sample, wherein the second biological sample is different from the first biological sample; and identifying, using Model G*, second instances of features of interest in the second biological sample, based at least in part on the fourth image and based at least in part on training of Model G* using at least the third patch comprising the virtual stain of the first aligned image patches. According to some embodiments, the method may further comprise generating, using Model G, a clinical score, based at least in part on the identified second instances of features of interest.

In another aspect, a system may comprise a computing system, which may comprise at least one first processor and a first non-transitory computer readable medium communicatively coupled to the at least one first processor. The first non-transitory computer readable medium may have stored thereon computer software comprising a first set of instructions that, when executed by the at least one first processor, causes the computing system to: receive a first image of a first biological sample, the first image comprising a first field of view ("FOV") of the first biological sample that has been stained with a first stain; receive a second image of the first biological sample, the second image comprising a second FOV of the first biological sample that has been stained with at least a second stain; align the first image with the second image to create first aligned images, by aligning one or more features of interest in the first biological sample as depicted in the first image with the same one or more features of interest in the first biological sample as depicted in the second image; autonomously create first aligned image patches from the first aligned images, by extracting a portion of the first aligned images, the portion of the first aligned images comprising a first patch corresponding to the extracted portion of the first image and a second patch corresponding to the extracted portion of the second image; train, using an artificial intelligence ("AI") system, a first AI model ("Model F") to generate a third patch comprising a virtual stain of the first aligned image patches, based at least in part on the first patch and the second patch, the virtual stain simulating staining by at least the second stain of features of interest in the first biological sample as shown in the second patch; and train, using the AI system, a second model ("Model G*") to identify or classify first instances of features of interest in the first biological sample, based at least in part on the third patch and based at least in part on results from an external instance classification process or a region of interest detection process.

In some embodiments, the computing system may comprise one of a computing system disposed in a work environment, a remote computing system disposed external to the work environment and accessible over a network, a web server, a web browser, or a cloud computing system, and/or the like. In some cases, the work environment may comprise at least one of a laboratory, a clinic, a medical facility, a research facility, a healthcare facility, or a room, and/or the like. In some instances, the AI system may comprise at least one of a machine learning system, a deep learning system, a model architecture, a statistical model-based system, or a deterministic analysis system, and/or the like. In some instances, the model architecture may comprise at least one of a neural network, a convolutional neural network ("CNN"), or a fully convolutional network ("FCN"), and/or the like.

According to some embodiments, the first biological sample may comprise one of a human tissue sample, an animal tissue sample, a plant tissue sample, or an artificially produced tissue sample, and/or the like, wherein the features of interest may comprise at least one of normal cells, abnormal cells, damaged cells, cancer cells, tumors, subcellular structures, or organ structures, and/or the like.

In some embodiments, the first image may comprise highlighting of first features of interest in the first biological sample by the first stain that had been applied to the first biological sample. In some cases, the third patch may comprise one of highlighting of the first features of interest by the first stain and highlighting of second features of interest in the first biological sample by the virtual stain that simulates the second stain having been applied to the first biological sample or highlighting of the first features of interest by the first stain and highlighting of first features of interest by the virtual stain, the second features of interest being different from the first features of interest. In some instances, the second stain may be one of the same as the first stain but used to stain the second features of interest or different from the first stain.

According to some embodiments, the first image may comprise one of a first set of color or brightfield images, a first fluorescence image, a first phase image, or a first spectral image, and/or the like, wherein the first set of color or brightfield images may comprise a first red-filtered ("R") image, a first green-filtered ("G") image, and a first blue-filtered ("B") image, and/or the like. The first fluorescence image may comprise at least one of a first autofluorescence image or a first labelled fluorescence image having one or more channels with different excitation or emission characteristics, and/or the like. The first spectral image may comprise at least one of a first Raman spectroscopy image, a first near infrared ("NIR") spectroscopy image, a first multispectral image, a first hyperspectral image, or a first full spectral image, and/or the like. In some instances, the second image may comprise one of a second set of color or brightfield images, a second fluorescence image, a second phase image, or a second spectral image, and/or the like, wherein the second set of color or brightfield images may comprise a second R image, a second G image, and a second B image, and/or the like. The second fluorescence image may comprise at least one of a second autofluorescence image or a second labelled fluorescence image having one or more channels with different excitation or emission characteristics, and/or the like. The second spectral image may comprise at least one of a second Raman spectroscopy image, a second NIR spectroscopy image, a second multispectral image, a second hyperspectral image, or a second full spectral image, and/or the like. In some cases, the third patch may comprise one of a third set of color or brightfield images, a third fluorescence image, a third phase image, or a third spectral image, and/or the like, wherein the third set of color or brightfield images may comprise a third R image, a third G image, and a third B image, and/or the like. The third fluorescence image may comprise at least one of a third autofluorescence image or a third labelled fluorescence image having one or more channels with different excitation or emission characteristics, and/or the like. The third spectral image may comprise at least one of a third Raman spectroscopy image, a third NIR spectroscopy image, a third multispectral image, a third hyperspectral image, or a third full spectral image, and/or the like.

In some embodiments, training the AI system to update Model F may comprise: receiving, with an encoder, the first patch; receiving the second patch; encoding, with the encoder, the received first patch; decoding, with the decoder, the encoded first patch; generating an intensity map based on the decoded first patch; simultaneously operating on the encoded first patch to generate a color vector; combining the generated intensity map with the generated color vector to generate an image of the virtual stain; adding the generated image of the virtual stain to the received first patch to produce a predicted virtually stained image patch; determining a first loss value between the predicted virtually stained image patch and the second patch; calculating a loss value using a loss function, based on the first loss value between the predicted virtually stained image patch and the second patch; and updating, with the AI system, Model F to generate the third patch, by updating one or more parameters of Model F based on the calculated loss value. In some instances, the loss function may comprise one of a mean squared error loss function, a mean squared logarithmic error loss function, a mean absolute error loss function, a Huber loss function, or a weighted sum of squared differences loss function, and/or the like.

According to some embodiments, the first loss value may comprise one of a pixel loss value between each pixel in the predicted virtually stained image patch and a corresponding pixel in the second patch or a generative adversarial network ("GAN") loss value between the predicted virtually stained image patch and the second patch, and/or the like, wherein the GAN loss value may be generated based on one of a minimax GAN loss function, a non-saturating GAN loss function, a least squares GAN loss function, or a Wasserstein GAN loss function, and/or the like.

In some embodiments, the first set of instructions, when executed by the at least one first processor, may further cause the computing system to: receive a fourth image, the fourth image comprising one of a fourth FOV of the first biological sample different from the first FOV and the second FOV or a fifth FOV of a second biological sample, wherein the second biological sample is different from the first biological sample; and identify, using Model G*, second instances of features of interest in the second biological sample, based at least in part on the fourth image and based at least in part on training of Model G* using at least the third patch comprising the virtual stain of the first aligned image patches. According to some embodiments, the first set of instructions, when executed by the at least one first processor, may further cause the computing system to: generate, using Model G*, a clinical score, based at least in part on the identified second instances of features of interest.

In yet another aspect, a method may comprise receiving, with a computing system, a first image of a first biological sample, the first image comprising a first field of view ("FOV") of the first biological sample; and identifying, using a first model ("Model G*") that is generated or updated by a trained AI system, first instances of features of interest in the first biological sample, based at least in part on the first image and based at least in part on training of Model G* using at least a first patch comprising a virtual stain of first aligned image patches, the first patch being generated by a second artificial intelligence ("AI") model (Model F) that is generated or updated by the trained AI system by using a second patch. In some cases, the first aligned image patches may comprise an extracted portion of first aligned images. The first aligned images may comprise a second image and a third image that have been aligned. The second image may comprise a second FOV of a second biological sample that is different from the first biological sample that has been stained with a first stain. The second patch may comprise the extracted portion of the second image. The third image may comprise a third FOV of the second biological sample that has been stained with at least a second stain.

In still another aspect, a system may comprise a computing system, which may comprise at least one first processor and a first non-transitory computer readable medium communicatively coupled to the at least one first processor. The first non-transitory computer readable medium may have stored thereon computer software comprising a first set of instructions that, when executed by the at least one first processor, causes the computing system to: receive a first image of a first biological sample, the first image comprising a first field of view ("FOV") of the first biological sample; and identify, using a first model ("Model G*") that is generated or updated by a trained AI system, first instances of features of interest in the first biological sample, based at least in part on the first image and based at least in part on training of Model G* using at least a first patch comprising a virtual stain of first aligned image patches, the first patch being generated by a second artificial intelligence ("AI") model (Model F) that is generated or updated by the trained AI system by using a second patch, wherein the first aligned image patches may comprise an extracted portion of first aligned images, wherein the first aligned images may comprise a second image and a third image that have been aligned, wherein the second image may comprise a second FOV of a second biological sample that is different from the first biological sample that has been stained with a first stain, wherein the second patch may comprise the extracted portion of the second image, wherein the third image may comprise a third FOV of the second biological sample that has been stained with at least a second stain.

Various modifications and additions can be made to the embodiments discussed without departing from the scope of the invention. For example, while the embodiments described above refer to particular features, the scope of this invention also includes embodiments having different combination of features and embodiments that do not include all of the above described features.

SPECIFIC EXEMPLARY EMBODIMENTS

I. Tissue Staining Methodology

In the following detailed description, for purposes of explanation and not limitation, representative embodiments disclosing specific details are set forth in order to provide a thorough understanding of the present teachings. Descriptions or details of known systems, compounds, materials, methods of use and methods of manufacture may be omitted so as to avoid obscuring the description of the example embodiments. Nonetheless, systems, moieties and methods that are within the purview of one of ordinary skill in the art may be used in accordance with the representative embodiments.

In many methods for diagnosing a disease or disorder or for determining an appropriate therapy for an individual suffering from a disease or disorder, it is desirable to detect multiple target molecules in a biological sample. In some embodiments, the target molecules may be molecules which are indicative of a disease state such as a tumor or molecules indicative of particular cell types, such as immune cells. For example, in some methods, such as those described in U.S. Pat. No. 10,613,092 (the disclosure of which is incorporated herein in its entirety), the number of PD-L1 positive tumor cells and the number of PD-L1 mononuclear inflammatory cells in a tumor tissue may be identified. Such methods may utilize antibodies which specifically bind to PD-L1 as well as antibodies which recognize target molecules found on mononuclear inflammatory cells, such as CD3, CD5, CD4, CD7, CD8, CD20 or CD68 in order to identify PD-L1 positive tumor cells and PD-L1 positive mononuclear inflammatory cells. Based on the results of this analysis, an appropriate therapy may be recommended for a particular individual. In some embodiments, the methods and compounds described herein may be used to sequentially detect cells expressing PD-L1 and mononuclear inflammatory cells such as lymphocytes or to develop digital imaging analyses which can be used to perform diagnostic methods or to assist in recommending an appropriate therapy.

In one aspect, a method for generating cell-level annotations from a biological sample comprising cells comprises: exposing the biological sample to a first ligand that recognizes a first antigen thereby forming a first ligand-antigen complex; exposing the first ligand-antigen complex to a first labeling reagent binding to the first ligand, the first labeling reagent forming a first detectable reagent, whereby the first detectable reagent is precipitated around the first antigen and visible in brightfield; exposing the biological sample to a second ligand that recognizes a second antigen thereby forming a second ligand-antigen complex; exposing the second ligand-antigen complex to a second labeling reagent binding to the second ligand, the second labeling reagent comprising a substrate not visible in brightfield, whereby the substrate is precipitated around the second antigen; obtaining a first image of the biological sample in brightfield to visualize the first detectable reagent precipitated in the biological sample using a detection method; exposing the biological sample to a third labeling reagent that recognizes the substrate, thereby forming a third ligand-antigen complex, the third labeling reagent forming a second detectable reagent, whereby the second detectable reagent is precipitated around the second antigen; obtaining a second image of the biological sample at a wavelength with the second detectable reagent precipitated in the biological sample using the detection method; creating a mask from the second image; applying the mask to the first image so as to obtain an image of the biological sample annotated with the second antigen.

In one aspect, the biological sample comprises one of a human tissue sample, an animal tissue sample, or a plant tissue sample, wherein the objects of interest comprise at least one of normal cells, cell type, abnormal cells, damaged cells, cancer cells, tumors, subcellular structures, or organ structures.

In one aspect, the detectable reagent is a chromogen. In one aspect the visibility or invisibility in brightfield can be in parts of or the whole brightfield spectra. In one aspect, the obtaining of the image can be through using a digital scanner.

In one aspect, the method further comprises, applying a target retrieval buffer and protein blocking solution to the biological sample, whereby the first and second antigens are retrieved for the subsequent steps. In one aspect the applying a target retrieval buffer and protein blocking solution to the biological sample occurs prior to exposure of the biological sample.

In one aspect, the method comprises the first and third labeling reagents comprising an enzyme that acts on a detectable reagent to form the first and second detectable reagents, respectively. In one aspect, the detectable reagents are chromogenic substrates to form the first and second chromogens, respectively.

In one aspect, the method further comprises the first and/or second antigens are selected from the group consisting of non-nuclear proteins, non-nuclear antigens, membranal antigens, cytoplasmic antigens, and nuclear antigens.

In one aspect, method comprises, following exposing the first ligand-antigen complex to a first labeling reagent binding to the first ligand, reversing the binding of the first ligand. In one aspect, the reversing the binding can be through denaturing.

In one aspect, the method further comprises, following exposing the second detectable reagent to a second labeling reagent binding to the second ligand, i) counterstaining cell nuclei of the biological sample, and ii) dehydrating and mounting the sample on a slide using a mounting medium.

In one aspect, the method further comprises, following obtaining a first image of the biological sample in brightfield to visualize the first chromogen precipitated in the biological sample, i) removing mounting medium from the slide, and ii) rehydrating the biological sample.

In one aspect, the method further comprises, following exposing the biological sample to a third labeling reagent that recognizes the substrate, i) counterstaining cell nuclei of the biological sample, and ii) dehydrating and mounting the sample on a slide.

In one aspect, the method further comprising the first antigen comprises a lymphocyte-specific antigen, the first ligand comprises an anti-lymphocyte-specific antigen antibody ("primary antibody"), the first labeling reagent comprises a horseradish peroxidase (HRP)-coupled polymer capable of binding to the primary antibody, the first detectable reagent comprises an HRP substrate comprising HRP Magenta (available from Agilent Technologies, Inc.) or 3,3'-diaminobenzidine tetrahydrochloride (DAB), the second antigen comprises PD-L1, the second ligand comprises anti-PD-L1 antibodies, the second labeling reagent comprises an HRP-coupled polymer capable of binding to anti-PD-L1 antibodies, the substrate comprises fluorescein-coupled long single-chained polymer (fer-4-flu linker), third labeling reagent an anti-FITC antibody coupled to HRP, and the second detectable reagent comprises HRP Magenta or DAB. It will be appreciated that the antigens may be stained in any order. For example, the lymphocyte-specific antigen may be stained first, followed by PD-L1. Alternatively, PD-L1 may be stained first, followed by the lymphocyte-specific antigen.

In one aspect, the first antigen comprises a lymphocyte-specific antigen, the first labeling reagent comprises a horseradish peroxidase (HRP)-coupled polymer capable of binding to the primary antibody, the first detectable reagent comprises an HRP substrate comprising HRP Magenta or 3,3'-diaminobenzidine tetrahydrochloride (DAB), the second antigen comprises p40, the second ligand comprises anti-p40 antibodies, the second labeling reagent comprises an HRP-coupled polymer capable of binding to anti-p40 antibodies, the substrate comprises fluorescein-coupled long single-chained polymer (fer-4-flu linker), the third labeling reagent comprises an anti-FITC antibody coupled to HRP, and the second detectable reagent comprises HRP Magenta or DAB. In one aspect, an annotated image is obtained. It will be appreciated that the antigens may be stained in any order. For example, the p40 antigen may be stained first, followed by the lymphocyte-specific antigen. Alternatively, the lymphocyte-specific antigen may be stained first, followed by the p40 antigen.

In some embodiments, the detectable reagents of the present disclosure absorb and/or emit light in the range from about 450 nm to about 600 nm. In some embodiments, the detectable reagent absorbs light at 536 nm and the color of stain may be defined as magenta. In some embodiments, the detectable reagent is yellow and absorbs light at 450 nm. In some embodiments, the detectable reagent is purple and absorbs light close to 600 nm. In some embodiments, the present detectable reagents can serve as substrates of a peroxidase enzyme, e.g. HRP, and they are spectrally narrow, non-dichromatic, and do not change their spectral characteristics upon precipitation. In some embodiments, the stains produced via enzymatic precipitation of the detectable reagents are poorly soluble, if at all, in water or organic solutions and do not bleach when exposed to light sources used for imaging of stained samples. These features make the present detectable reagents particularly suitable for automated image analyses and multiplexing. Further, the molecules of the detectable reagents have well-defined chemical structures.

In one aspect, a method for generating cell-level annotations from a biological sample comprising cells comprises: exposing the biological sample to a first ligand that recognizes a first antigen thereby forming a first ligand-antigen complex; exposing the first ligand-antigen complex to a first labeling reagent binding to the first ligand, the first labeling reagent forming a first detectable reagent, whereby the first detectable reagent is precipitated around the first antigen; exposing the biological sample to a second ligand that recognizes a second antigen thereby forming a second ligand-antigen complex; exposing the second ligand-antigen complex to a second labeling reagent binding to the second ligand, the second labeling reagent forming a second detectable reagent, whereby the second detectable reagent is precipitated around the second antigen; obtaining a first image of the biological sample with the first and second detectable reagents precipitated in the biological sample an image is obtained; incubating the tissue sample with an agent which dissolves the second detectable reagent; obtaining a second image of the biological sample with the first detectable reagent precipitated in the biological sample; creating a mask from the first image; and applying the mask to the second image so as to obtain an annotated image of the biological sample with the second antigen.

In one aspect, the method further comprises, wherein the first biological sample comprises one of a human tissue sample, an animal tissue sample, or a plant tissue sample, wherein the objects of interest comprise at least one of normal cells, abnormal cells, damaged cells, cancer cells, tumors, subcellular structures, or organ structures.

In one aspect, the method further comprises, applying a target retrieval buffer and protein blocking solution to the biological sample, whereby the first and second antigens are exposed for the subsequent steps and endogenous peroxidases are inactivated. In one aspect, the first and second labeling reagents comprise an enzyme that acts on a detectable substrate to form the first and second detectable reagents, respectively.

In one aspect, the method comprises denaturing the first ligands to retrieve the first antigens available. In one aspect, the method further comprises, following exposing the second ligand-antigen complex to a second labeling reagent binding to the second ligand, counterstaining cell nuclei of the biological sample, and dehydrating and mounting the sample on a slide using a mounting medium. In one aspect, the method further comprises, following obtaining a first image of the biological sample, removing mounting medium from the slide, and rehydrating the biological sample. In one aspect, the method further comprises, dehydrating and mounting the sample on a slide. In one aspect, the first antigen comprises a lymphocyte-specific antigen, the first ligand comprises an anti-lymphocyte-specific antigen antibody ("primary antibody"), the first labeling reagent comprises a horseradish peroxidase (HRP)-coupled polymer capable of binding to the primary antibody, the first detectable reagent comprises an HRP substrate comprising HRP Magenta or 3,3'-diaminobenzidine tetrahydrochloride (DAB), the second antigen comprises PD-Lithe second ligand comprises anti-PD-L1 antibodies, the second labeling reagent comprises an HRP-coupled polymer capable of binding to anti-PD-L1 antibodies, the second detectable reagent comprises amino ethyl carbazole (AEC), and the agent which dissolves the second detectable reagent is alcohol or acetone. It will be appreciated that the antigens may be stained in any order. For example, the lymphocyte-specific antigen may be stained first, followed by PD-L1. Alternatively, PD-L1 may be stained first, followed by the lymphocyte-specific antigen.

In one aspect, the first antigen comprises a lymphocyte-specific antigen, the first ligand comprises an anti-lymphocyte-specific antigen antibody ("primary antibody"), the first labeling reagent comprises a horseradish peroxidase (HRP)-coupled polymer capable of binding to the primary antibody, the first detectable reagent comprises an HRP substrate comprising HRP Magenta or 3,3'-diaminobenzidine tetrahydrochloride (DAB), the second antigen comprises p40 the second ligand comprises anti-p40 antibodies, the second labeling reagent comprises an HRP-coupled polymer capable of binding to anti-p40 antibodies, the second detectable reagent comprises amino ethyl carbazole (AEC), and the agent which dissolves the second detectable reagent is alcohol or acetone. It will be appreciated that the antigens may be stained in any order. For example, the p40 antigen may be stained first, followed by the lymphocyte-specific antigen. Alternatively, the lymphocyte-specific antigen may be stained first, followed by the p40 antigen. In one aspect, the counterstaining agent is hematoxylin. In one aspect, an annotated image is obtained.

In one aspect, a method for generating cell-level annotations from a biological sample comprising cells comprises: exposing the biological sample to a first ligand that recognizes a first antigen thereby forming a first ligand-antigen complex; exposing the first ligand-antigen complex to a first labeling reagent binding to the first ligand, the first labeling reagent forming a first detectable reagent, wherein the first detectable reagent is visible in brightfield; whereby the first detectable reagent is precipitated around the first antigen; exposing the biological sample to a second ligand that recognizes a second antigen thereby forming a second ligand-antigen complex; exposing the second ligand-antigen complex to a second labeling reagent binding to the second ligand, the second labeling reagent forming a second detectable reagent, wherein the second detectable reagent is visible in fluorescence; whereby the second detectable reagent is precipitated around the second antigen; obtaining a first brightfield image of the biological sample with the first detectable reagent precipitated in the biological sample; obtaining a second fluorescent image of the biological sample with the second detectable reagent precipitated in the biological sample; creating a mask from the second image; applying the mask to the first image so as to obtain an annotated image of the tissue sample with the second marker.

In one aspect, the first biological sample comprises one of a human tissue sample, an animal tissue sample, or a plant tissue sample, wherein the objects of interest comprise at least one of normal cells, abnormal cells, damaged cells, cancer cells, tumors, subcellular structures, or organ structures. In one aspect, applying a target retrieval buffer and protein blocking solution to the biological sample, whereby the first and second antigens are exposed for the subsequent steps and endogenous peroxidases are inactivated.

In one aspect, the first and second labeling reagents comprise an enzyme that acts on a detectable substrate to form the first and second detectable reagents, respectively. In one aspect, the antigens are selected from the group consisting of non-nuclear proteins, non-nuclear antigens, membranal antigens, cytoplasmic antigens, and nuclear antigens. In one aspect, further comprising denaturing the first ligands to retrieve the first antigens available. In one aspect, further comprising, following exposing the first ligand-antigen complex, counterstaining cell nuclei of the biological sample, and dehydrating and mounting the sample on a slide using a mounting medium.

In one aspect, the first antigen comprises a lymphocyte-specific antigen, the first ligand comprises an anti-lymphocyte-specific antigen antibody ("primary antibody"), the first labeling reagent comprises a horseradish peroxidase (HRP)-coupled polymer capable of binding to the primary antibody, the first detectable reagent comprises an HRP substrate comprising HRP Magenta or 3,3'-diaminobenzidine tetrahydrochloride (DAB), the second antigen comprises PD-L, the second ligand comprises anti-PD-L1 antibodies, the second labeling reagent comprises an HRP-coupled polymer capable of binding to anti-PD-L1 antibodies, and the second detectable reagent comprises a rhodamine-based fluorescent compound coupled to a long single-chain polymer. It will be appreciated that the antigens may be stained in any order. For example, the lymphocyte-specific antigen may be stained first, followed by PD-L1. Alternatively, PD-L1 may be stained first, followed by the lymphocyte-specific antigen. In one aspect, first antigen comprises a lymphocyte-specific antigen, the first ligand comprises an anti-lymphocyte-specific antigen antibody ("primary antibody"), the first labeling reagent comprises a horseradish peroxidase (HRP)-coupled polymer capable of binding to the primary antibody, the first detectable reagent comprises an HRP substrate comprising HRP Magenta or 3,3'-diaminobenzidine tetrahydrochloride (DAB), the second antigen comprises p40, the second ligand comprises anti-p40 antibodies, the second labeling reagent comprises an HRP-coupled polymer capable of binding to anti-p40 antibodies, and the second detectable reagent comprises rhodamine-based fluorescent compound coupled to a long single-chain polymer. It will be appreciated that the antigens may be stained in any order. For example, the p40 antigen may be stained first, followed by the lymphocyte-specific antigen. Alternatively, the lymphocyte-specific antigen may be stained first, followed by the p40 antigen. In one aspect, the counterstaining agent is hematoxylin. In one aspect, an annotated image is obtained.

In one aspect, a method for detecting multiple target molecules in a biological sample comprising cells comprises: contacting the biological sample with one or more first reagents which generate a detectable signal in cells comprising a first target molecule; contacting the biological sample with one or more second reagents which are capable of generating a detectable signal in cells comprising a second target molecule under conditions in which the one or more second reagents do not generate a detectable signal; detecting the signal generated by the one or more first reagents; creating conditions in which the one or more second reagents generate a signal in cells comprising the second target molecule; and detecting the signal generated by the one or more second reagents.

In one aspect, the method further comprises: obtaining a first digital image of the signal generated by the one or more first reagents; obtaining a second digital image of the signal generated by the one or more first reagents and the signal generated by the one or more second reagents; and copying a mask of the second digital image to the first digital image.

In one aspect, a method for detecting multiple target molecules in a biological sample comprising cells comprises: contacting the biological sample with one or more first reagents which generate a detectable signal in cells comprising a first target molecule; contacting the biological sample with one or more second reagents which generate a detectable signal in cells comprising a second target molecule, wherein the detectable signal generated by the one or more second reagents is removable; detecting the signal generated by the one or more first reagents and the signal generated by the one or more second reagents; creating conditions in which the signal generated by the one or more second reagents is removed; and detecting the signal generated by the one or more first reagents.

In one aspect the method further comprises, obtaining a first digital image of the signal generated by the one or more first reagents and the signal generated by the one or more second reagents; obtaining a second digital image of the signal generated by the one or more first reagents; and copying a mask of the first digital image to the second digital image.

In one aspect, a method for detecting multiple target molecules in a biological sample comprising cells comprises: contacting the biological sample with one or more first reagents which generate a first detectable signal in cells comprising a first target molecule, wherein said first detectable signal is detectable using a first detection method; contacting the biological sample with one or more second reagents which generate a second detectable signal in cells comprising a second target molecule, wherein the second detectable signal is detectable using a second detection method and is substantially undetectable using the first detection method and wherein the first detectable signal is substantially undetectable using the second detection method; detecting the signal generated by the one or more first reagents using the first detection method; and detecting the signal generated by the one or more second reagents using the second detection method.

In one aspect, the chromogenic conjugate comprises (a) a chromogenic moiety, and (b) peroxides substrate moiety, wherein the chromogenic moieties and the peroxidase substrate moieties are linked together via a linker, and wherein the linker comprises at least one linear chain of at least 5 consecutively connected atoms. For example, the chromogenic conjugate can be a compound of formula IV.

As described in the examples below, the following compounds may be used as chromogens, or detectable reagents. These compounds are not intended to be limiting. The carboxylic acid forms of these structures are colored and, when converted into their cyclic forms, the compounds become uncolored.

In some aspects, the compound comprises: Formula IV:

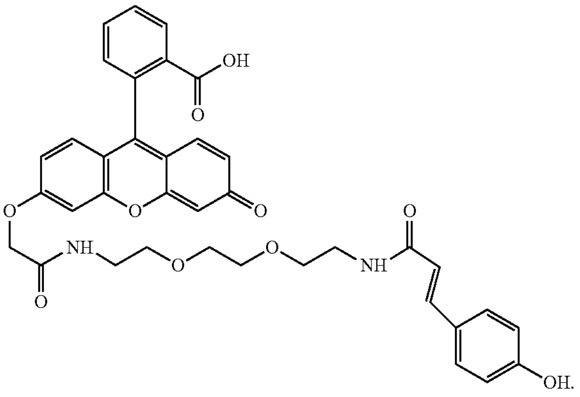 [SMILES: O=C(/C=C/c1ccc(O)cc1)NCCOCCOCCNC(=O)COc1ccc2c(-c3ccccc3C(=O)O)c3ccc(=O)cc-3oc2c1]

In some aspects, the reagent is yellow in color.

In some aspects, the carboxylic acid of Formula IV can have a second carbon (i.e., can be $CH_2COOH$). In some aspects, the ether can be a linker and attaches to a peroxidase substrate moiety.

In some aspects, the compound comprises: Formula VII:

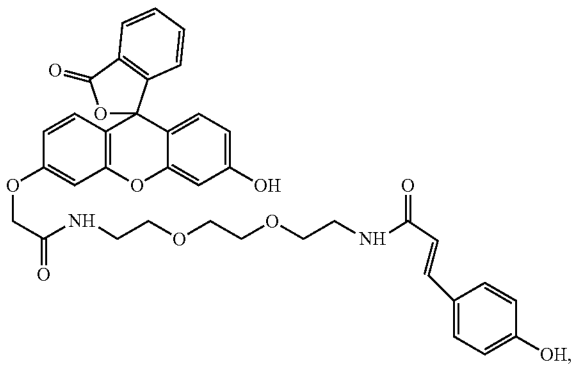 [SMILES: O=C(/C=C/c1ccc(O)cc1)NCCOCCOCCNC(=O)COc1ccc2c(c1)Oc1cc(O)ccc1C21OC(=O)c2ccccc21]

wherein following the conversion to the ring structure of the carboxylic acid, the compound is colorless and does not fluoresce.

In some aspects, the compound comprises: Formula V:

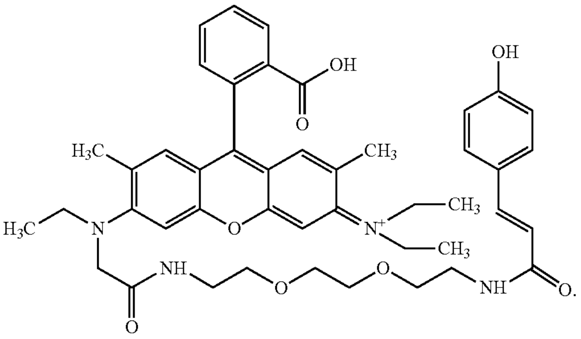 [SMILES: CCN(CC(=O)NCCOCCOCCNC(=O)/C=C/c1ccc(O)cc1)c1cc2oc3cc(=[N+](CC)CC)c(C)cc-3c(-c3ccccc3C(=O)O)c2cc1C]

In some aspects, the compound comprises: Formula VI:

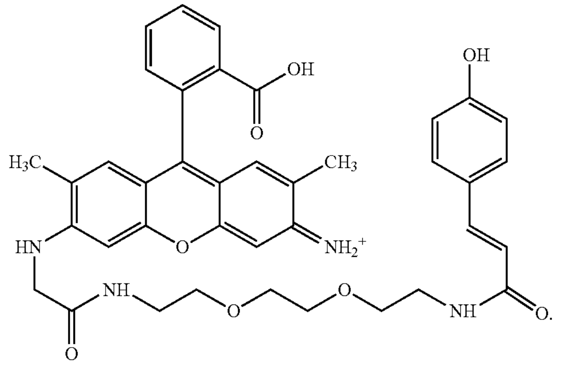 [SMILES: Cc1cc2c(-c3ccccc3C(=O)O)c3cc(C)c(=[NH2+])cc-3oc2cc1NCC(=O)NCCOCCOCCNC(=O)/C=C/c1ccc(O)cc1]

In some aspects, the compound comprises: Formula VIII:

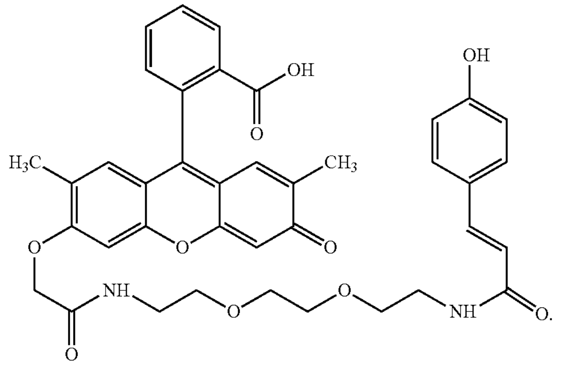 [SMILES: Cc1cc2c(-c3ccccc3C(=O)O)c3cc(C)c(=O)cc-3oc2cc1OCC(=O)NCCOCCOCCNC(=O)/C=C/c1ccc(O)cc1]

II. Sequential Imaging of Biological Samples for Generating Training Data for Developing Deep Learning Based Models for Image Analysis, for Cell Classification, for Feature of Interest Identification, and/or for Virtual Staining of the Biological Sample Training and Applying a Deep Learning Model The pair of images acquired in one of the methods described above (i.e., Methods 1 through 3) may be used to train a model that should be able to recognize patterns based on some digitization of antigen B. Two computational pipelines have been constructed to exploit the additional layer of information arriving from the sequential staining process.

Figure 4A:
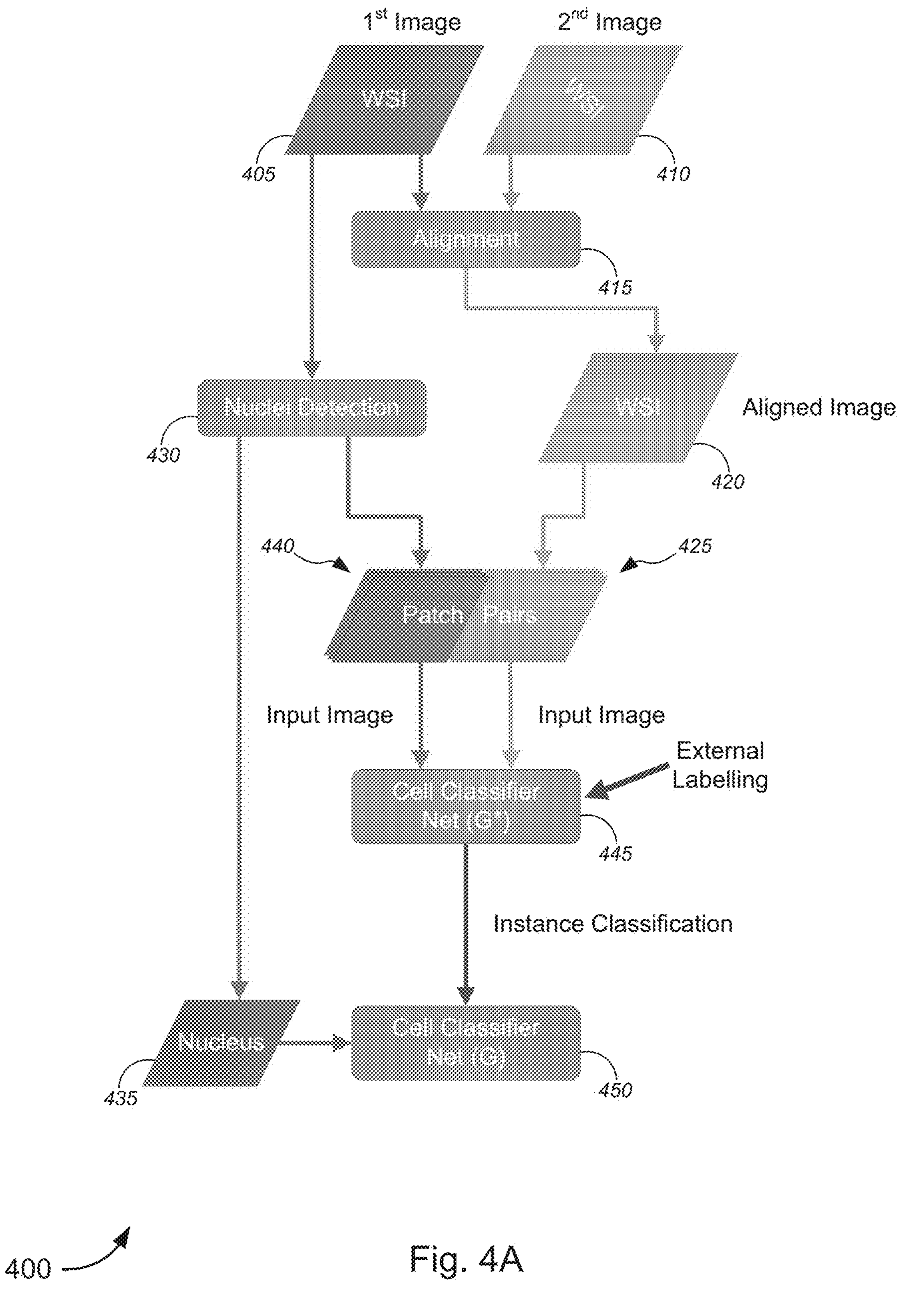
FIGS. 4A-4C are process flow diagrams illustrating various non-limiting examples of training of one or more artificial intelligence ("AI") models and inferencing performed by a trained AI model when implementing sequential imaging of biological samples for generating training data for developing deep learning based models for image analysis, for cell classification, and/or for features of interest identification of biological samples, in accordance with various embodiments.

The first pipeline (as depicted in FIG. 4A, herein also referred to as "pipeline A") uses both whole slide image ("WSI") scans to train an internal model ("G*") that takes as input aligned image patches of cells (e.g., pairs of aligned image patches of cells, although not limited to pairs) and (in some cases) external labelling, and provides a patch classification. Model G* can be considered as a ground truth generator (or "GT generator" or the like), and it could be either a deep-learning model or based purely on traditional image-processing techniques. The GT generator automates the tedious process of assigning each patch its correct label. Patches from the original image, containing antigen A, together with labels provided by the GT generator may be used to train a cell-classifier deep-learning model ("G").

Figure 7A:
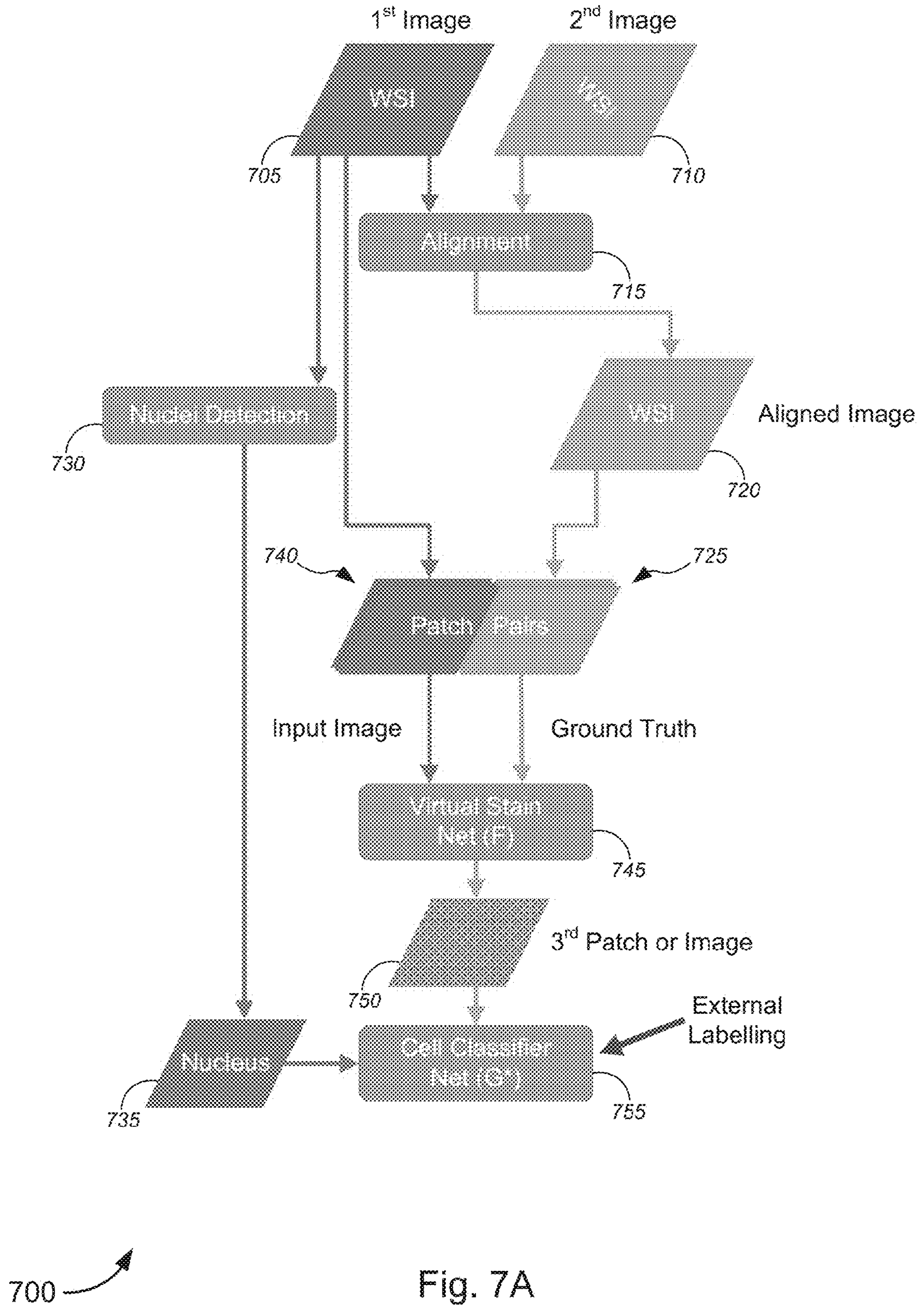
FIGS. 7A-7D are process flow diagrams illustrating various non-limiting examples of training of an artificial intelligence ("AI") model to generate a virtual stain and inferencing performed by a trained AI model when implementing sequential imaging of biological samples for generating training data for developing deep learning based models for virtual staining of biological samples and for generating training data for developing deep learning based models for image analysis, cell classification, and/or features of interest identification of biological samples, in accordance with various embodiments.

The second pipeline (as depicted in FIG. 7A, herein also referred to as "pipeline B") involves a different intermediate module (i.e., virtual-stain network ("F")) that is trained to simulate the antigen B staining patterns on a pixel-to-pixel basis. The virtual-stain network F takes as an input image stained with the original antigen A and adds a virtual antigen B staining on top of it, as if they were stained simultaneously. The virtual-stain layer can then be passed to a cell-classifier module ("G*" in pipeline B) that is trained to classify nuclei and/or cells. Module G* can take as an input both the original stain and the virtual stain (similar to the intermediate module G* of pipeline A) and (in some cases) external labelling, or can operate solely with the virtual stain image and (in some cases) external labelling to provide predictions. The additional intermediate process may assist in the training process and may provide meaningful regularization to the process. However, even without scoring and/or classifying the whole slide, the additional virtual-staining can provide useful and crucial information to a pathologist and can be used as a decision-support system. An important advantage of the virtual-staining model is that it does not requires a nuclei and/or cell detection module (although, in some cases, it might utilize external labelling as an additional input) for the training process. It only requires an accurate alignment.

Both pipelines rely on a reliable alignment between the sequential tissue scans to train the inner modules, and (in some cases) may eventually a nuclei detection mechanism, to provide overall scoring and/or diagnosis for the whole slide.

In some scenarios, where the staining patterns allow (e.g., nuclear staining), the process can be automated end to end. In such a case, a digital mask of the localization of antigen B can be done by a suitable method that separates the relevant color from the image where the location second antigen B is revealed. Following alignment of the uncontaminated first image containing only visible precipitation of antigen A and the digital mask of antigen B, the digital mask can be considered annotation data.

The system, processes, and results are described in detail below with respect to FIGS. 3-9.

III. Embodiments as Illustrated in the Drawings

We now turn to the embodiments as illustrated by the drawings. FIGS. 1-11 illustrate some of the features of tissue staining, for detectable reagents capable of serving as substrates of an enzyme with peroxidase activity, and/or for detecting multiple target molecules in biological samples comprising cells, and/or some of the features for implementing annotation data collection and autonomous annotation, and, more particularly, to methods, systems, and apparatuses for implementing sequential imaging of biological samples for generating training data for developing deep learning based models for image analysis, for cell classification, for feature of interest identification, and/or for virtual staining of biological samples, as referred to above. The methods, systems, and apparatuses illustrated by FIGS. 1-11 refer to examples of different embodiments that include various components and steps, which can be considered alternatives or which can be used in conjunction with one another in the various embodiments. The description of the illustrated methods, systems, and apparatuses shown in FIGS. 1-11 is provided for purposes of illustration and should not be considered to limit the scope of the different embodiments.

A. Non-Limiting Examples for Tissue Staining Methodology

Example 1

Method for using a chromogen visible in brightfield to mark the second antigen in IHC The purpose of this method is to run a normal IHC staining to visualize an antigen, and to precipitate an invisible reagent in the tissue, which can withstand the process of dehydration and rehydration and be "developed" in a subsequent reaction. Following the initial reaction where only one antigen (antigen A) is visible in brightfield due to precipitation of chromogen in the tissue, the slide in mounted and imaged using a digital slide scanner. The slide is then rehydrated, the second antigen (antigen B) is visualized by precipitating a different chromogen around the secondary antigen, the slide is dehydrated, mounted and imaged. Hence, the first image is a single stain, uncontaminated by the invisible reagent that is precipitated around the antigen B. In one aspect, the method may use compounds, such as those described herein, which are colored in their carboxylic acid forms and uncolored or less colored when the carboxylic acid cyclizes. In one aspect, this could also be Biotin which is invisible, and then visualized with streptavidin HRP and chromogen. Following imaging, the second stain can then be "developed" by precipitating another chromogen visible around the site of antigen B.

Copying a mask created from the second stain to the first uncontaminated image makes it possible to do massive annotation of the uncontaminated image of whatever the second stain represents. Following from the example, it could be used to reveal PD-L1 positive lymphocytes. In another investigation, revealing tumor cell nuclei using p40 as antigen B was successfully demonstrated.

TABLE 1

| Step | Reagent | Net Result |
|---|---|---|
| Target retrieval/dewax | Target retrieval buffer | Antigens in tissue are exposed for the reaction |
| Protein block | Peroxidase blocking solution (3% $H_2O_2$) | Endogenous peroxidases are inactivated |
| Mark antigen A | Primary antibody A against antigen A | Antigen A reacted with antibody A |
| Bind HRP enzymes around antigen A | HRP-coupled polymer that binds primary antibodies | Site of antigen A covered with HRP-coupled polymer |
| Precipitate chromogen around antigen A | Chromogen which is HRP substrate (DAB or HRP Magenta) | Chromogen precipitated around antigen A and visible in brightfield |
| Denature available antibodies bound to tissue | Sulfuric acid (300 mM) | All antibodies are denatured, but retrieved antigens still available |
| Mark antigen B | Primary antibody B against antigen B | Antigen B reacted with antibody B |
| Bind HRP enzymes around antigen B | HRP-coupled polymer that binds primary antibodies | Site of antigen B covered with HRP-coupled polymer |
| Precipitate substrate around antigen B | Fluorescein-coupled long single-chained polymer (fer-4-flu linker) | fer-4-flu linker precipitated in tissue (invisible in brightfield) |
| Counterstain | Hematoxylin | Nuclei counterstained |
| Dehydrate and mount | Alcohol, xylene, and organic mounting medium | Slide dehydrated and mounted |
| | Digital slide scan | |
| Remove coverslip, rehydrate | Alcohol and xylene | Glass and mounting medium removed |
| Bind HRP enzymes around antigen B | Anti-FITC antibody coupled to HRP | Anti-FITC antibody recognizes Fluorescein molecules on the fer-4-flu linker |
| Precipitate chromogen around antigen B | Chromogen which is HRP substrate (DAB or HRP Magenta) | Chromogen precipitated around antigen B and visible in brightfield |
| Counterstain | Hematoxylin | Nuclei counterstained |
| Dehydrate and mount | Alcohol, xylene, and organic mounting medium | Slide dehydrated and mounted |
| | Digital slide scan | |

Example 2

Method for Using a Dissolvable Chromogen Visible in Brightfield to Mark the Second Antigen in IHC The purpose of this method is to run a normal IHC staining with to visualize an antigen with a non dissolvable chromogen, and to precipitate a dissolvable chromogen around a second antigen. After the initial reaction, both antigens A and B are visible and brightfield and can be mounted with aqueous mounting medium and imaged using a digital slide scanner. The slide is then incubated in organic solvent (such as 96% ethanol) which dissolves the dissolvable chromogen. After this step, the slide is dehydrated, mounted and imaged. Hence, the first image is a double stain of antigens A and B, whereas the second image contains only antigen A. Copying a mask of antigen B created from the first stain to the second image containing only antigen A makes it possible to do massive annotation of the second image of whatever the stain of dissolvable chromogen represents. Following from the example mentioned in section A, it could be used to reveal PD-L1 positive lymphocytes.

TABLE 2

| Step | Reagent | Net Result |
|---|---|---|
| Target retrieval/dewax | Target retrieval buffer | Antigens in tissue are exposed for the reaction |
| Protein block | Peroxidase blocking solution (3% $H_20_2$) | Endogenous peroxidases are inactivated |
| Mark antigen A | Primary antibody A against antigen A | Antigen A reacted with antibody A |
| Bind HRP enzymes around antigen A | HRP-coupled polymer that binds primary antibodies | Site of antigen A covered with HRP-coupled polymer |
| Precipitate chromogen around antigen A | Chromogen which is HRP substrate (DAB or HRP Magenta) | Chromogen precipitated around antigen A and visible in brightfield |
| Denature available antibodies bound to tissue | Sulfuric acid (300 mM) | All antibodies are denatured, but retrieved antigens still available |
| Mark antigen B | Primary antibody B against antigen B | Antigen B reacted with antibody B |
| Bind HRP enzymes around antigen B | HRP-coupled polymer that binds primary antibodies | Site of antigen B covered with HRP-coupled polymer |
| Precipitate substrate around antigen B | Amino ethyl carbazole ("AEC") | Chromogen precipitated around antigen B |
| Counterstain | Hematoxylin | Nuclei counterstained |
| Mount in aqueous mounting medium | Aqueous mounting medium, e.g., faramount | Slide mounted |
| | Digital slide scan | |
| Remove dissolvable chromogen | Alcohol or acetone | AEC is dissolved |
| Dehydrate and mount | Alcohol, xylene, and organic mounting medium | Slide dehydrated and mounted |
| | Digital slide scan | |

Example 3

Method for Using a Fluorescence Marker Invisible in Brightfield to Mark the Second Antigen in IHC Another method that avoids the mechanical stress associated with mounting and unmounting slides, with resultant tissue shear and difficulties with the alignment of images to transfer the mask, is to precipitate a chromogen invisible in brightfield, but visible in fluorescence during the staining process. This allows for a belier alignment between the first and second image. Steps are shown below:

TABLE 3

| Step | Reagent | Net Result |
|---|---|---|
| Target retrieval/dewax | Target retrieval buffer | Antigens in tissue are exposed for the reaction |
| Protein block | Peroxidase blocking solution (3% $H_20_2$) | Endogenous peroxidases are inactivated |
| Mark antigen A | Primary antibody A against antigen A | Antigen A reacted with antibody A |
| Bind HRP enzymes around antigen A | HRP-coupled polymer that binds primary antibodies | Site of antigen A covered with HRP-coupled polymer |
| Precipitate chromogen around antigen A | Chromogen which is HRP substrate (DAB or HRP Magenta) | Chromogen precipitated around antigen A and visible in brightfield |
| Denature available antibodies bound to tissue | Sulfuric acid (300 mM) | All antibodies are denatured, but retrieved antigens still available |

TABLE 3-continued

| Step | Reagent | Net Result |
|---|---|---|
| Mark antigen B | Primary antibody B against antigen B | Antigen B reacted with antibody B |
| Bind HRP enzymes around antigen B | HRP-coupled polymer that binds primary antibodies | Site of antigen B covered with HRP-coupled polymer |
| Precipitate fluorescent substrate around antigen B | Rhodamine-based fluorescent compound coupled to long single-chained polymer | Fluorescent compound precipitated in tissue (invisible in brightfield) |
| Counterstain | Hematoxylin | Nuclei counterstained |
| Dehydrate and mount | Alcohol, xylene, and organic mounting medium | Slide dehydrated and mounted |
| Digital slide scan using both fluorescence and brightfield | | |

Example 4

Method for Using a Chromogen Visible in Brightfield to Mark the Second Target Nucleic Acid in ISH The purpose of this method is to run a normal ISH staining to visualize a first target nucleic acid, and to precipitate an invisible reagent in the tissue, which can be "developed" in a subsequent reaction. Following the initial reaction where only one target nucleic acid (target A) is visible in brightfield due to precipitation of chromogen in the tissue, the slide in mounted and imaged using a digital slide scanner. A second ISH staining is then performed and the second target nucleic acid (target B) is visualized by precipitating a different chromogen around the second target nucleic acid. The slide is then imaged. Hence, the first image is a single stain, uncontaminated by the invisible reagent that is precipitated around target B. Following imaging, the second stain can then be "developed" by precipitating another chromogen visible around the site of target B. It will be appreciated that, rather than using precipitation of a chromogen to detect one of the target nucleic acids, a directly labeled nucleic acid probe, such as a nucleic acid probe having a fluorescent moiety, may be used.

Copying a mask created from the second stain to the first uncontaminated image makes it possible to do massive annotation of the uncontaminated image of whatever the second stain represents.

TABLE 4

| Step | Reagent | Net Result |
|---|---|---|
| Dewax | Xylene or Clearify | Paraffin removed |
| Hydrate | Ethanols | Tissue rehydrated |
| Heat pretreatment | Pretreatment buffer | Probe access improved |
| Enzyme pretreatment | Pepsin reagent | Probe access improved |
| Dehydrate | Ethanols | Water removed |
| Denature Nucleic Acids in Tissue Sample and probe A | Agilent IQFISH Fast Hybridization Buffer with probe A | Nucleic acids are denatured |
| Hybridize first nucleic acid probe to target nucleic acid A where the probe is modified with moieties which can be observed by fluorescence or recognized by a primary antibody | Agilent IQFISH Fast Hybridization Buffer, Modified nucleic acid probes (for example first nucleic acid probe modified with CY3) | Modified probe hybridized to target nucleic acid A |
| Mark target nucleic acid A | First primary antibody against modified probe for target nucleic acid A labelled with HRP (for example antibody against CY3) | First nucleic acid probe bound to first primary antibody labelled with HRP |
| Precipitate chromogen around target nucleic acid A | Chromogen which is HRP substrate (DAB or HRP Magenta) | Chromogen precipitated around antigen A and visible in brightfield |
| Dehydrate and mount | Alcohol, xylene and organic mounting medium | Slide dehydrated and mounted |
| | Digital slide scan | |
| Remove coverslip, rehydrate | Alcohol and xylene | Glass and mounting medium removed |
| Denature antibodies bound to tissue | Sulfuric acid (300 mM) | All antibodies denatured and HRP activity inactivated |
| Dehydrate | Ethanols | Water removed |
| Denature Nucleic Acids in Tissue Sample and probe B | Agilent IQFISH Fast Hybridization Buffer with probe B | Nucleic acids are denatured |
| Hybridize second nucleic acid probe to target nucleic acid B where the probe is modified with moieties which can be observed by fluorescence or recognized by a primary antibody | Agilent IQFISH Fast Hybridization Buffer, Modified nucleic acid probes (for example, first nucleic acid probe modified with fluorescein) | Modified probes hybridized to target nucleic acid B |
| Mark target nucleic acid B | Second primary antibody against modified probe for target nucleic acid B labelled with HRP (for example antibody against fluorescein) | Second nucleic acid probe bound to second primary antibody labeled with HRP |
| Precipitate substrate around target nucleic acid B | Fluorescein-coupled long single-chained polymer (fer-4-flu linker) | fer-4-flu linker precipitated in tissue (invisible in brightfield) |
| Counterstain | Hematoxylin | Nuclei counterstained |
| Dehydrate and mount | Alcohol, xylene and organic mounting medium | Slide dehydrated and mounted |
| | Digital slide scan | |

Example 5

Method for Using a Dissolvable Chromogen Visible in Brightfield to Mark the Second Target Nucleic Acid in ISH The purpose of this method is to run a normal ISH staining to visualize a first target nucleic acid with a non dissolvable chromogen, and to precipitate a dissolvable chromogen around a second target nucleic acid. After the initial reaction, both target nucleic acids A and B are visible and brightfield and can be mounted with aqueous mounting medium and imaged using a digital slide scanner. The slide is then incubated in organic solvent (such as 96% ethanol) which dissolves the dissolvable chromogen. After this step, the slide is dehydrated, mounted and imaged. Hence, the first image is a double stain of target nucleic acids A and B, whereas the second image contains only target nucleic acid A. It will be appreciated that, rather than using precipitation of a chromogen to detect one of the target nucleic acids, a directly labeled nucleic acid probe, such as a nucleic acid probe modified with a fluorescent moiety, may be used.

Copying a mask of target nucleic acid B created from the first stain to the second image containing only target nucleic acid A makes it possible to do massive annotation of the second image of whatever the stain of dissolvable chromogen represents.

TABLE 5

| Step | Reagent | Net Result |
|---|---|---|
| Dewax | Xylene or Clearify | Paraffin removed |
| Hydrate | Ethanols | Tissue rehydrated |
| Heat pretreatment | Pretreatment buffer | Probe access improved |
| Enzyme pretreatment | Pepsin reagent | Probe access improved |
| Dehydrate | Ethanols | Water removed |
| Denature Nucleic Acids in Tissue Sample and probe A | Agilent IQFISH Fast Hybridization Buffer with probe A | Nucleic acids are denatured |
| Hybridize first nucleic acid probe to target nucleic acid A where the probe is modified with a moiety which can be recognized by a first primary antibody | Agilent IQFISH Fast Hybridization Buffer, Modified nucleic acid probe (for example, nucleic acid probe modified with fluorescein) | Modified probe hybridized to target nucleic acid A |
| Mark target nucleic acid A | First primary antibody against modified probe for target nucleic acid A labelled with HRP (for example, antibody against fluorescein) | First nucleic acid probe bound to first primary antibody labelled with HRP |
| Precipitate chromogen around target nucleic acid A | Chromogen which is HRP substrate (DAB or HRP Magenta) | Chromogen precipitated around target nucleic acid A and visible in brightfield |
| Denature antibodies bound to tissue | Sulfuric acid (300 mM) | All antibodies denatured and HRP activity inactivated |
| Dehydrate | Ethanols | Water removed |
| Denature Nucleic Acids in Tissue Sample and probe B | Agilent IQFISH Fast Hybridization Buffer with probe B | Nucleic acids and probe denatured |
| Hybridize second nucleic acid probe to target nucleic acid B where the probe is modified with a moiety which can be recognized by a second primary antibody | Agilent IQFISH Fast Hybridization Buffer, Modified nucleic acid probe B (for example, nucleic acid probe modified with CY3) | Modified probe hybridized to target nucleic acid B |
| Mark target nucleic acid B | Second primary antibody against modified probe for target nucleic acid B labelled with HRP (for example, antibody against CY3) | Second nucleic acid probe bound to second primary antibody labelled with HRP |
| Precipitate substrate around target nucleic acid B | Amino ethyl carbazole (AEC) | Chromogen precipitated around target nucleic acid B |
| Counterstain | Hematoxylin | Nuclei counterstained |
| Mount in aqueous mounting medium | Aqueous mounting medium e.g. faramount | Slide mounted |
| | Digital slide scan | |
| Remove dissolved chromogen | Alcohol or acetone | AEC is dissolved |
| Dehydrate and mount | Alcohol, xylene, and organic mounting medium | Slide dehydrated and mounted |
| | Digital slide scan | |

Example 6

Method for Using a Chromogen Visible in Brightfield to Mark the First Marker in IHC And a Fluorescence Marker Invisible in Brightfield to Mark the Second Target Nucleic Acid in ISH Another option is to precipitate a chromogen invisible in brightfield, but visible in fluorescence during the staining process in combination with an IHC reaction to precipitate a chromogen visible in brightfield around a certain marker. It will be appreciated that, rather than using precipitation of a chromogen to detect one of the target nucleic acids, a directly labeled nucleic acid probe, such as a nucleic acid probe modified with a fluorescent moiety, may be used. Steps are shown below:

TABLE 6

| Step | Reagent | Net Result |
|---|---|---|
| Denature Nucleic Acids in Tissue Sample | Agilent IQFISH Fast Hybridization Buffer | Nucleic acids are denatured |
| Hybridize first nucleic acid probe to target nucleic acid A where the probe is modified with a moiety which can be recognized by a first primary antibody | Agilent IQFISH Fast Hybridization Buffer, Modified nucleic acid probe | Modified probe hybridized to target nucleic acid A |
| Mark target nucleic acid A | First primary antibody against modified probe for target nucleic acid A | First nucleic acid probe bound to first primary antibody |
| Bind HRP enzymes around target nucleic acid A | HRP-coupled polymer that binds primary antibodies | Site of target nucleic acid A covered with HRP-coupled polymer |
| Precipitate chromogen around target nucleic acid A | Chromogen which is HRP substrate (DAB or HRP Magenta) | Chromogen precipitated around target nucleic acid A and visible in brightfield |
| Denature first nucleic acid probe bound to target nucleic acid A, remove probe with wash procedure | Agilent IQFISH Fast Hybridization Buffer | First nucleic acid probe removed |
| Hybridize second nucleic acid probe to target nucleic acid B where the probe is modified with a moiety which can be recognized by a second primary antibody | Agilent IQFISH Fast Hybridization Buffer, Modified nucleic acid probe | Modified probe hybridized to target nucleic acid B |
| | Digital slide scan | |
| Target retrieval/dewax | Target retrieval buffer | Antigens in tissue are exposed for the reaction |
| Protein block | Peroxidase blocking solution (3% $H_2O_2$) | Endogenous peroxidases are inactivated |
| Mark antigen B | Primary antibody B against antigen B | Antigen B reacted with antibody B |
| Bind HRP enzymes around antigen B | HRP-coupled polymer that binds primary antibodies | Site of antigen B covered with HRP-coupled polymer |
| Precipitate chromogen around antigen B | Chromogen which is HRP substrate (DAB or HRP Magenta) | Chromogen precipitated around antigen B and visible in brightfield) |
| Counterstain | Hematoxylin | Nuclei counterstained |
| | Digital slide scan | |

Example 7

Method for Doing a Dissolvable Primary Stain Visible in Brightfield, Followed by a Second Reaction to Mark an Antigen in IHC The purpose of this method is to do a primary stain (such as H&F), followed by dissolution of this stain, imaging, followed by a normal IHC staining with to visualize an antigen with a non-dissolvable chromogen. After the initial reaction, the primary stain is visible. The slide is then incubated in organic solvent (such as 96% ethanol) which dissolves the dissolvable primary stain. After this step, the slide is dehydrated, mounted, and imaged. After this, a normal IHC reaction is run to mark a certain antigen, followed by mounting and imaging. The mask from the IHC stain can then be applied to the primary stain to reveal cell identity.

TABLE 7

| Step | Reagent | Net Result |
|---|---|---|
| Target retrieval/dewax | Target retrieval buffer | Antigens in tissue are exposed for the reaction |
| Primary stain | Hematoxylin and Eosin | Primary stain completed |
| Mount in aqueous mounting medium | Aqueous mounting medium e.g. faramount | Slide mounted |
| | Digital slide scan | |
| Protein block | Peroxidase blocking solution (3% $H_2O_2$) | Endogenous peroxidases are inactivated |
| Mark antigen A | Primary antibody A against antigen A | Antigen A reacted with antibody A |
| Bind HRP enzymes around antigen A | HRP-coupled polymer that binds primary antibodies | Site of antigen A covered with HRP-coupled polymer |
| Precipitate chromogen around antigen A | Chromogen which is HRP substrate (DAB or HRP Magenta) | Chromogen precipitated around antigen A and visible in brightfield |
| Counterstain | Hematoxylin | Nuclei counterstained |
| Dehydrate and mount | Alcohol, xylene, and organic mounting medium | Slide dehydrated and mounted |
| | Digital slide scan | |

Example 8

In one experiment, PD-L1 was used. A notorious problem with PD-L1 stains are PD-L1 positive lymphocytes which are very hard to distinguish from tumor cells. Hence, marking several types of lymphocytes using a computational approach is challenging. Adenocarcinomas of the lung as well as squamous carcinomas of the lung were stained, first with PD-L1 with DAB chromogen as well as an invisible tag, fer4flu around a lymphocyte/macrophage marker in the same reaction. The tissue was stained for CD3 (T-cells/NK cells), CD20 (B-cells) and CD68 (macrophages). An invisible tag was used because the process of organic mounting made it very difficult to just do a whole new reaction from scratch. The antigens are very severely affected by the process of organic mounting, whereas this is not the case for aqueous mounting. This is important, because the image used for prediction has to be as it will be in the clinic—and here, it will almost always be permanently mounted in organic mounting medium. Aqueous mounting media look very different, have different refractive indices. This allows for an uncontaminated first image in organic mounting medium. The result of this experiment (following optimization), was that it was possible to do this workflow. In all the cases stained, the sequential imaging and staining for the said markers was done. The magenta staining was then used a training mask to create a virtual prediction of the staining of each marker, only based on the PD-L1 stain. See FIG. 1A showing after the first stain—PD-L1 visible precipitated with DAB. Invisible fer4flu linker also precipitated at sites of CD68 antigen. Slide is mounted in organic mounting medium and imaged. FIG. 1B shows Development of fer4flu bound at CD68 positive sites with HRP magenta.

For p40, adenocarcinomas of the lung was studied. A permanently mounted uncontaminated first image was obtained through precipitating the fer4flu linker around the p40 sites, mounted in organic medium, imaged, removed coverslip and developed the p40 stain using HRP magenta. See FIG. 2A showing after first stain. Fer4flu linker is precipitated around p40 sites. Slide is mounted in organic mounting medium and imaged. FIG. 2B shows p40 positivity is developed using HRP Magenta at sites of fer4flu linker.

In both cases, the proper positive and negative controls ensured that the quality of the method is sufficient.

Example 9

High affinity antibodies, which ensure robust staining reactions, can sometime be very difficult to denature using heat or harsh conditions. A method of obtaining effective antibody stripping between reactions has therefore been designed, as described in Table 8 below. The designed method was also shown be an effective way to remove plastic coverslips without compromising subsequent reaction (see, steps 5-12 in the below Table 8), a process which can be used in different settings.

TABLE 8

| Step | Action |
|---|---|
| 1 | IHC reaction: Stain A visualized by precipitation of an HRP substrate (FL or BF) |
| 2 | Dehydrate in gradients of alcohol and xylene |
| 3 | Mounting using Sakura TissueTek resin-covered plastic tape (xylene is added to dissolve tape into tissue) |
| 4 | Image in brightfield scan |
| 5 | Remove plastic tape start |
| 6 | Incubate for 5-7 minutes in 100% acetone, covering the slides completely |
| 7 | Plastic tape is loosed, remove using pincers |
| 8 | Move slides to fresh 100% acetone bath with magnet stirrer at 1000 rpms to dissolve remaining plastic |
| 9 | Move slides to 96% ethanol for 2 minutes |
| 10 | Move slides to 96% ethanol for 2 minutes |
| 11 | Move slides to 70% ethanol for 2 minutes |
| 12 | Move slides 1X RT Dako Wash buffer for 5 minutes |
| 13 | Preheat vertical containers with a stripping buffer* to exactly 56° C. in closed, shaking water-bath in fume hood |
| 14 | Incubate slides for 30 minutes at 56° C. with shaking |
| 15 | Transfer to 1X RT Dako wash buffer; 5 minutes times 3 (change buffer every 5 minutes for 15 minutes) |
| 16 | Transfer to 1X RT Dako wash buffer; 5 minutes times 3 (change buffer every 15 minutes for 45 minutes) |
| 17 | Ready for next IHC reaction (precipitate HPR substrate around antigen B) |

*Stripping buffer was prepared as follows:
200 ml 1X (prepare and refrigerate without the 2-ME)
20 ml SDS 10%
12.5 ml Tris HCl pH 6.8 (0.5M)
167.5 ml Distilled $H_2O$
Before use, add 0.8 ml 2-mercaptoethanol; once added, the half-life is about100 hrs.
Work under a fume hood. Scale up or down the volumes and chemicals accordingly.

Example 10

Dark Quenchers

It has been observed that DAB was a potent dark quencher for fluorescent excitations and emissions. Dark quenchers are molecules that, by virtual of their physiochemical properties, absorb light of certain wavelengths, which are converted to heat.

A method that is usable in certain types of multiplexing or sequential staining experiments was designed. Since high-affinity antibodies are hard to elute after binding, especially because HRP substrates become covalently attached to adjacent molecules by process of free radical generation, there are significant challenges of cross-reactivity between reactions when multiple stainings are applied. For example, if a mouse-anti-target1 antibody is applied, visualized with an HRP-polymer and HRP substrate 1, followed by enzyme deactivation (with sulfuric acid for example), and a different mouse-anti-target2 antibody is applied, and visualized that with HRP substrate 2, there may be some crossover for the visualization system between target 1 and target 2, depending on the sensitivity of these HRP substrates.

Figure 19:
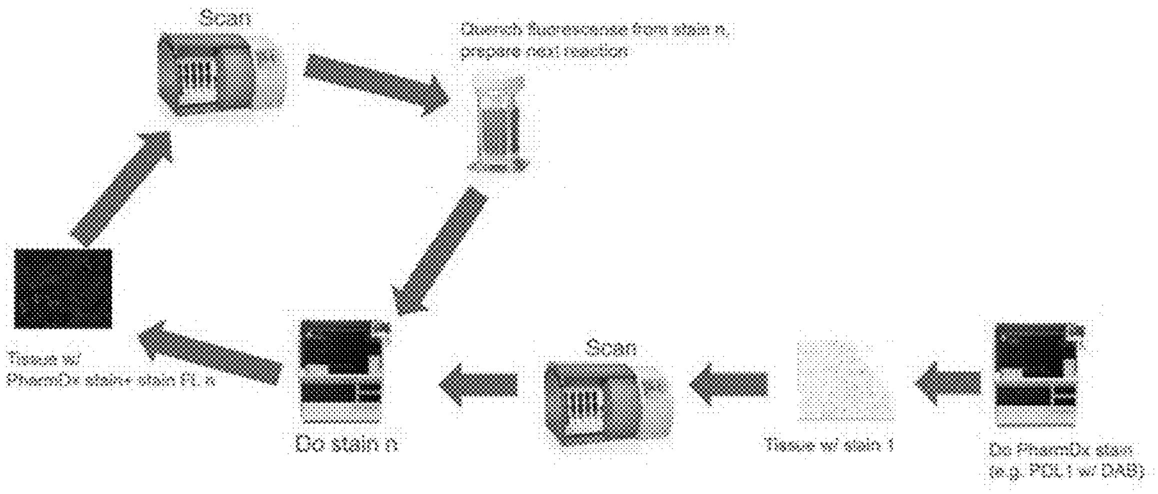
FIG. 19 is a schematic illustration of an exemplary sequential staining using a dark quenche, according to some embodiments of the present invention.

DAB was therefore used to quench the signal from a previous reaction by exploiting the crossover between reactions, as depicted in Table 9 and in FIG. 19.

TABLE 9

| Step | Description |
|---|---|
| 1 | Do PharmDx stain (e.g. PDL1 with DAB) |
| 2 | Mount, Scan in BF, unmount and clear counterstain (hematoxylin) |
| 3 | Do mouse-anti human stain n1 (for instance CD68) with fer4flu as visualizer |
| 4 | Mount, Scan in FL, unmount |
| 5 | Incubate with secondary reagent (goat-anti mouse-HRP conjugated polymer) and precipitate DAB. Stain n1 is now hidden in FL mode and is not visualized even if more fer4flu is precipiated |
| 6 | Do mouse-anti human stain n2 (for instance CD20) with fer4flu as visualizer |
| 7 | Mount, scan in FL, unmount |
| 8 | Cycle back between steps 5 and 8. |

Using the described methodology allows using the same fluorochromes for sequential reactions without crossover.

Figure 20:
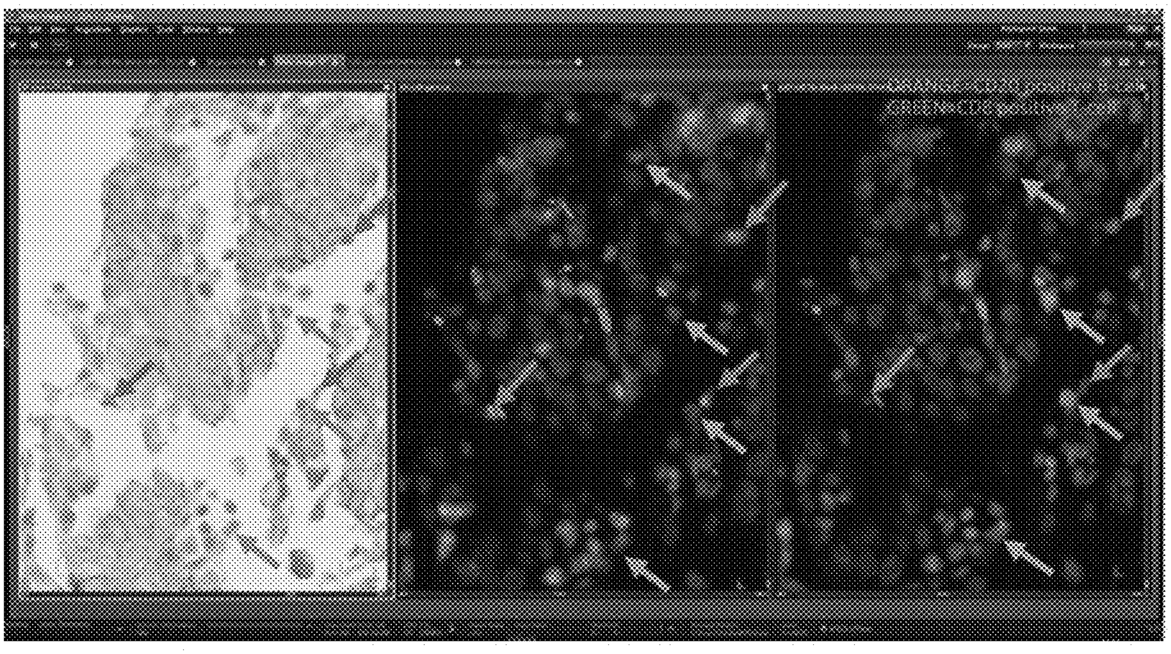
FIG. 20 presents images of a tissue section where multiple round of staining has been done using DAB as a quencher between reactions. First PDL1 (left), then CD8 for cytotoxic T-cells (center) which was subsequently dark quenched and stained for B-cells (right).

FIG. 20 presents an exemplary image of a tissue section where multiple round of staining has been done using DAB as a quencher between reactions. First PDL1 (left), then CD8 for cytotoxic T-cells (center) which was subsequently dark quenched and stained for B-cells (right).

Example 11

RNA-CISH/IHC Multiplex

Information about RNA transcripts was used in determining cell identity. This was achieved with sequential reactions of first using an RNA CISH kit from Bioteche (RNAscope) for a LAG3 transcript, which was visualised using a dissolvable chromogen (AEC). Following this, another reaction was added on top with LAG3 IHC (unreleased clone, internal development) and DAB using the normal IHC protocol. Thus, on the brightfield image, there is the RNA-scope mask for which cells had RNA transcripts.

Example 12

Specific antibody use for labeling nuclear periphery in sequential reactions

Figure 21:
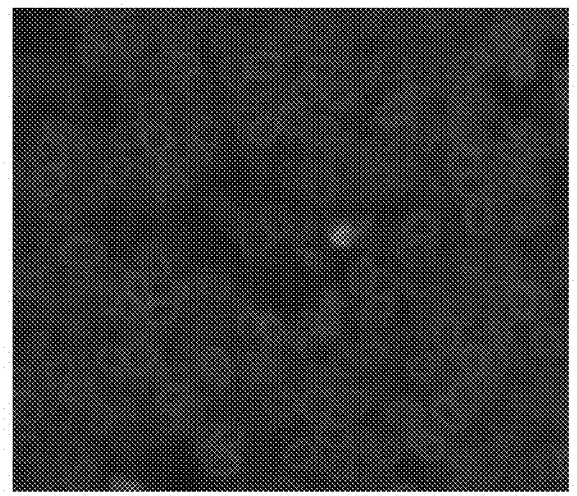
FIG. 21 presents an immunofluorescence image of an antibody against LaminB1, and a nuclear envelope protein which effectively stains the nuclear periphery.

A deep learning based nuclear classifier was built by labeling nuclei centroids as well as the nuclear periphery, in order to predict the two surfaces and combine that information to generate a nuclear mask. FIG. 21 presents an immunofluorescence image of an antibody against LaminB1, and a nuclear envelope protein which effectively stains the nuclear periphery (Coumaric acid-L42-Rhodamine101, different from fer4flu-LaminB1).

Such stains improve the nuclear classifier, by using large-scale biological annotations to create annotations for the nuclear periphery.

B. Non-Limiting Examples for Sequential Imaging of Biological Samples for Generating Training Data for Developing Deep Learning Based Models for Image Analysis, for Cell Classification, for Feature of Interest Identification, and/or for Virtual Staining of the Biological Sample With reference to the figures, FIG. 3 is a schematic diagram illustrating a system 300 for implementing sequential imaging of biological samples for generating training data for developing deep learning based models for image analysis, for cell classification, and/or for features of interest identification of biological samples, in accordance with various embodiments.

Figure 3:
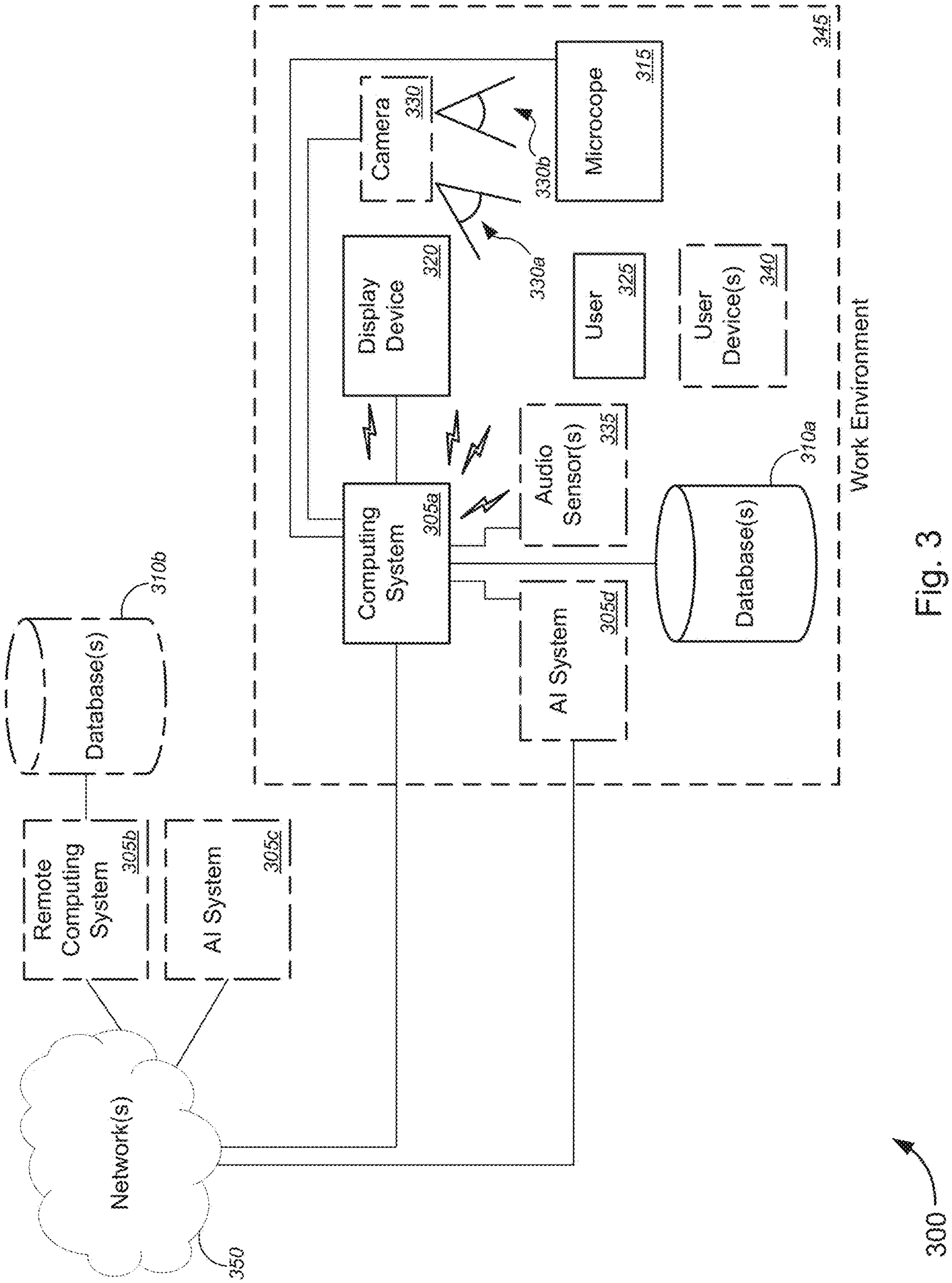
FIG. 3 is a schematic diagram illustrating a system for implementing sequential imaging of biological samples for generating training data for developing deep learning based models for image analysis, for cell classification, for features of interest identification, and/or for virtual staining of biological samples, in accordance with various embodiments.

In the non-limiting embodiment of FIG. 3, system 300 may comprise a computing system 305*a*, an artificial intelligence ("AI") system 305*d* (optional), and a data store or database 310*a* that is local to the computing system 305*a* and/or the AI system 305*d*. In some cases, the database 310*a* may be external, yet communicatively coupled, to the computing system 305*a*. In other cases, the database 310*a* may be integrated within the computing system 305*a*. In some embodiments, the AI system 305*d*—which may include, but is not limited to, at least one of a machine learning system, a deep learning system, a model architecture, a statistical model-based system, or a deterministic analysis system, and/or the like—may be external, yet communicatively coupled, to the computing system 305*a* or may be integrated within the computing system 305*a*. In some instances, the model architecture may comprise at least one of a neural network, a convolutional neural network ("CNN"), or a fully convolutional network ("FCN") (which may include a U-Net framework or the like), and/or the like.

System 300, according to some embodiments, may further comprise a display device 320 that may allow a user 325 to view a field of view ("FOV") of a biological sample or an image(s) or video(s) of the biological sample. System 300 may further comprise one or more user devices 340 (optional), one or more audio sensors 335 (optional), a camera(s) 330 (optional), and a microscope 315. In some instances, the one or more user devices 340 may include, without limitation, smart phones, mobile phones, tablet computers, laptop computers, desktop computers, keyboards, keypads, computer mice, or monitors, and/or the like. In some cases, the one or more audio sensors 335 may include, but are not limited to, one or more microphones, one or more voice recorders, or one or more audio recorders, and/or the like. In some instances, the camera 330 may include, without limitation, one or more eye tracking sensors, one or more motion sensors, or one or more tracking sensors, and/or the like.

According to some embodiments, the one or more user devices 340 may be used to receive user input from the user 325 indicative of annotations or labeling of objects of interest observed by the user 325 while viewing the field of view of the biological sample, whether viewing on a display screen of the display device 320 or viewing through an eyepiece(s) of the microscope 315. The one or more audio sensors 335 may be used to record vocal or spoken annotations by the user 325 while the user 325 is viewing the FOV 330*b* of the biological sample either on the display device 320 or through the eyepiece(s) of the microscope 315. The camera 330 may capture images or videos of the user 325 (in some cases, capturing images or videos of at least one eye of the user 325) while the user 325 is within the FOV 330*a* of camera 330. The features of gaze tracking and voice annotation are described in greater detail in the '105 Application, which has already been incorporated by reference in its entirety for all purposes.

Computing system 305*a* may communicatively couple (either via wireless (as depicted by lightning bolt symbols, or the like) or wired connection (as depicted by connecting lines)) with one or more of the AI system 305*d*, the database(s) 310*a*, the display device 320, the one or more user devices 340, the one or more audio sensors 335, the camera 330, and/or the microscope 315. Computing system 305*a*, the AI system 305*d*, the database(s) 310*a*, the display device 320, the one or more user devices 340, the one or more audio sensors 335, the camera 330, and/or the microscope 315 may be disposed or located within work environment 345, which may include, but is not limited to, one of a laboratory, a clinic, a medical facility, a research facility, a healthcare facility, or a room, and/or the like.

System 300 may further comprise remote computing system 305*b* (optional), AI system 305*c* (optional), and database(s) 310*b* (optional) that may communicatively couple with computing system 305*a* and/or AI system 305*d* via network(s) 350. In some cases, the remote computing system 305*b* may include, but is not limited to, a web server, a web browser, or a cloud computing system, and/or the like. Remote computing system 305*b*, AI system 305*c*, and database(s) 310*b* may otherwise be similar, if not identical, to computing system 305*a*, the AI system 305*d*, and the database(s) 310*a*, respectively.

Merely by way of example, network(s) 350 may each include a local area network ("LAN"), including, without limitation, a fiber network, an Ethernet network, a Token-Ring™ network, and/or the like; a wide-area network ("WAN"); a wireless wide area network ("WWAN"); a virtual network, such as a virtual private network ("VPN"); the Internet; an intranet; an extranet; a public switched telephone network ("PSTN"); an infra-red network; a wireless network, including, without limitation, a network operating under any of the IEEE 802.11 suite of protocols, the Bluetooth™ protocol known in the art, and/or any other wireless protocol; and/or any combination of these and/or other networks. In a particular embodiment, network(s) 350 may each include an access network of an Internet service provider ("ISP"). In another embodiment, network(s) 350 may each include a core network of the ISP, and/or the Internet.

In operation, computing system 305*a* or 305*b* and/or AI system 305*d* or 305*c* (collectively, "computing system") may receive a first image of a first biological sample, the first image comprising a first field of view ("FOV") of the first biological sample that has been stained with a first stain; and may receive a second image of the first biological sample, the second image comprising a second FOV of the first biological sample that has been stained with a second stain. The computing system may autonomously create a first set of image patches based on the first image and the second image, by extracting a portion of the first image and extracting a corresponding portion of the second image, the first set of image patches comprising a first patch corresponding to the extracted portion of the first image and a second patch corresponding to the extracted portion of the second image. In such cases, the first set of image patches may comprise labeling of instances of features of interest in the first biological sample that is based at least in part on at least one of information contained in the first patch, information contained in the second patch, or information contained in one or more external labeling sources.

The computing system may utilize an AI system (e.g., AI system 305*d* or 305*c*, or the like) to train a first model ("Model G*" or "(AI) Model G*"; which may be an AI model or can, instead, be either a statistical model or a deterministic algorithm model, or the like) to generate first instance classification of features of interest ("Ground Truth") in the first biological sample, based at least in part on the first set of image patches and the labeling of instances of features of interest contained in the first set of image patches; and may utilize the AI system to train a second AI model ("Model G") to identify instances of features of interest in the first biological sample, based at least in part on the first patch and the first instance classification of features of interest generated by Model G*.

According to some embodiments, the first biological sample may include, without limitation, one of a human tissue sample, an animal tissue sample, a plant tissue sample, or an artificially produced tissue sample, and/or the like. In some cases, the artificially produced tissue sample may include, but is not limited to, at least one of an artificial lab-grown tissue sample, an artificial commercially produced tissue sample, an artificially produced heart valve tissue sample, an artificially produced organ tissue sample, a 3D printed tissue sample, a 3D produced cell culture, and/or the like. In some instances, the features of interest may include, but are not limited to, at least one of normal cells, abnormal cells, damaged cells, cancer cells, tumors, subcellular structures, or organ structures, and/or the like.

In some embodiments, the first image may comprise highlighting of first features of interest in the first biological sample (including, but not limited to, at least one of first antigens, first nuclei, first cell walls, first cell structures, first antibodies, first normal cells, first abnormal cells, first damaged cells, first cancer cells, first tumors, first subcellular structures, first organ structures, or other features of interest, or the like) by the first stain that had been applied to the first biological sample. Similarly, the second image may comprise one of highlighting of second features of interest in the first biological sample (including, but not limited to, at least one of second antigens, second nuclei, second cell walls, second cell structures, second antibodies, second normal cells, second abnormal cells, second damaged cells, second cancer cells, second tumors, second subcellular structures, second organ structures, or other features of interest, or the like) by the second stain that had been applied to the first biological sample in addition to highlighting of the first features of interest by the first stain or highlighting of the second features of interest by the second stain without highlighting of the first features of interest by the first stain, the second features of interest being different from the first features of interest. In some cases, the second stain may be one of the same as the first stain but used to stain the second features of interest or different from the first stain, or the like.

Merely by way of example, in some cases, the first stain may include, without limitation, at least one of Hematoxylin, Acridine orange, Bismarck brown, Carmine, Coomassie blue, Cresyl violet, Crystal violet, 4',6-diamidino-2-phenylindole ("DAPI"), Eosin, Ethidium bromide intercalates, Acid fuchsine, Hoechst stain, Iodine, Malachite green, Methyl green, Methylene blue, Neutral red, Nile blue, Nile red, Osmium tetroxide, Propidium Iodide, Rhodamine, Safranine, programmed death-ligand 1 ("PD-L1") stain, 3,3'-Diaminobenzidine ("DAB") chromogen, Magenta chromogen, cyanine chromogen, cluster of differentiation ("CD") 3 stain, CD20 stain, CD68 stain, 40S ribosomal protein SA ("p40") stain, antibody-based stain, or label-free imaging marker (which may result from the use of imaging techniques including, but not limited to, Raman spectroscopy, near infrared ("NIR") spectroscopy, autofluorescence imaging, or phase imaging, and/or the like, and which may be used to highlight features of interest without an external dye, or the like), and/or the like. In some cases, the contrast when using label-free imaging techniques may be generated without additional markers such as fluorescent dyes or chromogen dyes, or the like. Likewise, the second stain may include, but is not limited to, at least one of Hematoxylin, Acridine orange, Bismarck brown, Carmine, Coomassie blue, Cresyl violet, Crystal violet, DAPI, Eosin, Ethidium bromide intercalates, Acid fuchsine, Hoechst stain, Iodine, Malachite green, Methyl green, Methylene blue, Neutral red, Nile blue, Nile red, Osmium tetroxide, Propidium Iodide, Rhodamine, Safranine, PD-L1 stain, DAB chromogen, Magenta chromogen, cyanine chromogen, CD3 stain, CD20 stain, CD68 stain, p40 stain, antibody-based stain, or label-free imaging marker, and/or the like.

According to some embodiments, the first image may include, without limitation, one of a first set of color or brightfield images, a first fluorescence image, a first phase image, or a first spectral image, and/or the like, where the first set of color or brightfield images may include, but is not limited to, a first red-filtered ("R") image, a first green-filtered ("G") image, and a first blue-filtered ("B") image, and/or the like. "Color or brightfield image(s)" may refer to either a color image(s) each resulting from the use of one or a combination or appropriate color sensors or color filters (in some cases, embodied by an RGB image, but is not limited to red, green, and/or blue colored images) or a brightfield image(s) each resulting from the use of a light source(s); for simplicity, these terms are intended herein to be interchangeable. The first fluorescence image may include, but is not limited to, at least one of a first autofluorescence image (also referred to as "intrinsic fluorescence image" or the like) or a first labelled fluorescence image (also referred to as "extrinsic fluorescence image" or the like) having one or more channels with different excitation or emission characteristics, and/or the like. The first spectral image may include, but is not limited to, at least one of a first Raman spectroscopy image, a first near infrared ("NIR") spectroscopy image, a first multispectral image, a first hyperspectral image, or a first full spectral image, and/or the like. Similarly, the second image may include, without limitation, one of a second set of color or brightfield images, a second fluorescence image, a second phase image, or a second spectral image, and/or the like, where the second set of color or brightfield images may include, but is not limited to, a second R image, a second G image, and a second B image, and/or the like. The second fluorescence image may include, but is not limited to, at least one of second autofluorescence image or a second labelled fluorescence image having one or more channels with different excitation or emission characteristics, and/or the like. The second spectral image may include, but is not limited to, at least one of a second Raman spectroscopy image, a second NIR spectroscopy image, a second multispectral image, a second hyperspectral image, or a second full spectral image, and/or the like.

In some embodiments, the computing system may align the first image with the second image to create first set of aligned images, by aligning one or more features of interest in the first biological sample as depicted in the first image with the same one or more features of interest in the first biological sample as depicted in the second image. In some instances, aligning the first image with the second image may be one of performed manually using manual inputs to the computing system or performed autonomously, where autonomous alignment may comprise alignment using at least one of automated global alignment techniques or optical flow alignment techniques, or the like. In some cases, the first set of aligned images may comprise a third FOV of the first biological sample, the third FOV being either different from each of the first FOV of the first image and the second FOV of the second image, or the same as one of the first FOV or the second FOV. Herein, FOV may refer to a region of the biological sample as captured in the first image or the second image. Prior to alignment (assuming alignment is necessary), the (first) FOV of the first image, although overlapping with the (second) FOV of the second image, may be slightly different from the FOV of the second image. The aligned image is intended to depict the FOV of the area of interest in the image of the first biological sample, and thus may be referred to as the intended, desired, or target FOV. In the case that alignment is not needed (either where the first and second images are pre-aligned or where the process that produces the first and second images results in automatically aligned images), the first FOV and the second FOV would be identical.

According to some embodiments, the computing system may receive a third image of the first biological sample, the third image comprising a third FOV of the first biological sample that has been stained with a third stain different from each of the first stain and the second stain; and may autonomously perform one of: aligning the third image with each of the first image and the second image to create second aligned images, by aligning one or more features of interest in the first biological sample as depicted in the third image with the same one or more features of interest in the first biological sample as depicted in each of the first image and the second image; or aligning the third image with the first aligned images to create second aligned images, by aligning one or more features of interest in the first biological sample as depicted in the third image with the same one or more features of interest in the first biological sample as depicted in the first aligned images.

The computing system may partially or fully autonomously create second aligned image patches from the second aligned images, by extracting a portion of the second aligned images, the portion of the second aligned images comprising a first patch corresponding to the extracted portion of the first image, a second patch corresponding to the extracted portion of the second image, and a third patch corresponding to the extracted portion of the third image; may train the AI system to update Model G* to generate second instance classification of features of interest in the first biological sample, based at least in part on the second aligned image patches and the labeling of instances of features of interest contained in the first set of image patches; and may train the AI system to update Model G to identify instances of features of interest in the first biological sample, based at least in part on the first patch and the second instance classification of features of interest generated by Model G*.

In some embodiments, the first image may comprise highlighting or designation of first features of interest in the first biological sample (including, but not limited to, at least one of first antigens, first nuclei, first cell walls, first cell structures, first antibodies, first normal cells, first abnormal cells, first damaged cells, first cancer cells, first tumors, first subcellular structures, first organ structures, or other features of interest, or the like) by the first stain that had been applied to the first biological sample. In some cases, the second image may comprise one of highlighting of second features of interest in the first biological sample (including, but not limited to, at least one of second antigens, second nuclei, second cell walls, second cell structures, second antibodies, second normal cells, second abnormal cells, second damaged cells, second cancer cells, second tumors, second subcellular structures, second organ structures, or other features of interest, or the like) by the second stain that had been applied to the first biological sample in addition to highlighting or designation of the first features of interest by the first stain or highlighting of the second features of interest by the second stain without highlighting of the first features of interest by the first stain, the second features of interest being different from the first features of interest. In some instances, the third image may comprise one of highlighting of third features of interest in the first biological sample (including, but not limited to, at least one of third antigens, third nuclei, third cell walls, third cell structures, third antibodies, third normal cells, third abnormal cells, third damaged cells, third cancer cells, third tumors, third subcellular structures, third organ structures, or other features of interest, or the like) by the third stain that had been applied to the first biological sample in addition to highlighting of the first features of interest by the first stain and highlighting of the second features of interest by the second stain, highlighting of the third features of interest by the third stain in addition to only one of highlighting of the first features of interest by the first stain or highlighting of the second features of interest by the second stain, or highlighting of the third features of interest by the third stain without any of highlighting of the first features of interest by the first stain or highlighting of the second features of interest by the second stain, and/or the like, the third features of interest being different from each of the first features of interest and the second features of interest.

According to some embodiments, the first image may include, without limitation, one of a first set of color or brightfield images, a first fluorescence image, a first phase image, or a first spectral image, and/or the like, where the first set of color or brightfield images may include, but is not limited to, a first red-filtered ("R") image, a first green-filtered ("G") image, and a first blue-filtered ("B") image, and/or the like. The first fluorescence image may include, but is not limited to, at least one of a first autofluorescence image or a first labelled fluorescence image having one or more channels with different excitation or emission characteristics, and/or the like. The first spectral image may include, but is not limited to, at least one of a first Raman spectroscopy image, a first near infrared ("NIR") spectroscopy image, a first multispectral image, a first hyperspectral image, or a first full spectral image, and/or the like. Likewise, the second image may include, without limitation, one of a second set of color or brightfield images, a second fluorescence image, a second phase image, or a second spectral image, and/or the like, where the second set of color or brightfield images may include, but is not limited to, a second R image, a second G image, and a second B image, and/or the like. The second fluorescence image may include, but is not limited to, at least one of a second autofluorescence image or a second labelled fluorescence image having one or more channels with different excitation or emission characteristics, and/or the like. The second spectral image may include, but is not limited to, at least one of a second Raman spectroscopy image, a second NIR spectroscopy image, a second multispectral image, a second hyperspectral image, or a second full spectral image, and/or the like. Similarly, the third image may include, without limitation, one of a third set of color or brightfield images, a third fluorescence image, a third phase image, or a third spectral image, and/or the like, where the third set of color or brightfield images may include, but is not limited to, a third R image, a third G image, and a third B image, and/or the like. The third fluorescence image may include, but is not limited to, at least one of a third autofluorescence image or a third labelled fluorescence image having one or more channels with different excitation or emission characteristics, and/or the like. The third spectral image may include, but is not limited to, at least one of a third Raman spectroscopy image, a third NIR spectroscopy image, a third multispectral image, a third hyperspectral image, or a third full spectral image, and/or the like.

In some embodiments, the computing system may receive a fourth image, the fourth image comprising one of a fourth FOV of the first biological sample different from the first FOV and the second FOV or a fifth FOV of a second biological sample, where the second biological sample may be different from the first biological sample; and may identify, using Model G, second instances of features of interest in the second biological sample, based at least in part on the fourth image and based at least in part on training of Model G using the first patch and the first instance classification of features of interest generated by Model G*. In some cases, the fourth image may comprise the fifth FOV and may further comprise only highlighting of first features of interest in the second biological sample by the first stain that had been applied to the second biological sample. According to some embodiments, the computing system may generate, using Model G, a clinical score, based at least in part on the identified second instances of features of interest.

In another aspect, the computing system may receive a first image of a first biological sample, the first image comprising a first field of view ("FOV") of the first biological sample; and may identify, using a first AI model ("Model G") that is generated or updated by a trained AI system, first instances of features of interest in the first biological sample, based at least in part on the first image and based at least in part on training of Model G using a first patch and first instance classification of features of interest generated by a second model (Model G*) that is generated or updated by the trained AI system by using first aligned image patches and labeling of instances of features of interest contained in the first patch. In some cases, the first aligned image patches may comprise an extracted portion of first aligned images, which may comprise a second image and a third image that have been aligned. The second image may comprise a second FOV of a second biological sample that has been stained with a first stain, the second biological sample being different from the first biological sample. The third image may comprise a third FOV of the second biological sample that has been stained with a second stain. The second patch may comprise labeling of instances of features of interest as shown in the extracted portion of the second image of the first aligned images. The first image may comprise highlighting of first features of interest in the second biological sample (including, but not limited to, at least one of first antigens, first nuclei, first cell walls, first cell structures, first antibodies, first normal cells, first abnormal cells, first damaged cells, first cancer cells, first tumors, first subcellular structures, first organ structures, or other features of interest, or the like) by the first stain that had been applied to the second biological sample. The second patch may comprise one of highlighting of second features of interest in the second biological sample (including, but not limited to, at least one of second antigens, second nuclei, second cell walls, second cell structures, second antibodies, second normal cells, second abnormal cells, second damaged cells, second cancer cells, second tumors, second subcellular structures, second organ structures, or other features of interest, or the like) by the second stain that had been applied to the second biological sample in addition to highlighting of the first features of interest by the first stain or highlighting of the second features of interest by the second stain without highlighting of the first features of interest by the first stain.

In yet another aspect, the computing system may receive first instance classification of features of interest ("Ground Truth") in a first biological sample that has been sequentially stained, the Ground Truth having been generated by a trained first model ("Model G*") that has been trained or updated by an AI system, wherein the Ground Truth is generated by using first aligned image patches and labeling of instances of features of interest contained in the first aligned image patches, wherein the first aligned image patches comprise an extracted portion of first aligned images, wherein the first aligned images comprise a first image and a second image that have been aligned, wherein the first image comprises a first FOV of the first biological sample that has been stained with a first stain, wherein the second image comprises a second FOV of the first biological sample that has been stained with a second stain, wherein the first aligned image patches comprise labeling of instances of features of interest as shown in the extracted portion of the first aligned images; and may utilize the AI system to train a second AI model ("Model G") to identify instances of features of interest in the first biological sample, based at least in part on the first instance classification of features of interest generated by Model G*.

In still another aspect, the computing system may generate ground truth for developing accurate AI models for biological image interpretation, based at least in part on images of a first biological sample depicting sequential staining of the first biological sample.

In an aspect, the computing system may receive a first image of a first biological sample, the first image comprising a first field of view ("FOV") of the first biological sample that has been stained with a first stain; may receive a second image of the first biological sample, the second image comprising a second FOV of the first biological sample that has been stained with at least a second stain; and may align the first image with the second image to create first aligned images, by aligning one or more features of interest in the first biological sample as depicted in the first image with the same one or more features of interest in the first biological sample as depicted in the second image.

The computing system may autonomously create first aligned image patches from the first aligned images, by extracting a portion of the first aligned images, the portion of the first aligned images comprising a first patch corresponding to the extracted portion of the first image and a second patch corresponding to the extracted portion of the second image; may utilize an AI system to train a first AI model ("Model F") to generate a third patch comprising a virtual stain of the first aligned image patches, based at least in part on the first patch and the second patch, the virtual stain simulating staining by at least the second stain of features of interest in the first biological sample as shown in the second patch; and may utilize the AI system to train a second model ("Model G*") to identify or classify first instances of features of interest in the first biological sample, based at least in part on the third patch and based at least in part on results from an external instance classification process or a region of interest detection process.

According to some embodiments, the first image may comprise highlighting of first features of interest in the first biological sample (including, but not limited to, at least one of first antigens, first nuclei, first cell walls, first cell structures, first antibodies, first normal cells, first abnormal cells, first damaged cells, first cancer cells, first tumors, first subcellular structures, first organ structures, or other features of interest, or the like) by the first stain that had been applied to the first biological sample. In some cases, the third patch may comprise one of highlighting of the first features of interest by the first stain and highlighting of second features of interest in the first biological sample (including, but not limited to, at least one of second antigens, second nuclei, second cell walls, second cell structures, second antibodies, second normal cells, second abnormal cells, second damaged cells, second cancer cells, second tumors, second subcellular structures, second organ structures, or other features of interest, or the like) by the virtual stain that simulates the second stain having been applied to the first biological sample or highlighting of the first features of interest by the first stain and highlighting of first features of interest by the virtual stain, the second features of interest being different from the first features of interest. In some instances, the second stain may be one of the same as the first stain but used to stain the second features of interest or different from the first stain. In some embodiments, the second FOV of the first biological sample that has been stained with at least the second stain may comprise one o: (a) an image or FOV of sequentially staining of the first biological sample with two or more stains, the two or more stains comprising the first stain and the at least the second stain; (b) an image or FOV of fluorescent staining of the first biological sample with the second stain without the first stain; (c) an image or FOV of single channel grayscale staining of the first biological sample; or (d) an image or FOV of fluorescent, single channel, grayscale staining of the first biological sample; and/or the like.

Merely by way of example, in some cases, the first stain may include, without limitation, at least one of Hematoxylin, Acridine orange, Bismarck brown, Carmine, Coomassie blue, Cresyl violet, Crystal violet, 4',6-diamidino-2-phenylindole ("DAPI"), Eosin, Ethidium bromide intercalates, Acid fuchsine, Hoechst stain, Iodine, Malachite green, Methyl green, Methylene blue, Neutral red, Nile blue, Nile red, Osmium tetroxide, Propidium Iodide, Rhodamine, Safranine, programmed death-ligand 1 ("PD-L1") stain, 3,3'-Diaminobenzidine ("DAB") chromogen, Magenta chromogen, cyanine chromogen, cluster of differentiation ("CD") 3 stain, CD20 stain, CD68 stain, 40S ribosomal protein SA ("p40") stain, antibody-based stain, or label-free imaging marker, and/or the like. Similarly, the second stain may include, but is not limited to, at least one of Hematoxylin, Acridine orange, Bismarck brown, Carmine, Coomassie blue, Cresyl violet, Crystal violet, DAPI, Eosin, Ethidium bromide intercalates, Acid fuchsine, Hoechst stain, Iodine, Malachite green, Methyl green, Methylene blue, Neutral red, Nile blue, Nile red, Osmium tetroxide, Propidium Iodide, Rhodamine, Safranine, PD-L1 stain, DAB chromogen, Magenta chromogen, cyanine chromogen, CD3 stain, CD20 stain, CD68 stain, p40 stain, antibody-based stain, or label-free imaging marker, and/or the like.

In some embodiments, the first image may include, without limitation, one of a first set of color or brightfield images, a first fluorescence image, a first phase image, or a first spectral image, and/or the like, where the first set of color or brightfield images may include, but is not limited to, a first red-filtered ("R") image, a first green-filtered ("G") image, and a first blue-filtered ("B") image, and/or the like. The first fluorescence image may include, but is not limited to, at least one of a first autofluorescence image or a first labelled fluorescence image having one or more channels with different excitation or emission characteristics, and/or the like. The first spectral image may include, but is not limited to, at least one of a first Raman spectroscopy image, a first near infrared ("NIR") spectroscopy image, a first multispectral image, a first hyperspectral image, or a first full spectral image, and/or the like. In some instances, the second image may include, without limitation, one of a second set of color or brightfield images, a second fluorescence image, a second phase image, or a second spectral image, and/or the like, where the second set of color or brightfield images may include, but is not limited to, a second R image, a second G image, and a second B image, and/or the like. The second fluorescence image may include, but is not limited to, at least one of a second autofluorescence image or a second labelled fluorescence image having one or more channels with different excitation or emission characteristics, and/or the like. The second spectral image may include, but is not limited to, at least one of a second Raman spectroscopy image, a second NIR spectroscopy image, a second multispectral image, a second hyperspectral image, or a second full spectral image, and/or the like. In some cases, the third patch may include, without limitation, one of a third set of color or brightfield images, a third fluorescence image, a third phase image, or a third spectral image, and/or the like, where the third set of color or brightfield images may include, but is not limited to, a third R image, a third G image, and a third B image, and/or the like. The third fluorescence image may include, but is not limited to, at least one of a third autofluorescence image or a third labelled fluorescence image having one or more channels with different excitation or emission characteristics, and/or the like. The third spectral image may include, but is not limited to, at least one of a third Raman spectroscopy image, a third NIR spectroscopy image, a third multispectral image, a third hyperspectral image, or a third full spectral image, and/or the like.

According to some embodiments, aligning the first image with the second image may be one of performed manually using manual inputs to the computing system or performed autonomously, where autonomous alignment may comprise alignment using at least one of automated global alignment techniques or optical flow alignment techniques.

In some embodiments, training, using the AI system, Model G* to identify or classify instances of features of interest in the first biological sample may comprise training, using the AI system, Model G* to identify or classify instances of features of interest in the first biological sample, based at least in part on one or more of the first patch, the second patch, or the third patch and based at least in part on the results from the external instance classification process or the region of interest detection process. In some cases, the external instance classification process or the region of interest detection process may each include, without limitation, at least one of detection of nuclei in the first image or the first patch by a nuclei detection method, identification of nuclei in the first image or the first patch by a pathologist, detection of features of interest in the first image or the first patch by a feature detection method, or identification of features of interest in the first image or the first patch by the pathologist, and/or the like.

According to some embodiments, training the AI system to update Model F may comprise: receiving, with an encoder, the first patch; receiving the second patch; encoding, with the encoder, the received first patch; decoding, with the decoder, the encoded first patch; generating an intensity map based on the decoded first patch; simultaneously operating on the encoded first patch to generate a color vector; combining the generated intensity map with the generated color vector to generate an image of the virtual stain; adding the generated image of the virtual stain to the received first patch to produce a predicted virtually stained image patch; determining a first loss value between the predicted virtually stained image patch and the second patch; calculating a loss value using a loss function, based on the first loss value between the predicted virtually stained image patch and the second patch; and updating, with the AI system, Model F to generate the third patch, by updating one or more parameters of Model F based on the calculated loss value. In some instances, the loss function may include, but is not limited to, one of a mean squared error loss function, a mean squared logarithmic error loss function, a mean absolute error loss function, a Huber loss function, or a weighted sum of squared differences loss function, and/or the like.

In some embodiments, the first patch may include, without limitation, one of a first set of color or brightfield images, a first fluorescence image, a first phase image, or a first spectral image, and/or the like, where the first set of color or brightfield images may include, but is not limited to, a first red-filtered ("R") image, a first green-filtered ("G") image, and a first blue-filtered ("B") image, and/or the like. The first fluorescence image may include, but is not limited to, at least one of a first autofluorescence image or a first labelled fluorescence image having one or more channels with different excitation or emission characteristics, and/or the like. The first spectral image may include, but is not limited to, at least one of a first Raman spectroscopy image, a first near infrared ("NIR") spectroscopy image, a first multispectral image, a first hyperspectral image, or a first full spectral image, and/or the like. In some cases, the second image may include, without limitation, one of a second set of color or brightfield images, a second fluorescence image, a second phase image, or a second spectral image, and/or the like, where the second set of color or brightfield images may include, but is not limited to, a second R image, a second G image, and a second B image, and/or the like. The second fluorescence image may include, but is not limited to, at least one of a second autofluorescence image or a second labelled fluorescence image having one or more channels with different excitation or emission characteristics, and/or the like. The second spectral image may include, but is not limited to, at least one of a second Raman spectroscopy image, a second NIR spectroscopy image, a second multispectral image, a second hyperspectral image, or a second full spectral image, and/or the like. In some instances, the predicted virtually stained image patch may include, without limitation, one of a third set of color or brightfield images, a third fluorescence image, a third phase image, or a third spectral image, and/or the like, where the third set of color or brightfield images may include, but is not limited to, a third R image, a third G image, and a third B image, and/or the like. The third fluorescence image may include, but is not limited to, at least one of a third autofluorescence image or a third labelled fluorescence image having one or more channels with different excitation or emission characteristics, and/or the like. The third spectral image may include, but is not limited to, at least one of a third Raman spectroscopy image, a third NIR spectroscopy image, a third multispectral image, a third hyperspectral image, or a third full spectral image, and/or the like.

According to some embodiments, operating on the encoded first patch to generate the color vector may comprise operating on the encoded first patch to generate a color vector, using a color vector output and one of a model architecture, a statistical model-based system, or a deterministic analysis system, and/or the like. In some instances, the model architecture may comprise at least one of a neural network, a convolutional neural network ("CNN"), or a fully convolutional network ("FCN"), and/or the like. In some cases, the color vector may be one of a fixed color vector or a learned color vector that is not based on the encoded first patch, and/or the like.

In some embodiments, the image of the virtual stain may include, but is not limited to, one of a 3-channel image of the virtual stain, a RGB-transform image of the virtual stain, or a logarithmic transform image of the virtual stain, and/or the like. In some instances, generating the predicted virtually stained image patch may include, without limitation, adding the generated image of the virtual stain to the received first patch to produce the predicted virtually stained image patch. In some cases, determining the first loss value between the predicted virtually stained image patch and the second patch may be performed without adding the generated image of the virtual stain to the received first patch.

According to some embodiments, the first loss value may include, without limitation, one of a pixel loss value between each pixel in the predicted virtually stained image patch and a corresponding pixel in the second patch or a generative adversarial network ("GAN") loss value between the predicted virtually stained image patch and the second patch, and/or the like. In some instances, the GAN loss value may be generated based on one of a minimax GAN loss function, a non-saturating GAN loss function, a least squares GAN loss function, or a Wasserstein GAN loss function, and/or the like.

Alternatively, training the AI system to update Model F may comprise: receiving, with the AI system, the first patch; receiving, with the AI system, the second patch; generating, with a second model of the AI system, an image of the virtual stain; adding the generated image of the virtual stain to the received first patch to produce a predicted virtually stained image patch; determining a first loss value between the predicted virtually stained image patch and the second patch; calculating a loss value using a loss function, based on the first loss value between the predicted virtually stained image patch and the second patch; and updating, with the AI system, Model F to generate the third patch, by updating one or more parameters of Model F based on the calculated loss value.

In some embodiments, the second model may include, without limitation, at least one of a convolutional neural network ("CNN"), a U-Net, an artificial neural network ("ANN"), a residual neural network ("ResNet"), an encode/decode CNN, an encode/decode U-Net, an encode/decode ANN, or an encode/decode ResNet, and/or the like.

According to some embodiments, the computing system may receive a fourth image, the fourth image comprising one of a fourth FOV of the first biological sample different from the first FOV and the second FOV or a fifth FOV of a second biological sample, where the second biological sample may be different from the first biological sample; and may identify, using Model G*, second instances of features of interest in the second biological sample, based at least in part on the fourth image and based at least in part on training of Model G* using at least the third patch comprising the virtual stain of the first aligned image patches. According to some embodiments, the computing system may generate, using Model G*, a clinical score, based at least in part on the identified second instances of features of interest.

In some embodiments, the first image may comprise highlighting of first features of interest in the first biological sample (including, but not limited to, at least one of first antigens, first nuclei, first cell walls, first cell structures, first antibodies, first normal cells, first abnormal cells, first damaged cells, first cancer cells, first tumors, first subcellular structures, first organ structures, or other features of interest, or the like) by the first stain that had been applied to the first biological sample. In some cases, the third patch may comprise one of highlighting of the first features of interest by the first stain and highlighting of second features of interest in the first biological sample (including, but not limited to, at least one of second antigens, second nuclei, second cell walls, second cell structures, second antibodies, second normal cells, second abnormal cells, second damaged cells, second cancer cells, second tumors, second subcellular structures, second organ structures, or other features of interest, or the like) by the virtual stain that simulates the second stain having been applied to the first biological sample or highlighting of the first features of interest by the first stain and highlighting of first features of interest by the virtual stain, the second features of interest being different from the first features of interest. In some instances, the second stain may be one of the same as the first stain but used to stain the second features of interest or different from the first stain.

According to some embodiments, the first image may include, without limitation, one of a first set of color or brightfield images, a first fluorescence image, a first phase image, or a first spectral image, and/or the like, where the first set of color or brightfield images may include, but is not limited to, a first red-filtered ("R") image, a first green-filtered ("G") image, and a first blue-filtered ("B") image, and/or the like. The first fluorescence image may include, but is not limited to, at least one of a first autofluorescence image or a first labelled fluorescence image having one or more channels with different excitation or emission characteristics, and/or the like. The first spectral image may include, but is not limited to, at least one of a first Raman spectroscopy image, a first near infrared ("NIR") spectroscopy image, a first multispectral image, a first hyperspectral image, or a first full spectral image, and/or the like. In some instances, the second image may include, without limitation, one of a second set of color or brightfield images, a second fluorescence image, a second phase image, or a second spectral image, and/or the like, where the second set of color or brightfield images may include, but is not limited to, a second R image, a second G image, and a second B image, and/or the like. The second fluorescence image may include, but is not limited to, at least one of a second autofluorescence image or a second labelled fluorescence image having one or more channels with different excitation or emission characteristics, and/or the like. The second spectral image may include, but is not limited to, at least one of a second Raman spectroscopy image, a second NIR spectroscopy image, a second multispectral image, a second hyperspectral image, or a second full spectral image, and/or the like. In some cases, the third patch may include, without limitation, one of a third set of color or brightfield images, a third fluorescence image, a third phase image, or a third spectral image, and/or the like, where the third set of color or brightfield images may include, but is not limited to, a third R image, a third G image, and a third B image, and/or the like. The third fluorescence image may include, but is not limited to, at least one of a third autofluorescence image or a third labelled fluorescence image having one or more channels with different excitation or emission characteristics, and/or the like. The third spectral image may include, but is not limited to, at least one of a third Raman spectroscopy image, a third NIR spectroscopy image, a third multispectral image, a third hyperspectral image, or a third full spectral image, and/or the like.

In some embodiments, training the AI system to update Model F may comprise: receiving, with an encoder, the first patch; receiving the second patch; encoding, with the encoder, the received first patch; decoding, with the decoder, the encoded first patch; generating an intensity map based on the decoded first patch; simultaneously operating on the encoded first patch to generate a color vector; combining the generated intensity map with the generated color vector to generate an image of the virtual stain; adding the generated image of the virtual stain to the received first patch to produce a predicted virtually stained image patch; determining a first loss value between the predicted virtually stained image patch and the second patch; calculating a loss value using a loss function, based on the first loss value between the predicted virtually stained image patch and the second patch; and updating, with the AI system, Model F to generate the third patch, by updating one or more parameters of Model F based on the calculated loss value. In some instances, the loss function may include, but is not limited to, one of a mean squared error loss function, a mean squared logarithmic error loss function, a mean absolute error loss function, a Huber loss function, or a weighted sum of squared differences loss function, and/or the like.

According to some embodiments, the first loss value may include, without limitation, one of a pixel loss value between each pixel in the predicted virtually stained image patch and a corresponding pixel in the second patch or a generative adversarial network ("GAN") loss value between the predicted virtually stained image patch and the second patch, and/or the like. In some cases, the GAN loss value may be generated based on one of a minimax GAN loss function, a non-saturating GAN loss function, a least squares GAN loss function, or a Wasserstein GAN loss function, and/or the like.

In yet another aspect, the computing system may receive a first image of a first biological sample, the first image comprising a first field of view ("FOV") of the first biological sample; and may identify, using a first model ("Model G*") that is generated or updated by a trained AI system, first instances of features of interest in the first biological sample, based at least in part on the first image and based at least in part on training of Model G* using at least a first patch comprising a virtual stain of first aligned image patches, the first patch being generated by a second AI model (Model F) that is generated or updated by the trained AI system by using a second patch. In some cases, the first aligned image patches may comprise an extracted portion of first aligned images. The first aligned images may comprise a second image and a third image that have been aligned. The second image may comprise a second FOV of a second biological sample that is different from the first biological sample that has been stained with a first stain. The second patch may comprise the extracted portion of the second image. The third image may comprise a third FOV of the second biological sample that has been stained with at least a second stain.

In general, in some embodiments, the training of the (AI) Models may leverage the following: (1) A set of biological samples (i.e., one or more samples) represents the tissue of interest; (2) Each such sample may also have annotation associated with it (e.g., nuclei position, pathologist marking, other labeling as described herein, etc.); (3) Each such biological sample may be stained and images may be scanned or captured in the following manner: (a) "First" staining (for example H+DAB, although not limited to such), followed by at least one multiple "sequential" staining steps; (b) After each staining step, the tissue is scanned, resulting in production of a set of Whole-Slide-Image ("WSI") for each biological sample produced, one WSI for each staining; (4) For each biological sample, a large set of regions (not just one) may be selected, such a region in some cases being referred to as a FOV or sample FOV; (5) For each such FOV (or sample FOV), a "patches-set" may reflect the collection of corresponding image patches (one for each WSI for this biological sample), together with the "annotation patch," corresponding to the associated annotation for the biological sample. According to some embodiments, the scans of the images of one or more biological samples may include, without limitation, at least one of a brightfield scan, a fluorescence scan (e.g., autofluorescence scan, or the like), and/or a spectral scan, and/or the like, with the patches-set including such multitude of scans (if available for that biological sample). Here, a patches-set may correspond to a specific FOV(s), within a specific biological sample, and may have one member for each staining+ annotation. The Training process takes this whole multitude of patches-sets and trains an (AI) model with them. This model will be able to predict various annotations and/or to generate a clinical score, given an arbitrary image patch from a scan of a biological sample stained with only the "First" staining above. Training of the (AI) Models is not necessarily limited to training based on only one biological sample, or based on there being only one FOV, or based on there being only one sequential staining. Rather, training of the (AI) Models may be based on training of one or more biological samples, based on one or more FOVs of each biological sample, and/or based on a single staining or sequential staining or unmixing of particular staining, and/or the like. Herein also, "the (AI) Models" may refer to AI models or to models that are not necessarily AI-based (e.g., statistical model-based, deterministic analysis, etc.).

These and other functions of the system 100 (and its components) are described in greater detail below with respect to FIGS. 4-9.

Figure 4B:
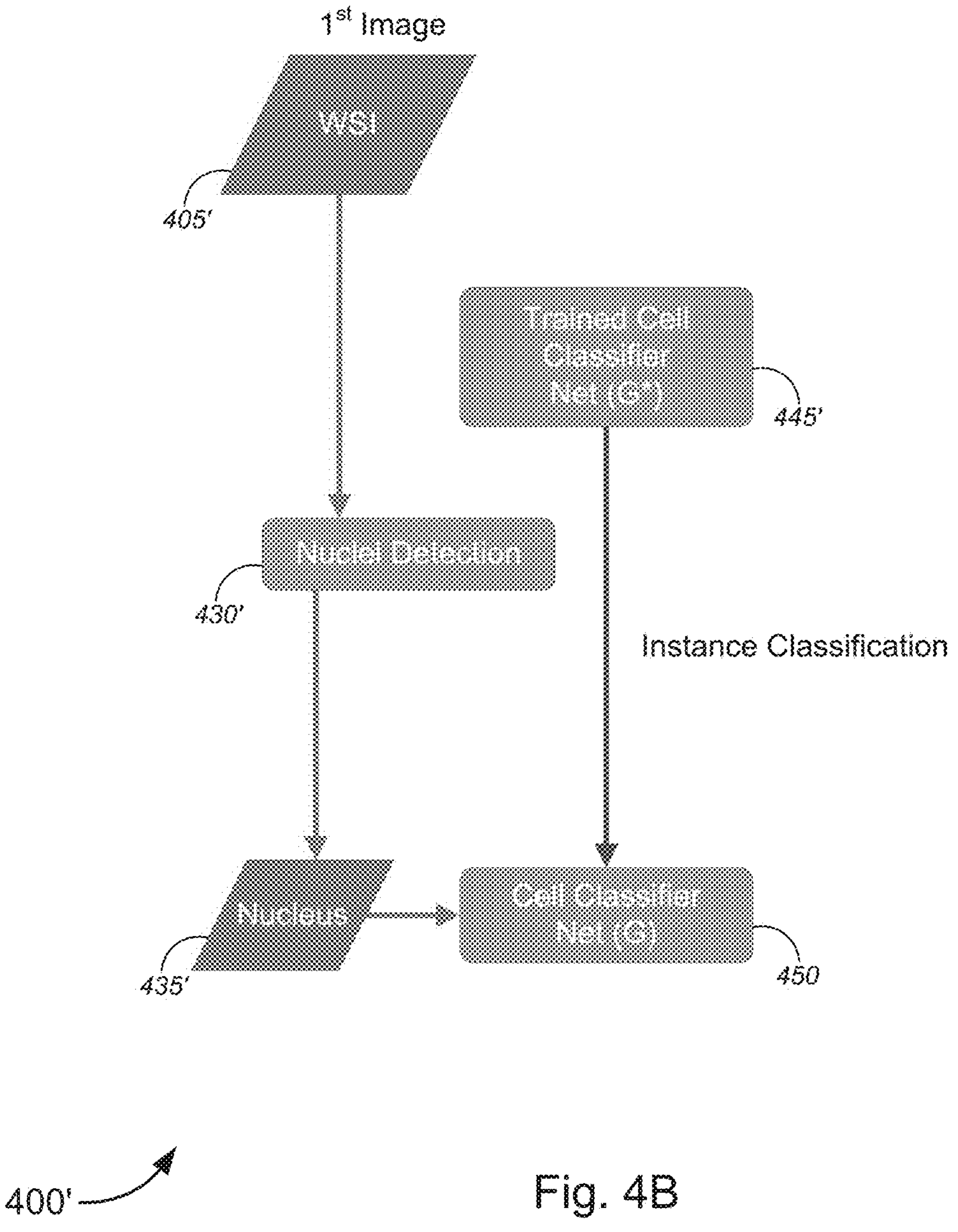
Figure 4C:
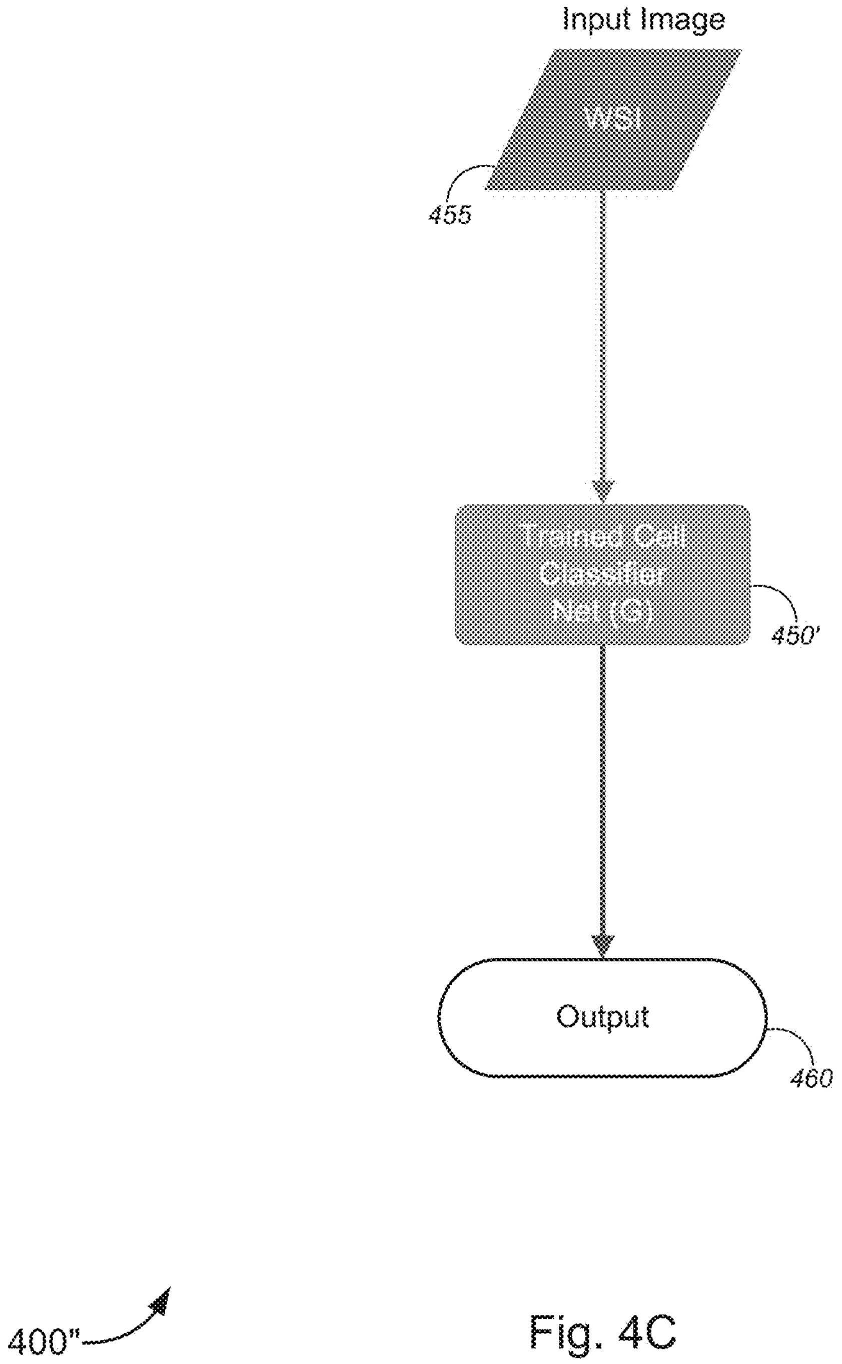

FIGS. 4A-4C (collectively, "FIG. 4") are process flow diagrams illustrating various non-limiting examples 400 and 400' of training of one or more artificial intelligence ("AI") models and non-limiting example 400" of associated inferencing performed by a trained AI model, when implementing sequential imaging of biological samples for generating training data for developing deep learning based models for image analysis, for cell classification, and/or for features of interest identification of biological samples, in accordance with various embodiments. FIG. 4 is directed to the process of generating ground truth for developing accurate AI models for biological image interpretation, based at least in part on images of a first biological sample depicting sequential staining of the first biological sample. Such a process, in some cases, may be performed by computing system **305*a* or 305*b* and/or AI system 305*d* or 305*c* (collectively, "computing system") of FIG. 3**, or the like.

Although FIG. 4 is focused on specific examples that utilize particular components (including, but not limited to, whole slide images ("WSIs"), nuclei detection, using pairs of patches or images, using alignment of images, etc.) in a particular order, the various embodiments are not so limited, and some of these components may be replaced with other types of components, may be omitted, may be reordered, or may otherwise by changed, as necessary or as desired, without deviating from the scope of the various embodiments. For instance, images of biological samples other than WSIs may be used, detection of other features of interest (not necessarily nuclei or cells) may be utilized, sets of three or more patches or images may be used rather than pairs, and/or images may already have been aligned or do not require alignment, or the like. Further, although specific examples of biological markers or stains may be referred to with respect to FIG. 4, this is merely for purposes of illustration, and the various embodiments are not so limited, as any suitable biological marker(s) and/or stain(s) may be used, as appropriate or as desired.

With reference to the non-limiting embodiment 400 of FIG. 4A, a first image 405 of a first biological sample and a second image 410 of the first biological sample may be received. According to some embodiments, the first biological sample may include, without limitation, one of a human tissue sample, an animal tissue sample, a plant tissue sample, or an artificially produced tissue sample, and/or the like. The first image 405 (which may comprise a WSI, although not limited to such) may include a first field of view ("FOV") of the first biological sample that has been stained with a first stain. The second image 410 (which may comprise a WSI, although not limited to such) may include a second FOV of the first biological sample that has been stained with a second stain. In some cases, while the first image 405 may include highlighting of first features of interest in the first biological sample (including, but not limited to, at least one of first antigens, first nuclei, first cell walls, first cell structures, first antibodies, first normal cells, first abnormal cells, first damaged cells, first cancer cells, first tumors, first subcellular structures, first organ structures, or other features of interest, or the like) by the first stain, the second image 410 may include either highlighting of second features of interest in the first biological sample (including, but not limited to, at least one of second antigens, second nuclei, second cell walls, second cell structures, second antibodies, second normal cells, second abnormal cells, second damaged cells, second cancer cells, second tumors, second subcellular structures, second organ structures, or other features of interest, or the like) by the second stain in addition to highlighting of the first features of interest by the first stain or highlighting of the second features of interest by the second stain without highlighting of the first features of interest by the first stain. In some instances, the second features of interest may be different from the first features of interest.

In some embodiments, the second stain either may be the same as the first stain but used to stain the second features of interest or may be different from the first stain. In some instances, the first stain and the second stain may each include, but is not limited to, at least one of Hematoxylin, Acridine orange, Bismarck brown, Carmine, Coomassie blue, Cresyl violet, Crystal violet, 4',6-diamidino-2-phenylindole ("DAPI"), Eosin, Ethidium bromide intercalates, Acid fuchsine, Hoechst stain, Iodine, Malachite green, Methyl green, Methylene blue, Neutral red, Nile blue, Nile red, Osmium tetroxide, Propidium Iodide, Rhodamine, Safranine, programmed death-ligand 1 ("PD-L1") stain, 3,3'-Diaminobenzidine ("DAB") chromogen, Magenta chromogen, cyanine chromogen, cluster of differentiation ("CD") 3 stain, CD20 stain, CD68 stain, 40S ribosomal protein SA ("p40") stain, antibody-based stain, or label-free imaging marker, and/or the like. In some cases, the first image 405 and the second image 410 may each include, without limitation, one of a set of color or brightfield images, a fluorescence image, or a spectral image, and/or the like, where the set of color or brightfield images may include, but is not limited to, a red-filtered ("R") image, a green-filtered ("G") image, and a blue-filtered ("B") image, and/or the like.

As depicted in FIG. 4A (with the notation "WSI" being at a different angle in the second image 410 compared with corresponding notation in the first image 405), the first image 405 and the second image 410 may initially be misaligned, and thus may require alignment by alignment system 415. The alignment system 415 may perform alignment of the first image 405 relative to the second image 410 (or vice versa) either using manual input from a user (e.g., pathologist or other operator, or the like) or via autonomous alignment processes (in some cases, utilizing AI system functionality, or the like). In some cases, autonomous alignment may include, but is not limited to, alignment using at least one of automated global alignment techniques or optical flow alignment techniques, or the like.

In some embodiments, automated global alignment may include the following computational details: (i) finding foreground tiles (in some cases, using entropy threshold criterion, or the like); (ii) performing feature-based (e.g., with oriented fast and rotated brief ("ORB") features, or the like) matching on low resolution images (e.g., default pyramid level 4, or the like); and (iii) computing affine alignment transformation from matched features. Computational steps (i) to (iii) are applicable to both serial and sequential staining. For sequential staining, the following additional details may apply for automated global alignment: (iv) finding all high resolution (e.g., level 0) tiles spanning the matched low resolution features; (v) matching high resolution tiles based on low resolution alignment; (vi) performing feature based matching on high resolution features within matched tiles; and (vii) computing global affine alignment as composition of the high and low resolution alignment transformation matrices; and/or the like.

Even with sequential staining, there may be misalignments and deformations between scans. Global, affine alignment accounts for translation, rotation, or uniform deformation of the whole slide image, but cannot account for non-uniform deformation of the slide image. Large scale deformation may result in misalignment of paired FOVs, while small scale deformation may result in non-uniform misalignment within a FOV (which may be apparent as horizontal stretching of the FOV, for example). Such misalignment introduces noise to the training of models based on the sequentially stained image as ground truth. Alignment characterization may be optimized as follows: (a) optimization may be performed on either H channel alone, or on the sum of H+DAB channels (combined); (b) optimization may be performed by non-overlapping square micro-patches of equal size having patch sides in 1000, 500, 100, or 50 pixels in length; (c) manual global rigid alignment may be performed for micro-patch matching; (d) for each patch-pair, rigid transform (i.e., rotation+translation) parameters may be found that minimize the mis-match cost; (e) no continuity constraints across patches may be enforced—free optimization; (f) several cost functions may be evaluated by patch-level random self-alignment test, with the best (most stable) results being attained by pixel-wise MSE (L2) loss or the like; and (g) each micro-patch may be padded by adding extra pixels around the patch to allow for required transformation range, which was not always possible (due to FOV edges).

Quantitative evaluation of alignment characterization may alternatively or additionally be performed as follows: (1) quantitative evaluation may be performed by measuring cell-center distances in paired FOVS, with FOVs annotated using the predictions of segmentation models, with segmentation net trained or retrained and running on the H channel only, and with centroids calculated using region_props from segmentation predictions; (2) annotation in paired FOVs may be matched by k=1 nearest neighbour ("NN") matching; (3) NN matching may be applied with threshold on NN distance ratio (k=1, 2); (4) NN matching may also be applied with threshold on a global distance threshold; and (5) matched distance histograms pre and post-optimization may be generated for each FOV. Distance histograms pre and post optimization for micro-patches may be used for quantitative evaluation of the alignment characterization.

According to some embodiments, optical flow alignment may utilize dense inverse search ("DIS"), which may include the following characteristics: (A) optical flow dense (per-pixel) displacement field; (B) "coarse to fine" micro-patch based optimization with partial patch overlap; (C) utilizing an open-sourced implementation (e.g., Python bindings to a C implementation, or the like); (D) integrating into a computing platform (e.g., Matlab calling Python, or the like); (E) the algorithm's patch size and overlap may be empirically tuned for robustness over various tissue samples and various image pyramid levels; and (F) achieving latency per tile (including padding) of <100 ms (in some evaluations, ~40-50 ms was achieved). The algorithm details for optical flow alignment may include the following: (I) dividing the image into a grid of equally sized micro-patches; (II) for each micro-patch in the image, finding the displacement to its optimal position in the paired image (under MSE loss, or the like); (III) starting with coarse (low resolution) patches, and using optimal displacement as the initial condition for the next (finer) level; (IV) overlapping partial micro-patch with similarity-weighted densification for continuity and smoothness; and (V) applying variational refinement on intensity functions for further smoothness and conservation constraints (e.g., divergence of brightness, color, and gradients, or the like). Distance histograms pre and post optimization for DIS may be used for quantitative evaluation of the optical flow alignment. In summary, to account for local, non-uniform deformations, a second tier of local alignment—namely, optical flow alignment—may be used. Optical flow alignment refines the global alignment. Optical flow alignment can account for paired-FOV misalignment as well as non-uniform misalignment within a FOV. With optical flow alignment, pixel-perfect registration of the sequentially stained images can be achieved.

In some cases, the received first and second images may be pre-aligned prior to being received, or may not require alignment (such as in the case of output images of a fluorescence staining scanning protocol, or the like), and thus alignment by the alignment system 415 may be omitted. After alignment (if needed), aligned image 420 may be used to extract at least one second image patch 425 (a plurality of which is depicted in FIG. 4A). In some instances, aligned image 420 may be divided into equal sized (and shaped) grids, with each image patch 425 representing a grid. In some cases, the grids may be of different sizes and/or different shapes (e.g., rectangles, squares, trapezoids, circles, triangles, or other polygons, etc.).

Meanwhile, a nuclei detection system 430 (or other feature detection system (not shown), or the like) may be used to detect nuclei (or other features of interest) in the first image 405, with the resultant image 435 being used to extract at least one first image patch 440 (a plurality of which is depicted in FIG. 4A), in a similar manner as the at least one second image patch 425, each of the at least one first image patch 440 corresponding to each of the at least one second image patch 425 to form patch pairs (although a set of corresponding three or more images, not limited to a pair, may be used, such as in the case of a third image (not shown) being used to highlight a third stain or a combination of stains).

The at least one first image patch 440 and the at least one second image patch 425 (or patch pairs, or the like) may serve as input images for training a first cell classifier net, a first AI module, or a first model ("G*"; collectively, "first AI model G*" or "first (AI) model G*" or "Model G*" or the like) 445, which may also be referred to herein as a "ground truth generator" or the like. The first model G* 445 (which may, in some cases, receive external labelling data, or the like, in addition to the nuclei or other feature detection data, or the like) may generate first instance classification of features of interest ("Ground Truth") in the first biological sample, based at least in part on the aligned image patches 440 and 425, based at least in part on the labeling of instances of features of interest contained in the at least one second patch 425, and (in some cases) based at least in part on additional external labelling data.

The generated first instance classification or Ground Truth, along with the image 435 (containing results of the nuclei or other feature detection, or the like) may be used as inputs to train a second cell classifier net, a second AI module, or a second AI model ("G"; collectively, "second AI model G" or the like) 450 to identify instances of features of interest in the first biological sample. The process flow as depicted in FIG. 4A represents a computational pipeline (also referred to herein as "pipeline A") for generating ground truth based on images of a sequentially stained biological sample, and using such generated ground truth to train another AI model (in this case, model G) to identify features of interest in biological samples. Such ground truth generation would improve upon the technical field of annotation collection or autonomous annotation collection, by increasing the speed of annotation collection, while, in some cases, identifying features of interest that are difficult if not impossible for a human to identify.

Turning to the non-limiting embodiment 400' of FIG. 4B, an already trained first model G* 445' (which may be trained in a manner similar to that described above with respect to FIG. 4A, or the like) may be used to generate ground truth to train the second AI model G 450, which may also use, as inputs for training, image 435' (containing results of the nuclei or other feature detection, or the like, by nuclei detection system (or other feature detection system) 430' being used to detect nuclei or other features in first image 405'). The embodiment 400' may otherwise be similar to embodiment 400 of FIG. 4A.

Referring to the non-limiting embodiment 400" of FIG. 4C, after the second AI model G has been trained, the second AI model G 450' may be used to receive as an input, input image 455, and to identify features of interest in input image 455 and to generate an output 460 containing labelling of identified features of interest in input image 455. In some embodiments, the output 460 may include, without limitation, at least one of a clinical score and/or a labelled image (identifying features of interest), or the like. Such inferencing or overall scoring or diagnosis would improve upon the technical field of annotation collection or autonomous annotation collection, by improving precision and accuracy in identifying features of interest and/or avoiding observer/pathologist biases or human error effects, or the like. Additionally, pipeline A provides a simple, straight forward approach, with relatively low complexity (in some cases, using binary classification, or the like).

These and other features are similar, if not identical to the features, processes, and techniques described herein with respect to FIGS. 3 and 5-9, or the like.

Figure 5A:
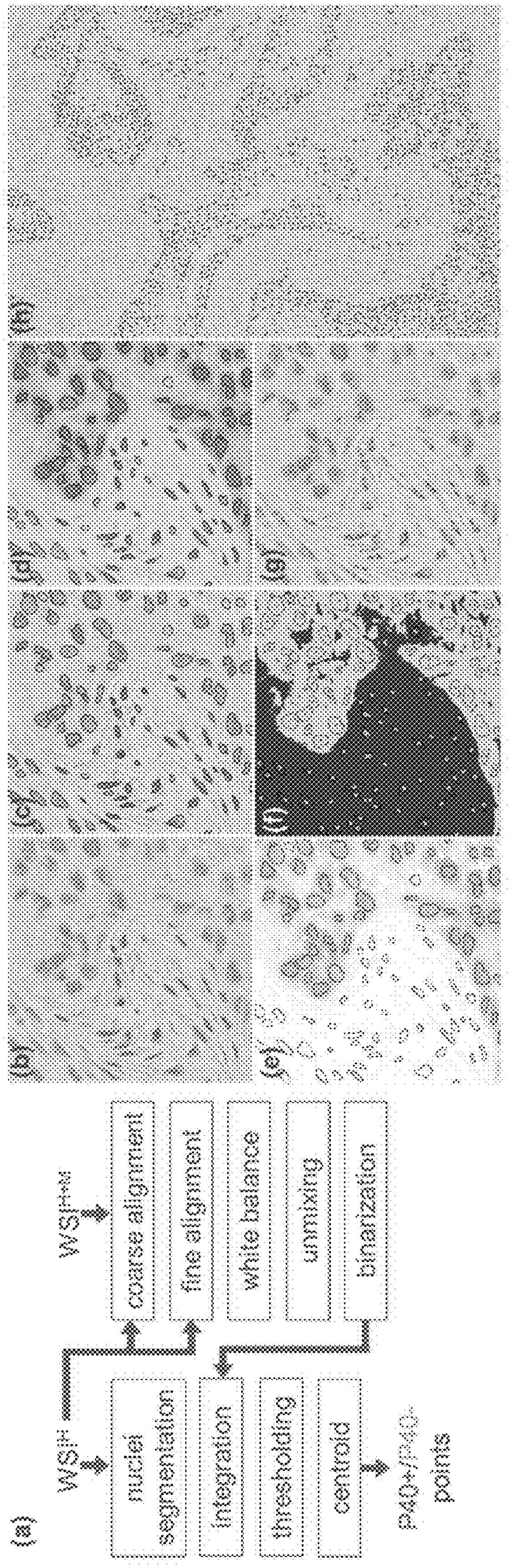
FIGS. 5A-5N are schematic diagrams illustrating anon-limiting example of various process steps performed by the system when implementing sequential imaging of biological samples for generating training data for developing deep learning based models for image analysis, for cell classification, and/or for features of interest identification of biological samples in conjunction with corresponding images of the biological sample during each process (and in some cases, at varying levels of magnification), in accordance with various embodiments.
Figure 5B:
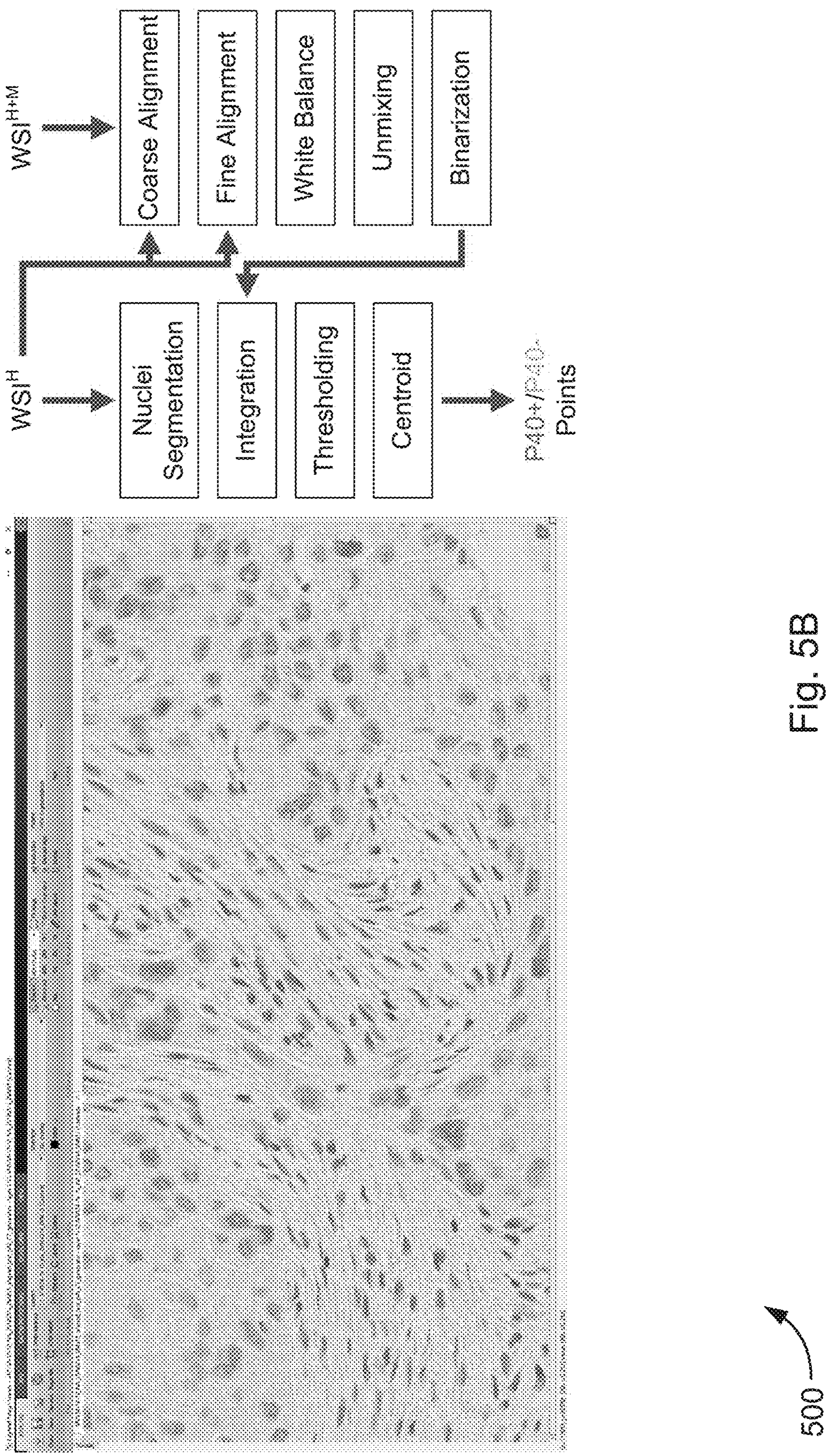
Figure 5C:
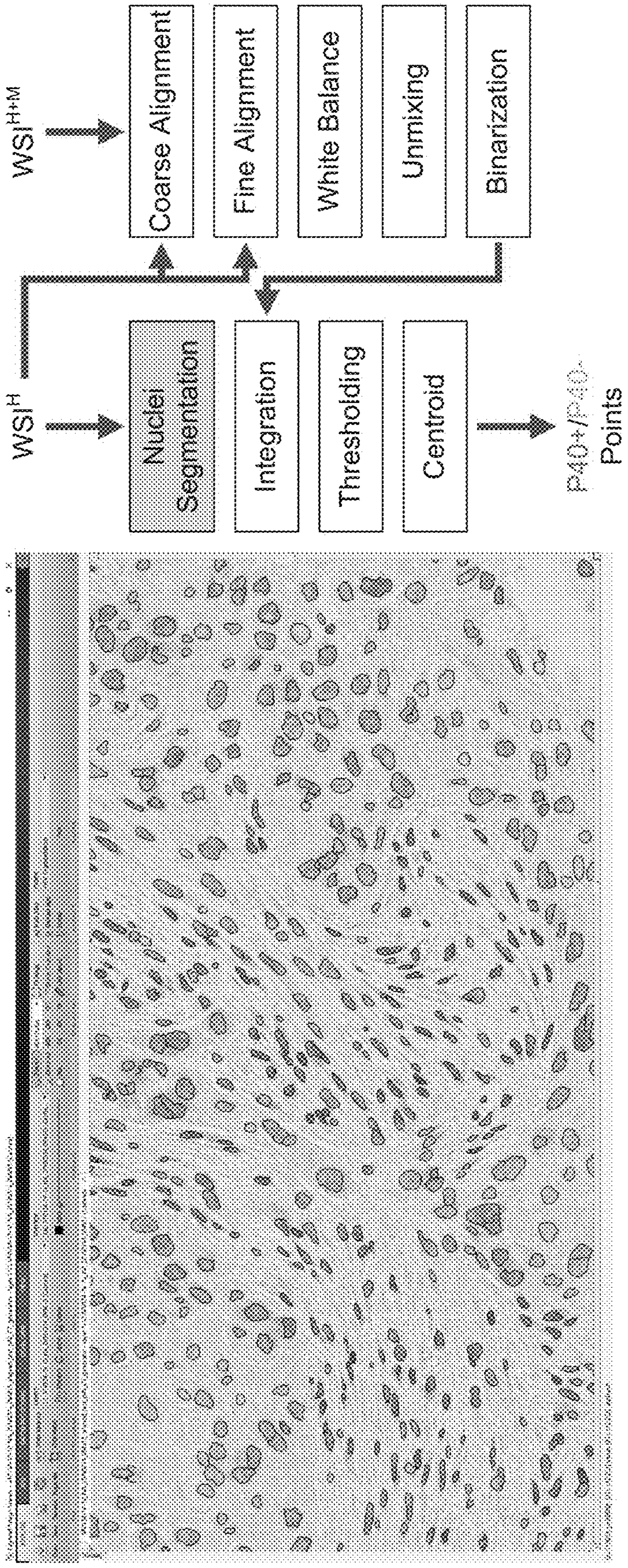
Figure 5D:
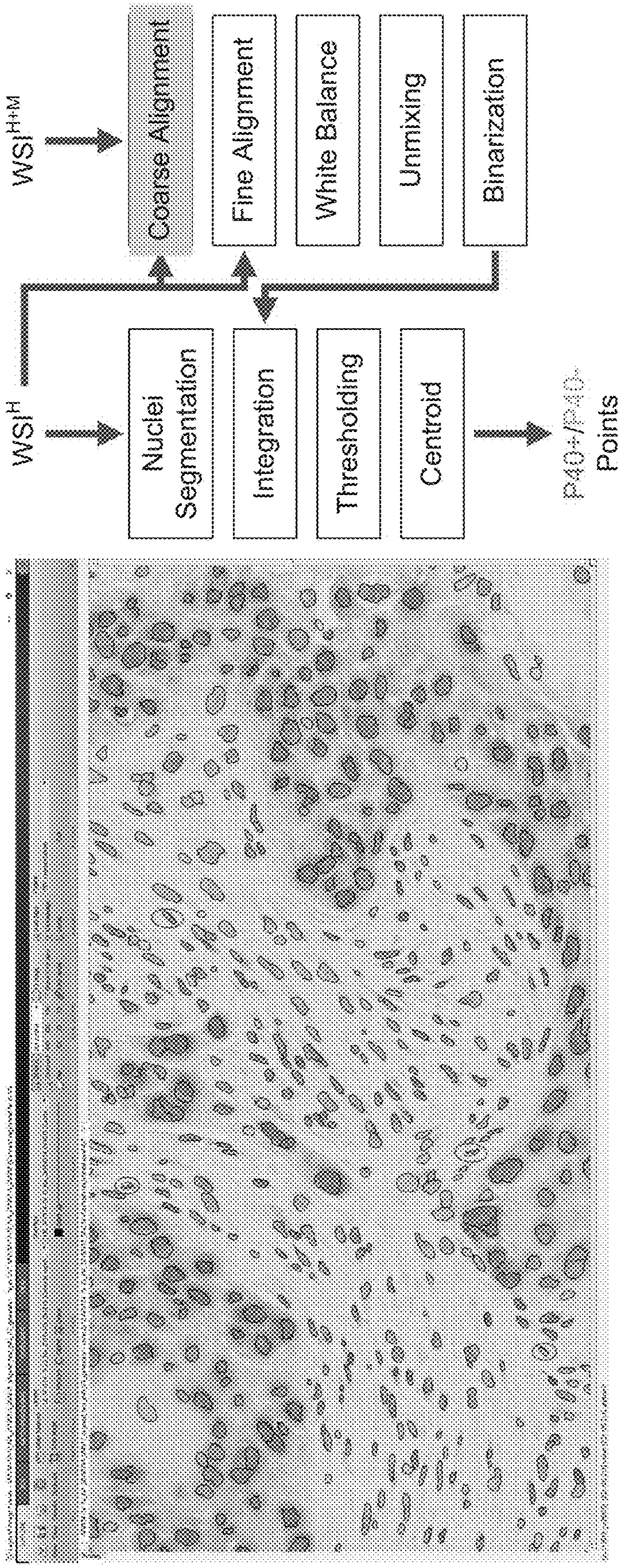
Figure 5E:
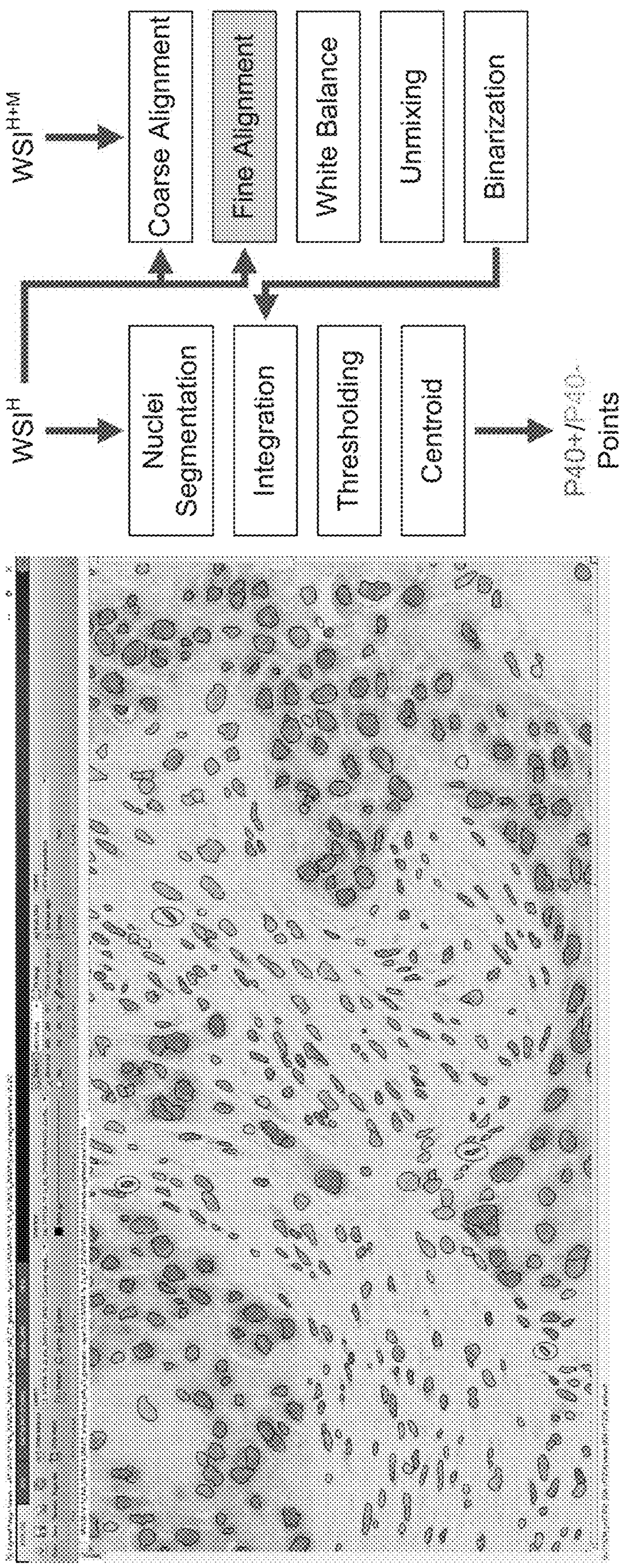
Figure 5F:
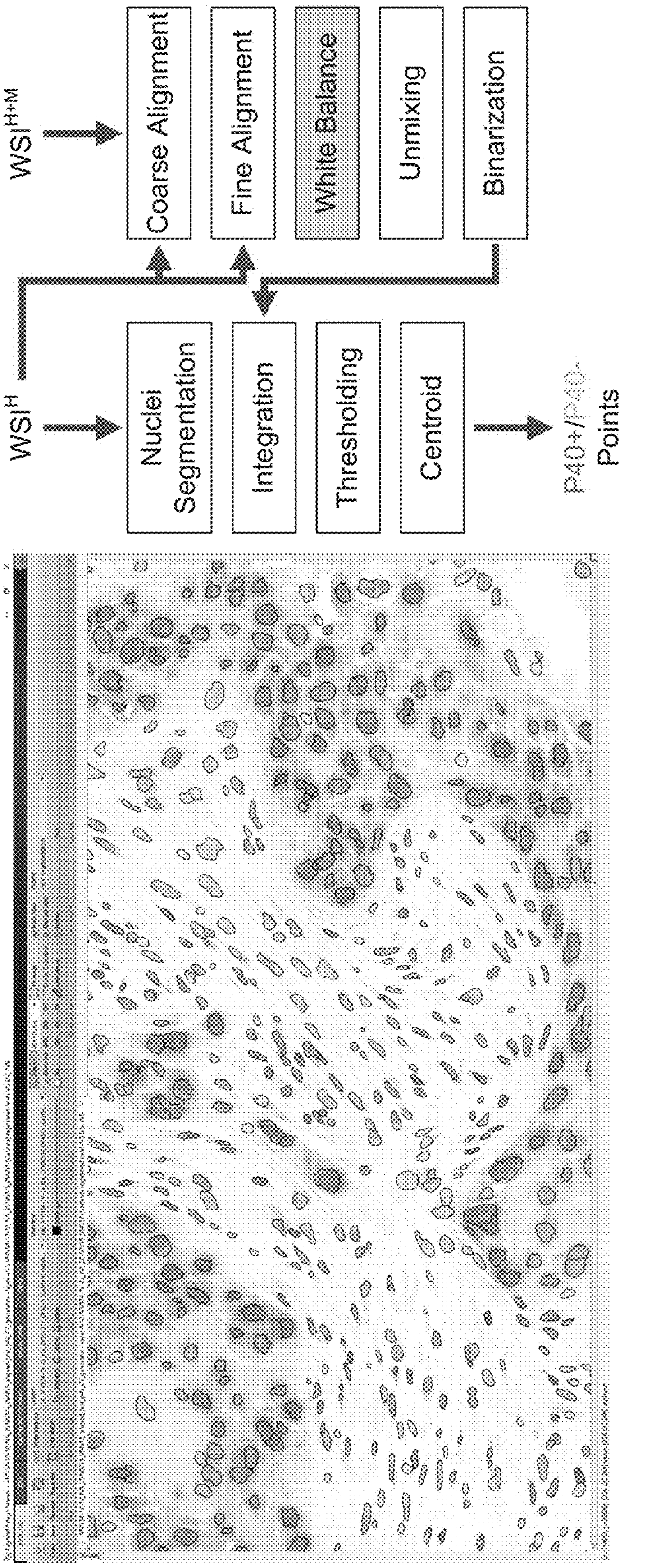
Figure 5G:
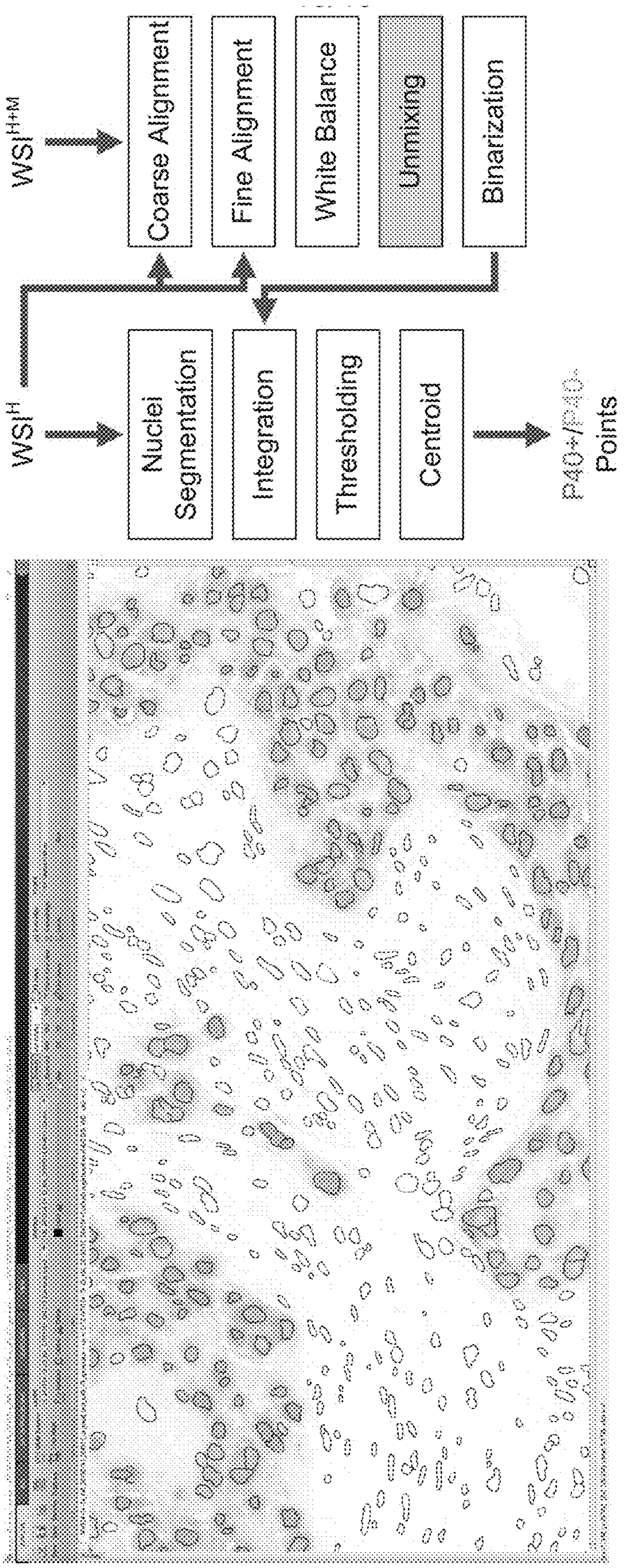
Figure 5H:
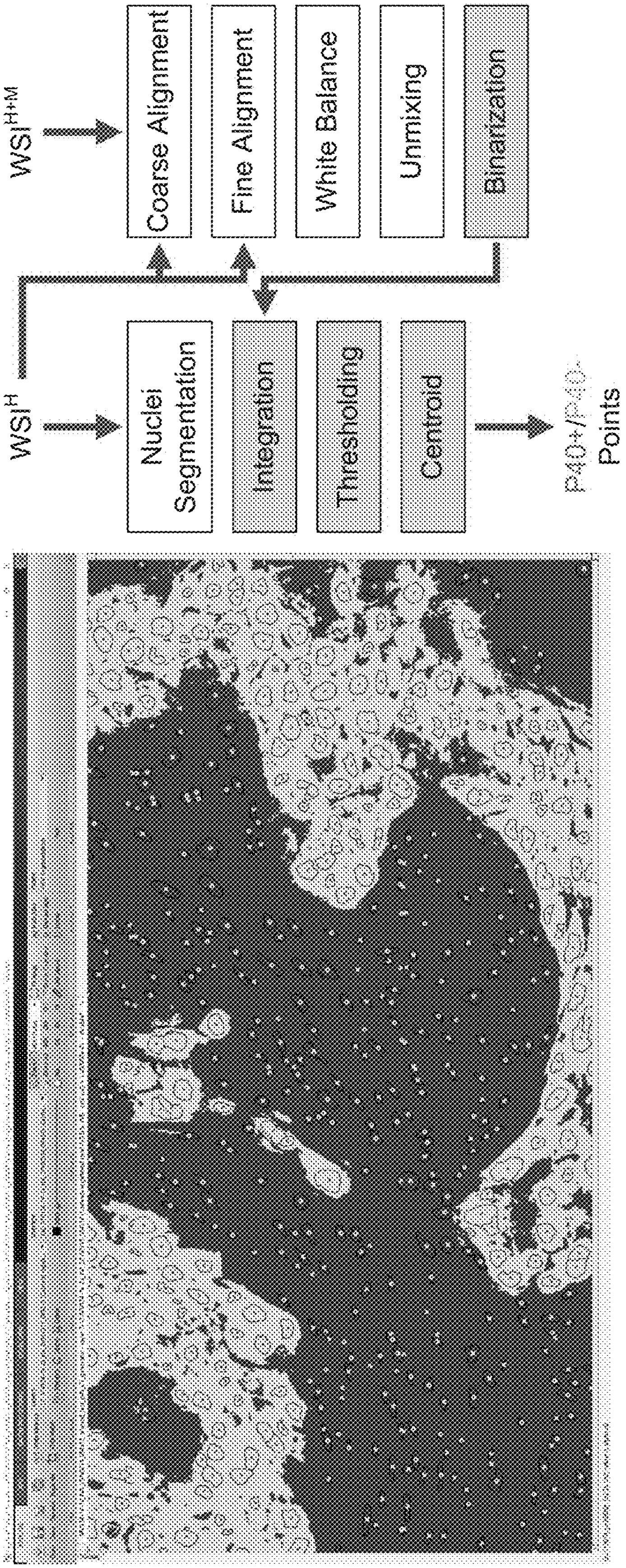
Figure 5I:
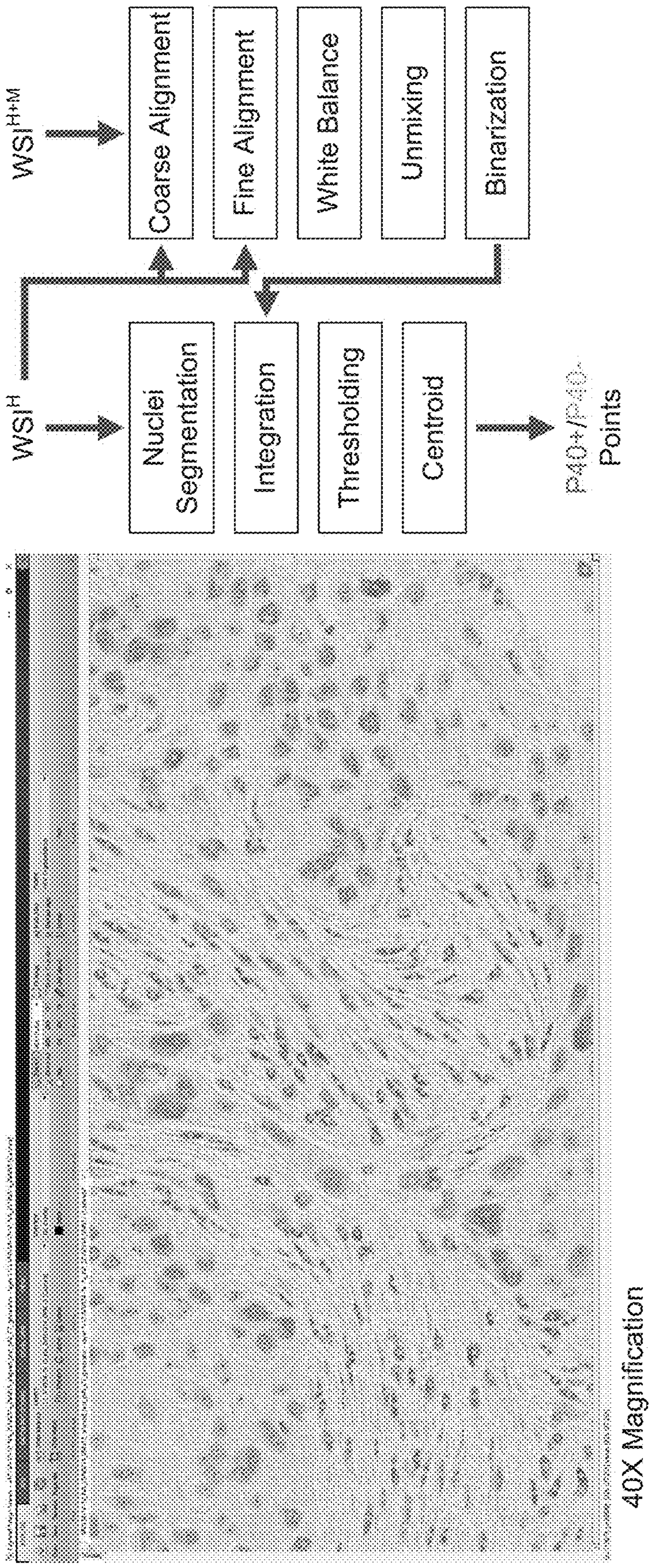
Figure 5J:
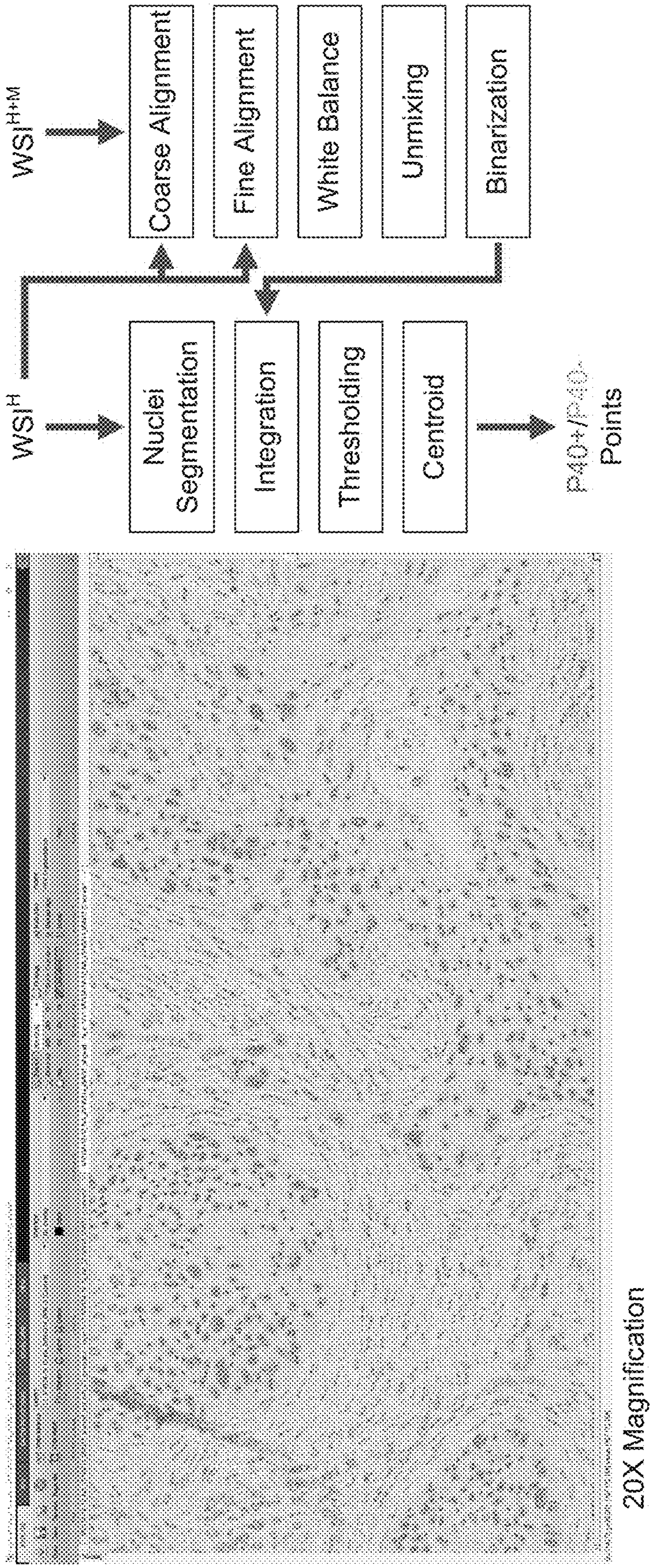
Figure 5K:
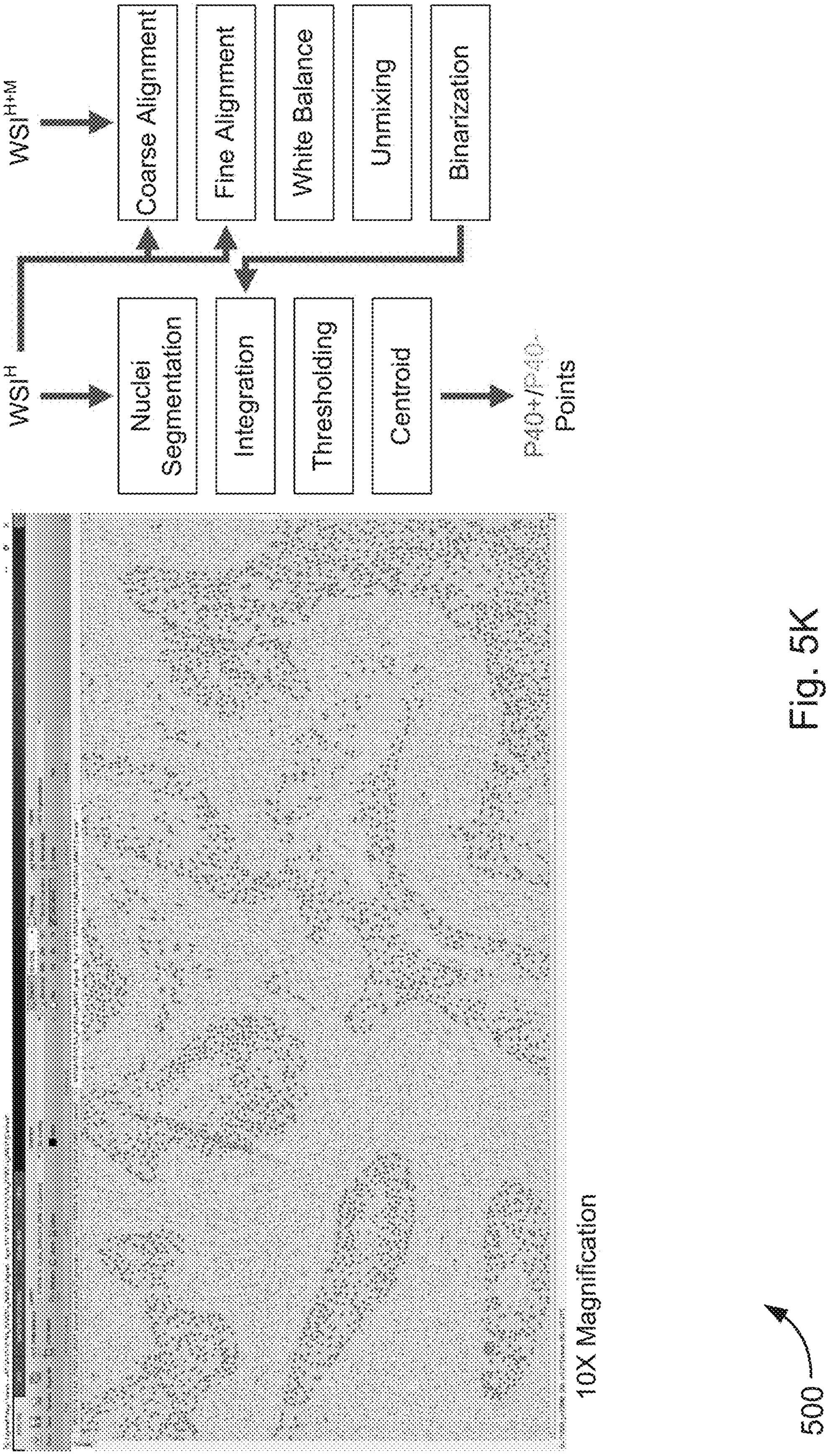
Figure 5L:
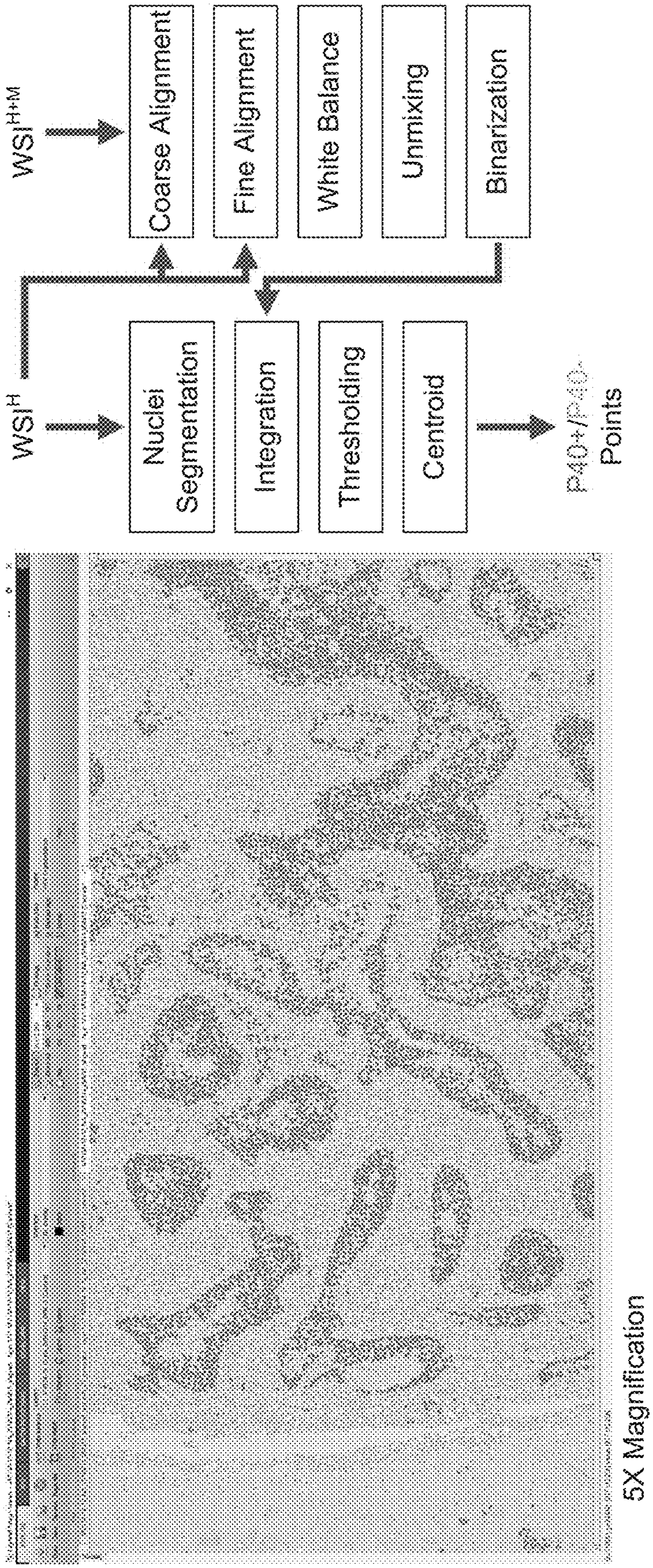
Figure 5M:
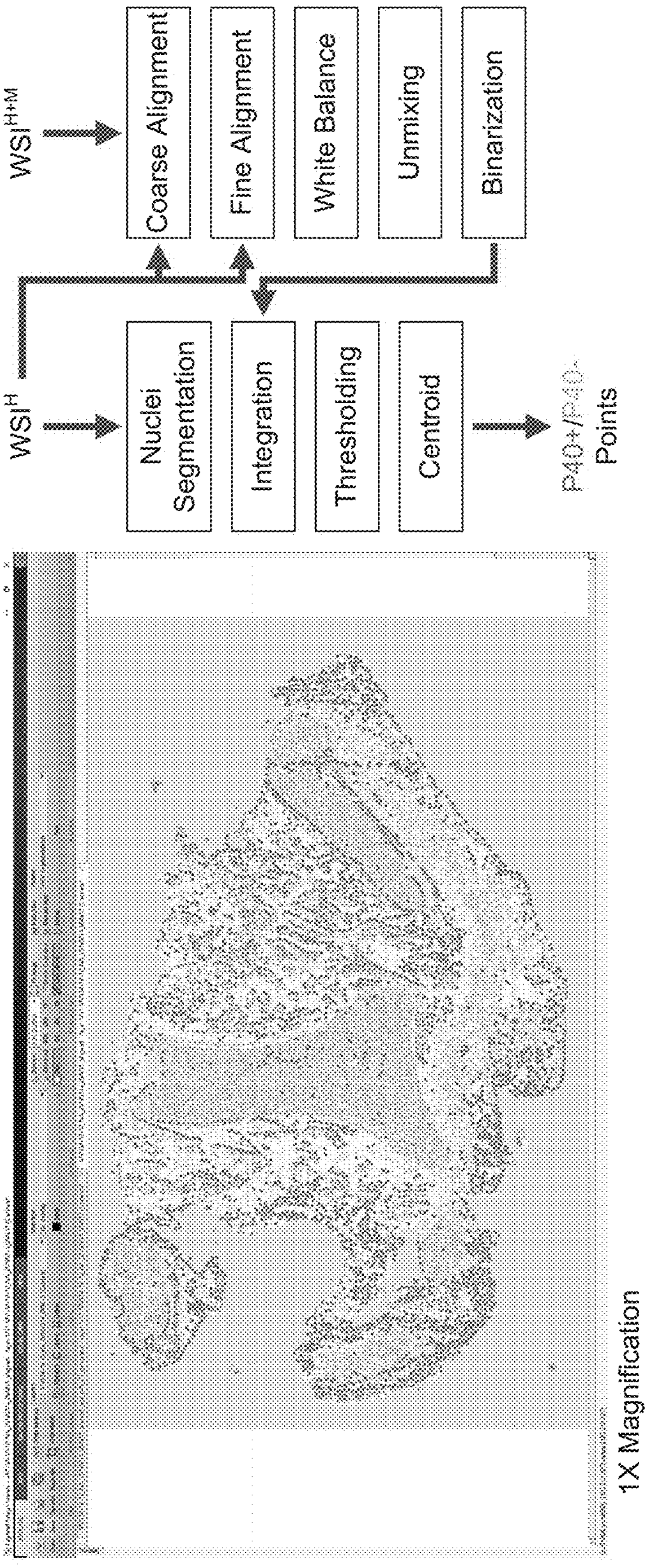
Figure 5N:
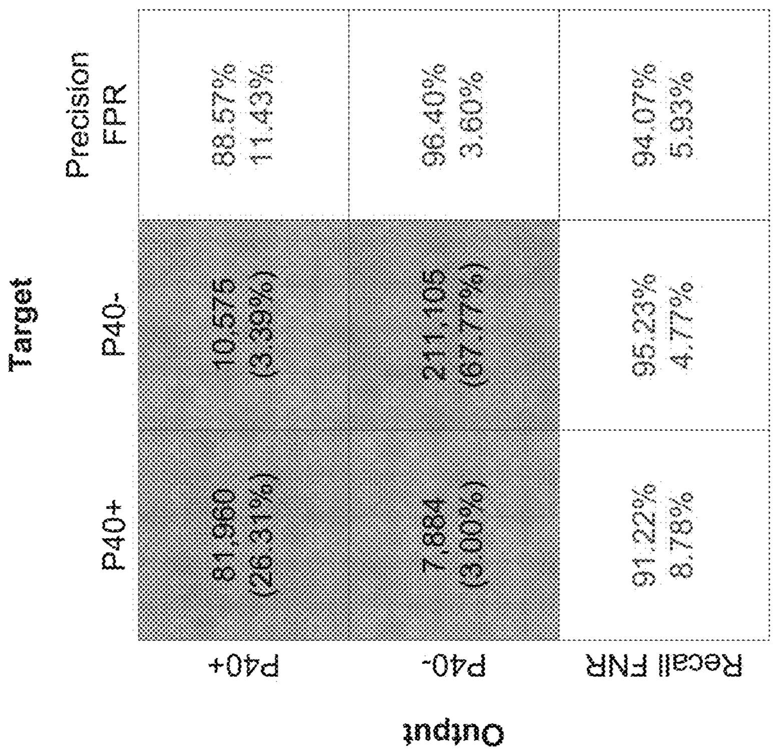

FIGS. 5A-5N (collectively, "FIG. 5") are schematic diagrams illustrating a non-limiting example 500 of various process steps performed by the system when implementing sequential imaging of biological samples for generating training data for developing deep learning based models for image analysis, for cell classification, and/or for features of interest identification of biological samples in conjunction with corresponding images of the biological sample during each process (and in some cases, at varying levels of magnification), in accordance with various embodiments.

Although FIG. 5 is focused on specific examples that utilize particular components (including, but not limited to, whole slide images ("WSIs"), nuclei segmentation, using hematoxylin ("H") and the combination of H and Magenta (e.g., attached/staining p40 antibody, or the like) ("H+M"), generating p40 ground truth, using alignment of images, etc.) in a particular order, the various embodiments are not so limited, and some of these components may be replaced with other types of components, may be omitted, may be reordered, or may otherwise by changed, as necessary or as desired, without deviating from the scope of the various embodiments. For instance, images of biological samples other than WSIs may be used, detection of other features of interest (not necessarily nuclei or cells) may be utilized, stains other than H or H+M may be used, ground truth other than for p40 antibody based ground truth may be generated, and/or images may already have been aligned or do not require alignment, or the like.

The non-limiting embodiment 500 of FIG. 5 demonstrates automatic processing of p40-positive (or p40+) tumor nuclear marker in squamous cell carcinoma sequential stain tissue slides for ground truth generation (i.e., by cell classifier G* without external labeling in pipeline A as shown in FIG. 4A). This ground truth is then used for training nuclei patch based classification deep neural network (i.e., cell classifier G in pipeline A as shown in FIG. 4A) on Hematoxylin patches extracted from WSI around detected nuclei. In some instances, classifier architecture known as Resnet50 or the like may be used. The cell classifier (or neural network) may be trained from scratch on one or more 101×101×RGB Hematoxylin patches extracted from one or more WSIs. Performances of the trained classifier, evaluated on validation FOVs (similar to that depicted in FIG. 8E, or the like), that were not used during training, from the same WSIs, can be seen in the confusion matrix shown in FIG. 5N.

With reference to FIGS. 5A-5M, an alternative depiction of computational pipeline A for WSI ground truth generator from sequential stains for training nuclei patch based classification deep neural network is shown in (a). A Hematoxylin patch is shown in (b) as well as in FIG. 5B, while a Hematoxylin patch overlaid with segmented nuclei is shown in (c) as well as in FIG. 5C, and an aligned Hematoxylin+ p40 Magenta marker patch overlaid with segmented nuclei from Hematoxylin patch is shown in (d) as well as in FIG. 5D or FIG. 5E. The patch as depicted in (d) after unmixing following white balancing is shown in (e) as well as in FIG. 5F or FIG. 5G. The patch as depicted in (e) after binarization, integration over segmented nuclei, thresholding, and grouping calculated nuclei centroids to p40+(pink colored points) and p40− (cyan colored points) is shown in (f) as well as in FIG. 5H. The resultant patch depicting nuclei shown as p40+(pink colored points) and p40− (cyan colored points) is shown in (g) as well as in FIG. 5I. The patches shown in (a)-(g) as well as in FIGS. 5B-5I are depicted in 40× magnification. 10× magnification Hematoxylin region marked in p40+/p40− points is shown in (h). FIG. 5J illustrates the patch as depicted FIG. 5I in 20× magnification, while FIGS. 5K, 5L, and 5M illustrate the patch as depicted FIG. 5I in 10×, 5×, and 1× magnification, respectively. As shown in the non-limiting embodiment of FIG. 5M, the whole slide image may contain 420,016 nuclei, 95,751 p40+, and 324,265 p40−.

FIG. 5N depicts a non-limiting example of evaluation of trained nuclei patch based classification deep neural network on validation FOVs from 11 WSIs, embodied by a confusion matrix. The output and target represent the predicted and ground truth classes, respectively. Precision and recall are represented by blue colored numbers. False negative rate ("FNR") and false positive rate ("FPR") are represented by red colored numbers. The cell in the bottom right of the confusion matrix depicts the overall accuracy in blue colored numbers. For the classification evaluated in the accuracy, precision, recall, confusion matrix of FIG. 5N, the Resnet50 was trained from scratch using about 3 million nuclei from the 11 WSIs, with evaluation of 0.3 million validation nuclei from 11 WSIs.

FIGS. 6A-6E (collectively, "FIG. 6") are flow diagrams illustrating a method 600 for implementing sequential imaging of biological samples for generating training data for developing deep learning based models for image analysis, for cell classification, and/or for features of interest identification of biological samples, in accordance with various embodiments. Method 600 of FIG. 6A continues onto FIG. 6B following the circular marker denoted, "A," and returns to FIG. 6A following the circular marker denoted, "B." Method 600 of FIG. 6A continues onto FIG. 6C following the circular marker denoted, "C."

While the techniques and procedures are depicted and/or described in a certain order for purposes of illustration, it should be appreciated that certain procedures may be reordered and/or omitted within the scope of various embodiments. Moreover, while the method 600 illustrated by FIG. 6 can be implemented by or with (and, in some cases, are described below with respect to) the systems, examples, or embodiments 300, 400, 400', 400", and 500 of FIGS. 3, 4A, 4B, 4C, and 5, respectively (or components thereof), such methods may also be implemented using any suitable hardware (or software) implementation. Similarly, while each of the systems, examples, or embodiments 300, 400, 400', 400", and 500 of FIGS. 3, 4A, 4B, 4C, and 5, respectively (or components thereof), can operate according to the method 600 illustrated by FIG. 6 (e.g., by executing instructions embodied on a computer readable medium), the systems, examples, or embodiments 300, 400, 400', 400", and 500 of FIGS. 3, 4A, 4B, 4C, and 5 can each also operate according to other modes of operation and/or perform other suitable procedures.

Figure 6A:
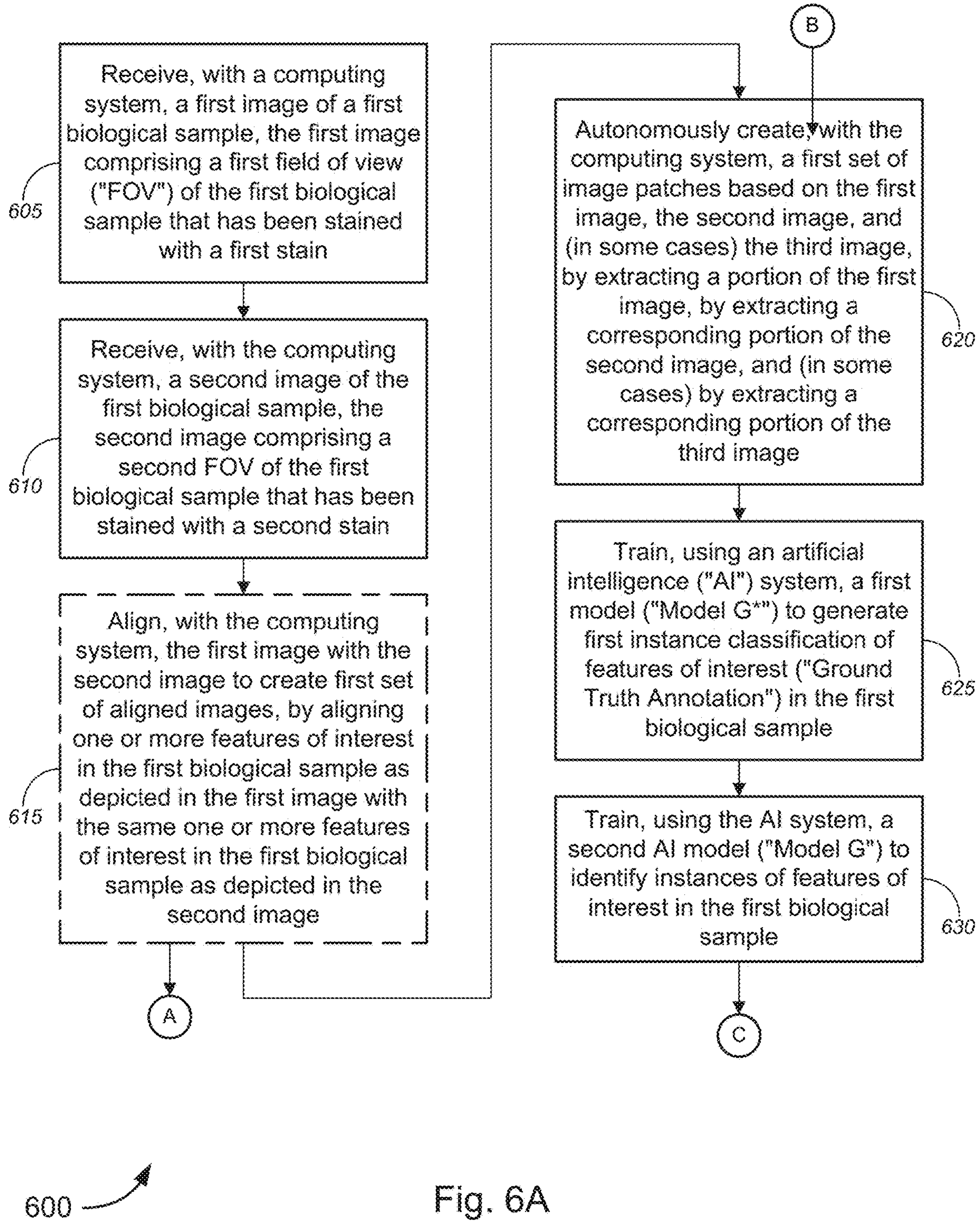

In the non-limiting embodiment of FIG. 6A, method 600, at block 605, may comprise receiving, with a computing system, a first image of a first biological sample, the first image comprising a first field of view ("FOV") of the first biological sample that has been stained with a first stain. Method 600 may comprise receiving, with the computing system, a second image of the first biological sample, the second image comprising a second FOV of the first biological sample that has been stained with a second stain (block 610).

In some embodiments, the computing system may include, without limitation, one of a computing system disposed in a work environment, a remote computing system disposed external to the work environment and accessible over a network, a web server, a web browser, or a cloud computing system, and/or the like. In some instances, the work environment may include, but is not limited to, at least one of a laboratory, a clinic, a medical facility, a research facility, a healthcare facility, or a room, and/or the like. In some cases, the first biological sample may include, without limitation, one of a human tissue sample, an animal tissue sample, a plant tissue sample, or an artificially produced tissue sample, and/or the like, and the features of interest may include, but are not limited to, at least one of normal cells, abnormal cells, damaged cells, cancer cells, tumors, subcellular structures, or organ structures, and/or the like.

Merely by way of example, in some cases, the first image may comprise highlighting of first features of interest in the first biological sample (including, but not limited to, at least one of first antigens, first nuclei, first cell walls, first cell structures, first antibodies, first normal cells, first abnormal cells, first damaged cells, first cancer cells, first tumors, first subcellular structures, first organ structures, or other features of interest, or the like) by the first stain that had been applied to the first biological sample. The second image may comprise one of highlighting of second features of interest in the first biological sample (including, but not limited to, at least one of second antigens, second nuclei, second cell walls, second cell structures, second antibodies, second normal cells, second abnormal cells, second damaged cells, second cancer cells, second tumors, second subcellular structures, second organ structures, or other features of interest, or the like) by the second stain that had been applied to the first biological sample in addition to highlighting of the first features of interest by the first stain or highlighting of the second features of interest by the second stain without highlighting of the first features of interest by the first stain, the second features of interest being different from the first features of interest. In some instances, the second stain may be one of the same as the first stain but used to stain the second features of interest or different from the first stain.

According to some embodiments, the first stain and the second stain may each include, without limitation, at least one of Hematoxylin, Acridine orange, Bismarck brown, Carmine, Coomassie blue, Cresyl violet, Crystal violet, 4',6-diamidino-2-phenylindole ("DAPI"), Eosin, Ethidium bromide intercalates, Acid fuchsine, Hoechst stain, Iodine, Malachite green, Methyl green, Methylene blue, Neutral red, Nile blue, Nile red, Osmium tetroxide, Propidium Iodide, Rhodamine, Safranine, programmed death-ligand 1 ("PD-L1") stain, 3,3'-Diaminobenzidine ("DAB") chromogen, Magenta chromogen, cyanine chromogen, cluster of differentiation ("CD") 3 stain, CD20 stain, CD68 stain, 40S ribosomal protein SA ("p40") stain, antibody-based stain, or label-free imaging marker, and/or the like.

In some embodiments, the first image may include, but is not limited to, one of a first set of color or brightfield images, a first fluorescence image, a first phase image, or a first spectral image, and/or the like. The first set of color or brightfield images may include, without limitation, a first red-filtered ("R") image, a first green-filtered ("G") image, and a first blue-filtered ("B") image, and/or the like. The first fluorescence image may include, but is not limited to, at least one of a first autofluorescence image or a first labelled fluorescence image having one or more channels with different excitation or emission characteristics, and/or the like. The first spectral image may include, but is not limited to, at least one of a first Raman spectroscopy image, a first near infrared ("NIR") spectroscopy image, a first multispectral image, a first hyperspectral image, or a first full spectral image, and/or the like. Similarly, the second image may include, but is not limited to, one of a second set of color or brightfield images, a second fluorescence image, a second phase image, or a second spectral image, and/or the like. The second set of color or brightfield images may include, without limitation, a second R image, a second G image, and a second B image, and/or the like. The second fluorescence image may include, but is not limited to, at least one of a second autofluorescence image or a second labelled fluorescence image having one or more channels with different excitation or emission characteristics, and/or the like. The second spectral image may include, but is not limited to, at least one of a second Raman spectroscopy image, a second NIR spectroscopy image, a second multispectral image, a second hyperspectral image, or a second full spectral image, and/or the like.

At optional block 615, method 600 may comprise aligning, with the computing system, the first image with the second image to create first set of aligned images, by aligning one or more features of interest in the first biological sample as depicted in the first image with the same one or more features of interest in the first biological sample as depicted in the second image. In some instances, aligning the first image with the second image may either be performed manually using manual inputs to the computing system or performed autonomously, where autonomous alignment may comprise alignment using at least one of automated global alignment techniques or optical flow alignment techniques, or the like.

Method 600 may continue onto the process at block 620. Alternatively, method 600 may continue onto the process at block 635 in FIG. 6B following the circular marker denoted, "A," and may return from FIG. 6B to the process at block 620 in FIG. 6A following the circular marker denoted, "B."

Figure 6B:
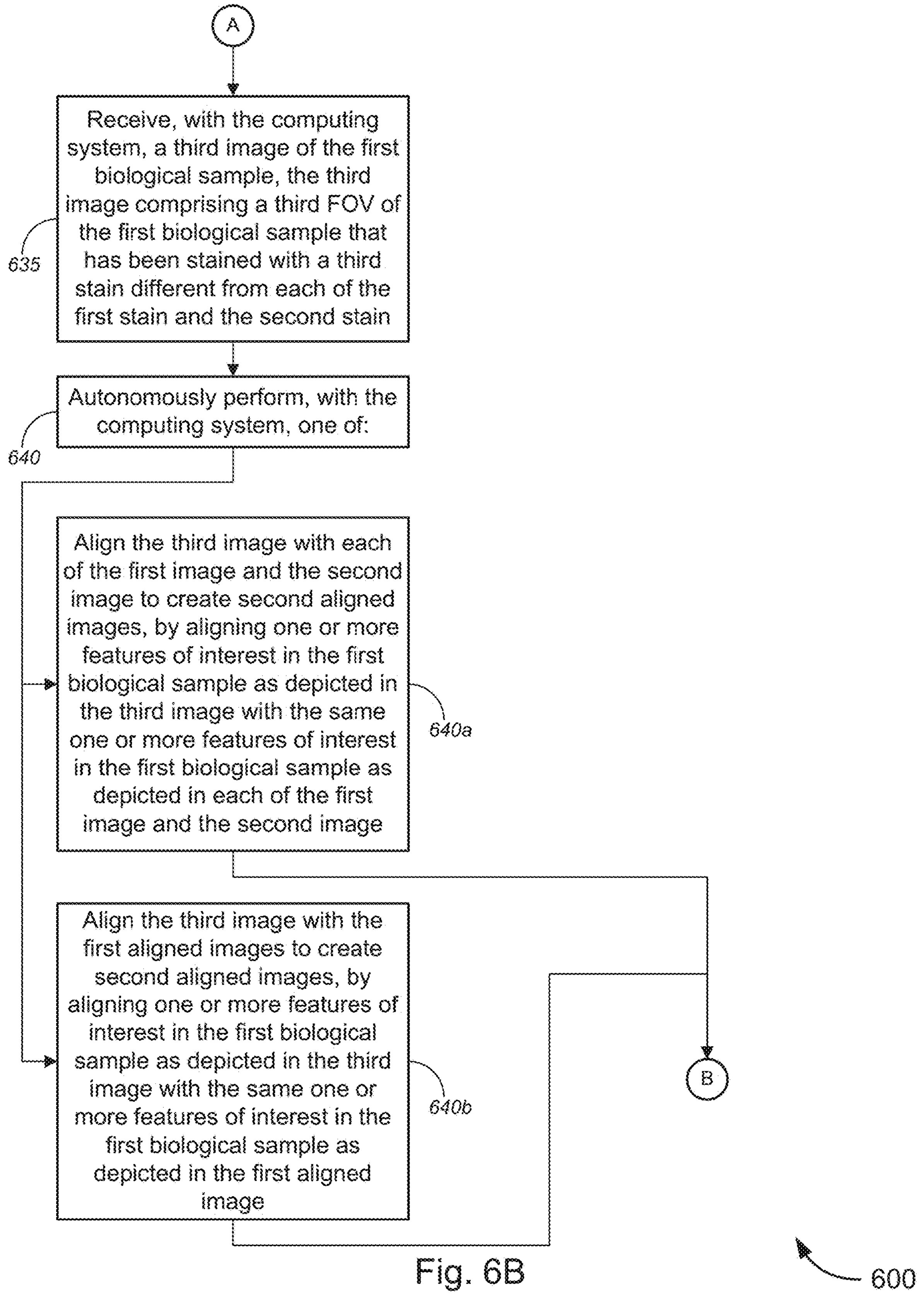

At block 635 in FIG. 6B (following the circular marker denoted, "A"), method 600 may comprise receiving, with the computing system, a third image of the first biological sample, the third image comprising a third FOV of the first biological sample that has been stained with a third stain different from each of the first stain and the second stain. Method 600 may further comprise, at block 640, autonomously performing, with the computing system, one of: aligning the third image with each of the first image and the second image to create second aligned images, by aligning one or more features of interest in the first biological sample as depicted in the third image with the same one or more features of interest in the first biological sample as depicted in each of the first image and the second image (block 640*a*); or aligning the third image with the first aligned images to create second aligned images, by aligning one or more features of interest in the first biological sample as depicted in the third image with the same one or more features of interest in the first biological sample as depicted in the first aligned images (block 640*b*). Method 400 may return to the process at block 620 in FIG. 6A following the circular marker denoted, "B."

Method 600 may further comprise, at block 620, autonomously creating, with the computing system, a first set of image patches based on the first image and the second image (and, in some cases, the third image), by extracting a portion of the first image and by extracting a corresponding portion of the second image (and, in some cases, by extracting a corresponding portion of the third image). In some cases, the first set of image patches may include, without limitation, a first patch corresponding to the extracted portion of the first image and a second patch corresponding to the extracted portion of the second image (and, in some cases, a third patch corresponding to the extracted portion of the third image). In some instances, the first set of image patches may comprise labeling of instances of features of interest in the first biological sample that is based at least in part on at least one of information contained in the first patch, information contained in the second patch, information contained in one or more external labeling sources, and/or information contained in the third patch (if applicable).

In some cases, the third image may comprise one of highlighting of third features of interest in the first biological sample (including, but not limited to, at least one of third antigens, third nuclei, third cell walls, third cell structures, third antibodies, third normal cells, third abnormal cells, third damaged cells, third cancer cells, third tumors, third subcellular structures, third organ structures, or other features of interest, or the like) by the third stain that had been applied to the first biological sample in addition to highlighting of the first features of interest by the first stain and highlighting of the second features of interest by the second stain, highlighting of the third features of interest by the third stain in addition to only one of highlighting of the first features of interest by the first stain or highlighting of the second features of interest by the second stain, or highlighting of the third features of interest by the third stain without any of highlighting of the first features of interest by the first stain or highlighting of the second features of interest by the second stain, the third features of interest being different from each of the first features of interest and the second features of interest.

In some instances, the third image may include, but is not limited to, one of a third set of color or brightfield images, a third fluorescence image, a third phase image, or a third spectral image, and/or the like. The third set of color or brightfield images may include, without limitation, a third R image, a third G image, and a third B image, and/or the like. The third fluorescence image may include, but is not limited to, at least one of a third autofluorescence image or a third labelled fluorescence image having one or more channels with different excitation or emission characteristics, and/or the like. The third spectral image may include, but is not limited to, at least one of a third Raman spectroscopy image, a third NIR spectroscopy image, a third multispectral image, a third hyperspectral image, or a third full spectral image, and/or the like.

Method 600 may further comprise training, using an artificial intelligence ("AI") system, a first model ("Model G*") to generate first instance classification of features of interest ("Ground Truth") in the first biological sample, based at least in part on the first set of image patches and the labeling of instances of features of interest contained in the first set of image patches (block 625); and training, using the AI system, a second AI model ("Model G") to identify instances of features of interest in the first biological sample, based at least in part on the first patch and the first instance classification of features of interest generated by Model G* (block 630). In some embodiments, the AI system may include, but is not limited to, at least one of a machine learning system, a deep learning system, a model architecture, a statistical model-based system, or a deterministic analysis system, and/or the like. In some instances, the model architecture may comprise at least one of a neural network, a convolutional neural network ("CNN"), or a fully convolutional network ("FCN"), and/or the like.

Figure 6C:
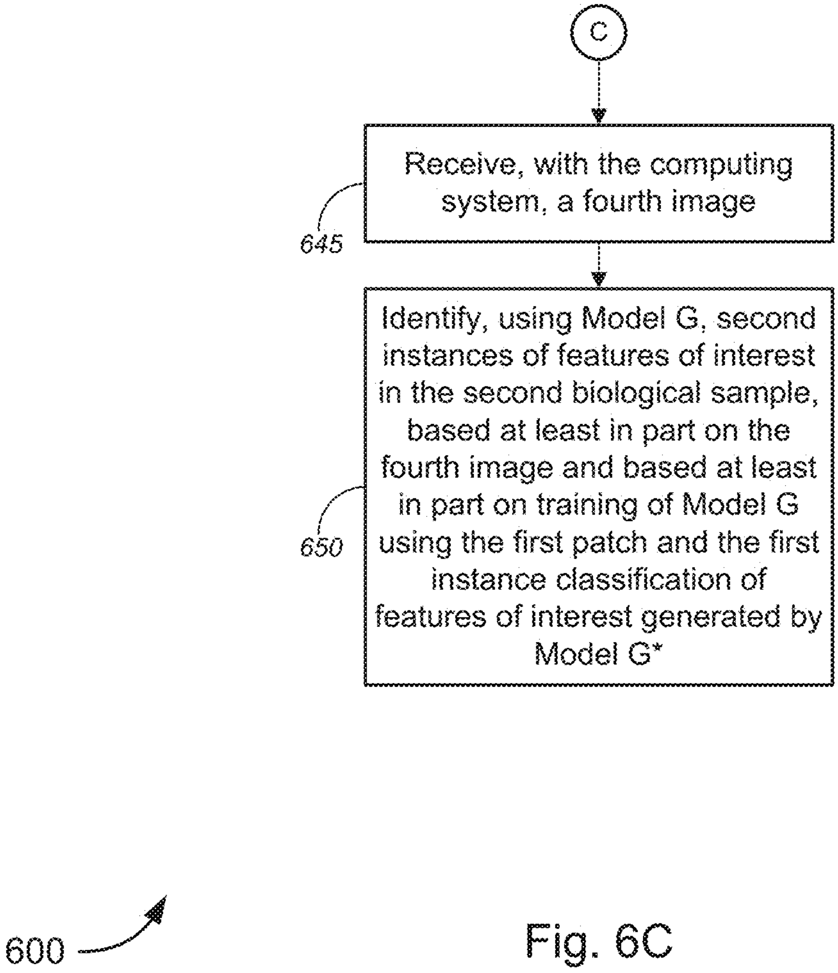

Method 600 may continue onto the process at block 645 in FIG. 6C following the circular marker denoted, "C."

At block 645 in FIG. 6C (following the circular marker denoted, "C"), method 600 may comprise receiving, with the computing system, a fourth image, the fourth image comprising one of a fourth FOV of the first biological sample different from the first FOV and the second FOV or a fifth FOV of a second biological sample, where the second biological sample is different from the first biological sample. Method 600 may further comprise, at block 650, identifying, using Model G, second instances of features of interest in the second biological sample, based at least in part on the fourth image and based at least in part on training of Model G using the first patch and the first instance classification of features of interest generated by Model G*. In some cases, the fourth image may comprise the fifth FOV and may further comprise only highlighting of first features of interest in the second biological sample by the first stain that had been applied to the second biological sample. According to some embodiments, method 600 may further comprise generating, using Model G, a clinical score, based at least in part on the identified second instances of features of interest.

With reference to FIG. 6D, method 600 may comprise receiving, with a computing system, first instance classification of features of interest ("Ground Truth") in a first biological sample that has been sequentially stained, the Ground Truth having been generated by a trained first model ("Model G*") that has been trained or updated by an artificial intelligence ("AI") system (block 655); and training, using the AI system, a second AI model ("Model G") to identify instances of features of interest in the first biological sample, based at least in part on the first instance classification of features of interest generated by Model G* (block 660). In some cases, the Ground Truth may be generated by using first aligned image patches and labeling of instances of features of interest contained in the first aligned image patches, wherein the first aligned image patches comprise an extracted portion of first aligned images, wherein the first aligned images comprise a first image and a second image that have been aligned, wherein the first image comprises a first FOV of the first biological sample that has been stained with a first stain, wherein the second image comprises a second FOV of the first biological sample that has been stained with a second stain, wherein the first aligned image patches comprise labeling of instances of features of interest as shown in the extracted portion of the first aligned images.

Referring to FIG. 6E, method 600 may comprise, at block 665, receiving, with a computing system, a first image of a first biological sample, the first image comprising a first field of view ("FOV") of the first biological sample. At block 670, method 600 may comprise identifying, using a first artificial intelligence ("AI") model ("Model G") that is trained by an AI system, first instances of features of interest in the first biological sample, based at least in part on the first image and based at least in part on training of Model G using a first patch and first instance classification of features of interest generated by a second model (Model G*) that is trained by the AI system by using first aligned image patches and labeling of instances of features of interest contained in the first patch. In some instances, the first aligned image patches may comprise an extracted portion of first aligned images. The first aligned images may comprise a second image and a third image that have been aligned. The second image may comprise a second FOV of a second biological sample that has been stained with a first stain, the second biological sample being different from the first biological sample. The third image may comprise a third FOV of the second biological sample that has been stained with a second stain. The second patch may comprise labeling of instances of features of interest as shown in the extracted portion of the second image of the first aligned images. The first image may comprise highlighting of first features of interest in the second biological sample by the first stain that had been applied to the second biological sample. The second patch may comprise one of highlighting of second features of interest in the second biological sample by the second stain that had been applied to the second biological sample in addition to highlighting of the first features of interest by the first stain or highlighting of the second features of interest by the second stain without highlighting of the first features of interest by the first stain.

FIGS. 7A-7D (collectively, "FIG. 7") are process flow diagrams illustrating various non-limiting examples 700, 700", and 700''' of training of an artificial intelligence ("AI") model to generate a virtual stain and a non-limiting example 700' of inferencing performed by a trained AI model when implementing sequential imaging of biological samples for generating training data for developing deep learning based models for virtual staining of biological samples and for generating training data for developing deep learning based models for image analysis, cell classification, and/or features of interest identification of biological samples, in accordance with various embodiments. FIG. 7 is directed to the process of generating virtual staining for simulating sequential staining of biological samples for developing accurate AI models for biological image interpretation. Such a process, in some cases, may be performed by computing system 305*a* or 305*b* and/or AI system 305*d* or 305*c* (collectively, "computing system") of FIG. 3, or the like.

Although FIG. 7 is focused on specific examples that utilize particular components (including, but not limited to, whole slide images ("WSIs"), nuclei detection, using pairs of patches or images, using alignment of images, etc.) in a particular order, the various embodiments are not so limited, and some of these components may be replaced with other types of components, may be omitted, may be reordered, or may otherwise by changed, as necessary or as desired, without deviating from the scope of the various embodiments. For instance, images of biological samples other than WSIs may be used, detection of other features of interest (not necessarily nuclei or cells) may be utilized, sets of three or more patches or images may be used rather than pairs, and/or images may already have been aligned or do not require alignment, or the like. Further, although specific examples of biological markers or stains may be referred to with respect to FIG. 7, this is merely for purposes of illustration, and the various embodiments are not so limited, as any suitable biological marker(s) and/or stain(s) may be used, as appropriate or as desired.

With reference to the non-limiting embodiment 700 of FIG. 7A, a first image 705 of a first biological sample and a second image 710 of the first biological sample may be received. According to some embodiments, the first biological sample may include, without limitation, one of a human tissue sample, an animal tissue sample, a plant tissue sample, or an artificially produced tissue sample, and/or the like. The first image 705 (which may comprise a WSI, although not limited to such) may include a first field of view ("FOV") of the first biological sample that has been stained with a first stain. The second image 710 (which may comprise a WSI, although not limited to such) may include a second FOV of the first biological sample that has been stained with a second stain. In some cases, while the first image 705 may include highlighting of first features of interest in the first biological sample (including, but not limited to, at least one of first antigens, first nuclei, first cell walls, first cell structures, first antibodies, first normal cells, first abnormal cells, first damaged cells, first cancer cells, first tumors, first subcellular structures, first organ structures, or other features of interest, or the like) by the first stain, the second image 710 may include either highlighting of second features of interest in the first biological sample (including, but not limited to, at least one of second antigens, second nuclei, second cell walls, second cell structures, second antibodies, second normal cells, second abnormal cells, second damaged cells, second cancer cells, second tumors, second subcellular structures, second organ structures, or other features of interest, or the like) by the second stain in addition to highlighting of the first features of interest by the first stain or highlighting of the second features of interest by the second stain without highlighting of the first features of interest by the first stain. In some instances, the second features of interest may be different from the first features of interest.

In some embodiments, the second stain either may be the same as the first stain but used to stain the second features of interest or may be different from the first stain. In some instances, the first stain and the second stain may each include, but is not limited to, at least one of Hematoxylin, Acridine orange, Bismarck brown, Carmine, Coomassie blue, Cresyl violet, Crystal violet, 4',6-diamidino-2-phenylindole ("DAPI"), Eosin, Ethidium bromide intercalates, Acid fuchsine, Hoechst stain, Iodine, Malachite green, Methyl green, Methylene blue, Neutral red, Nile blue, Nile red, Osmium tetroxide, Propidium Iodide, Rhodamine, Safranine, programmed death-ligand 1 ("PD-L1") stain, 3,3'-Diaminobenzidine ("DAB") chromogen, Magenta chromogen, cyanine chromogen, cluster of differentiation ("CD") 3 stain, CD20 stain, CD68 stain, 40S ribosomal protein SA ("p40") stain, antibody-based stain, or label-free imaging marker, and/or the like. In some cases, the first image 705 and the second image 710 may each include, without limitation, one of a set of color or brightfield images, a fluorescence image, or a spectral image, and/or the like, where the set of color or brightfield images may include, but is not limited to, a red-filtered ("R") image, a green-filtered ("G") image, and a blue-filtered ("B") image, and/or the like.

As depicted in FIG. 7A (with the notation "WSI" being at a different angle in the second image 710 compared with corresponding notation in the first image 705), the first image 705 and the second image 710 may initially be misaligned, and thus may require alignment by alignment system 715. The alignment system 715 may perform alignment of the first image 705 relative to the second image 710 (or vice versa) either using manual input from a user (e.g., pathologist or other operator, or the like) or via autonomous alignment processes (in some cases, utilizing AI system functionality, or the like). In some cases, autonomous alignment may include, but is not limited to, alignment using at least one of automated global alignment techniques or optical flow alignment techniques, or the like.

In some embodiments, automated global alignment may include the following computational details: (i) finding foreground tiles (in some cases, using entropy threshold criterion, or the like); (ii) performing feature-based (e.g., with oriented fast and rotated brief ("ORB") features, or the like) matching on low resolution images (e.g., default pyramid level 4, or the like); and (iii) computing affine alignment transformation from matched features. Computational steps (i) to (iii) are applicable to both serial and sequential staining. For sequential staining, the following additional details may apply for automated global alignment: (iv) finding all high resolution (e.g., level 0) tiles spanning the matched low resolution features; (v) matching high resolution tiles based on low resolution alignment; (vi) performing feature based matching on high resolution features within matched tiles; and (vii) computing global affine alignment as composition of the high and low resolution alignment transformation matrices; and/or the like.

Even with sequential staining, there may be misalignments and deformations between scans. Global, affine alignment accounts for translation, rotation, or uniform deformation of the whole slide image, but cannot account for non-uniform deformation of the slide image. Large scale deformation may result in misalignment of paired FOVs, while small scale deformation may result in non-uniform misalignment within a FOV (which may be apparent as horizontal stretching of the FOV, for example). Such misalignment introduces noise to the training of models based on the sequentially stained image as ground truth. Alignment characterization may be optimized as follows: (a) optimization may be performed on either H channel alone, or on the sum of H+DAB channels (combined); (b) optimization may be performed by non-overlapping square micro-patches of equal size having patch sides in 1000, 500, 100, or 50 pixels in length; (c) manual global rigid alignment may be performed for micro-patch matching; (d) for each patch-pair, rigid transform (i.e., rotation+translation) parameters may be found that minimize the mis-match cost; (e) no continuity constraints across patches may be enforced—free optimization; (f) several cost functions may be evaluated by patch-level random self-alignment test, with the best (most stable) results being attained by pixel-wise MSE (L2) loss or the like; and (g) each micro-patch may be padded by adding extra pixels around the patch to allow for required transformation range, which was not always possible (due to FOV edges).

Quantitative evaluation of alignment characterization may alternatively or additionally be performed as follows: (1) quantitative evaluation may be performed by measuring cell-center distances in paired FOVS, with FOVs annotated using the predictions of segmentation models, with segmentation net trained or retrained and running on the H channel only, and with centroids calculated using region_props from segmentation predictions; (2) annotation in paired FOVs may be matched by k=1 nearest neighbour ("NN") matching; (3) NN matching may be applied with threshold on NN distance ratio (k=1, 2); (4) NN matching may also be applied with threshold on a global distance threshold; and (5) matched distance histograms pre and post-optimization may be generated for each FOV. Distance histograms pre and post optimization for micro-patches may be used for quantitative evaluation of the alignment characterization.

According to some embodiments, optical flow alignment may utilize dense inverse search ("DIS"), which may include the following characteristics: (A) optical flow dense (per-pixel) displacement field; (B) "coarse to fine" micro-patch based optimization with partial patch overlap; (C) utilizing an open-sourced implementation (e.g., Python bindings to a C implementation, or the like); (D) integrating into a computing platform (e.g., Matlab calling Python, or the like); (E) the algorithm's patch size and overlap may be empirically tuned for robustness over various tissue samples and various image pyramid levels; and (F) achieving latency per tile (including padding) of <100 ms (in some evaluations, ~40-50 ms was achieved). The algorithm details for optical flow alignment may include the following: (I) dividing the image into a grid of equally sized micro-patches; (II) for each micro-patch in the image, finding the displacement to its optimal position in the paired image (under MSE loss, or the like); (III) starting with coarse (low resolution) patches, and using optimal displacement as the initial condition for the next (finer) level; (IV) overlapping partial micro-patch with similarity-weighted densification for continuity and smoothness; and (V) applying variational refinement on intensity functions for further smoothness and conservation constraints (e.g., divergence of brightness, color, and gradients, or the like). Distance histograms pre and post optimization for DIS may be used for quantitative evaluation of the optical flow alignment. In summary, to account for local, non-uniform deformations, a second tier of local alignment—namely, optical flow alignment—may be used. Optical flow alignment refines the global alignment. Optical flow alignment can account for paired-FOV misalignment as well as non-uniform misalignment within a FOV. With optical flow alignment, pixel-perfect registration of the sequentially stained images can be achieved.

In some cases, the received first and second images may be pre-aligned prior to being received, or may not require alignment (such as in the case of output images of a fluorescence staining scanning protocol, or the like), and thus alignment by the alignment system 715 may be omitted. After alignment (if needed), aligned image 720 may be used to extract at least one second image patch 725 (a plurality of which is depicted in FIG. 7A). In some instances, aligned image 720 may be divided into equal sized (and shaped) grids, with each image patch 725 representing a grid. In some cases, the grids may be of different sizes and/or different shapes (e.g., rectangles, squares, trapezoids, circles, triangles, or other polygons, etc.).

Meanwhile, a nuclei detection system 730 (or other feature detection system (not shown), or the like) may be used to detect nuclei (or other features of interest) in the first image 705, with the resultant image 735 being used to train a second cell classifier net, a second AI module, or a second model ("G*"; collectively, "second AI model G*" or "Model G*" or the like) 755. Unlike in the embodiment 400 of FIG. 4A, nuclei detection is not necessary for virtual staining, and thus at least one first image patch 740 (a plurality of which is depicted in FIG. 7A) is extracted from the first image 705 rather than image 735, in a similar manner as the at least one second image patch 725. Each of the at least one first image patch 740 may correspond to each of the at least one second image patch 725 to form patch pairs (although a set of corresponding three or more images, not limited to a pair, may be used, such as in the case of a third image (not shown) being used to highlight a third stain or a combination of stains).

The at least one first image patch 740 and the at least one second image patch 725 (or patch pairs, or the like) may serve as input images for training a first cell classifier net, a first AI module, or a first AI model ("F"; collectively, "first AI model F" or the like) 745, which may also be referred to herein as a "virtual staining generator" or the like. The first model G* 745 (which may, in some cases, receive external labelling data, or the like, in addition to the nuclei or other feature detection data, or the like) may generate a third patch or image 750 comprising a virtual stain of the first aligned image patches, based at least in part on the at least one first patch 725 and the at least one second patch 740, the virtual stain simulating staining by at least the second stain of features of interest in the first biological sample as shown in the at least one second patch 725.

The generated third patch or image 750, along with the image 735 (containing results of the nuclei or other feature detection, or the like) may be used as inputs to train the second AI model G 750 to identify instances of features of interest in the first biological sample. The process flow as depicted in FIG. 7A represents a computational pipeline (also referred to herein as "pipeline B") for using an AI model (in this case, model F) for generating virtual staining for simulating sequentially stained biological sample, and using such generated virtual staining to train another model (in this case, model G*) to identify features of interest in biological samples.

Figure 7B:
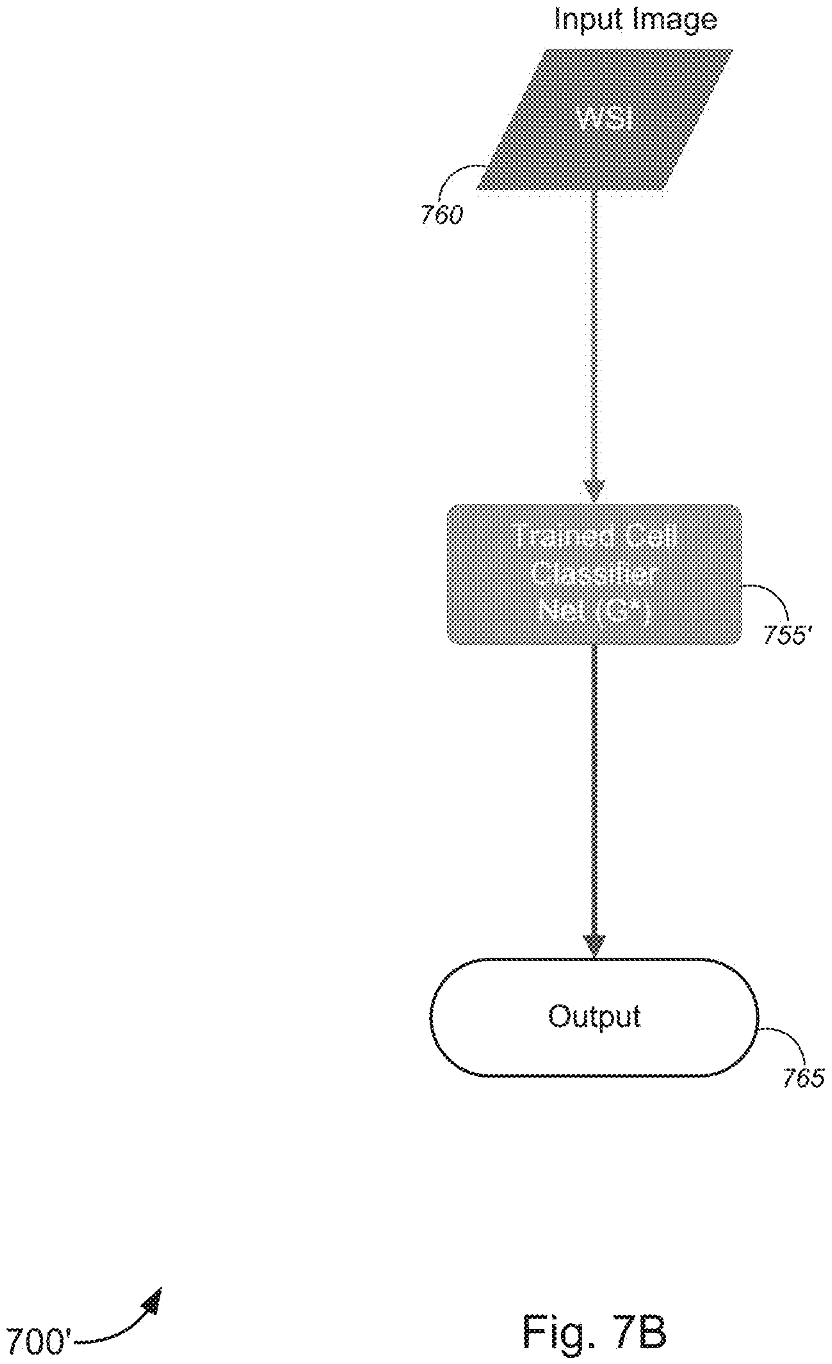

Turning to the non-limiting embodiment 700' of FIG. 7B, after the second AI model G has been trained, the second AI model G 755' may be used to receive as an input, input image 760, and to identify features of interest in input image 760 and to generate an output 765 containing labelling of identified features of interest in input image 760. In some embodiments, the output 765 may include, without limitation, at least one of a clinical score and/or a labelled image (identifying features of interest), or the like. Such inferencing or overall scoring or diagnosis would improve upon the technical field of annotation collection or autonomous annotation collection, by improving precision and accuracy in identifying features of interest, avoiding observer/pathologist biases or human error effects, increasing the speed of annotation collection, while, in some cases, identifying features of interest that are difficult if not impossible for a human to identify. Additionally, pipeline B provides a simple, straight forward approach, with relatively low complexity (in some cases, using binary classification, or the like).

These and other features are similar, if not identical to the features, processes, and techniques described herein with respect to FIGS. 3-6, 8, and 9, or the like.

Figure 7C:
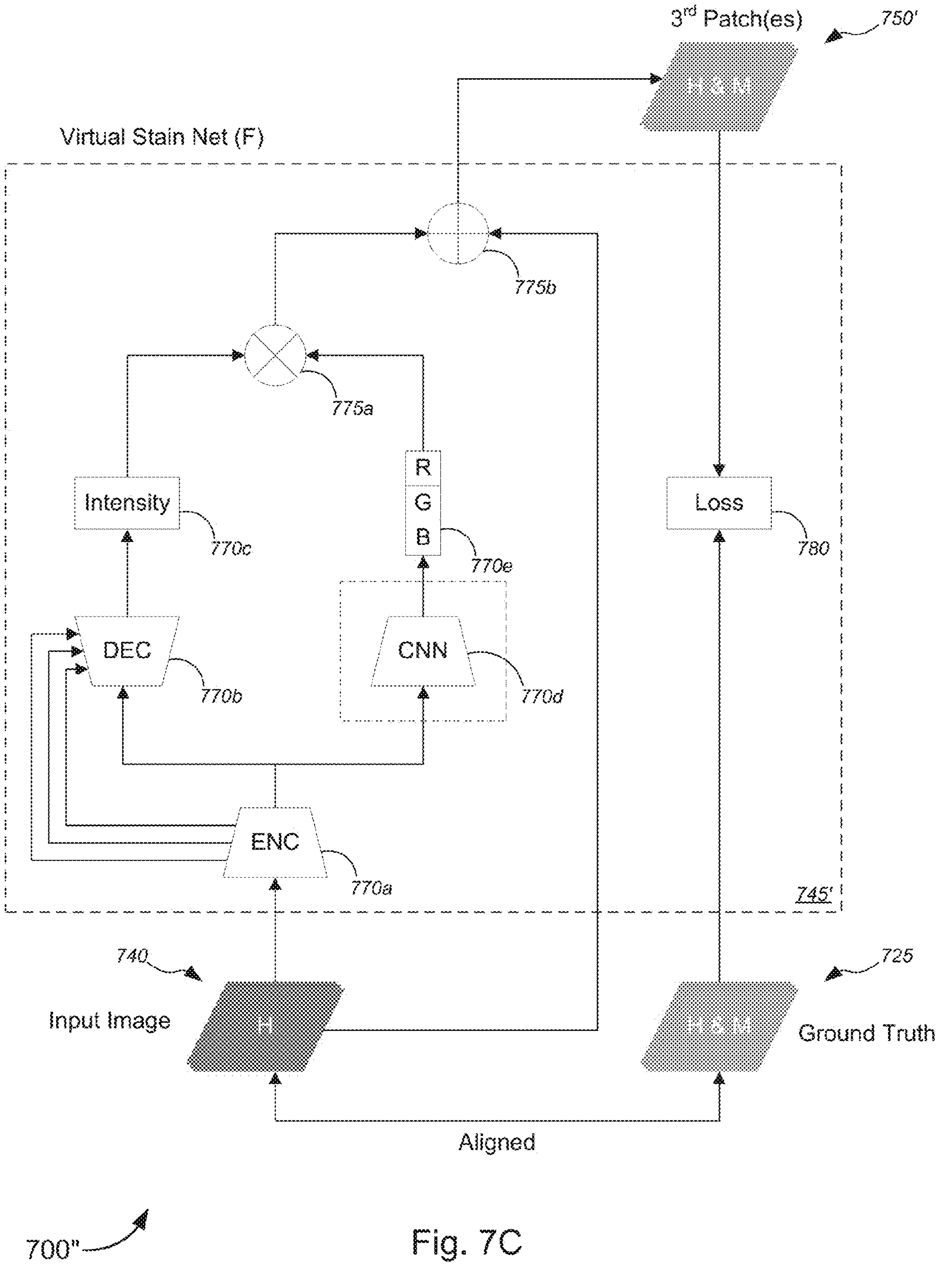
Figure 7D:
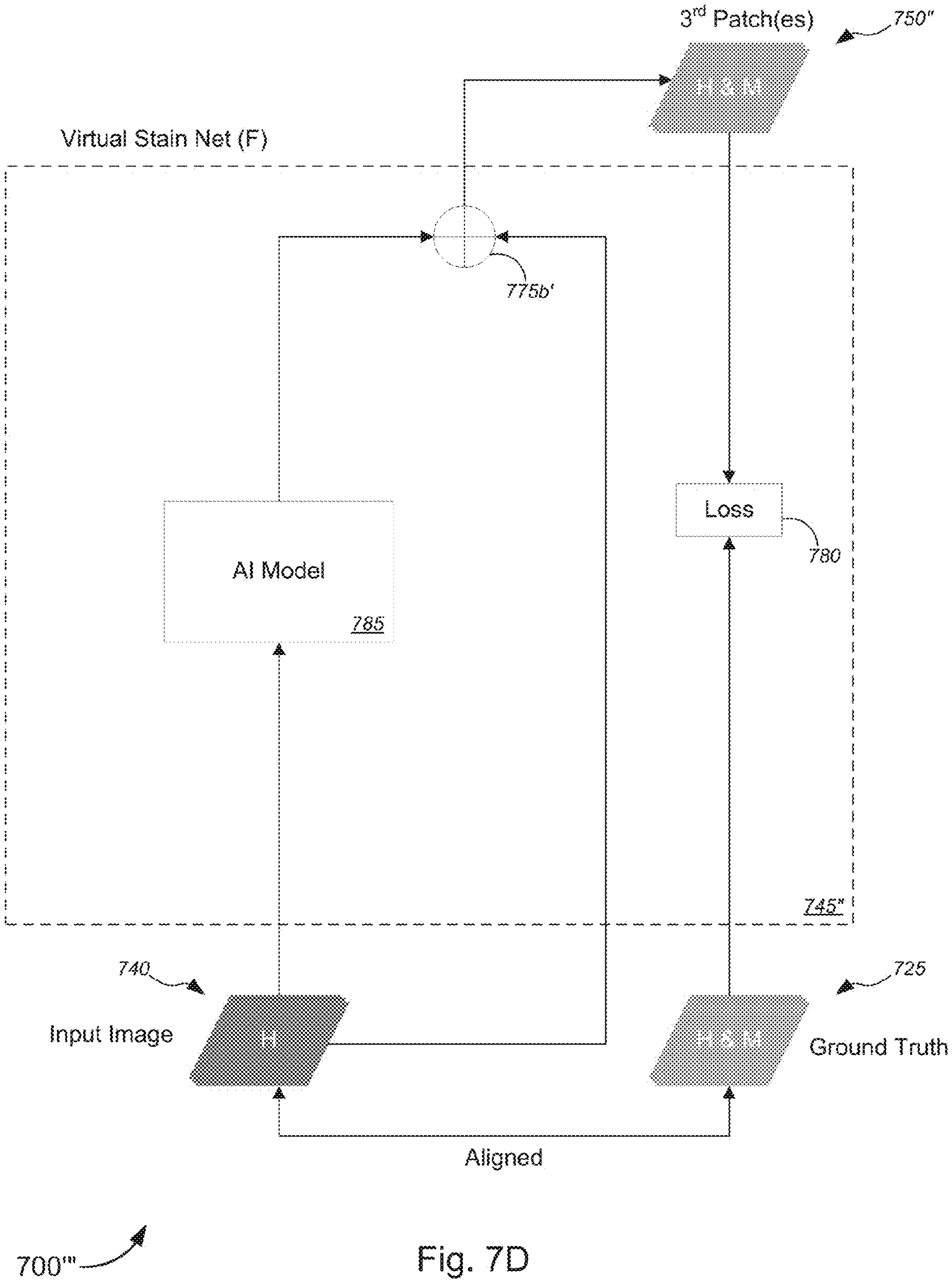

FIGS. 7C and 7D may illustrate various process flows depicting virtual staining performed by various embodiments of virtual stain net F or AI model F 745 of FIG. 7A. Although Hematoxylin stain and Hematoxylin plus Magenta sequential staining are depicted in FIGS. 7C and 7D for the input image 740 and the ground truth image 725, respectively, the various embodiments are not so limited, and the biological sample depicted in the input image 740 and in the ground truth image 725 may each include, without limitation, at least one of Hematoxylin, Acridine orange, Bismarck brown, Carmine, Coomassie blue, Cresyl violet, Crystal violet, 4',6-diamidino-2-phenylindole ("DAPI"), Eosin, Ethidium bromide intercalates, Acid fuchsine, Hoechst stain, Iodine, Malachite green, Methyl green, Methylene blue, Neutral red, Nile blue, Nile red, Osmium tetroxide, Propidium Iodide, Rhodamine, Safranine, programmed death-ligand 1 ("PD-L1") stain, 3,3'-Diaminobenzidine ("DAB") chromogen, Magenta chromogen, cyanine chromogen, cluster of differentiation ("CD") 3 stain, CD20 stain, CD68 stain, 40S ribosomal protein SA ("p40") stain, antibody-based stain, or label-free imaging marker, and/or the like.

As shown in the non-limiting embodiment 700" of FIG. 7C, one embodiment of virtual stain net F or AI model F 745' may receive an input image 740 (which may include, without limitation, an image of Hematoxylin stained biological sample, or the like) and ground truth image 725 (which may include, without limitation, an image of Hematoxylin plus Magenta sequentially stained biological sample, or the like), which are first aligned (if not already aligned or if alignment is not necessary). The virtual stain net F or AI model F 745' may include, but is not limited to, an encoder 770*a*, a decoder 770*b*, an intensity map 770*c*, an additional convolutional neural network ("CNN") 770*d* (optional), a color vector 770*e* (e.g., an RGB vector or the like), a mixer 775*a*, an adder 775*b*, and a loss function device 780. An input image 740 is input to the encoder/decoder network (e.g., the network of encoder 770*a* and decoder 770*b*, or the like), which may be similar to a U-Net, with a single channel output of the same spatial size as the input image (i.e., output of Intensity Map 770*c*). In some cases, the additional CNN 770*d* (optional) may operate on the output of the encoder 770*a*, with a color vector output (i.e., output of RGB vector 770*e*). The outputs of the intensity map 770*c* and the color vector 770*e* may be combined using mixer 775*a* to produce a 3-channel image of the virtual stain (i.e., virtual magenta). The predicted virtual stain may be added using adder 775*b* to the input image 740 to produce the outputs—i.e., the predicted virtually stained patch(es) or image(s) 750'. The network may then be trained with a loss function (by the loss function device 780) between the virtually stained patch(es) or image(s) 750' and its paired sequentially stained ground truth image 725. In some embodiments, the loss function may include, but is not limited to, one of a mean squared error loss function, a mean squared logarithmic error loss function, a mean absolute error loss function, a Huber loss function, or a weighted sum of squared differences loss function, and/or the like.

Alternatively, as shown in the non-limiting embodiment 700'" of FIG. 7D, another embodiment of virtual stain net F or AI model F 745" may receive an input image 740 (which may include, without limitation, an image of Hematoxylin stained biological sample, or the like) and ground truth image 725 (which may include, without limitation, an image of Hematoxylin plus Magenta sequentially stained biological sample, or the like), which are first aligned (if not already aligned or if alignment is not necessary). The virtual stain net F or AI model F 745" may include, but is not limited to, an AI model 785 and a loss function device 780 (similar to loss function device 780 of FIG. 7C). An input image 740 is input to the AI model 785, which may output predicted virtual stain may be added using adder 775*b'* to the input image 740 to produce the outputs—i.e., the predicted virtually stained patch(es) or image(s) 750". The network may then be trained with a loss function (by the loss function device 780) between the virtually stained patch(es) or image(s) 750" and its paired sequentially stained ground truth image 725. In some embodiments, the loss function may include, but is not limited to, one of a mean squared error loss function, a mean squared logarithmic error loss function, a mean absolute error loss function, a Huber loss function, or a weighted sum of squared differences loss function, and/or the like.

Figure 8A:
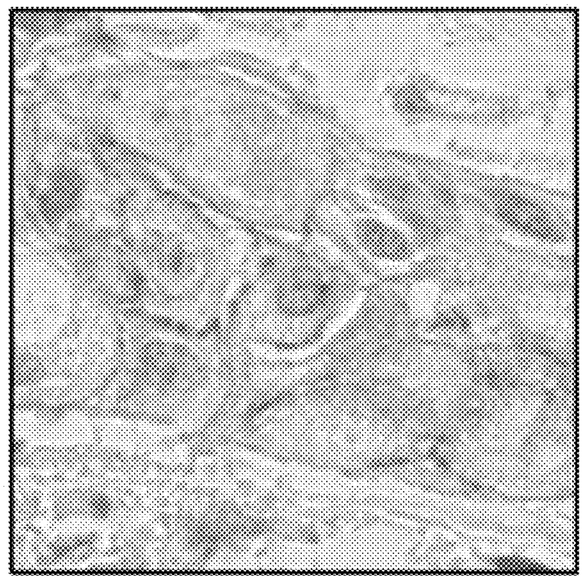
FIGS. 8A-8O are schematic diagrams illustrating various non-limiting examples of images of biological samples that have been virtually stained when implementing sequential imaging of biological samples for generating training data for developing deep learning based models for virtual staining of biological samples and for developing deep learning based models for image analysis, cell classification, and/or features of interest identification of biological samples, in accordance with various embodiments.
Figure 8B:
Figure 8C:
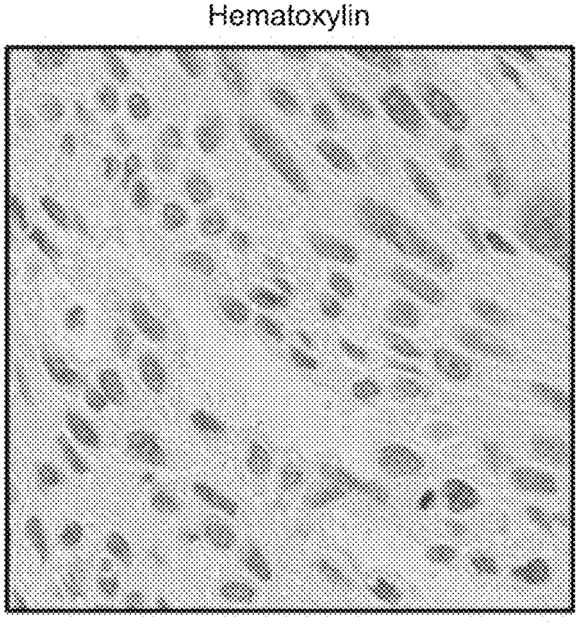
Figure 8D:
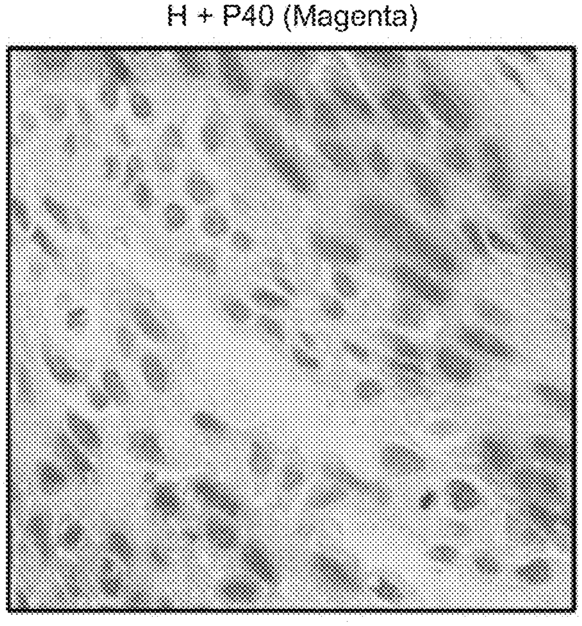
Figure 8F:
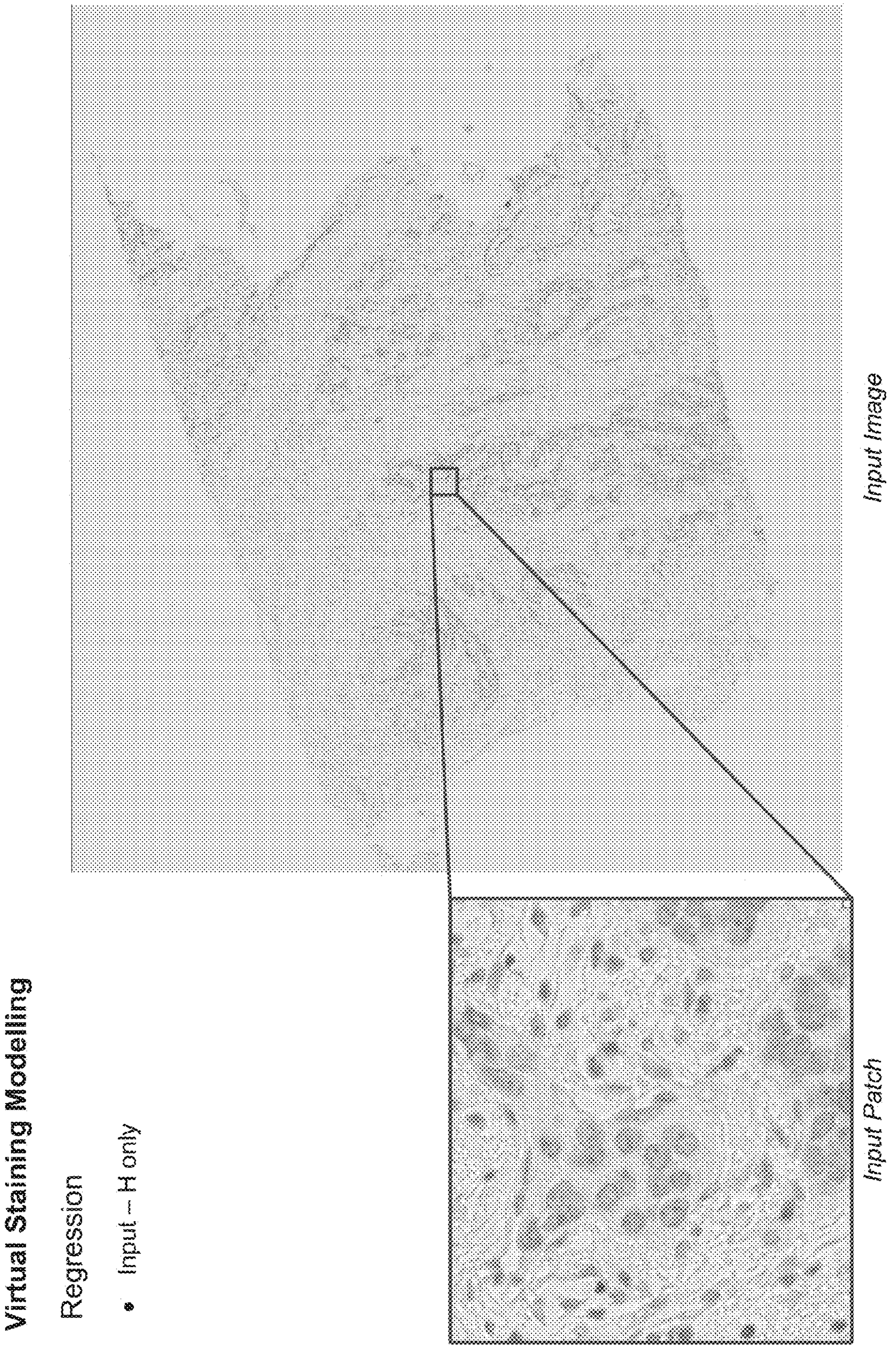
Figure 8G:
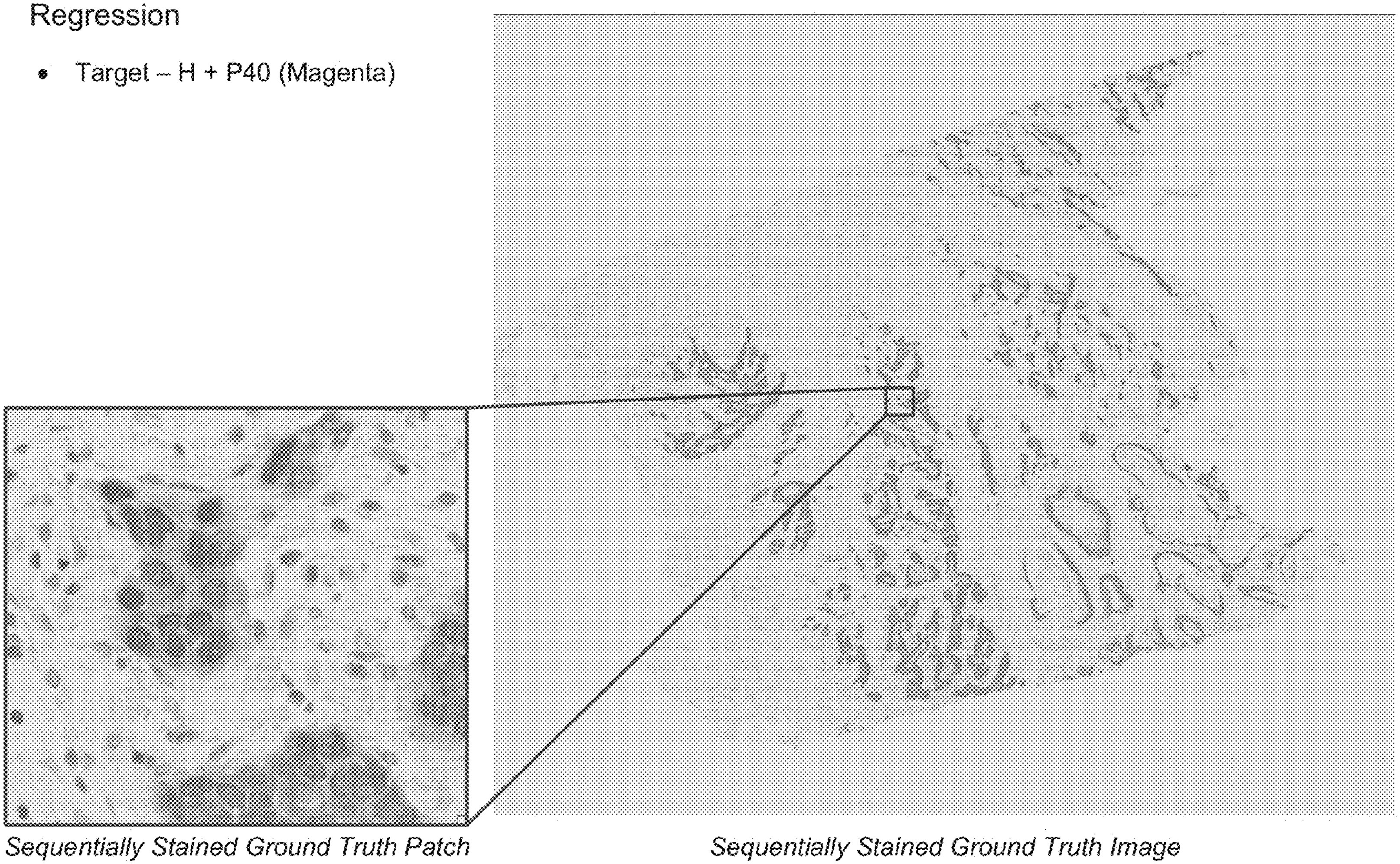
Figure 8H:
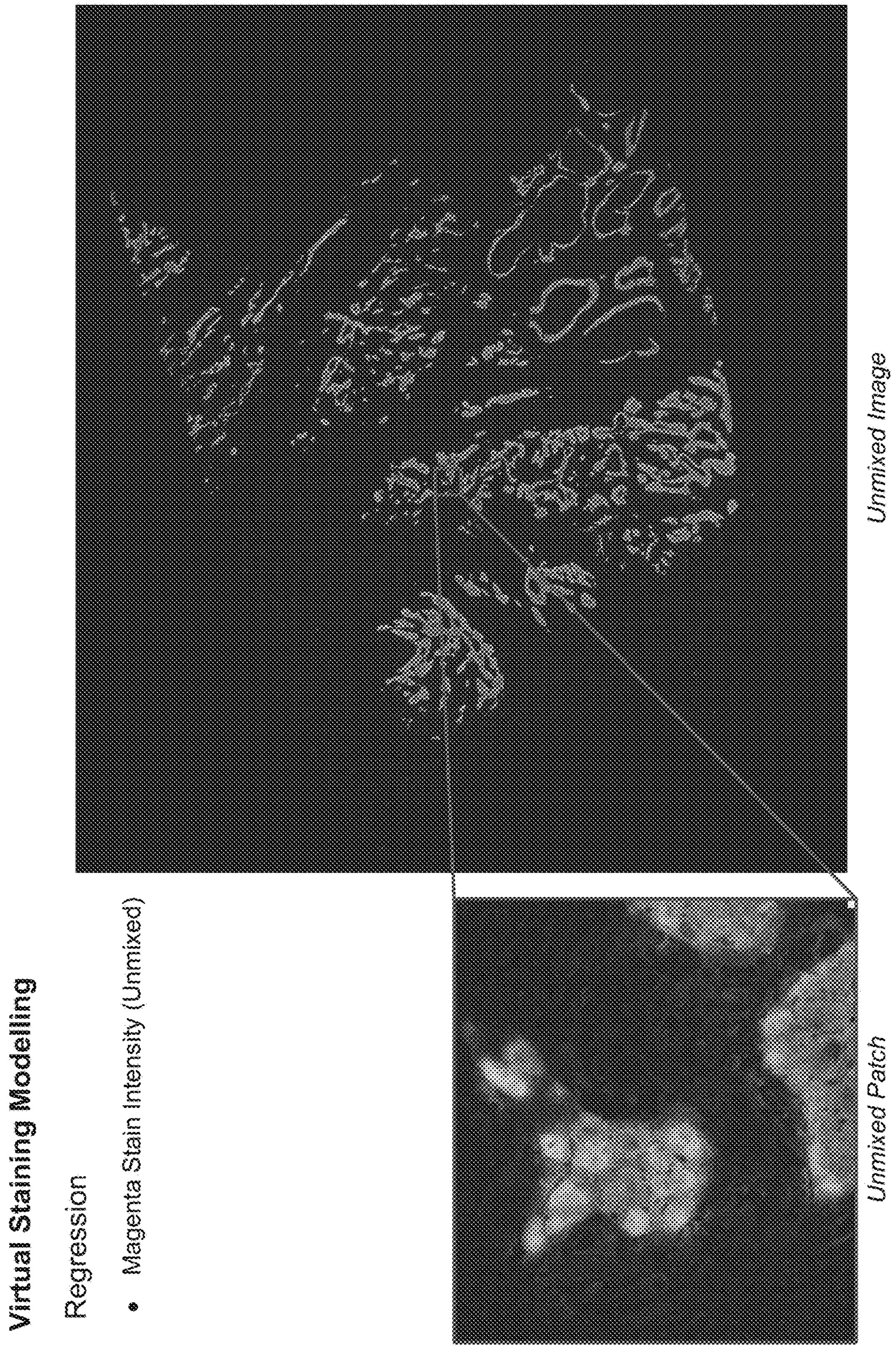
Figure 8I:
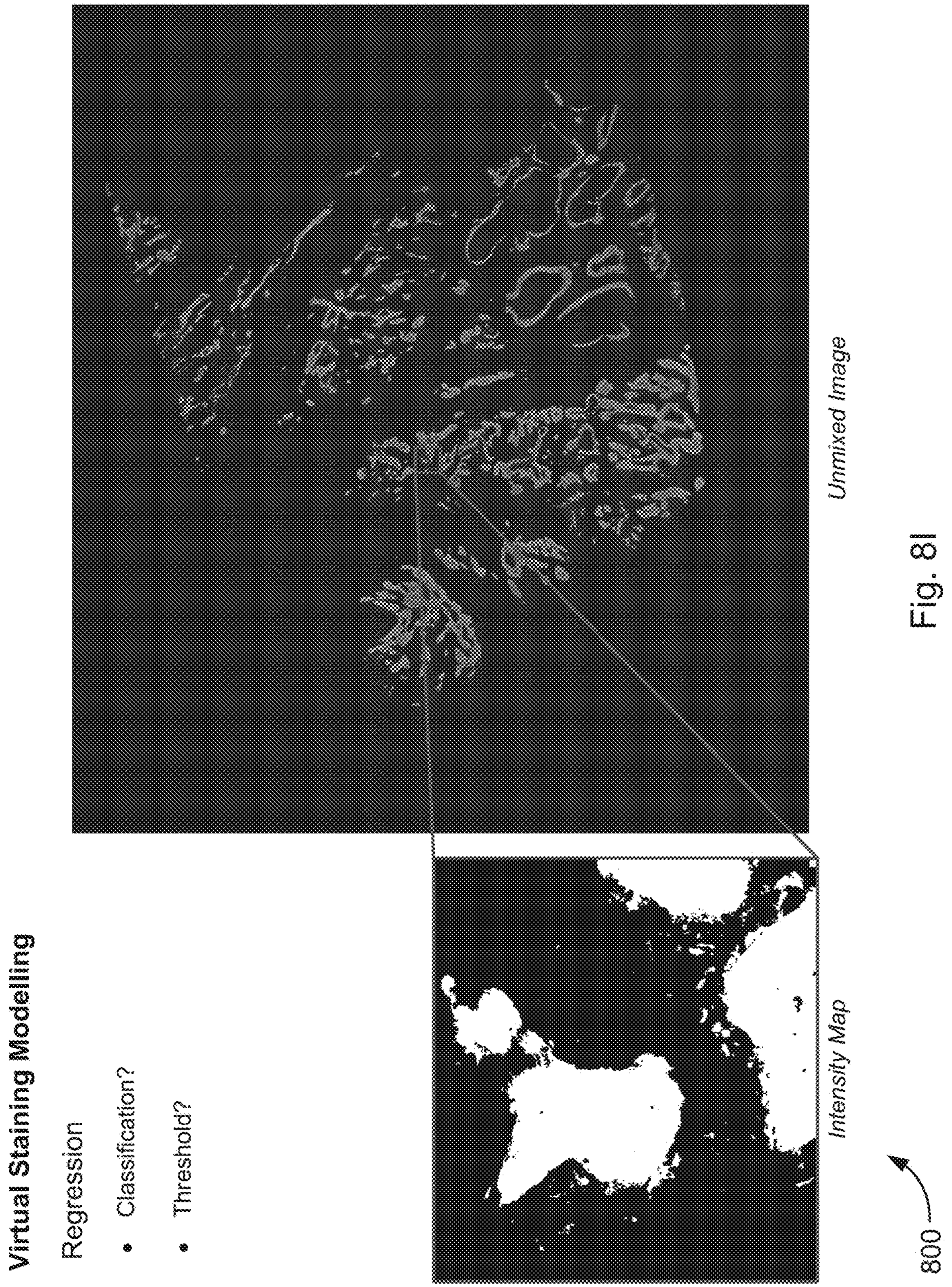
Figure 8J:
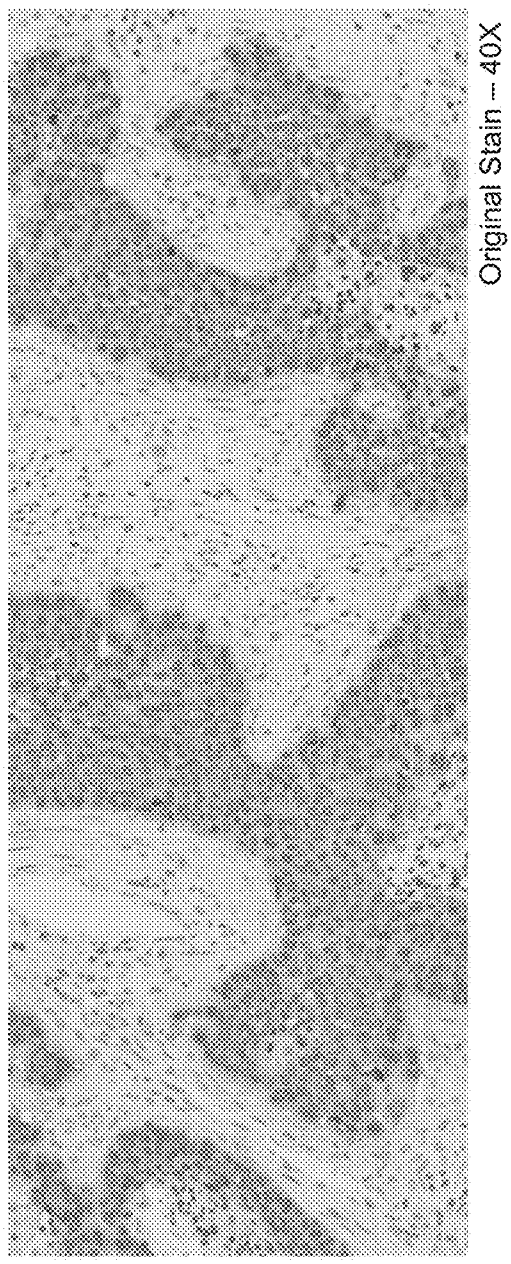
Figure 8K:
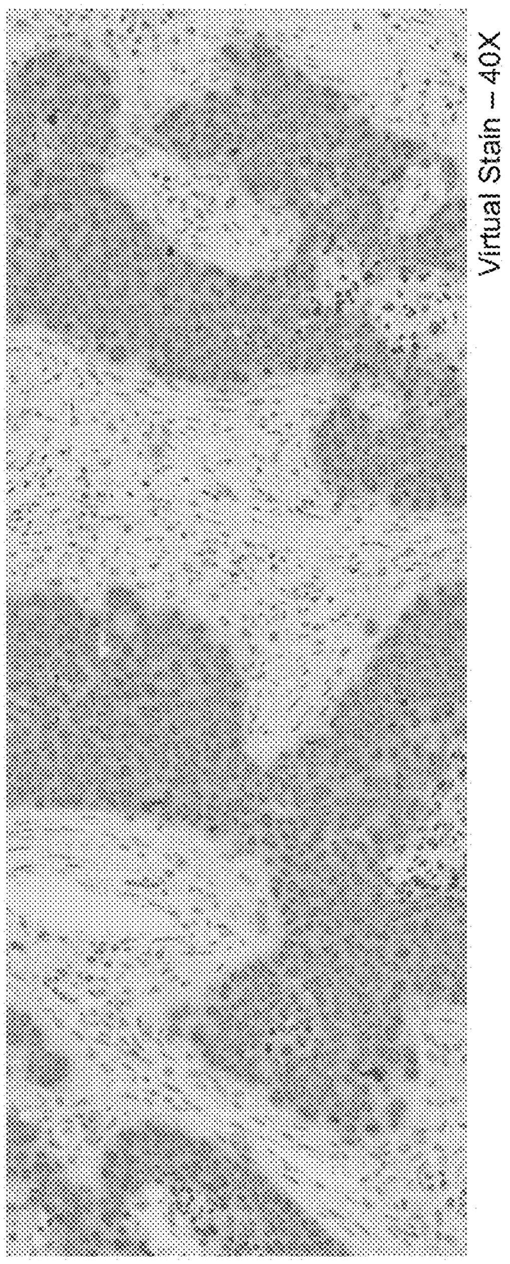
Figure 8L:
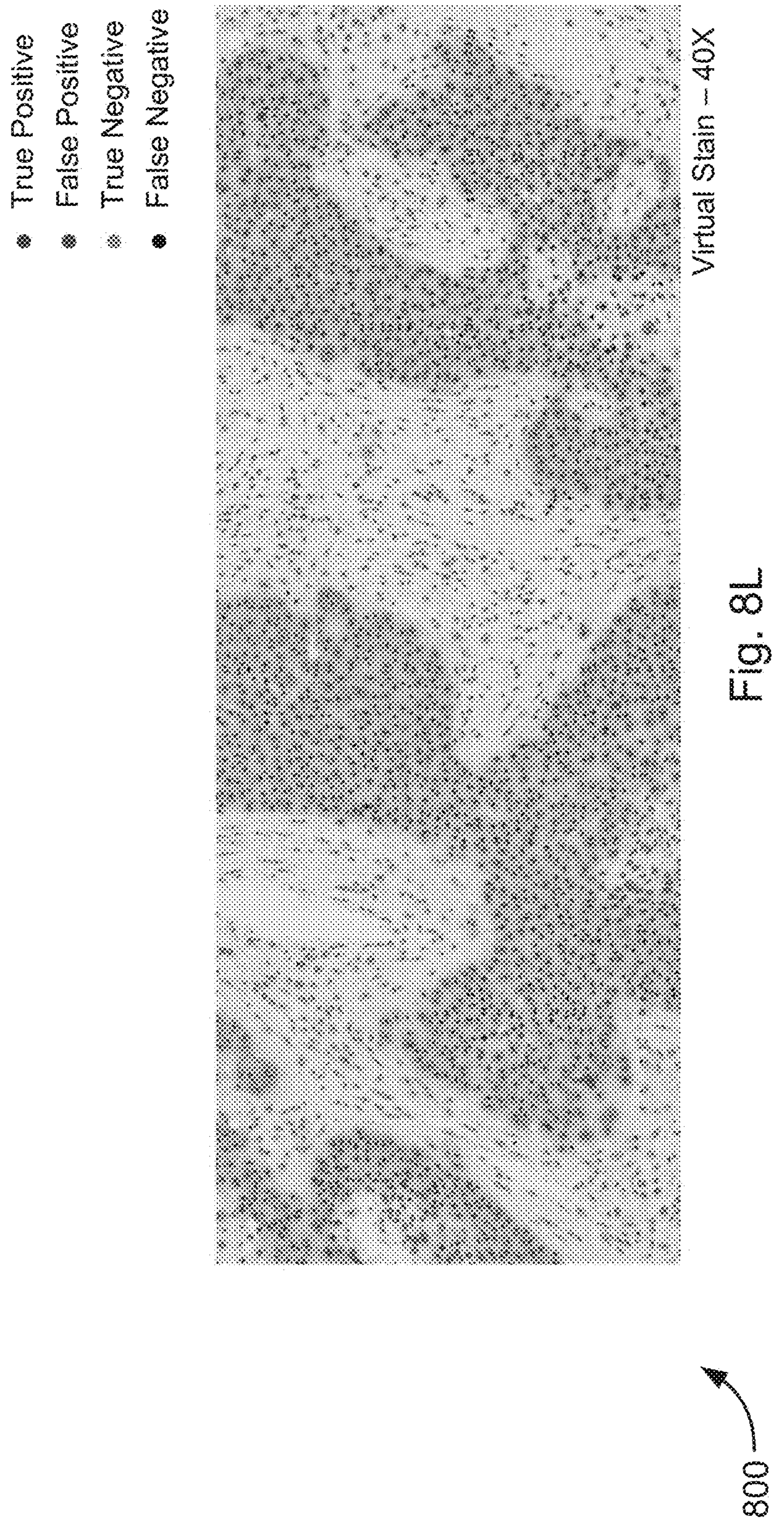
Figure 8O:
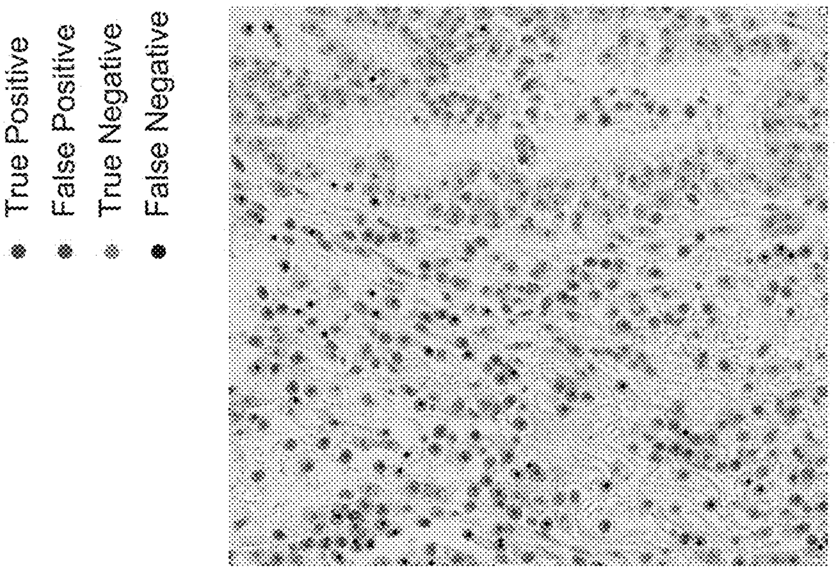

FIGS. 8A-8O (collectively, "FIG. 8") are schematic diagrams illustrating various non-limiting examples 800 of images of biological samples that have been virtually stained when implementing sequential imaging of biological samples for generating training data for generating training data for developing deep learning based models for virtual staining of biological samples and for developing deep learning based models for image analysis, cell classification, and/or features of interest identification of biological samples, in accordance with various embodiments.

Although Hematoxylin plus DAB sequential staining and Hematoxylin plus DAB plus Magenta sequential staining are depicted in FIGS. 8A and 8B for the input image and the ground truth image, respectively, or Hematoxylin stain and Hematoxylin plus p40 Magenta sequential staining are depicted in FIGS. 8C and 8D for the input image and the ground truth image, respectively, the various embodiments are not so limited, and the biological sample depicted in the input image and in the ground truth image may each include, without limitation, at least one of Hematoxylin, Acridine orange, Bismarck brown, Carmine, Coomassie blue, Cresyl violet, Crystal violet, 4',6-diamidino-2-phenylindole ("DAPI"), Eosin, Ethidium bromide intercalates, Acid fuchsine, Hoechst stain, Iodine, Malachite green, Methyl green, Methylene blue, Neutral red, Nile blue, Nile red, Osmium tetroxide, Propidium Iodide, Rhodamine, Safranine, programmed death-ligand 1 ("PD-L1") stain, 3,3'-Diaminobenzidine ("DAB") chromogen, Magenta chromogen, cyanine chromogen, cluster of differentiation ("CD") 3 stain, CD20 stain, CD68 stain, 40S ribosomal protein SA ("p40") stain, antibody-based stain, or label-free imaging marker, and/or the like.

FIGS. 8A-8B depict a non-limiting example of an input image of a first biological sample having been stained with sequential staining of Hematoxylin stain and programmed death-ligand 1 ("PD-L1") stain (e.g., 3,3'-Diaminobenzidine ("DAB") chromogen, or the like) (as shown in FIG. 8A) and a ground truth image of the first biological sample having been stained with sequential staining of Hematoxylin stain, PD-L1 stain (e.g., DAB chromogen, or the like), and cluster of differentiation ("CD") 68 stain (e.g., Magenta chromogen,) (as shown in FIG. 8B).

FIGS. 8C-8D depict a non-limiting example of an input image of a first biological sample having been stained with Hematoxylin stain (as shown in FIG. 8C) and a ground truth image of the first biological sample having been stained with sequential staining of Hematoxylin stain and p40 stain (e.g., Magenta chromogen,) (as shown in FIG. 8D).

FIG. 8E depicts an image of a biological sample with selected validation FOVs (denoted by blue rectangles).

Virtual Staining Modelling is depicted in FIGS. 8F-8I, with a magnified image of a patch of the image containing the biological sample. FIG. 8F depicts an input image (and corresponding image patch) illustrating only Hematoxylin stain, while FIG. 8G depicts a target image (and corresponding image patch) illustrating sequential staining with Hematoxylin stain and p40 (Magenta) stain, and FIG. 8H depicts unmixed Magenta stain intensity image (and corresponding image patch). FIG. 8I depicts the Magenta stain intensity image of FIG. 8H, with an image patch that represents an intensity map, which can be used for regression, that is the prediction of a continuous value of the virtual stain intensity. FIG. 8I depicts a binarization of 8H that can be used to train the network or model F as a classification network (binary classification). Training the classification network may require defining a threshold intensity value, beyond which a pixel will be considered a positive pixel for virtual stain. The question marks in FIG. 8I (i.e., "classification?" and "threshold?") are indicative of the possibility of solving this as a classification problem and/or the requirement of determining a threshold if doing so. In some non-limiting example models that have been trained, a regression solution was selected that solved for the kind of intensity image shown in FIG. 8I, after combining it with the color vector and adding to the input image.

Figure 8N:
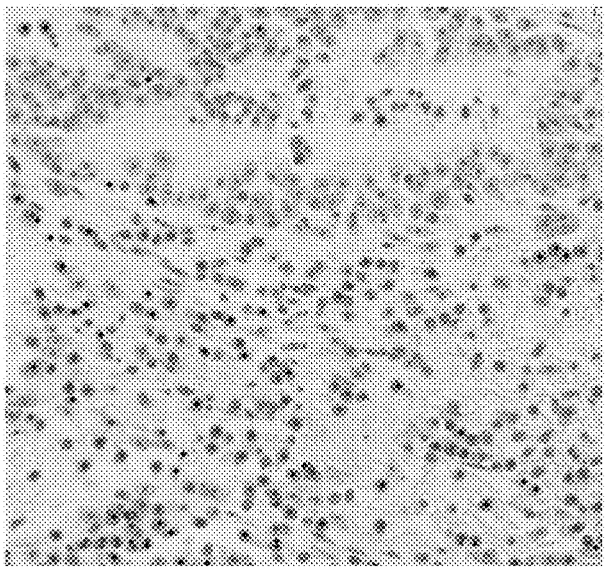
Figure 8M:
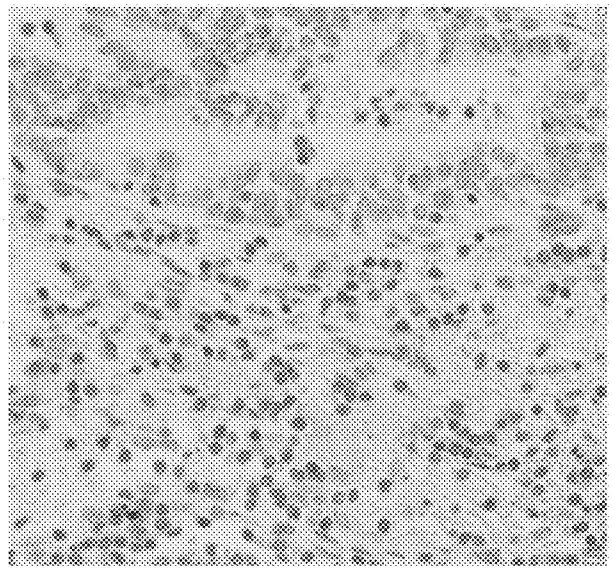

FIGS. 8J-8O depict evaluation of the virtual staining technique (in this case, p40 nucleic virtual staining (FIGS. 8J-8L) and CD3 virtual staining (FIGS. 8M-8O)). FIGS. 8J and 8K depict an originally stained image of a biological sample and a virtually stained image of the biological sample, respectively, both at 40× magnification, while FIG. 8L depicts a color-coded evaluation of the virtually stained image of FIG. 8K, with true positive nuclei detection denoted by blue dots, false positive nuclei detection denoted by red dots, true negative nuclei detection denoted by green dots, and false negative nuclei detection denoted by black dots. FIGS. 8N and 8O similarly depict color-coded evaluation of the virtually stained image of FIG. 8M, with true positive nuclei detection denoted by blue dots, false positive nuclei detection denoted by red dots, true negative nuclei detection denoted by green dots, and false negative nuclei detection denoted by black dots.

FIGS. 9A-9E (collectively, "FIG. 9") are flow diagrams illustrating a method 900 for implementing sequential imaging of biological samples for generating training data for generating training data for developing deep learning based models for virtual staining of biological samples and for developing deep learning based models for image analysis, cell classification, and/or features of interest identification of biological samples, in accordance with various embodiments.

Figure 9A:
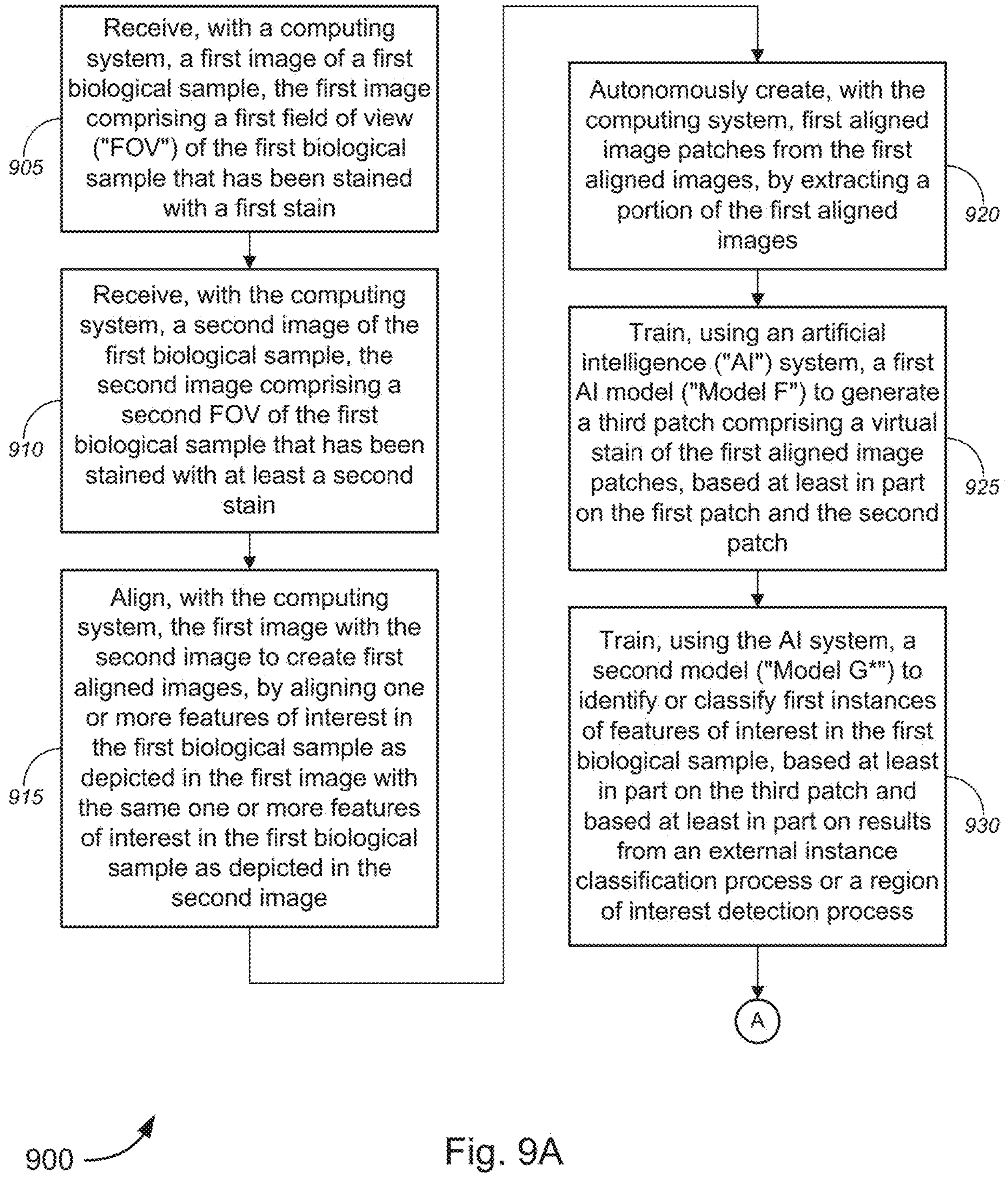
FIGS. 9A-9E are flow diagrams illustrating a method for implementing sequential imaging of biological samples for generating training data for developing deep learning based models for virtual staining of biological samples and for developing deep learning based models for image analysis, cell classification, and/or features of interest identification of biological samples, in accordance with various embodiments.
Figure 9B:
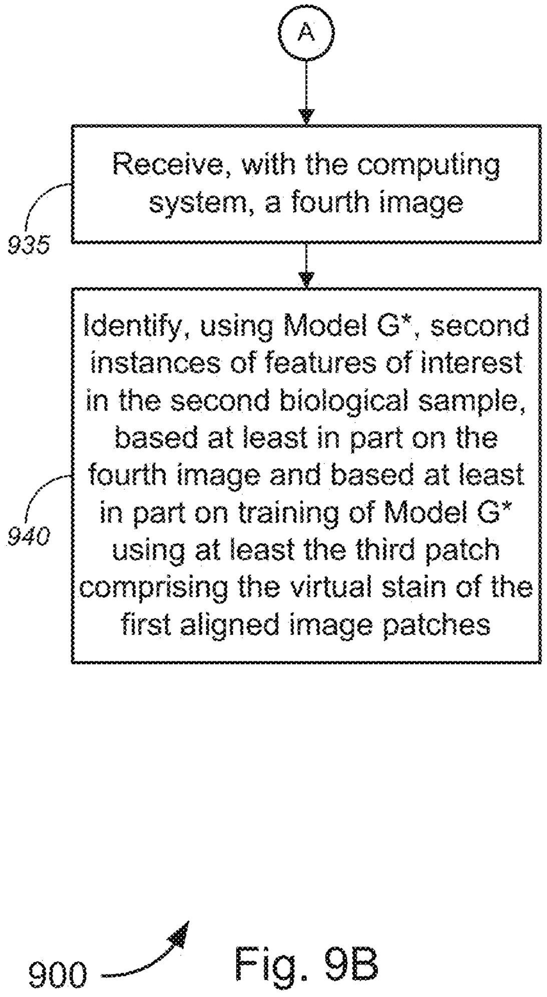

Method 900 of FIG. 9A continues onto FIG. 9B following the circular marker denoted, "A."

While the techniques and procedures are depicted and/or described in a certain order for purposes of illustration, it should be appreciated that certain procedures may be reordered and/or omitted within the scope of various embodiments. Moreover, while the method 900 illustrated by FIG. 9 can be implemented by or with (and, in some cases, are described below with respect to) the systems, examples, or embodiments 300, 700, 700', 700", 700'", and 800 of FIGS. 3, 7A, 7B, 7C, 7D, and 8, respectively (or components thereof), such methods may also be implemented using any suitable hardware (or software) implementation. Similarly, while each of the systems, examples, or embodiments 300, 700, 700', 700", 700'", and 800 of FIGS. 3, 7A, 7B, 7C, 7D, and 8, respectively (or components thereof), can operate according to the method 900 illustrated by FIG. 9 (e.g., by executing instructions embodied on a computer readable medium), the systems, examples, or embodiments 300, 700, 700', 700", 700'", and 800 of FIGS. 3, 7A, 7B, 7C, 7D, and 8 can each also operate according to other modes of operation and/or perform other suitable procedures.

In the non-limiting embodiment of FIG. 9A, method 900, at block 905, may comprise receiving, with a computing system, a first image of a first biological sample, the first image comprising a first field of view ("FOV") of the first biological sample that has been stained with a first stain. Method 900 may comprise receiving, with the computing system, a second image of the first biological sample, the second image comprising a second FOV of the first biological sample that has been stained with at least a second stain (block 910).

At block 915, method 900 may comprise aligning, with the computing system, the first image with the second image to create first aligned images, by aligning one or more features of interest in the first biological sample as depicted in the first image with the same one or more features of interest in the first biological sample as depicted in the second image. According to some embodiments, aligning the first image with the second image may be either performed manually using manual inputs to the computing system or performed autonomously, where autonomous alignment may comprise alignment using at least one of automated global alignment techniques or optical flow alignment techniques.

Method 900 may further comprise, at block 920, autonomously creating, with the computing system, first aligned image patches from the first aligned images, by extracting a portion of the first aligned images. In some cases, the portion of the first aligned images may comprise a first patch corresponding to the extracted portion of the first image and a second patch corresponding to the extracted portion of the second image.

Method 900 may further comprise training, using an artificial intelligence ("AI") system, a first AI model ("Model F") to generate a third patch comprising a virtual stain of the first aligned image patches, based at least in part on the first patch and the second patch, the virtual stain simulating staining by at least the second stain of features of interest in the first biological sample as shown in the second patch (block 925); and training, using the AI system, a second model ("Model G*") to identify or classify first instances of features of interest in the first biological sample, based at least in part on the third patch and based at least in part on results from an external instance classification process or a region of interest detection process (block 730).

In some embodiments, training, using the AI system, Model G* to identify or classify instances of features of interest in the first biological sample may comprise training, using the AI system, Model G* to identify or classify instances of features of interest in the first biological sample, based at least in part on one or more of the first patch, the second patch, or the third patch and based at least in part on the results from the external instance classification process or the region of interest detection process. According to some embodiments, the external instance classification process or the region of interest detection process may each include, without limitation, at least one of detection of nuclei in the first image or the first patch by a nuclei detection method, identification of nuclei in the first image or the first patch by a pathologist, detection of features of interest in the first image or the first patch by a feature detection method, or identification of features of interest in the first image or the first patch by the pathologist, and/or the like.

In some embodiments, the computing system may include, without limitation, one of a computing system disposed in a work environment, a remote computing system disposed external to the work environment and accessible over a network, a web server, a web browser, or a cloud computing system, and/or the like. According to some embodiments, the AI system may include, but is not limited to, at least one of a machine learning system, a deep learning system, a model architecture, a statistical model-based system, or a deterministic analysis system, and/or the like.

In some cases, the model architecture may comprise at least one of a neural network, a convolutional neural network ("CNN"), or a fully convolutional network ("FCN"), and/or the like. In some instances, the work environment may include, but is not limited to, at least one of a laboratory, a clinic, a medical facility, a research facility, a healthcare facility, or a room, and/or the like. In some cases, the first biological sample may include, without limitation, one of a human tissue sample, an animal tissue sample, a plant tissue sample, or an artificially produced tissue sample, and/or the like, and the features of interest may include, but are not limited to, at least one of normal cells, abnormal cells, damaged cells, cancer cells, tumors, subcellular structures, or organ structures, and/or the like.

Merely by way of example, in some cases, the first image may comprise highlighting of first features of interest in the first biological sample (including, but not limited to, at least one of first antigens, first nuclei, first cell walls, first cell structures, first antibodies, first normal cells, first abnormal cells, first damaged cells, first cancer cells, first tumors, first subcellular structures, first organ structures, or other features of interest, or the like) by the first stain that had been applied to the first biological sample. The third patch may comprise one of highlighting of the first features of interest by the first stain and highlighting of second features of interest in the first biological sample (including, but not limited to, at least one of second antigens, second nuclei, second cell walls, second cell structures, second antibodies, second normal cells, second abnormal cells, second damaged cells, second cancer cells, second tumors, second subcellular structures, second organ structures, or other features of interest, or the like) by the virtual stain that simulates the second stain having been applied to the first biological sample or highlighting of the first features of interest by the first stain and highlighting of first features of interest by the virtual stain, the second features of interest being different from the first features of interest. In some instances, the second stain may be one of the same as the first stain but used to stain the second features of interest or different from the first stain.

According to some embodiments, the first stain and the second stain may each include, without limitation, at least one of Hematoxylin, Acridine orange, Bismarck brown, Carmine, Coomassie blue, Cresyl violet, Crystal violet, 4',6-diamidino-2-phenylindole ("DAPI"), Eosin, Ethidium bromide intercalates, Acid fuchsine, Hoechst stain, Iodine, Malachite green, Methyl green, Methylene blue, Neutral red, Nile blue, Nile red, Osmium tetroxide, Propidium Iodide, Rhodamine, Safranine, programmed death-ligand 1 ("PD-L1") stain, 3,3'-Diaminobenzidine ("DAB") chromogen, Magenta chromogen, cyanine chromogen, cluster of differentiation ("CD") 3 stain, CD20 stain, CD68 stain, 40S ribosomal protein SA ("p40") stain, antibody-based stain, or label-free imaging marker, and/or the like.

In some embodiments, the first image may include, but is not limited to, one of a first set of color or brightfield images, a first fluorescence image, a first phase image, or a first spectral image, and/or the like. The first set of color or brightfield images may include, without limitation, a first red-filtered ("R") image, a first green-filtered ("G") image, and a first blue-filtered ("B") image, and/or the like. The first fluorescence image may include, but is not limited to, at least one of a first autofluorescence image or a first labelled fluorescence image having one or more channels with different excitation or emission characteristics, and/or the like. The first spectral image may include, but is not limited to, at least one of a first Raman spectroscopy image, a first near infrared ("NIR") spectroscopy image, a first multispectral image, a first hyperspectral image, or a first full spectral image, and/or the like. Similarly, the second image may include, but is not limited to, one of a second set of color or brightfield images, a second fluorescence image, a second phase image, or a second spectral image, and/or the like. The second set of color or brightfield images may include, without limitation, a second R image, a second G image, and a second B image, and/or the like. The second fluorescence image may include, but is not limited to, at least one of a second autofluorescence image or a second labelled fluorescence image having one or more channels with different excitation or emission characteristics, and/or the like. The second spectral image may include, but is not limited to, at least one of a second Raman spectroscopy image, a second NIR spectroscopy image, a second multispectral image, a second hyperspectral image, or a second full spectral image, and/or the like. Likewise, the third patch may include, but is not limited to, one of a third set of color or brightfield images, a third fluorescence image, a third phase image, or a third spectral image, and/or the like. The third set of color or brightfield images may include, without limitation, a third R image, a third G image, and a third B image, and/or the like. The third fluorescence image may include, but is not limited to, at least one of a third autofluorescence image or a third labelled fluorescence image having one or more channels with different excitation or emission characteristics, and/or the like. The third spectral image may include, but is not limited to, at least one of a third Raman spectroscopy image, a third NIR spectroscopy image, a third multispectral image, a third hyperspectral image, or a third full spectral image, and/or the like.

Method 900 may continue onto the process at block 935 in FIG. 9B following the circular marker denoted, "A."

At block 935 in FIG. 9B (following the circular marker denoted, "A"), method 900 may comprise receiving, with the computing system, a fourth image, the fourth image comprising one of a fourth FOV of the first biological sample different from the first FOV and the second FOV or a fifth FOV of a second biological sample, where the second biological sample is different from the first biological sample. Method 900 may further comprise identifying, using Model G*, second instances of features of interest in the second biological sample, based at least in part on the fourth image and based at least in part on training of Model G* using at least the third patch comprising the virtual stain of the first aligned image patches (block 940). According to some embodiments, method 900 may further comprise generating, using Model G*, a clinical score, based at least in part on the identified second instances of features of interest.

Figure 9C:
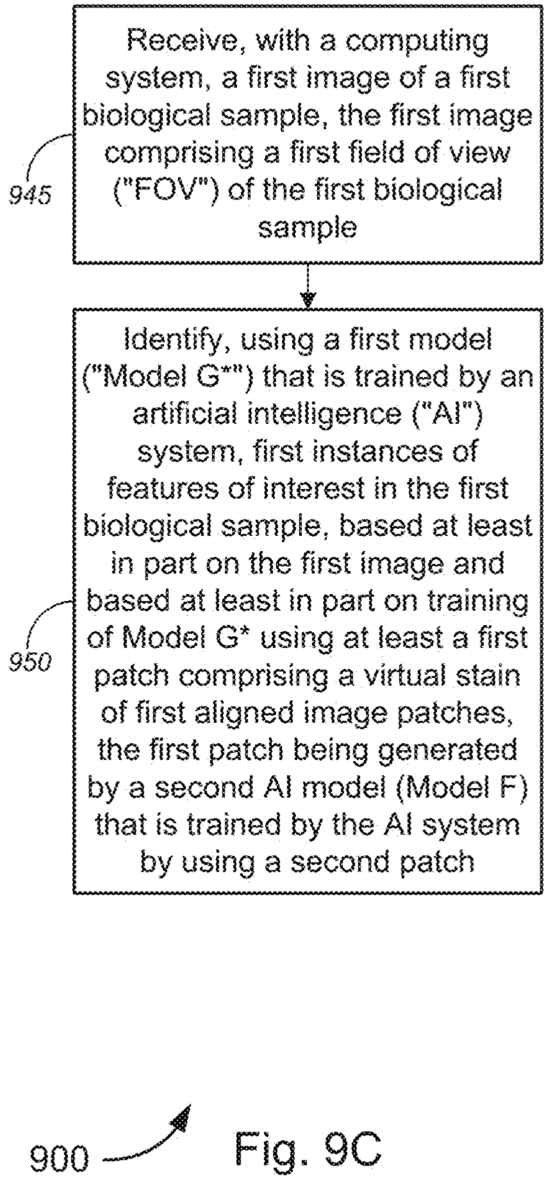

Turning to FIG. 9C, method 900 may comprise, at block 945, receiving, with a computing system, a first image of a first biological sample, the first image comprising a first field of view ("FOV") of the first biological sample. At block 950, method 900 may comprise identifying, using a first model ("Model G*") that is trained by an artificial intelligence ("AI") system, first instances of features of interest in the first biological sample, based at least in part on the first image and based at least in part on training of Model G* using at least a first patch comprising a virtual stain of first aligned image patches. In some cases, the first patch may be generated by a second AI model (Model F) that is generated or updated by the trained AI system by using a second patch. The first aligned image patches may comprise an extracted portion of first aligned images. The first aligned images may comprise a second image and a third image that have been aligned. The second image may comprise a second FOV of a second biological sample that is different from the first biological sample that has been stained with a first stain. The second patch may comprise the extracted portion of the second image. The third image may comprise a third FOV of the second biological sample that has been stained with at least a second stain.

Figure 9D:
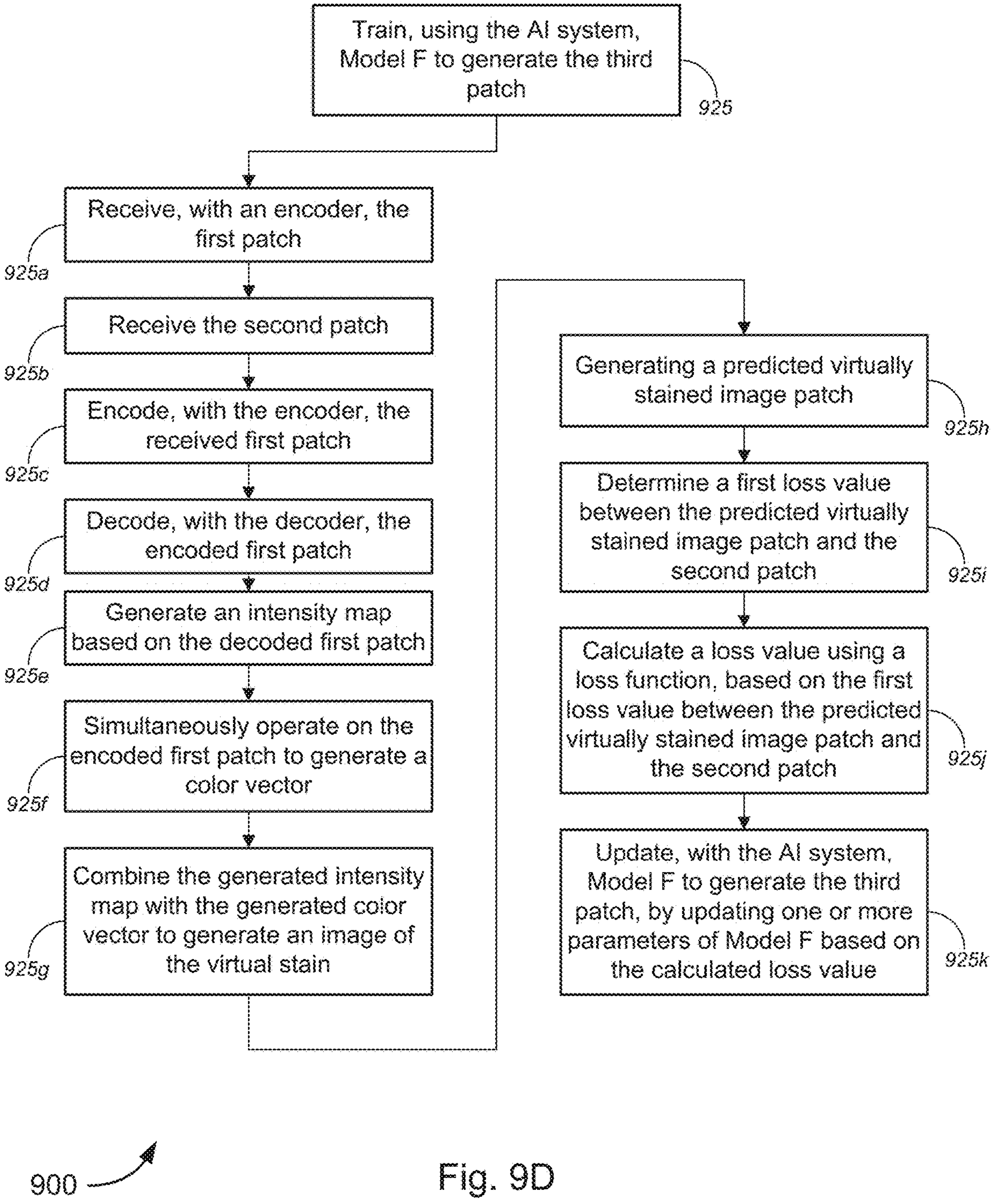
Figure 9E:
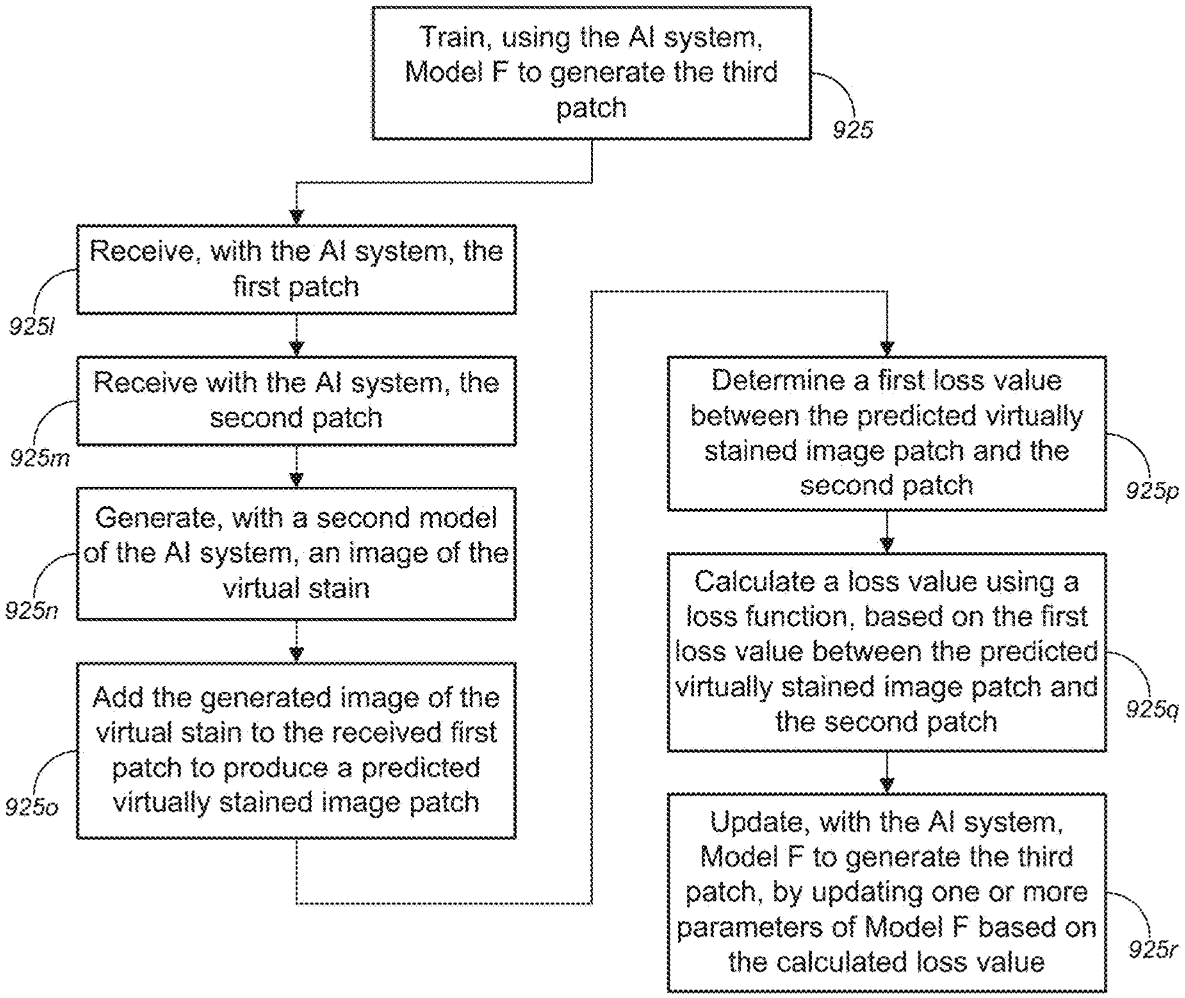

With reference to FIGS. 9D and 9E, training the AI system to update Model F may comprise (as shown in FIG. 9D): receiving, with an encoder, the first patch (block 925*a*); receiving the second patch (block 925*b*); encoding, with the encoder, the received first patch (block 925*c*); decoding, with the decoder, the encoded first patch (block 925*d*); generating an intensity map based on the decoded first patch (block 925*e*); simultaneously operating on the encoded first patch to generate a color vector (block 925*f*); combining the generated intensity map with the generated color vector to generate an image of the virtual stain (block 925*g*); generating a predicted virtually stained image patch (block 925*h*); determining a first loss value between the predicted virtually stained image patch and the second patch (block 925*i*); calculating a loss value using a loss function, based on the first loss value between the predicted virtually stained image patch and the second patch (block 925*j*); and updating, using the AI system, Model F to generate the third patch, by updating one or more parameters of Model F based on the calculated loss value (block 925*k*). According to some embodiments, generating the predicted virtually stained image patch (at block 925*h*) may comprise adding the generated image of the virtual stain to the received first patch to produce the predicted virtually stained image patch. In some cases, determining the first loss value between the predicted virtually stained image patch and the second patch may be performed without adding the generated image of the virtual stain to the received first patch.

In some embodiments, the loss function may include, without limitation, one of a mean squared error loss function, a mean squared logarithmic error loss function, a mean absolute error loss function, a Huber loss function, or a weighted sum of squared differences loss function, and/or the like.

In some cases, the first patch may include, but is not limited to, one of a first set of color or brightfield images, a first fluorescence image, a first phase image, or a first spectral image, and/or the like. The first set of color or brightfield images may include, without limitation, a first red-filtered ("R") image, a first green-filtered ("G") image, and a first blue-filtered ("B") image, and/or the like. The first fluorescence image may include, but is not limited to, at least one of a first autofluorescence image or a first labelled fluorescence image having one or more channels with different excitation or emission characteristics, and/or the like. The first spectral image may include, but is not limited to, at least one of a first Raman spectroscopy image, a first near infrared ("NIR") spectroscopy image, a first multispectral image, a first hyperspectral image, or a first full spectral image, and/or the like. The second image may include, but is not limited to, one of a second set of color or brightfield images, a second fluorescence image, a second phase image, or a second spectral image, and/or the like. The second set of color or brightfield images may include, without limitation, a second R image, a second G image, and a second B image, and/or the like. The second fluorescence image may include, but is not limited to, at least one of a second autofluorescence image or a second labelled fluorescence image having one or more channels with different excitation or emission characteristics, and/or the like. The second spectral image may include, but is not limited to, at least one of a second Raman spectroscopy image, a second NIR spectroscopy image, a second multispectral image, a second hyperspectral image, or a second full spectral image, and/or the like. The predicted virtually stained image patch may include, but is not limited to, one of a third set of color or brightfield images, a third fluorescence image, a third phase image, or a third spectral image, and/or the like. The third set of color or brightfield images may include, without limitation, a third R image, a third G image, and a third B image, and/or the like. The third fluorescence image may include, but is not limited to, at least one of a third autofluorescence image or a third labelled fluorescence image having one or more channels with different excitation or emission characteristics, and/or the like. The third spectral image may include, but is not limited to, at least one of a third Raman spectroscopy image, a third NIR spectroscopy image, a third multispectral image, a third hyperspectral image, or a third full spectral image, and/or the like.

In some instances, operating on the encoded first patch to generate the color vector may comprise operating on the encoded first patch to generate a color vector, using a color vector output and one of a model architecture, a statistical model-based system, or a deterministic analysis system, and/or the like. In some instances, the model architecture may comprise at least one of a neural network, a convolutional neural network ("CNN"), or a fully convolutional network ("FCN"), and/or the like. The color vector may include, without limitation, one of a fixed color vector or a learned color vector that is not based on the encoded first patch, and/or the like. In some cases, the image of the virtual stain may include, but is not limited to, one of a 3-channel image of the virtual stain, a RGB-transform image of the virtual stain, or a logarithmic transform image of the virtual stain, and/or the like. In some embodiments, when the virtual stain is the logarithmic transform of the virtual stain, it may be added to the logarithmic transform of the input image (i.e., the first patch). After the addition, the logarithmically transformed virtually stained image is transformed, using an exponential transform, back to the common domain of RGB images (i.e., the reverse transform of the logarithmic transform). In such a case, the loss during training may be computed on the logarithmically transformed virtually stained image (or log transformed virtual stain directly in some cases), compared to the log transformed second patch (e.g., sequentially stained magenta, fluorescence, etc.). In some cases, there may be no exponentiation before calculating the loss, but the loss can also be calculated on the common RGB images domain, after exponentiating the virtually stained image and comparing to the second patch directly (i.e., not log-transformed).

According to some embodiments, the first loss value may include, without limitation, one of a pixel loss value between each pixel in the predicted virtually stained image patch and a corresponding pixel in the second patch or a generative adversarial network ("GAN") loss value between the predicted virtually stained image patch and the second patch, and/or the like. In some instances, the GAN loss value may be generated based on one of a minimax GAN loss function, a non-saturating GAN loss function, a least squares GAN loss function, or a Wasserstein GAN loss function, and/or the like.

Alternatively, training the AI system to update Model F may comprise (as shown in FIG. 9E): receiving, with the AI system, the first patch (block 925*l*); receiving, with the AI system, the second patch (block 925*m*); generating, with a second model of the AI system, an image of the virtual stain (block 925*n*); adding the generated image of the virtual stain to the received first patch to produce a predicted virtually stained image patch (block 925*o*); determining a first loss value between the predicted virtually stained image patch and the second patch (block 925*p*); calculating a loss value using a loss function, based on the first loss value between the predicted virtually stained image patch and the second patch (block 925*q*); and updating, with the AI system, Model F to generate the third patch, by updating one or more parameters of Model F based on the calculated loss value (block 925*r*).

In some embodiments, the second model may include, without limitation, at least one of a convolutional neural network ("CNN"), a U-Net, an artificial neural network ("ANN"), a residual neural network ("ResNet"), an encode/decode CNN, an encode/decode U-Net, an encode/decode ANN, or an encode/decode ResNet, and/or the like.

Exemplary System and Hardware Implementation

Figure 10:
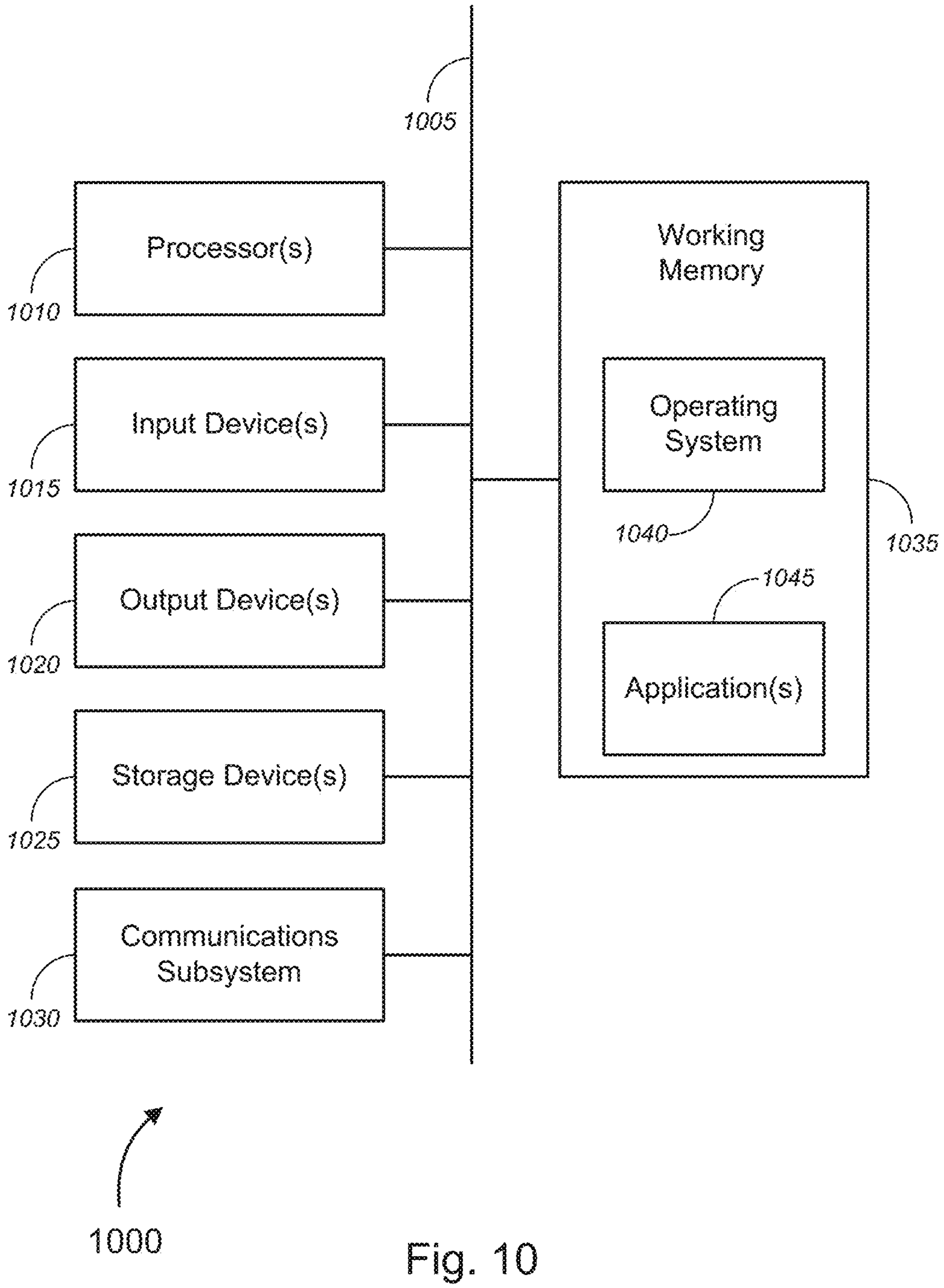
FIG. 10 is a block diagram illustrating an exemplary computer or system hardware architecture, in accordance with various embodiments.

FIG. 10 is a block diagram illustrating an exemplary computer or system hardware architecture, in accordance with various embodiments. FIG. 10 provides a schematic illustration of one embodiment of a computer system 1000 of the service provider system hardware that can perform the methods provided by various other embodiments, as described herein, and/or can perform the functions of computer or hardware system (i.e., computing systems 305*a* and 305*b*, artificial intelligence ("AI") systems 305*c* and 305*d* and/or AI system architecture 445, 445', 450, 450', 745, 745', 745", 755, and 755', display device 320, user device(s) 340, image alignment systems 415 and 715, and nuclei detection systems 430 and 730, etc.), as described above. It should be noted that FIG. 10 is meant only to provide a generalized illustration of various components, of which one or more (or none) of each may be utilized as appropriate. FIG. 10, therefore, broadly illustrates how individual system elements may be implemented in a relatively separated or relatively more integrated manner.

The computer or hardware system 1000—which might represent an embodiment of the computer or hardware system (i.e., computing systems 305*a* and 305*b*, AI systems 305*c* and 305*d* and/or AI system architecture 445, 445', 450, 450', 745, 745', 745", 755, and 755', display device 320, user device(s) 340, image alignment systems 415 and 715, and nuclei detection systems 430 and 730, etc.), described above with respect to FIGS. 3-9—is shown comprising hardware elements that can be electrically coupled via a bus 1005 (or may otherwise be in communication, as appropriate). The hardware elements may include one or more processors 1010, including, without limitation, one or more general-purpose processors and/or one or more special-purpose processors (such as microprocessors, digital signal processing chips, graphics acceleration processors, and/or the like); one or more input devices 1015, which can include, without limitation, a mouse, a keyboard, and/or the like; and one or more output devices 1020, which can include, without limitation, a display device, a printer, and/or the like.

The computer or hardware system 1000 may further include (and/or be in communication with) one or more storage devices 1025, which can comprise, without limitation, local and/or network accessible storage, and/or can include, without limitation, a disk drive, a drive array, an optical storage device, solid-state storage device such as a random access memory ("RAM") and/or a read-only memory ("ROM"), which can be programmable, flash-updateable, and/or the like. Such storage devices may be configured to implement any appropriate data stores, including, without limitation, various file systems, database structures, and/or the like.

The computer or hardware system 1000 might also include a communications subsystem 1030, which can include, without limitation, a modem, a network card (wireless or wired), an infra-red communication device, a wireless communication device and/or chipset (such as a Bluetooth™ device, an 802.11 device, a WiFi device, a WiMax device, a WWAN device, cellular communication facilities, etc.), and/or the like. The communications subsystem 1030 may permit data to be exchanged with a network (such as the network described below, to name one example), with other computer or hardware systems, and/or with any other devices described herein. In many embodiments, the computer or hardware system 1000 will further comprise a working memory 1035, which can include a RAM or ROM device, as described above.

The computer or hardware system 1000 also may comprise software elements, shown as being currently located within the working memory 1035, including an operating system 1040, device drivers, executable libraries, and/or other code, such as one or more application programs 1045, which may comprise computer programs provided by various embodiments (including, without limitation, hypervisors, VMs, and the like), and/or may be designed to implement methods, and/or configure systems, provided by other embodiments, as described herein. Merely by way of example, one or more procedures described with respect to the method(s) discussed above might be implemented as code and/or instructions executable by a computer (and/or a processor within a computer); in an aspect, then, such code and/or instructions can be used to configure and/or adapt a general purpose computer (or other device) to perform one or more operations in accordance with the described methods.

A set of these instructions and/or code might be encoded and/or stored on a non-transitory computer readable storage medium, such as the storage device(s) 1025 described above. In some cases, the storage medium might be incorporated within a computer system, such as the system 1000. In other embodiments, the storage medium might be separate from a computer system (i.e., a removable medium, such as a compact disc, etc.), and/or provided in an installation package, such that the storage medium can be used to program, configure, and/or adapt a general purpose computer with the instructions/code stored thereon. These instructions might take the form of executable code, which is executable by the computer or hardware system 1000 and/or might take the form of source and/or installable code, which, upon compilation and/or installation on the computer or hardware system 1000 (e.g., using any of a variety of generally available compilers, installation programs, compression/decompression utilities, etc.) then takes the form of executable code.

It will be apparent to those skilled in the art that substantial variations may be made in accordance with specific requirements. For example, customized hardware (such as programmable logic controllers, field-programmable gate arrays, application-specific integrated circuits, and/or the like) might also be used, and/or particular elements might be implemented in hardware, software (including portable software, such as applets, etc.), or both. Further, connection to other computing devices such as network input/output devices may be employed.

As mentioned above, in one aspect, some embodiments may employ a computer or hardware system (such as the computer or hardware system 1000) to perform methods in accordance with various embodiments of the invention. According to a set of embodiments, some or all of the procedures of such methods are performed by the computer or hardware system 1000 in response to processor 1010 executing one or more sequences of one or more instructions (which might be incorporated into the operating system 1040 and/or other code, such as an application program 1045) contained in the working memory 1035. Such instructions may be read into the working memory 1035 from another computer readable medium, such as one or more of the storage device(s) 1025. Merely by way of example, execution of the sequences of instructions contained in the working memory 1035 might cause the processor(s) 1010 to perform one or more procedures of the methods described herein.

The terms "machine readable medium" and "computer readable medium," as used herein, refer to any medium that participates in providing data that causes a machine to operate in a specific fashion. In an embodiment implemented using the computer or hardware system 1000, various computer readable media might be involved in providing instructions/code to processor(s) 1010 for execution and/or might be used to store and/or carry such instructions/code (e.g., as signals). In many implementations, a computer readable medium is a non-transitory, physical, and/or tangible storage medium. In some embodiments, a computer readable medium may take many forms, including, but not limited to, non-volatile media, volatile media, or the like. Non-volatile media includes, for example, optical and/or magnetic disks, such as the storage device(s) 1025. Volatile media includes, without limitation, dynamic memory, such as the working memory 1035. In some alternative embodiments, a computer readable medium may take the form of transmission media, which includes, without limitation, coaxial cables, copper wire, and fiber optics, including the wires that comprise the bus 1005, as well as the various components of the communication subsystem 1030 (and/or the media by which the communications subsystem 1030 provides communication with other devices). In an alternative set of embodiments, transmission media can also take the form of waves (including without limitation radio, acoustic, and/or light waves, such as those generated during radio-wave and infra-red data communications).

Common forms of physical and/or tangible computer readable media include, for example, a floppy disk, a flexible disk, a hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read instructions and/or code.

Various forms of computer readable media may be involved in carrying one or more sequences of one or more instructions to the processor(s) 1010 for execution. Merely by way of example, the instructions may initially be carried on a magnetic disk and/or optical disc of a remote computer. A remote computer might load the instructions into its dynamic memory and send the instructions as signals over a transmission medium to be received and/or executed by the computer or hardware system 1000. These signals, which might be in the form of electromagnetic signals, acoustic signals, optical signals, and/or the like, are all examples of carrier waves on which instructions can be encoded, in accordance with various embodiments of the invention.

The communications subsystem 1030 (and/or components thereof) generally will receive the signals, and the bus 1005 then might carry the signals (and/or the data, instructions, etc. carried by the signals) to the working memory 1035, from which the processor(s) 1005 retrieves and executes the instructions. The instructions received by the working memory 1035 may optionally be stored on a storage device 1025 either before or after execution by the processor (s) 1010.

As noted above, a set of embodiments comprises methods and systems for implementing annotation data collection and autonomous annotation, and, more particularly, to methods, systems, and apparatuses for implementing sequential imaging of biological samples for generating training data for developing deep learning based models for image analysis, for cell classification, for feature of interest identification, and/or for virtual staining of biological samples. FIG. 11 illustrates a schematic diagram of a system 1100 that can be used in accordance with one set of embodiments. The system 1100 can include one or more user computers, user devices, or customer devices 1105. A user computer, user device, or customer device 1105 can be a general purpose personal computer (including, merely by way of example, desktop computers, tablet computers, laptop computers, handheld computers, and the like, running any appropriate operating system, several of which are available from vendors such as Apple, Microsoft Corp., and the like), cloud computing devices, a server(s), and/or a workstation computer(s) running any of a variety of commercially-available UNIX™ or UNIX-like operating systems. A user computer, user device, or customer device 1105 can also have any of a variety of applications, including one or more applications configured to perform methods provided by various embodiments (as described above, for example), as well as one or more office applications, database client and/or server applications, and/or web browser applications. Alternatively, a user computer, user device, or customer device 1105 can be any other electronic device, such as a thin-client computer, Internet-enabled mobile telephone, and/or personal digital assistant, capable of communicating via a network (e.g., the network(s) 1110 described below) and/or of displaying and navigating web pages or other types of electronic documents. Although the exemplary system 1100 is shown with two user computers, user devices, or customer devices 1105, any number of user computers, user devices, or customer devices can be supported.

Certain embodiments operate in a networked environment, which can include a network(s) 1110. The network(s) 1110 can be any type of network familiar to those skilled in the art that can support data communications using any of a variety of commercially-available (and/or free or proprietary) protocols, including, without limitation, TCP/IP, SNA™, IPX™, AppleTalk™, and the like. Merely by way of example, the network(s) 1110 (similar to network(s) 350 of FIG. 3, or the like) can each include a local area network ("LAN"), including, without limitation, a fiber network, an Ethernet network, a Token-Ring™ network, and/or the like; a wide-area network ("WAN"); a wireless wide area network ("WWAN"); a virtual network, such as a virtual private network ("VPN"); the Internet; an intranet; an extranet; a public switched telephone network ("PSTN"); an infra-red network; a wireless network, including, without limitation, a network operating under any of the IEEE 802.11 suite of protocols, the Bluetooth™ protocol known in the art, and/or any other wireless protocol; and/or any combination of these and/or other networks. In a particular embodiment, the network might include an access network of the service provider (e.g., an Internet service provider ("ISP")). In another embodiment, the network might include a core network of the service provider, and/or the Internet.

Embodiments can also include one or more server computers 1115. Each of the server computers 1115 may be configured with an operating system, including, without limitation, any of those discussed above, as well as any commercially (or freely) available server operating systems. Each of the servers 1115 may also be running one or more applications, which can be configured to provide services to one or more clients 1105 and/or other servers 1115.

Merely by way of example, one of the servers 1115 might be a data server, a web server, a cloud computing device(s), or the like, as described above. The data server might include (or be in communication with) a web server, which can be used, merely by way of example, to process requests for web pages or other electronic documents from user computers 1105. The web server can also run a variety of server applications, including HTTP servers, FTP servers, CGI servers, database servers, Java servers, Matlab servers, and the like. In some embodiments of the invention, the web server may be configured to serve web pages that can be operated within a web browser on one or more of the user computers 1105 to perform methods of the invention.

The server computers 1115, in some embodiments, might include one or more application servers, which can be configured with one or more applications accessible by a client running on one or more of the client computers 1105 and/or other servers 1115. Merely by way of example, the server(s) 1115 can be one or more general purpose computers capable of executing programs or scripts in response to the user computers 1105 and/or other servers 1115, including, without limitation, web applications (which might, in some cases, be configured to perform methods provided by various embodiments). Merely by way of example, a web application can be implemented as one or more scripts or programs written in any suitable programming language, such as Java™, C, C#™ or C++, and/or any scripting language, such as Perl, Python, or TCL, as well as combinations of any programming and/or scripting languages. The application server(s) can also include database servers, including, without limitation, those commercially available from Oracle™, Microsoft™, Sybase™, IBM™, and the like, which can process requests from clients (including, depending on the configuration, dedicated database clients, API clients, web browsers, etc.) running on a user computer, user device, or customer device 1105 and/or another server 1115.

In some embodiments, an application server can perform one or more of the processes for implementing annotation data collection and autonomous annotation, and, more particularly, to methods, systems, and apparatuses for implementing sequential imaging of biological sample for generating training data for developing deep learning based models for image analysis, for cell classification, for feature of interest identification, and/or for virtual staining of biological samples, as described in detail above. Data provided by an application server may be formatted as one or more web pages (comprising HTML, JavaScript, etc., for example) and/or may be forwarded to a user computer 1105 via a web server (as described above, for example). Similarly, a web server might receive web page requests and/or input data from a user computer 1105 and/or forward the web page requests and/or input data to an application server. In some cases, a web server may be integrated with an application server.

In accordance with further embodiments, one or more servers 1115 can function as a file server and/or can include one or more of the files (e.g., application code, data files, etc.) necessary to implement various disclosed methods, incorporated by an application running on a user computer 1105 and/or another server 1115. Alternatively, as those skilled in the art will appreciate, a file server can include all necessary files, allowing such an application to be invoked remotely by a user computer, user device, or customer device 1105 and/or server 1115.

It should be noted that the functions described with respect to various servers herein (e.g., application server, database server, web server, file server, etc.) can be performed by a single server and/or a plurality of specialized servers, depending on implementation-specific needs and parameters.

In certain embodiments, the system can include one or more databases 1120*a*-1120*n* (collectively, "databases 1120"). The location of each of the databases 1120 is discretionary: merely by way of example, a database 1120*a* might reside on a storage medium local to (and/or resident in) a server 1115*a* (and/or a user computer, user device, or customer device 1105). Alternatively, a database 1120*n* can be remote from any or all of the computers 1105, 1115, so long as it can be in communication (e.g., via the network 1110) with one or more of these. In a particular set of embodiments, a database 1120 can reside in a storage-area network ("SAN") familiar to those skilled in the art. (Likewise, any necessary files for performing the functions attributed to the computers 1105, 1115 can be stored locally on the respective computer and/or remotely, as appropriate.) In one set of embodiments, the database 1120 can be a relational database, such as an Oracle database, that is adapted to store, update, and retrieve data in response to SQL-formatted commands. The database might be controlled and/or maintained by a database server, as described above, for example.

According to some embodiments, system 1100 might further comprise a computing system 1125 (similar to computing systems 305*a* of FIG. 3, or the like) and corresponding database(s) 1130 (similar to database(s) 310*a* of FIG. 3, or the like). System 1100 might further comprise a display device 1140 (similar to display device 320 of FIG. 3, or the like) that are used to allow a user 1145 to look at an optical view of a first biological sample that is displayed on the display device 1140. The user 1145 might use one or more user devices 1160 (similar to user device(s) 340 of FIG. 3, or the like; including, without limitation, smart phones, mobile phones, tablet computers, laptop computers, desktop computers, keyboards, keypads, computer mice, or monitors, and/or the like). In some embodiments, system 1100 might further comprise one or more audio sensors 1155 (optional; similar to audio sensor(s) 335 of FIG. 3, or the like; including, but not limited to, one or more microphones, one or more voice recorders, or one or more audio recorders, and/or the like), a camera 1150 (optional; similar to camera 330 of FIG. 3, or the like; including, without limitation, one or more eye tracking sensors, one or more motion sensors, or one or more tracking sensors, and/or the like), and a microscope 1135 (optional; similar to microscopes 315 of FIG. 3, or the like). In some cases, the audio sensors 1155 might be used to record vocal or spoken annotations by the user 1145 while the user is viewing the FOV of the first biological sample either on the display device 1140 or through an eyepiece(s) of the microscope 1135. The camera 1150 might capture images of the user 1145 (in some cases, capturing images of at least one eye of the user 1145) while the user 1145 is within the field of view ("FOV") 1150*a* of camera 1150, as the user is viewing the FOV of the first biological sample either on the display device 1140 or through an eyepiece(s) of the microscope 1135. The features of gaze tracking and voice annotation are described in greater detail in the '105 Application, which has already been incorporated by reference in its entirety for all purposes. In some instances, two or more of computing system 1125, database(s) 1130, display device 1140, user device(s) 1160, audio sensor(s) 1155 (optional), camera 1150 (optional), and/or microscope 1135 (optional) might be disposed in work environment 1165, which might include, but is not limited to, at least one of a laboratory, a clinic, a medical facility, a research facility, a healthcare facility, or a room, and/or the like.

Alternative, or additional, to computing system 1125 and corresponding database(s) 1130, system 1100 might further comprise remote computing system 1170 (similar to remote computing system 305*b* of FIG. 3, or the like) and corresponding database(s) 1175 (similar to database(s) 310*b* of FIG. 3, or the like). In some embodiments, system 1100 might further comprise artificial intelligence ("AI") system 1180. In some embodiments, computing system 1125 and/or 1170 might include, without limitation, one of a computing system disposed in a work environment, a remote computing system disposed external to the work environment and accessible over a network, a web server, a web browser, or a cloud computing system, and/or the like. According to some embodiments, the AI system 1180 might include, but is not limited to, at least one of a machine learning system, a deep learning system, a model architecture, and/or the like. In some instances, the model architecture may comprise at least one of a neural network, a convolutional neural network ("CNN"), or a fully convolutional network ("FCN"), and/or the like.

In operation, computing system 1125, remote computing system 1170, and/or AI system 1180 (collectively, "computing system") may receive a first image of a first biological sample, the first image comprising a first field of view ("FOV") of the first biological sample that has been stained with a first stain; and may receive a second image of the first biological sample, the second image comprising a second FOV of the first biological sample that has been stained with a second stain. The computing system may autonomously create a first set of image patches based on the first image and the second image, by extracting a portion of the first image and extracting a corresponding portion of the second image, the first set of image patches comprising a first patch corresponding to the extracted portion of the first image and a second patch corresponding to the extracted portion of the second image. In such cases, the first set of image patches may comprise labeling of instances of features of interest in the first biological sample that is based at least in part on at least one of information contained in the first patch, information contained in the second patch, or information contained in one or more external labeling sources.

The computing system utilize an AI system (e.g., AI system 305*d* or 305*c*, or the like) to train a first model ("Model G*") to generate first instance classification of features of interest ("Ground Truth") in the first biological sample, based at least in part on the first set of image patches and the labeling of instances of features of interest contained in the first set of image patches; and may utilize the AI system to train a second AI model ("Model G") to identify instances of features of interest in the first biological sample, based at least in part on the first patch and the first instance classification of features of interest generated by Model G*.

According to some embodiments, the first biological sample may include, without limitation, one of a human tissue sample, an animal tissue sample, a plant tissue sample, or an artificially produced tissue sample, and/or the like. In some instances, the features of interest may include, but are not limited to, at least one of normal cells, abnormal cells, damaged cells, cancer cells, tumors, subcellular structures, or organ structures, and/or the like.

In some embodiments, the first image may comprise highlighting of first features of interest in the first biological sample (including, but not limited to, at least one of first antigens, first nuclei, first cell walls, first cell structures, first antibodies, first normal cells, first abnormal cells, first damaged cells, first cancer cells, first tumors, first subcellular structures, first organ structures, or other features of interest, or the like) by the first stain that had been applied to the first biological sample. Similarly, the second image may comprise one of highlighting of second features of interest in the first biological sample (including, but not limited to, at least one of second antigens, second nuclei, second cell walls, second cell structures, second antibodies, second normal cells, second abnormal cells, second damaged cells, second cancer cells, second tumors, second subcellular structures, second organ structures, or other features of interest, or the like) by the second stain that had been applied to the first biological sample in addition to highlighting of the first features of interest by the first stain or highlighting of the second features of interest by the second stain without highlighting of the first features of interest by the first stain, the second features of interest being different from the first features of interest. In some cases, the second stain may be one of the same as the first stain but used to stain the second features of interest or different from the first stain, or the like.

Merely by way of example, in some cases, the first stain may include, without limitation, at least one of Hematoxylin, Acridine orange, Bismarck brown, Carmine, Coomassie blue, Cresyl violet, Crystal violet, 4',6-diamidino-2-phenylindole ("DAPI"), Eosin, Ethidium bromide intercalates, Acid fuchsine, Hoechst stain, Iodine, Malachite green, Methyl green, Methylene blue, Neutral red, Nile blue, Nile red, Osmium tetroxide, Propidium Iodide, Rhodamine, Safranine, programmed death-ligand 1 ("PD-L1") stain, 3,3'-Diaminobenzidine ("DAB") chromogen, Magenta chromogen, cyanine chromogen, cluster of differentiation ("CD") 3 stain, CD20 stain, CD68 stain, 40S ribosomal protein SA ("p40") stain, antibody-based stain, or label-free imaging marker, and/or the like. Likewise, the second stain may include, but is not limited to, at least one of Hematoxylin, Acridine orange, Bismarck brown, Carmine, Coomassie blue, Cresyl violet, Crystal violet, DAPI, Eosin, Ethidium bromide intercalates, Acid fuchsine, Hoechst stain, Iodine, Malachite green, Methyl green, Methylene blue, Neutral red, Nile blue, Nile red, Osmium tetroxide, Propidium Iodide, Rhodamine, Safranine, PD-L1 stain, DAB chromogen, Magenta chromogen, cyanine chromogen, CD3 stain, CD20 stain, CD68 stain, p40 stain, antibody-based stain, or label-free imaging marker, and/or the like.

According to some embodiments, the first image may include, without limitation, one of a first set of color or brightfield images, a first fluorescence image, a first phase image, or a first spectral image, and/or the like, where the first set of color or brightfield images may include, but is not limited to, a first red-filtered ("R") image, a first green-filtered ("G") image, and a first blue-filtered ("B") image, and/or the like. The first fluorescence image may include, but is not limited to, at least one of a first autofluorescence image or a first labelled fluorescence image having one or more channels with different excitation or emission characteristics, and/or the like. The first spectral image may include, but is not limited to, at least one of a first Raman spectroscopy image, a first near infrared ("NIR") spectroscopy image, a first multispectral image, a first hyperspectral image, or a first full spectral image, and/or the like. Similarly, the second image may include, without limitation, one of a second set of color or brightfield images, a second fluorescence image, a second phase image, or a second spectral image, and/or the like, where the second set of color or brightfield images may include, but is not limited to, a second R image, a second G image, and a second B image, and/or the like. The second fluorescence image may include, but is not limited to, at least one of a second autofluorescence image or a second labelled fluorescence image having one or more channels with different excitation or emission characteristics, and/or the like. The second spectral image may include, but is not limited to, at least one of a second Raman spectroscopy image, a second NIR spectroscopy image, a second multispectral image, a second hyperspectral image, or a second full spectral image, and/or the like.

In some embodiments, the computing system may align the first image with the second image to create first set of aligned images, by aligning one or more features of interest in the first biological sample as depicted in the first image with the same one or more features of interest in the first biological sample as depicted in the second image. In some instances, aligning the first image with the second image may be one of performed manually using manual inputs to the computing system or performed autonomously, where autonomous alignment may comprise alignment using at least one of automated global alignment techniques or optical flow alignment techniques, or the like.

According to some embodiments, the computing system may receive a third image of the first biological sample, the third image comprising a third FOV of the first biological sample that has been stained with a third stain different from each of the first stain and the second stain; and may autonomously perform one of: aligning the third image with each of the first image and the second image to create second aligned images, by aligning one or more features of interest in the first biological sample as depicted in the third image with the same one or more features of interest in the first biological sample as depicted in each of the first image and the second image; or aligning the third image with the first aligned images to create second aligned images, by aligning one or more features of interest in the first biological sample as depicted in the third image with the same one or more features of interest in the first biological sample as depicted in the first aligned images.

The computing system may autonomously create second aligned image patches from the second aligned images, by extracting a portion of the second aligned images, the portion of the second aligned images comprising a first patch corresponding to the extracted portion of the first image, a second patch corresponding to the extracted portion of the second image, and a third patch corresponding to the extracted portion of the third image; may train the AI system to update Model G* to generate second instance classification of features of interest in the first biological sample, based at least in part on the second aligned image patches and the labeling of instances of features of interest contained in the first set of image patches; and may train the AI system to update Model G to identify instances of features of interest in the first biological sample, based at least in part on the first patch and the second instance classification of features of interest generated by Model G*.

In some embodiments, the first image may comprise highlighting of first features of interest in the first biological sample (including, but not limited to, at least one of first antigens, first nuclei, first cell walls, first cell structures, first antibodies, first normal cells, first abnormal cells, first damaged cells, first cancer cells, first tumors, first subcellular structures, first organ structures, or other features of interest, or the like) by the first stain that had been applied to the first biological sample. In some cases, the second image may comprise one of highlighting of second features of interest in the first biological sample (including, but not limited to, at least one of second antigens, second nuclei, second cell walls, second cell structures, second antibodies, second normal cells, second abnormal cells, second damaged cells, second cancer cells, second tumors, second subcellular structures, second organ structures, or other features of interest, or the like) by the second stain that had been applied to the first biological sample in addition to highlighting of the first features of interest by the first stain or highlighting of the second features of interest by the second stain without highlighting of the first features of interest by the first stain, the second features of interest being different from the first features of interest. In some instances, the third image may comprise one of highlighting of third features of interest in the first biological sample (including, but not limited to, at least one of third antigens, third nuclei, third cell walls, third cell structures, third antibodies, third normal cells, third abnormal cells, third damaged cells, third cancer cells, third tumors, third subcellular structures, third organ structures, or other features of interest, or the like) by the third stain that had been applied to the first biological sample in addition to highlighting of the first features of interest by the first stain and highlighting of the second features of interest by the second stain, highlighting of the third features of interest by the third stain in addition to only one of highlighting of the first features of interest by the first stain or highlighting of the second features of interest by the second stain, or highlighting of the third features of interest by the third stain without any of highlighting of the first features of interest by the first stain or highlighting of the second features of interest by the second stain, and/or the like, the third features of interest being different from each of the first features of interest and the second features of interest.

According to some embodiments, the first image may include, without limitation, one of a first set of color or brightfield images, a first fluorescence image, a first phase image, or a first spectral image, and/or the like, where the first set of color or brightfield images may include, but is not limited to, a first red-filtered ("R") image, a first green-filtered ("G") image, and a first blue-filtered ("B") image, and/or the like. The first fluorescence image may include, but is not limited to, at least one of a first autofluorescence image or a first labelled fluorescence image having one or more channels with different excitation or emission characteristics, and/or the like. The first spectral image may include, but is not limited to, at least one of a first Raman spectroscopy image, a first near infrared ("NIR") spectroscopy image, a first multispectral image, a first hyperspectral image, or a first full spectral image, and/or the like. Likewise, the second image may include, without limitation, one of a second set of color or brightfield images, a second fluorescence image, a second phase image, or a second spectral image, and/or the like, where the second set of color or brightfield images may include, but is not limited to, a second R image, a second G image, and a second B image, and/or the like. The second fluorescence image may include, but is not limited to, at least one of a second autofluorescence image or a second labelled fluorescence image having one or more channels with different excitation or emission characteristics, and/or the like. The second spectral image may include, but is not limited to, at least one of a second Raman spectroscopy image, a second NIR spectroscopy image, a second multispectral image, a second hyperspectral image, or a second full spectral image, and/or the like. Similarly, the third image may include, without limitation, one of a third set of color or brightfield images, a third fluorescence image, a third phase image, or a third spectral image, and/or the like, where the third set of color or brightfield images may include, but is not limited to, a third R image, a third G image, and a third B image, and/or the like. The third fluorescence image may include, but is not limited to, at least one of a third autofluorescence image or a third labelled fluorescence image having one or more channels with different excitation or emission characteristics, and/or the like. The third spectral image may include, but is not limited to, at least one of a third Raman spectroscopy image, a third NIR spectroscopy image, a third multispectral image, a third hyperspectral image, or a third full spectral image, and/or the like.

In some embodiments, the computing system may receive a fourth image, the fourth image comprising one of a fourth FOV of the first biological sample different from the first FOV and the second FOV or a fifth FOV of a second biological sample, where the second biological sample may be different from the first biological sample; and may identify, using Model G, second instances of features of interest in the second biological sample, based at least in part on the fourth image and based at least in part on training of Model G using the first patch and the first instance classification of features of interest generated by Model G*. In some cases, the fourth image may comprise the fifth FOV and may further comprise only highlighting of first features of interest in the second biological sample by the first stain that had been applied to the second biological sample. According to some embodiments, the computing system may generate, using Model G, a clinical score, based at least in part on the identified second instances of features of interest.

In another aspect, the computing system may receive a first image of a first biological sample, the first image comprising a first field of view ("FOV") of the first biological sample; and may identify, using a first AI model ("Model G") that is generated or updated by a trained AI system, first instances of features of interest in the first biological sample, based at least in part on the first image and based at least in part on training of Model G using a first patch and first instance classification of features of interest generated by a second model (Model G*) that is generated or updated by the trained AI system by using first aligned image patches and labeling of instances of features of interest contained in the first patch. In some cases, the first aligned image patches may comprise an extracted portion of first aligned images, which may comprise a second image and a third image that have been aligned. The second image may comprise a second FOV of a second biological sample that has been stained with a first stain, the second biological sample being different from the first biological sample. The third image may comprise a third FOV of the second biological sample that has been stained with a second stain. The second patch may comprise labeling of instances of features of interest as shown in the extracted portion of the second image of the first aligned images. The first image may comprise highlighting of first features of interest in the second biological sample by the first stain that had been applied to the second biological sample. The second patch may comprise one of highlighting of second features of interest in the second biological sample by the second stain that had been applied to the second biological sample in addition to highlighting of the first features of interest by the first stain or highlighting of the second features of interest by the second stain without highlighting of the first features of interest by the first stain.

In yet another aspect, the computing system may receive first instance classification of features of interest ("Ground Truth") in a first biological sample that has been sequentially stained, the Ground Truth having been generated by a trained first model ("Model G*") that has been trained or updated by an AI system, wherein the Ground Truth is generated by using first aligned image patches and labeling of instances of features of interest contained in the first aligned image patches, wherein the first aligned image patches comprise an extracted portion of first aligned images, wherein the first aligned images comprise a first image and a second image that have been aligned, wherein the first image comprises a first FOV of the first biological sample that has been stained with a first stain, wherein the second image comprises a second FOV of the first biological sample that has been stained with a second stain, wherein the first aligned image patches comprise labeling of instances of features of interest as shown in the extracted portion of the first aligned images; and may utilize the AI system to train a second AI model ("Model G") to identify instances of features of interest in the first biological sample, based at least in part on the first instance classification of features of interest generated by Model G*.

In still another aspect, the computing system may generate ground truth for developing accurate AI models for biological image interpretation, based at least in part on images of a first biological sample depicting sequential staining of the first biological sample.

In an aspect, the computing system may receive a first image of a first biological sample, the first image comprising a first field of view ("FOV") of the first biological sample that has been stained with a first stain; may receive a second image of the first biological sample, the second image comprising a second FOV of the first biological sample that has been stained with at least a second stain; and may align the first image with the second image to create first aligned images, by aligning one or more features of interest in the first biological sample as depicted in the first image with the same one or more features of interest in the first biological sample as depicted in the second image.

The computing system may autonomously create first aligned image patches from the first aligned images, by extracting a portion of the first aligned images, the portion of the first aligned images comprising a first patch corresponding to the extracted portion of the first image and a second patch corresponding to the extracted portion of the second image; may utilize an AI system to train a first AI model ("Model F") to generate a third patch comprising a virtual stain of the first aligned image patches, based at least in part on the first patch and the second patch, the virtual stain simulating staining by at least the second stain of features of interest in the first biological sample as shown in the second patch; and may utilize the AI system to train a second model ("Model G*") to identify or classify first instances of features of interest in the first biological sample, based at least in part on the third patch and based at least in part on results from an external instance classification process or a region of interest detection process.

According to some embodiments, the first image may comprise highlighting of first features of interest in the first biological sample (including, but not limited to, at least one of first antigens, first nuclei, first cell walls, first cell structures, first antibodies, first normal cells, first abnormal cells, first damaged cells, first cancer cells, first tumors, first subcellular structures, first organ structures, or other features of interest, or the like) by the first stain that had been applied to the first biological sample. In some cases, the third patch may comprise one of highlighting of the first features of interest by the first stain and highlighting of second features of interest in the first biological sample (including, but not limited to, at least one of second antigens, second nuclei, second cell walls, second cell structures, second antibodies, second normal cells, second abnormal cells, second damaged cells, second cancer cells, second tumors, second subcellular structures, second organ structures, or other features of interest, or the like) by the virtual stain that simulates the second stain having been applied to the first biological sample or highlighting of the first features of interest by the first stain and highlighting of first features of interest by the virtual stain, the second features of interest being different from the first features of interest. In some instances, the second stain may be one of the same as the first stain but used to stain the second features of interest or different from the first stain.

Merely by way of example, in some cases, the first stain may include, without limitation, at least one of Hematoxylin, Acridine orange, Bismarck brown, Carmine, Coomassie blue, Cresyl violet, Crystal violet, 4',6-diamidino-2-phenylindole ("DAPI"), Eosin, Ethidium bromide intercalates, Acid fuchsine, Hoechst stain, Iodine, Malachite green, Methyl green, Methylene blue, Neutral red, Nile blue, Nile red, Osmium tetroxide, Propidium Iodide, Rhodamine, Safranine, programmed death-ligand 1 ("PD-L1") stain, 3,3'-Diaminobenzidine ("DAB") chromogen, Magenta chromogen, cyanine chromogen, cluster of differentiation ("CD") 3 stain, CD20 stain, CD68 stain, 40S ribosomal protein SA ("p40") stain, antibody-based stain, or label-free imaging marker, and/or the like. Similarly, the second stain may include, but is not limited to, at least one of Hematoxylin, Acridine orange, Bismarck brown, Carmine, Coomassie blue, Cresyl violet, Crystal violet, DAPI, Eosin, Ethidium bromide intercalates, Acid fuchsine, Hoechst stain, Iodine, Malachite green, Methyl green, Methylene blue, Neutral red, Nile blue, Nile red, Osmium tetroxide, Propidium Iodide, Rhodamine, Safranine, PD-L1 stain, DAB chromogen, Magenta chromogen, cyanine chromogen, CD3 stain, CD20 stain, CD68 stain, p40 stain, antibody-based stain, or label-free imaging marker, and/or the like.

In some embodiments, the first image may include, without limitation, one of a first set of color or brightfield images, a first fluorescence image, a first phase image, or a first spectral image, and/or the like, where the first set of color or brightfield images may include, but is not limited to, a first red-filtered ("R") image, a first green-filtered ("G") image, and a first blue-filtered ("B") image, and/or the like. The first fluorescence image may include, but is not limited to, at least one of a first autofluorescence image or a first labelled fluorescence image having one or more channels with different excitation or emission characteristics, and/or the like. The first spectral image may include, but is not limited to, at least one of a first Raman spectroscopy image, a first near infrared ("NIR") spectroscopy image, a first multispectral image, a first hyperspectral image, or a first full spectral image, and/or the like. In some instances, the second image may include, without limitation, one of a second set of color or brightfield images, a second fluorescence image, a second phase image, or a second spectral image, and/or the like, where the second set of color or brightfield images may include, but is not limited to, a second R image, a second G image, and a second B image, and/or the like. The second fluorescence image may include, but is not limited to, at least one of a second autofluorescence image or a second labelled fluorescence image having one or more channels with different excitation or emission characteristics, and/or the like. The second spectral image may include, but is not limited to, at least one of a second Raman spectroscopy image, a second NIR spectroscopy image, a second multispectral image, a second hyperspectral image, or a second full spectral image, and/or the like. In some cases, the third patch may include, without limitation, one of a third set of color or brightfield images, a third fluorescence image, a third phase image, or a third spectral image, and/or the like, where the third set of color or brightfield images may include, but is not limited to, a third R image, a third G image, and a third B image, and/or the like. The third fluorescence image may include, but is not limited to, at least one of a third autofluorescence image or a third labelled fluorescence image having one or more channels with different excitation or emission characteristics, and/or the like. The third spectral image may include, but is not limited to, at least one of a third Raman spectroscopy image, a third NIR spectroscopy image, a third multispectral image, a third hyperspectral image, or a third full spectral image, and/or the like.

According to some embodiments, aligning the first image with the second image may be one of performed manually using manual inputs to the computing system or performed autonomously, where autonomous alignment may comprise alignment using at least one of automated global alignment techniques or optical flow alignment techniques.

In some embodiments, training, using the AI system, Model G* to identify or classify instances of features of interest in the first biological sample may comprise training, using the AI system, Model G* to identify or classify instances of features of interest in the first biological sample, based at least in part on one or more of the first patch, the second patch, or the third patch and based at least in part on the results from the external instance classification process or the region of interest detection process. In some cases, the external instance classification process or the region of interest detection process may each include, without limitation, at least one of detection of nuclei in the first image or the first patch by a nuclei detection method, identification of nuclei in the first image or the first patch by a pathologist, detection of features of interest in the first image or the first patch by a feature detection method, or identification of features of interest in the first image or the first patch by the pathologist, and/or the like.

According to some embodiments, training the AI system to update Model F may comprise: receiving, with an encoder, the first patch; receiving the second patch; encoding, with the encoder, the received first patch; decoding, with the decoder, the encoded first patch; generating an intensity map based on the decoded first patch; simultaneously operating on the encoded first patch to generate a color vector; combining the generated intensity map with the generated color vector to generate an image of the virtual stain; adding the generated image of the virtual stain to the received first patch to produce a predicted virtually stained image patch; determining a first loss value between the predicted virtually stained image patch and the second patch; calculating a loss value using a loss function, based on the first loss value between the predicted virtually stained image patch and the second patch; and updating, with the AI system, Model F to generate the third patch, by updating one or more parameters of Model F based on the calculated loss value. In some instances, the loss function may include, but is not limited to, one of a mean squared error loss function, a mean squared logarithmic error loss function, a mean absolute error loss function, a Huber loss function, or a weighted sum of squared differences loss function, and/or the like.

In some embodiments, the first patch may include, without limitation, one of a first set of color or brightfield images, a first fluorescence image, a first phase image, or a first spectral image, and/or the like, where the first set of color or brightfield images may include, but is not limited to, a first red-filtered ("R") image, a first green-filtered ("G") image, and a first blue-filtered ("B") image, and/or the like. The first fluorescence image may include, but is not limited to, at least one of a first autofluorescence image or a first labelled fluorescence image having one or more channels with different excitation or emission characteristics, and/or the like. The first spectral image may include, but is not limited to, at least one of a first Raman spectroscopy image, a first near infrared ("NIR") spectroscopy image, a first multispectral image, a first hyperspectral image, or a first full spectral image, and/or the like. In some cases, the second image may include, without limitation, one of a second set of color or brightfield images, a second fluorescence image, a second phase image, or a second spectral image, and/or the like, where the second set of color or brightfield images may include, but is not limited to, a second R image, a second G image, and a second B image, and/or the like. The second fluorescence image may include, but is not limited to, at least one of a second autofluorescence image or a second labelled fluorescence image having one or more channels with different excitation or emission characteristics, and/or the like. The second spectral image may include, but is not limited to, at least one of a second Raman spectroscopy image, a second NIR spectroscopy image, a second multispectral image, a second hyperspectral image, or a second full spectral image, and/or the like. In some instances, the predicted virtually stained image patch may include, without limitation, one of a third set of color or brightfield images, a third fluorescence image, a third phase image, or a third spectral image, and/or the like, where the third set of color or brightfield images may include, but is not limited to, a third R image, a third G image, and a third B image, and/or the like. The third fluorescence image may include, but is not limited to, at least one of a third autofluorescence image or a third labelled fluorescence image having one or more channels with different excitation or emission characteristics, and/or the like. The third spectral image may include, but is not limited to, at least one of a third Raman spectroscopy image, a third NIR spectroscopy image, a third multispectral image, a third hyperspectral image, or a third full spectral image, and/or the like.

According to some embodiments, operating on the encoded first patch to generate the color vector may comprise operating on the encoded first patch to generate a color vector, using a color vector output and one of a model architecture, a statistical model-based system, or a deterministic analysis system, and/or the like. In some instances, the model architecture may comprise at least one of a neural network, a convolutional neural network ("CNN"), or a fully convolutional network ("FCN"), and/or the like. In some cases, the color vector may be one of a fixed color vector or a learned color vector that is not based on the encoded first patch, and/or the like.

In some embodiments, the image of the virtual stain may include, but is not limited to, one of a 3-channel image of the virtual stain, a RGB-transform image of the virtual stain, or a logarithmic transform image of the virtual stain, and/or the like. In some instances, generating the predicted virtually stained image patch may include, without limitation, adding the generated image of the virtual stain to the received first patch to produce the predicted virtually stained image patch. In some cases, determining the first loss value between the predicted virtually stained image patch and the second patch may be performed without adding the generated image of the virtual stain to the received first patch.

According to some embodiments, the first loss value may include, without limitation, one of a pixel loss value between each pixel in the predicted virtually stained image patch and a corresponding pixel in the second patch or a generative adversarial network ("GAN") loss value between the predicted virtually stained image patch and the second patch, and/or the like. In some instances, the GAN loss value may be generated based on one of a minimax GAN loss function, a non-saturating GAN loss function, a least squares GAN loss function, or a Wasserstein GAN loss function, and/or the like.

Alternatively, training the AI system to update Model F may comprise: receiving, with the AI system, the first patch; receiving, with the AI system, the second patch; generating, with a second model of the AI system, an image of the virtual stain; adding the generated image of the virtual stain to the received first patch to produce a predicted virtually stained image patch; determining a first loss value between the predicted virtually stained image patch and the second patch; calculating a loss value using a loss function, based on the first loss value between the predicted virtually stained image patch and the second patch; and updating, with the AI system, Model F to generate the third patch, by updating one or more parameters of Model F based on the calculated loss value.

In some embodiments, the second model may include, without limitation, at least one of a convolutional neural network ("CNN"), a U-Net, an artificial neural network ("ANN"), a residual neural network ("ResNet"), an encode/decode CNN, an encode/decode U-Net, an encode/decode ANN, or an encode/decode ResNet, and/or the like.

According to some embodiments, the computing system may receive a fourth image, the fourth image comprising one of a fourth FOV of the first biological sample different from the first FOV and the second FOV or a fifth FOV of a second biological sample, where the second biological sample may be different from the first biological sample; and may identify, using Model G*, second instances of features of interest in the second biological sample, based at least in part on the fourth image and based at least in part on training of Model G* using at least the third patch comprising the virtual stain of the first aligned image patches. According to some embodiments, the computing system may generate, using Model G*, a clinical score, based at least in part on the identified second instances of features of interest.

In some embodiments, the first image may comprise highlighting of first features of interest in the first biological sample (including, but not limited to, at least one of first antigens, first nuclei, first cell walls, first cell structures, first antibodies, first normal cells, first abnormal cells, first damaged cells, first cancer cells, first tumors, first subcellular structures, first organ structures, or other features of interest, or the like) by the first stain that had been applied to the first biological sample. In some cases, the third patch may comprise one of highlighting of the first features of interest by the first stain and highlighting of second features of interest in the first biological sample (including, but not limited to, at least one of second antigens, second nuclei, second cell walls, second cell structures, second antibodies, second normal cells, second abnormal cells, second damaged cells, second cancer cells, second tumors, second subcellular structures, second organ structures, or other features of interest, or the like) by the virtual stain that simulates the second stain having been applied to the first biological sample or highlighting of the first features of interest by the first stain and highlighting of first features of interest by the virtual stain, the second features of interest being different from the first features of interest. In some instances, the second stain may be one of the same as the first stain but used to stain the second features of interest or different from the first stain.

According to some embodiments, the first image may include, without limitation, one of a first set of color or brightfield images, a first fluorescence image, a first phase image, or a first spectral image, and/or the like, where the first set of color or brightfield images may include, but is not limited to, a first red-filtered ("R") image, a first green-filtered ("G") image, and a first blue-filtered ("B") image, and/or the like. The first fluorescence image may include, but is not limited to, at least one of a first autofluorescence image or a first labelled fluorescence image having one or more channels with different excitation or emission characteristics, and/or the like. The first spectral image may include, but is not limited to, at least one of a first Raman spectroscopy image, a first near infrared ("NIR") spectroscopy image, a first multispectral image, a first hyperspectral image, or a first full spectral image, and/or the like. In some instances, the second image may include, without limitation, one of a second set of color or brightfield images, a second fluorescence image, a second phase image, or a second spectral image, and/or the like, where the second set of color or brightfield images may include, but is not limited to, a second R image, a second G image, and a second B image, and/or the like. The second fluorescence image may include, but is not limited to, at least one of a second autofluorescence image or a second labelled fluorescence image having one or more channels with different excitation or emission characteristics, and/or the like. The second spectral image may include, but is not limited to, at least one of a second Raman spectroscopy image, a second NIR spectroscopy image, a second multispectral image, a second hyperspectral image, or a second full spectral image, and/or the like. In some cases, the third patch may include, without limitation, one of a third set of color or brightfield images, a third fluorescence image, a third phase image, or a third spectral image, and/or the like, where the third set of color or brightfield images may include, but is not limited to, a third R image, a third G image, and a third B image, and/or the like. The third fluorescence image may include, but is not limited to, at least one of a third autofluorescence image or a third labelled fluorescence image having one or more channels with different excitation or emission characteristics, and/or the like. The third spectral image may include, but is not limited to, at least one of a third Raman spectroscopy image, a third NIR spectroscopy image, a third multispectral image, a third hyperspectral image, or a third full spectral image, and/or the like.

In some embodiments, training the AI system to update Model F may comprise: receiving, with an encoder, the first patch; receiving the second patch; encoding, with the encoder, the received first patch; decoding, with the decoder, the encoded first patch; generating an intensity map based on the decoded first patch; simultaneously operating on the encoded first patch to generate a color vector; combining the generated intensity map with the generated color vector to generate an image of the virtual stain; adding the generated image of the virtual stain to the received first patch to produce a predicted virtually stained image patch; determining a first loss value between the predicted virtually stained image patch and the second patch; calculating a loss value using a loss function, based on the first loss value between the predicted virtually stained image patch and the second patch; and updating, with the AI system, Model F to generate the third patch, by updating one or more parameters of Model F based on the calculated loss value. In some instances, the loss function may include, but is not limited to, one of a mean squared error loss function, a mean squared logarithmic error loss function, a mean absolute error loss function, a Huber loss function, or a weighted sum of squared differences loss function, and/or the like.

According to some embodiments, the first loss value may include, without limitation, one of a pixel loss value between each pixel in the predicted virtually stained image patch and a corresponding pixel in the second patch or a generative adversarial network ("GAN") loss value between the predicted virtually stained image patch and the second patch, and/or the like. In some cases, the GAN loss value may be generated based on one of a minimax GAN loss function, a non-saturating GAN loss function, a least squares GAN loss function, or a Wasserstein GAN loss function, and/or the like.

In yet another aspect, the computing system may receive a first image of a first biological sample, the first image comprising a first field of view ("FOV") of the first biological sample; and may identify, using a first model ("Model G*") that is generated or updated by a trained AI system, first instances of features of interest in the first biological sample, based at least in part on the first image and based at least in part on training of Model G* using at least a first patch comprising a virtual stain of first aligned image patches, the first patch being generated by a second AI model (Model F) that is generated or updated by the trained AI system by using a second patch. In some cases, the first aligned image patches may comprise an extracted portion of first aligned images. The first aligned images may comprise a second image and a third image that have been aligned. The second image may comprise a second FOV of a second biological sample that is different from the first biological sample that has been stained with a first stain. The second patch may comprise the extracted portion of the second image. The third image may comprise a third FOV of the second biological sample that has been stained with at least a second stain.

These and other functions of the system 1100 (and its components) are described in greater detail above with respect to FIGS. 3-9.

Additional exemplary embodiments are now described.

According to an aspect of some embodiments of the present invention there is provided a method for detecting multiple target molecules in a biological sample comprising cells, the method comprising:

- contacting the biological sample with one or more first reagents which generate a detectable signal in cells comprising a first target molecule;
- contacting the biological sample with one or more second reagents which are capable of generating a detectable signal in cells comprising a second target molecule under conditions in which the one or more second reagents do not generate a detectable signal;
- detecting the signal generated by the one or more first reagents;
- creating conditions in which the one or more second reagents generate a signal in cells comprising the second molecule; and
- detecting the signal generated by the one or more second reagents.

Optionally, further comprising:

- obtaining a first digital image of the signal generated by the one or more first reagents;
- obtaining a second digital image of the signal generated by the one or more first reagents and the signal generated by the one or more second reagents; and
- copying a mask of the second digital image to the first digital image.

Optionally, the biological sample comprises one of a human tissue sample, an animal tissue sample, or a plant tissue sample.

Optionally, the target molecules are indicative of at least one of normal cells, cell type, abnormal cells, damaged cells, cancer cells, tumors, subcellular structures, a marker indicative of or associated with a disease, disorder or health condition, or organ structures.

Optionally, the target molecules are selected from the group consisting of nuclear proteins, cytoplasmic proteins, membrane proteins, nuclear antigens, cytoplasmic antigens, membrane antigens and nucleic acids.

Optionally, the target molecules are nucleic acids.

Optionally, the target molecules are polypeptides.

Optionally, the first reagents comprise a first primary antibody against a first target polypeptide, an HRP coupled polymer that binds to the first primary antibody and a chromogen which is an HRP substrate.

Optionally, the second reagents comprise a second primary antibody against a second target polypeptide, an HRP coupled polymer that binds to the second primary antibody, a fluorescein-coupled long single chained polymer, an antibody against FITC that binds to the fluorescein-coupled long single chained polymer and is coupled to HRP and a chromogen which is an HRP substrate.

Optionally, further comprising using a digital image of the signals detected in the biological sample to train a neural network.

Optionally, a neural network is trained using the method

According to an aspect of some embodiments of the present invention there is provided a method for generating cell-level annotations from a biological sample comprising cells comprising:

a) exposing the biological sample to a first ligand that recognizes a first antigen thereby forming a first ligand antigen complex;

b) exposing the first ligand antigen complex to a first labeling reagent binding to the first ligand, the first labeling reagent forming a first detectable reagent, whereby the first detectable reagent is precipitated around the first antigen and visible in brightfield;

c) exposing the biological sample to a second ligand that recognizes a second antigen thereby forming a second ligand antigen complex;

d) exposing the second ligand antigen complex to a second labeling reagent binding to the second ligand, the second labeling reagent comprising a substrate not visible in brightfield, whereby the substrate is precipitated around the second antigen;

e) obtaining a first image of the biological sample in brightfield to visualize the first chromogen precipitated in the biological sample;

f) exposing the biological sample to a third labeling reagent that recognizes the substrate, thereby forming a third ligand antigen complex, the third labeling reagent forming a second detectable reagent, whereby the second detectable reagent is precipitated around the second antigen;

g) obtaining a second image of the biological sample in brightfield with the second detectable reagent precipitated in the biological sample;

h) creating a mask from the second image; and i) applying the mask to the first image so as to obtain an image of the biological sample annotated with the second antigen.

Optionally, the biological sample comprises one of a human tissue sample, an animal tissue sample, or a plant tissue sample.

Optionally, the target molecules are indicative of at least one of normal cells, cell type, abnormal cells, damaged cells, cancer cells, tumors, subcellular structures, a marker indicative of or associated with a disease, disorder or health condition, or organ structures.

Optionally, the method further comprises, prior to step a), applying a target retrieval buffer and protein blocking solution to the biological sample, whereby the first and second antigens are exposed for the subsequent steps and endogenous peroxidases are inactivated.

Optionally, the first and third labeling reagents comprise an enzyme that acts on a detectable reagent substrate to form the first and second detectable reagents, respectively.

Optionally, the first and second antigens are non-nuclear proteins.

Optionally, the method further comprises, following step b), denaturing the first ligands to retrieve the first antigens available.

Optionally, the method further comprises, following step d), i) counterstaining cell nuclei of the biological sample, and ii) dehydrating and mounting the sample on a slide.

Optionally, the method further comprises, following step e), i) removing mounting medium from the slide, and ii) rehydrating the biological sample.

Optionally, the method further comprises, following step f), i) counterstaining cell nuclei of the biological sample, and ii) dehydrating and mounting the sample on a slide.

Optionally, the first ligand comprises an anti-lymphocyte-specific antigen antibody ("primary antibody"), the first labeling reagent comprises a horseradish peroxidase (HRP)-coupled polymer capable of binding to the primary antibody, the first detectable reagent comprises a chromogen comprising an HRP substrate comprising HRP Magenta or 3,3'-diaminobenzidine tetrahydrochloride (DAB), the second antigen comprises PD-L1, the second ligand comprises anti-PD-L1 antibodies, the second labeling reagent comprises an HRP-coupled polymer capable of binding to anti-PD-L1 antibodies, the substrate comprises fluorescein-coupled long single-chained polymer (fer-4-flu linker), third labeling reagent comprises an anti-FITC antibody coupled to HRP, and the second detectable reagent comprises a chromogen comprising HRP Magenta or DAB.

Optionally, the first antigen comprises PD-L1.

the first ligand comprises anti-PD-L1 antibodies, the first labeling reagent comprises an HRP-coupled polymer capable of binding to anti-PD-L1 antibodies, the substrate comprises fluorescein-coupled long single-chained polymer (fer-4-flu linker), the second ligand comprises an anti-lymphocyte-specific antigen antibody ("primary antibody"), the second labeling reagent comprises a horseradish peroxidase (HRP)-coupled polymer capable of binding to the primary antibody, the second detectable reagent comprises a chromogen comprising an HRP substrate comprising HRP Magenta or 3,3'-diaminobenzidine tetrahydrochloride (DAB), third labeling reagent comprises an anti-FITC antibody coupled to HRP, and the second detectable reagent comprises a chromogen comprising HRP Magenta or DAB.

Optionally, the first labeling reagent comprises a horseradish peroxidase (HRP)-coupled polymer capable of binding to the primary antibody, the first detectable reagent comprises a chromogen comprising an HRP substrate comprising HRP Magenta or 3,3'-diaminobenzidine tetrahydrochloride (DAB), the second antigen comprises p40, the second ligand comprises anti-p40 antibodies, the second labeling reagent comprises an HRP-coupled polymer capable of binding to anti-p40 antibodies, the substrate comprises fluorescein-coupled long single-chained polymer (fer-4-flu linker), third labeling reagent an anti-FITC antibody coupled to HRP, and the second detectable reagent comprises a chromogen comprising HRP Magenta or DAB.

Optionally, the first antigen comprises p40, the first ligand comprises anti-p40 antibodies, the first labeling reagent comprises an HRP-coupled polymer capable of binding to anti-p40 antibodies, the substrate comprises fluorescein-coupled long single-chained polymer (fer-4-flu linker), the second labeling reagent comprises a horseradish peroxidase (HRP)-coupled polymer capable of binding to the primary antibody, the second detectable reagent comprises a chromogen comprising an HRP substrate comprising HRP Magenta or 3,3'-diaminobenzidine tetrahydrochloride (DAB), third labeling reagent an anti-FITC antibody coupled to HRP, and the second detectable reagent comprises a chromogen comprising HRP Magenta or DAB.

Optionally, a counterstaining agent is hematoxylin.

Optionally, the method further comprises using a digital image of the signals detected in the biological sample to train a neural network.

Optionally, a neural network trained using the method.

Optionally, an annotated image obtained by the method.

According to an aspect of some embodiments of the present invention there is provided a method for detecting multiple target molecules in a biological sample comprising cells, the method comprising:

contacting the biological sample with one or more first reagents which generate a detectable signal in cells comprising a first target molecule;

contacting the biological sample with one or more second reagents which generate a detectable signal in cells comprising a second target molecule, wherein the detectable signal generated by the one or more second reagents is removable;

detecting the signal generated by the one or more first reagents and the signal generated by the one or more second reagents;

creating conditions in which the signal generated by the one or more second reagents is removed; and detecting the signal generated by the one or more first reagents.

Optionally, the method further comprises:

obtaining a first digital image of the signal generated by the one or more first reagents and the signal generated by the one or more second reagents;

obtaining a second digital image of the signal generated by the one or more first reagents; and copying a mask of the first digital image to the second digital image.

Optionally, the biological sample comprises one of a human tissue sample, an animal tissue sample, or a plant tissue sample.

Optionally, the target molecules are indicative of at least one of normal cells, cell type, abnormal cells, damaged cells, cancer cells, tumors, subcellular structures, a marker indicative of or associated with a disease, disorder or health condition, or organ structures.

Optionally, the target molecules are selected from the group consisting of nuclear proteins, cytoplasmic proteins, membrane proteins, nuclear antigens, cytoplasmic antigens, membrane antigens and nucleic acids.

Optionally, the target molecules are nucleic acids.

Optionally, the target molecules are polypeptides.

Optionally, the first reagents comprise a first primary antibody against a first target polypeptide, an HRP coupled polymer that binds to the first primary antibody and a chromogen which is an HRP substrate.

Optionally, the second reagents comprise a second primary antibody against a second target polypeptide, an HRP coupled polymer that binds to the second primary antibody, and amino ethyl carbazole.

Optionally, the method further comprises using a digital image of the signals detected in the biological sample to train a neural network.

Optionally, a neural network trained using the method.

According to an aspect of some embodiments of the present invention there is provided a method for generating cell-level annotations from a biological sample comprising cells, the method comprising:

a) exposing the biological sample to a first ligand that recognizes a first antigen thereby forming a first ligand antigen complex;

b) exposing the first ligand antigen complex to a first labeling reagent binding to the first ligand, the first labeling reagent forming a first detectable reagent, whereby the first detectable reagent is precipitated around the first antigen;

c) exposing the biological sample to a second ligand that recognizes a second antigen thereby forming a second ligand antigen complex;

d) exposing the second ligand antigen complex to a second labeling reagent binding to the second ligand, the second labeling reagent forming a second detectable reagent, whereby the second detectable reagent is precipitated around the second antigen;

e) obtaining a first image of the biological sample with the first and second detectable reagents precipitated in the biological sample;

f) incubating the tissue sample with an agent which dissolves the second detectable reagent;

g) obtaining a second image of the biological sample with the first detectable reagent precipitated in the biological sample;

h) creating a mask from the first image; and i) applying the mask to the second image so as to obtain an annotated image of the biological sample with the second antigen.

Optionally, the first biological sample comprises one of a human tissue sample, an animal tissue sample, or a plant tissue sample, wherein the objects of interest comprise at least one of normal cells, abnormal cells, damaged cells, cancer cells, tumors, subcellular structures, or organ structures.

Optionally, the method further comprises, prior to step a), applying a target retrieval buffer and protein blocking solution to the biological sample, whereby the first and second antigens are exposed for the subsequent steps and endogenous peroxidases are inactivated.

Optionally, the first and second labeling reagents comprise an enzyme that acts on a detectable reagent substrate to form the first and second detectable reagents, respectively.

Optionally, the first and second antigens are non-nuclear proteins.

Optionally, further comprising, following step b), denaturing the first ligands to retrieve the first antigens available.

Optionally, the method further comprises, following step d), i) counterstaining cell nuclei of the biological sample, and ii) dehydrating and mounting the sample on a slide.

Optionally, further comprising, following step e), i) removing mounting medium from the slide, and ii) rehydrating the biological sample.

Optionally, the method further comprises, following step f), dehydrating and mounting the sample on a slide.

Optionally, the first antigen comprises a lymphocyte-specific antigen, the first ligand comprises an anti-lymphocyte-specific antigen antibody ("primary antibody"), the first labeling reagent comprises a horseradish peroxidase (HRP)-coupled polymer capable of binding to the primary antibody, the first detectable reagent comprises an HRP substrate comprising HRP Magenta or 3,3'-diaminobenzidine tetrahydrochloride (DAB), the second antigen comprises PD-L1, the second ligand comprises anti-PD-L1 antibodies, the second labeling reagent comprises an HRP-coupled polymer capable of binding to anti-PD-L1 antibodies, the second detectable reagent comprises amino ethyl carbazole (AEC), and the agent which dissolves the second detectable reagent is alcohol or acetone.

Optionally, the first labeling reagent comprises a horseradish peroxidase (HRP)-coupled polymer capable of binding to the primary antibody, the first detectable reagent comprises an HRP substrate comprising HRP Magenta or 3,3'-diaminobenzidine tetrahydrochloride (DAB), the second antigen comprises p40, the second ligand comprises anti-p40 antibodies, the second labeling reagent comprises an HRP-coupled polymer capable of binding to anti-p40 antibodies, the second detectable reagent comprises amino ethyl carbazole (AEC), and the agent which dissolves the second detectable reagent is alcohol or acetone.

Optionally, a counterstaining agent is hematoxylin.

Optionally, the method further comprises using a digital image of the signals detected in the biological sample to train a neural network.

Optionally, a neural network trained using the method.

Optionally, an annotated image obtained by the method.

According to an aspect of some embodiments of the present invention there is provided a method for detecting multiple target molecules in a biological sample comprising cells comprising:

contacting the biological sample with one or more first reagents which generate a first detectable signal in cells comprising a first target molecule, wherein said first detectable signal is detectable using a first detection method;

contacting the biological sample with one or more second reagents which generate a second detectable signal in cells comprising a second target molecule, wherein the second detectable signal is detectable using a second detection method and is substantially undetectable using the first detection method and wherein the first detectable signal is substantially undetectable using the second detection method;

detecting the signal generated by the one or more first reagents using the first detection method; and detecting the signal generated by the one or more second reagents using the second detection method.

Optionally, the biological sample comprises one of a human tissue sample, an animal tissue sample, or a plant tissue sample.

Optionally, the target molecules are indicative of at least one of normal cells, cell type, abnormal cells, damaged cells, cancer cells, tumors, subcellular structures, a marker indicative of or associated with a disease, disorder or health condition, or organ structures.

Optionally, the target molecules are selected from the group consisting of nuclear proteins, cytoplasmic proteins, membrane proteins, nuclear antigens, cytoplasmic antigens, membrane antigens and nucleic acids.

Optionally, the target molecules are nucleic acids.

Optionally, the target molecules are polypeptides.

Optionally, the first reagents comprise a first primary antibody against a first target polypeptide, an HRP coupled polymer that binds to the first primary antibody and a chromogen which is an HRP substrate.

Optionally, the second reagents comprise a second primary antibody against a second target polypeptide, an HRP coupled polymer that binds to the second primary antibody, and a rhodamine based fluorescent compound coupled to a long single chained polymer.

Optionally, the method further comprises using a digital image of the signals detected in the biological sample to train a neural network.

Optionally, there is provided a neural network trained using the method.

According to an aspect of some embodiments of the present invention there is provided a method for generating cell-level annotations from a biological sample comprising cells, the method comprising:

a) exposing the biological sample to a first ligand that recognizes a first antigen thereby forming a first ligand antigen complex;

b) exposing the first ligand antigen complex to a first labeling reagent binding to the first ligand, the first labeling reagent forming a first detectable reagent, wherein the first detectable reagent is visible in brightfield; whereby the first detectable reagent is precipitated around the first antigen;

c) exposing the biological sample to a second ligand that recognizes a second antigen thereby forming a second ligand antigen complex;

d) exposing the second ligand antigen complex to a second labeling reagent binding to the second ligand, the second labeling reagent forming a second detectable reagent, wherein the second detectable reagent is visible in fluorescence; whereby the second detectable reagent is precipitated around the second antigen;

e) obtaining a first brightfield image of the biological sample with the first detectable reagent precipitated in the biological sample;

f) obtaining a second fluorescent image of the biological sample with the second detectable reagent precipitated in the biological sample;

g) creating a mask from the second image; and h) applying the mask to the first image so as to obtain an annotated image of the tissue sample with the second marker.

Optionally, the method further comprises, prior to step a), applying a target retrieval buffer and protein blocking solution to the biological sample, whereby the first and second antigens are exposed for the subsequent steps and endogenous peroxidases are inactivated.

Optionally, the first biological sample comprises one of a human tissue sample, an animal tissue sample, or a plant tissue sample.

Optionally, the target molecules are indicative of at least one of normal cells, cell type, abnormal cells, damaged cells, cancer cells, tumors, subcellular structures, a marker indicative of or associated with a disease, disorder or health condition, or organ structures.

Optionally, the first and second labeling reagents comprise an enzyme that acts on a detectable reagent substrate to form the first and second detectable reagents, respectively.

Optionally, the first and second antigens are non-nuclear proteins.

Optionally, the method further comprises, following step b), denaturing the first ligands to retrieve the first antigens available.

Optionally, the method further comprises, following step d), i) counterstaining cell nuclei of the biological sample, and ii) dehydrating and mounting the sample on a slide.

Optionally, the first labeling reagent comprises a horseradish peroxidase (HRP)-coupled polymer capable of binding to the primary antibody, the first detectable reagent comprises an HRP substrate comprising HRP Magenta or 3,3'-diaminobenzidine tetrahydrochloride (DAB), the second antigen comprises PD-L1, the second ligand comprises anti-PD-L1 antibodies, the second labeling reagent comprises an HRP-coupled polymer capable of binding to anti-PD-L1 antibodies, and the second detectable reagent comprises a rhodamine-based fluorescent compound coupled to a long single-chain polymer.

Optionally, the first antigen comprises PD-L1, the first ligand comprises anti-PD-L1 antibodies, the first labeling reagent comprises a horseradish peroxidase (HRP)-coupled polymer capable of binding to anti-PD-L1 antibodies, the first detectable reagent comprises a rhodamine-based fluorescent compound coupled to a long single-chain polymer, the second labeling reagent comprises an HRP-coupled polymer capable of binding to the primary antibody, and the second detectable reagent comprises an HRP substrate comprising HRP Magenta or 3,3'-diaminobenzidine tetrahydrochloride (DAB).

Optionally, the first antigen comprises a lymphocyte-specific antigen, the first ligand comprises an anti-lymphocyte-specific antigen antibody ("primary antibody"), the first labeling reagent comprises a horseradish peroxidase (HRP)-coupled polymer capable of binding to the primary antibody, the first detectable reagent comprises an HRP substrate comprising HRP Magenta or 3,3'-diaminobenzidine tetrahydrochloride (DAB), the second antigen comprises p40, the second ligand comprises anti-p40 antibodies, the second labeling reagent comprises an HRP-coupled polymer capable of binding to anti-p40 antibodies, and the second detectable reagent comprises rhodamine-based fluorescent compound coupled to a long single-chain polymer.

Optionally, the first antigen comprises p40, the first ligand comprises anti-p40 antibodies, the first labeling reagent comprises a horseradish peroxidase (HRP)-coupled polymer capable of binding to anti-p40 antibodies, the first detectable reagent comprises rhodamine-based fluorescent compound coupled to a long single-chain polymer, the second antigen comprises a lymphocyte-specific antigen, the second ligand comprises an anti-lymphocyte-specific antigen antibody ("primary antibody"), the second labeling reagent comprises HRP-coupled polymer capable of binding to the primary antibody, and the second detectable reagent comprises an HRP substrate comprising HRP Magenta or 3,3'-diaminobenzidine tetrahydrochloride (DAB).

Optionally, a counterstaining agent is hematoxylin.

Optionally, an annotated image obtained by the method.

According to an aspect of some embodiments of the present invention there is provided a method, comprising:

receiving, with a computing system, a first image of a first biological sample, the first image comprising a first field of view ("FOV") of the first biological sample that has been stained with a first stain;

receiving, with the computing system, a second image of the first biological sample, the second image comprising a second FOV of the first biological sample that has been stained with a second stain;

autonomously creating, with the computing system, a first set of image patches based on the first image and the second image, by extracting a portion of the first image and extracting a corresponding portion of the second image, the first set of image patches comprising a first patch corresponding to the extracted portion of the first image and a second patch corresponding to the extracted portion of the second image, wherein the first set of image patches comprises labeling of instances of features of interest in the first biological sample that is based at least in part on at least one of information contained in the first patch, information contained in the second patch, or information contained in one or more external labeling sources;

training, using an artificial intelligence ("AI") system, a first model ("Model G*") to generate first instance classification of features of interest ("Ground Truth") in the first biological sample, based at least in part on the first set of image patches and the labeling of instances of features of interest contained in the first set of image patches; and training, using the AI system, a second AI model ("Model G") to identify instances of features of interest in the first biological sample, based at least in part on the first patch and the first instance classification of features of interest generated by Model G*.

Optionally, the computing system comprises one of a computing system disposed in a work environment, a remote computing system disposed external to the work environment and accessible over a network, a web server, a web browser, or a cloud computing system, wherein the work environment comprises at least one of a laboratory, a clinic, a medical facility, a research facility, a healthcare facility, or a room.

Optionally, the AI system comprises at least one of a machine learning system, a deep learning system, a model architecture, a statistical model-based system, or a deterministic analysis system, wherein the model architecture comprises at least one of a neural network, a convolutional neural network ("CNN"), or a fully convolutional network ("FCN").

Optionally, the first biological sample comprises one of a human tissue sample, an animal tissue sample, a plant tissue sample, or an artificially produced tissue sample, wherein the features of interest comprise at least one of normal cells, abnormal cells, damaged cells, cancer cells, tumors, subcellular structures, or organ structures.

Optionally, the first image comprises highlighting of first features of interest in the first biological sample by the first stain that had been applied to the first biological sample, and wherein the second image comprises one of highlighting of second features of interest in the first biological sample by the second stain that had been applied to the first biological sample in addition to highlighting of the first features of interest by the first stain or highlighting of the second features of interest by the second stain without highlighting of the first features of interest by the first stain, the second features of interest being different from the first features of interest, wherein the second stain is one of the same as the first stain but used to stain the second features of interest or different from the first stain.

Optionally, the first stain comprises at least one of Hematoxylin, Acridine orange, Bismarck brown, Carmine, Coomassie blue, Cresyl violet, Crystal violet, 4',6-diamidino-2-phenylindole ("DAPI"), Eosin, Ethidium bromide intercalates, Acid fuchsine, Hoechst stain, Iodine, Malachite green, Methyl green, Methylene blue, Neutral red, Nile blue, Nile red, Osmium tetroxide, Propidium Iodide, Rhodamine, Safranine, programmed death-ligand 1 ("PD-L1") stain, 3,3'-Diaminobenzidine ("DAB") chromogen, Magenta chromogen, cyanine chromogen, cluster of differentiation ("CD") 3 stain, CD20 stain, CD68 stain, 40S ribosomal protein SA ("p40") stain, antibody-based stain, or label-free imaging marker, and wherein the second stain comprises at least one of Hematoxylin, Acridine orange, Bismarck brown, Carmine, Coomassie blue, Cresyl violet, Crystal violet, DAPI, Eosin, Ethidium bromide intercalates, Acid fuchsine, Hoechst stain, Iodine, Malachite green, Methyl green, Methylene blue, Neutral red, Nile blue, Nile red, Osmium tetroxide, Propidium Iodide, Rhodamine, Safranine, PD-L1 stain, DAB chromogen, Magenta chromogen, cyanine chromogen, CD3 stain, CD20 stain, CD68 stain, p40 stain, antibody-based stain, or label-free imaging marker.

Optionally, the first image comprises one of a first set of color or brightfield images, a first fluorescence image, a first phase image, or a first spectral image, wherein the first set of color or brightfield images comprises a first red-filtered ("R") image, a first green-filtered ("G") image, and a first blue-filtered ("B") image, wherein the first fluorescence image comprises at least one of a first autofluorescence image or a first labelled fluorescence image having one or more channels with different excitation or emission characteristics, wherein the first spectral image comprises at least one of a first Raman spectroscopy image, a first near infrared ("NIR") spectroscopy image, a first multispectral image, a first hyperspectral image, or a first full spectral image, wherein the second image comprises one of a second set of color or brightfield images, a second fluorescence image, a second phase image, or a second spectral image, and wherein the second set of color or brightfield images comprises a second R image, a second G image, and a second B image, wherein the second fluorescence image comprises at least one of second autofluorescence image or a second labelled fluorescence image having one or more channels with different excitation or emission characteristics, wherein the second spectral image comprises at least one of a second Raman spectroscopy image, a second NIR spectroscopy image, a second multispectral image, a second hyperspectral image, or a second full spectral image.

Optionally, the method further comprises:

aligning, with the computing system, the first image with the second image to create first set of aligned images, by aligning one or more features of interest in the first biological sample as depicted in the first image with the same one or more features of interest in the first biological sample as depicted in the second image, wherein aligning the first image with the second image is one of performed manually using manual inputs to the computing system or performed autonomously, wherein autonomous alignment might comprise alignment using at least one of automated global alignment techniques or optical flow alignment techniques.

Optionally, the method further comprises:

receiving, with the computing system, a third image of the first biological sample, the third image comprising a third FOV of the first biological sample that has been stained with a third stain;

autonomously performing, with the computing system, one of aligning the third image with each of the first image and the second image to create second aligned images, by aligning one or more features of interest in the first biological sample as depicted in the third image with the same one or more features of interest in the first biological sample as depicted in each of the first image and the second image; or aligning the third image with the first aligned images to create second aligned images, by aligning one or more features of interest in the first biological sample as depicted in the third image with the same one or more features of interest in the first biological sample as depicted in the first aligned images;

autonomously creating, with the computing system, second aligned image patches from the second aligned images, by extracting a portion of the second aligned images, the portion of the second aligned images comprising a first patch corresponding to the extracted portion of the first image, a second patch corresponding to the extracted portion of the second image, and a third patch corresponding to the extracted portion of the third image;

training the AI system to update Model G* to generate second instance classification of features of interest in the first biological sample, based at least in part on the second aligned image patches and the labeling of instances of features of interest contained in the first set of image patches; and training the AI system to update Model G to identify instances of features of interest in the first biological sample, based at least in part on the first patch and the second instance classification of features of interest generated by Model G*.

Optionally, the first image comprises highlighting of first features of interest in the first biological sample by the first stain that had been applied to the first biological sample, wherein the second image comprises one of highlighting of second features of interest in the first biological sample by the second stain that had been applied to the first biological sample in addition to highlighting of the first features of interest by the first stain or highlighting of the second features of interest by the second stain without highlighting of the first features of interest by the first stain, the second features of interest being different from the first features of interest, and wherein the third image comprises one of highlighting of third features of interest in the first biological sample by the third stain that had been applied to the first biological sample in addition to highlighting of the first features of interest by the first stain and highlighting of the second features of interest by the second stain, highlighting of the third features of interest by the third stain in addition to only one of highlighting of the first features of interest by the first stain or highlighting of the second features of interest by the second stain, or highlighting of the third features of interest by the third stain without any of highlighting of the first features of interest by the first stain or highlighting of the second features of interest by the second stain, the third features of interest being different from each of the first features of interest and the second features of interest.

Optionally, the first image comprises one of a first set of color or brightfield images, a first fluorescence image, a first phase image, or a first spectral image, wherein the first set of color or brightfield images comprises a first red-filtered ("R") image, a first green-filtered ("G") image, and a first blue-filtered ("B") image, wherein the first fluorescence image comprises at least one of first autofluorescence image or a first labelled fluorescence image having one or more channels with different excitation or emission characteristics, wherein the first spectral image comprises at least one of a first Raman spectroscopy image, a first near infrared ("NIR") spectroscopy image, a first multispectral image, a first hyperspectral image, or a first full spectral image, wherein the second image comprises one of a second set of color or brightfield images, a second fluorescence image, a second phase image, or a second spectral image, wherein the second set of color or brightfield images comprises a second R image, a second G image, and a second B image, wherein the second fluorescence image comprises at least one of second autofluorescence image or a second labelled fluorescence image having one or more channels with different excitation or emission characteristics, wherein the second spectral image comprises at least one of a second Raman spectroscopy image, a second NIR spectroscopy image, a second multispectral image, a second hyperspectral image, or a second full spectral image, wherein the third image comprises one of a third set of color or brightfield images, a third fluorescence image, a third phase image, or a third spectral image, and wherein the third set of color or brightfield images comprises a third R image, a third G image, and a third B image, wherein the third fluorescence image comprises at least one of a third autofluorescence image or a third labelled fluorescence image having one or more channels with different excitation or emission characteristics, wherein the third spectral image comprises at least one of a third Raman spectroscopy image, a third NIR spectroscopy image, a third multispectral image, a third hyperspectral image, or a third full spectral image.

Optionally, the method further comprises:

receiving, with the computing system, a fourth image, the fourth image comprising one of a fourth FOV of the first biological sample different from the first FOV and the second FOV or a fifth FOV of a second biological sample, wherein the second biological sample is different from the first biological sample; and identifying, using Model G, second instances of features of interest in the second biological sample, based at least in part on the fourth image and based at least in part on training of Model G using the first patch and the first instance classification of features of interest generated by Model G*.

Optionally, the fourth image comprises the fifth FOV and further comprises only highlighting of first features of interest in the second biological sample by the first stain that had been applied to the second biological sample.

Optionally, the method further comprises:

generating, using Model G, a clinical score, based at least in part on the identified second instances of features of interest.

According to an aspect of some embodiments of the present invention there is provided a system, comprising:

a computing system, comprising:

at least one first processor; and a first non-transitory computer readable medium communicatively coupled to the at least one first processor, the first non-transitory computer readable medium having stored thereon computer software comprising a first set of instructions that, when executed by the at least one first processor, causes the computing system to:

receive a first image of a first biological sample, the first image comprising a first field of view ("FOV") of the first biological sample that has been stained with a first stain;

receive a second image of the first biological sample, the second image comprising a second FOV of the first biological sample that has been stained with a second stain;

autonomously create a first set of image patches based on the first image and the second image, by extracting a portion of the first image and extracting a corresponding portion of the second image, the first set of image patches comprising a first patch corresponding to the extracted portion of the first image and a second patch corresponding to the extracted portion of the second image, wherein the first set of image patches comprises labeling of instances of features of interest in the first biological sample that is based at least in part on at least one of information contained in the first patch, information contained in the second patch, or information contained in one or more external labeling sources;

train, using an artificial intelligence ("AI") system, a first model ("Model G*") to generate first instance classification of features of interest ("Ground Truth") in the first biological sample, based at least in part on the first set of image patches and the labeling of instances of features of interest contained in the first set of image patches; and train, using the AI system, a second AI model ("Model G") to identify instances of features of interest in the first biological sample, based at least in part on the first patch and the first instance classification of features of interest generated by Model G*.

Optionally, the computing system comprises one of a computing system disposed in a work environment, a remote computing system disposed external to the work environment and accessible over a network, a web server, a web browser, or a cloud computing system, wherein the work environment comprises at least one of a laboratory, a clinic, a medical facility, a research facility, a healthcare facility, or a room.

Optionally, the AI system comprises at least one of a machine learning system, a deep learning system, a model architecture, a statistical model-based system, or a deterministic analysis system, wherein the model architecture comprises at least one of a neural network, a convolutional neural network ("CNN"), or a fully convolutional network ("FCN").

Optionally, the first biological sample comprises one of a human tissue sample, an animal tissue sample, a plant tissue sample, or an artificially produced tissue sample, wherein the features of interest comprise at least one of normal cells, abnormal cells, damaged cells, cancer cells, tumors, subcellular structures, or organ structures.

Optionally, the first image comprises highlighting of first features of interest in the first biological sample by the first stain that had been applied to the first biological sample, and wherein the second image comprises one of highlighting of second features of interest in the first biological sample by the second stain that had been applied to the first biological sample in addition to highlighting of the first features of interest by the first stain or highlighting of the second features of interest by the second stain without highlighting of the first features of interest by the first stain, the second features of interest being different from the first features of interest, wherein the second stain is one of the same as the first stain but used to stain the second features of interest or different from the first stain.

Optionally, the first image comprises one of a first set of color or brightfield images, a first fluorescence image, a first phase image, or a first spectral image, wherein the first set of color or brightfield images comprises a first red-filtered ("R") image, a first green-filtered ("G") image, and a first blue-filtered ("B") image, wherein the first fluorescence image comprises at least one of a first autofluorescence image or a first labelled fluorescence image having one or more channels with different excitation or emission characteristics, wherein the first spectral image comprises at least one of a first Raman spectroscopy image, a first near infrared ("NIR") spectroscopy image, a first multispectral image, a first hyperspectral image, or a first full spectral image, wherein the second image comprises one of a second set of color or brightfield images, a second fluorescence image, a second phase image, or a second spectral image, and wherein the second set of color or brightfield images comprises a second R image, a second G image, and a second B image, wherein the second fluorescence image comprises at least one of a second autofluorescence image or a second labelled fluorescence image having one or more channels with different excitation or emission characteristics, wherein the second spectral image comprises at least one of a second Raman spectroscopy image, a second NIR spectroscopy image, a second multispectral image, a second hyperspectral image, or a second full spectral image.

Optionally, the first set of instructions, when executed by the at least one first processor, further causes the computing system to:

receive a third image of the first biological sample, the third image comprising a third FOV of the first biological sample that has been stained with a third stain different from each of the first stain and the second stain;

autonomously perform one of aligning the third image with each of the first image and the second image images to create second aligned images, by aligning one or more features of interest in the first biological sample as depicted in the third image with the same one or more features of interest in the first biological sample as depicted in each of the first image and the second image; or aligning the third image with the first aligned images to create second aligned images, by aligning one or more features of interest in the first biological sample as depicted in the third image with the same one or more features of interest in the first biological sample as depicted in the first aligned images;

autonomously create second aligned image patches from the second aligned images, by extracting a portion of the second aligned images, the portion of the second aligned images comprising a first patch corresponding to the extracted portion of the first image, a second patch corresponding to the extracted portion of the second image, and a third patch corresponding to the extracted portion of the third image;

train the AI system to update Model G* to generate second instance classification of features of interest in the first biological sample, based at least in part on the second aligned image patches and the labeling of instances of features of interest contained in the first set of image patches; and train the AI system to update Model G to identify instances of features of interest in the first biological sample, based at least in part on the first patch and the second instance classification of features of interest generated by Model G*.

Optionally, the first set of instructions, when executed by the at least one first processor, further causes the computing system to:

receive a fourth image, the fourth image comprising one of a fourth FOV of the first biological sample different from the first FOV and the second FOV or a fifth FOV of a second biological sample, wherein the second biological sample is different from the first biological sample; and identify, using Model G, second instances of features of interest in the second biological sample, based at least in part on the fourth image and based at least in part on training of Model G using the first patch and the first instance classification of features of interest generated by Model G*.

According to an aspect of some embodiments of the present invention there is provided a method, comprising:

receiving, with a computing system, a first image of a first biological sample, the first image comprising a first field of view ("FOV") of the first biological sample; and identifying, using a first artificial intelligence ("AI") model ("Model G") that is generated or updated by a trained AI system, first instances of features of interest in the first biological sample, based at least in part on the first image and based at least in part on training of Model G using a first patch and first instance classification of features of interest generated by a second model (Model G*) that is generated or updated by the trained system by using first aligned image patches and labeling of instances of features of interest contained in the first patch, wherein the first aligned image patches comprise an extracted portion of first aligned images, wherein the first aligned images comprise a second image and a third image that have been aligned, wherein the second image comprises a second FOV of a second biological sample that has been stained with a first stain, the second biological sample being different from the first biological sample, wherein the third image comprises a third FOV of the second biological sample that has been stained with a second stain, wherein the second patch comprises labeling of instances of features of interest as shown in the extracted portion of the second image of the first aligned images, wherein the first image comprises highlighting of first features of interest in the second biological sample by the first stain that had been applied to the second biological sample, wherein the second patch comprises one of highlighting of second features of interest in the second biological sample by the second stain that had been applied to the second biological sample in addition to highlighting of the first features of interest by the first stain or highlighting of the second features of interest by the second stain without highlighting of the first features of interest by the first stain.

According to an aspect of some embodiments of the present invention there is provided a system, comprising:

a computing system, comprising:

at least one first processor; and a first non-transitory computer readable medium communicatively coupled to the at least one first processor, the first non-transitory computer readable medium having stored thereon computer software comprising a first set of instructions that, when executed by the at least one first processor, causes the computing system to:

receive a first image of a first biological sample, the first image comprising a first field of view ("FOV") of the first biological sample; and identify, using a first artificial intelligence ("AI") model ("Model G") that is generated or updated by a trained AI system, first instances of features of interest in the first biological sample, based at least in part on the first image and based at least in part on training of Model G using a first patch and first instance classification of features of interest generated by a second model (Model G*) that is generated or updated by the trained AI system by using first aligned image patches and labeling of instances of features of interest contained in the first patch, wherein the first aligned image patches comprise an extracted portion of first aligned images, wherein the first aligned images comprise a second image and a third image that have been aligned, wherein the second image comprises a second FOV of a second biological sample that has been stained with a first stain, the second biological sample being different from the first biological sample, wherein the third image comprises a third FOV of the second biological sample that has been stained with a second stain, wherein the second patch comprises labeling of instances of features of interest as shown in the extracted portion of the second image of the first aligned images, wherein the first image comprises highlighting of first features of interest in the second biological sample by the first stain that had been applied to the second biological sample wherein the second patch comprises one of highlighting of second features of interest in the second biological sample by the second stain that had been applied to the second biological sample in addition to highlighting of the first features of interest by the first stain or highlighting of the second features of interest by the second stain without highlighting of the first features of interest by the first stain.

According to an aspect of some embodiments of the present invention there is provided a method, comprising:

receiving, with a computing system, first instance classification of features of interest ("Ground Truth") in a first biological sample that has been sequentially stained, the Ground Truth having been generated by a trained first model ("Model G*") that has been trained or updated by an artificial intelligence ("AI") system, wherein the Ground Truth is generated by using first aligned image patches and labeling of instances of features of interest contained in the first aligned image patches, wherein the first aligned image patches comprise an extracted portion of first aligned images, wherein the first aligned images comprise a first image and a second image that have been aligned, wherein the first image comprises a first FOV of the first biological sample that has been stained with a first stain, wherein the second image comprises a second FOV of the first biological sample that has been stained with a second stain, wherein the first aligned image patches comprise labeling of instances of features of interest as shown in the extracted portion of the first aligned images; and training, using the AI system, a second AI model ("Model G") to identify instances of features of interest in the first biological sample, based at least in part on the first instance classification of features of interest generated by Model G*.

According to an aspect of some embodiments of the present invention there is provided a system, comprising:

a computing system, comprising:

at least one first processor; and a first non-transitory computer readable medium communicatively coupled to the at least one first processor, the first non-transitory computer readable medium having stored thereon computer software comprising a first set of instructions that, when executed by the at least one first processor, causes the computing system to:

receive first instance classification of features of interest ("Ground Truth") in a first biological sample that has been sequentially stained, the Ground Truth having been generated by a trained first model ("Model G*") that has been trained or updated by an artificial intelligence ("AI") system, wherein the Ground Truth is generated by using first aligned image patches and labeling of instances of features of interest contained in the first aligned image patches, wherein the first aligned image patches comprise an extracted portion of first aligned images, wherein the first aligned images comprise a first image and a second image that have been aligned, wherein the first image comprises a first FOV of the first biological sample that has been stained with a first stain, wherein the second image comprises a second FOV of the first biological sample that has been stained with a second stain, wherein the first aligned image patches comprise labeling of instances of features of interest as shown in the extracted portion of the first aligned images; and train, using the AI system, a second AI model ("Model G") to identify instances of features of interest in the first biological sample, based at least in part on the first. instance classification of features of interest generated by Model G*.

According to an aspect of some embodiments of the present invention there is provided a method, comprising:

generating, using a computing system, ground truth for developing accurate artificial intelligence ("AI") models for biological image interpretation, based at least in part on images of a first biological sample depicting sequential staining of the first biological sample. According to an aspect of some embodiments of the present invention there is provided a method, comprising:

receiving, with a computing system, a first image of a first biological sample, the first image comprising a first field of view ("FOV") of the first biological sample that has been stained with a first stain;

receiving, with the computing system, a second image of the first biological sample, the second image comprising a second FOV of the first biological sample that has been stained with at least a second stain;

aligning, with the computing system, the first image with the second image to create first aligned images, by aligning one or more features of interest in the first biological sample as depicted in the first image with the same one or more features of interest in the first biological sample as depicted in the second image;

autonomously creating, with the computing system, first aligned image patches from the first aligned images, by extracting a portion of the first aligned images, the portion of the first aligned images comprising a first patch corresponding to the extracted portion of the first image and a second patch corresponding to the extracted portion of the second image;

training, using an artificial intelligence ("AI") system, a first AI model ("Model F") to generate a third patch comprising a virtual stain of the first aligned image patches, based at least in part on the first patch and the second patch, the virtual stain simulating staining by at least the second stain of features of interest in the first biological sample as shown in the second patch; and training, using the AI system, a second model ("Model G*") to identify or classify first instances of features of interest in the first biological sample, based at least in part on the third patch and based at least in part on results from an external instance classification process or a region of interest detection process.

Optionally, the computing system comprises one of a computing system disposed in a work environment, a remote computing system disposed external to the work environment and accessible over a network, a web server, a web browser, or a cloud computing system, wherein the work environment comprises at least one of a laboratory, a clinic, a medical facility, a research facility, a healthcare facility, or a room.

Optionally, the AI system comprises at least one of a machine learning system, a deep learning system, a model architecture, a statistical model-based system, or a deterministic analysis system, wherein the model architecture comprises at least one of a neural network, a convolutional neural network ("CNN"), or a fully convolutional network ("FCN").

Optionally, the first biological sample comprises one of a human tissue sample, an animal tissue sample, a plant tissue sample, or an artificially produced tissue sample, wherein the features of interest comprise at least one of normal cells, abnormal cells, damaged cells, cancer cells, tumors, subcellular structures, or organ structures.

Optionally, the first image comprises highlighting of first features of interest in the first biological sample by the first stain that had been applied to the first biological sample, and wherein the third patch comprises one of highlighting of the first features of interest by the first stain and highlighting of second features of interest in the first biological sample by the virtual stain that simulates the second stain having been applied to the first biological sample or highlighting of the first features of interest by the first stain and highlighting of first features of interest by the virtual stain, the second features of interest being different from the first features of interest, wherein the second stain is one of the same as the first stain but used to stain the second features of interest or different from the first stain.

Optionally, the first stain comprises at least one of Hematoxylin, Acridine orange, Bismarck brown, Carmine, Coomassie blue, Cresyl violet, Crystal violet, 4',6-diamidino-2-phenylindole ("DAPI"), Eosin, Ethidium bromide intercalates, Acid fuchsine, Hoechst stain, Iodine, Malachite green, Methyl green, Methylene blue, Neutral red, Nile blue, Nile red, Osmium tetroxide, Propidium Iodide, Rhodamine, Safranine, programmed death-ligand 1 ("PD-L1") stain, 3,3'-Diaminobenzidine ("DAB") chromogen, Magenta chromogen, cyanine chromogen, cluster of differentiation ("CD") 3 stain, CD20 stain, CD68 stain, 40S ribosomal protein SA ("p40") stain, antibody-based stain, or label-free imaging marker, and wherein the second stain comprises at least one of Hematoxylin, Acridine orange, Bismarck brown, Carmine, Coomassie blue, Cresyl violet, Crystal violet, DAPI, Eosin, Ethidium bromide intercalates, Acid fuchsine, Hoechst stain, Iodine, Malachite green, Methyl green, Methylene blue, Neutral red, Nile blue, Nile red, Osmium tetroxide, Propidium Iodide, Rhodamine, Safranine, PD-L1 stain, DAB chromogen, Magenta chromogen, cyanine chromogen, CD3 stain, CD20 stain, CD68 stain, p40 stain, antibody-based stain, or label-free imaging marker.

Optionally, the first image comprises one of a first set of color or brightfield images, a first fluorescence image, a first phase image, or a first spectral image, wherein the first set of color or brightfield images comprises a first red-filtered ("R") image, a first green-filtered ("G") image, and a first blue-filtered ("B") image, wherein the first fluorescence image comprises at least one of a first autofluorescence image or a first labelled fluorescence image having one or more channels with different excitation or emission characteristics, wherein the first spectral image comprises at least one of a first Raman spectroscopy image, a first near infrared ("NIR") spectroscopy image, a first multispectral image, a first hyperspectral image, or a first full spectral image, wherein the second image comprises one of a second set of color or brightfield images, a second fluorescence image, a second phase image, or a second spectral image, wherein the second set of color or brightfield images comprises a second R image, a second G image, and a second B image, wherein the second fluorescence image comprises at least one of a second autofluorescence image or a second labelled fluorescence image having one or more channels with different excitation or emission characteristics, wherein the second spectral image comprises at least one of a second Raman spectroscopy image, a second NIR spectroscopy image, a second multispectral image, a second hyperspectral image, or a second full spectral image, wherein the third patch comprises one of a third set of color or brightfield images, a third fluorescence image, a third phase image, or a third spectral image, and wherein the third set of color or brightfield images comprises a third R image, a third G image, and a third B image, wherein the third fluorescence image comprises at least one of a third autofluorescence image or a third labelled fluorescence image having one or more channels with different excitation or emission characteristics, wherein the third spectral image comprises at least one of a third Raman spectroscopy image, a third NIR spectroscopy image, a third multispectral image, a third hyperspectral image, or a third full spectral image.

Optionally, aligning the first image with the second image is one of performed manually using manual inputs to the computing system or performed autonomously, wherein autonomous alignment might comprise alignment using at least one of automated global alignment techniques or optical flow alignment techniques.

Optionally, training, using the AI system, Model G* to identify or classify instances of features of interest in the first biological sample comprises training, using the AI system, Model G* to identify or classify instances of features of interest in the first biological sample, based at least in part on one or more of the first patch, the second patch, or the third patch and based at least in part on the results from the external instance classification process or the region of interest detection process.

Optionally, the external instance classification process or the region of interest detection process each comprises at least one of detection of nuclei in the first image or the first patch by a nuclei detection method, identification of nuclei in the first image or the first patch by a pathologist, detection of features of interest in the first image or the first patch by a feature detection method, or identification of features of interest in the first image or the first patch by the pathologist.

Optionally, training the AI system to update Model F comprises:

receiving, with an encoder, the first patch;

receiving the second patch;

encoding, with the encoder, the received first patch;

decoding, with the decoder, the encoded first patch;

generating an intensity map based on the decoded first patch;

simultaneously operating on the encoded first patch to generate a color vector;

combining the generated intensity map with the generated color vector to generate an image of the virtual stain;

generating a predicted virtually stained image patch;

determining a first loss value between the predicted virtually stained image patch and the second patch;

calculating a loss value using a loss function, based on the first loss value between the predicted virtually stained image patch and the second patch; and updating, with the AI system, Model F to generate the third patch, by updating one or more parameters of Model F based on the calculated loss value.

Optionally, the loss function comprises one of a mean squared error loss function, a mean squared logarithmic error loss function, a mean absolute error loss function, a Huber loss function, or a weighted sum of squared differences loss function.

Optionally, the first patch comprises one of a first set of color or brightfield images, a first fluorescence image, a first phase image, or a first spectral image, wherein the first set of color or brightfield images comprises a first red-filtered ("R") image, a first green-filtered ("G") image, and a first blue-filtered ("B") image, wherein the first fluorescence image comprises at least one of a first autofluorescence image or a first labelled fluorescence image having one or more channels with different excitation or emission characteristics, wherein the first spectral image comprises at least one of a first Raman spectroscopy image, a first near infrared ("NIR") spectroscopy image, a first multispectral image, a first hyperspectral image, or a first full spectral image, wherein the second image comprises one of a second set of color or brightfield images, a second fluorescence image, a second phase image, or a second spectral image, wherein the second set of color or brightfield images comprises a second R image, a second G image, and a second B image, wherein the second fluorescence image comprises at least one of a second autofluorescence image or a second labelled fluorescence image having one or more channels with different excitation or emission characteristics, wherein the second spectral image comprises at least one of a second Raman spectroscopy image, a second NIR spectroscopy image, a second multispectral image, a second hyperspectral image, or a second full spectral image, wherein the predicted virtually stained image patch comprises one of a third set of color or brightfield images, a third fluorescence image, a third phase image, or a third spectral image, wherein the third set of color or brightfield images comprises a third R image, a third G image, and a third B image, wherein the third fluorescence image comprises at least one of a third autofluorescence image or a third labelled fluorescence image having one or more channels with different excitation or emission characteristics, wherein the third spectral image comprises at least one of a third Raman spectroscopy image, a third NIR spectroscopy image, a third multispectral image, a third hyperspectral image, or a third full spectral image.

Optionally, operating on the encoded first patch to generate the color vector comprises operating on the encoded first patch to generate a color vector, using a color vector output and one of a neural network, a model architecture, a statistical model-based system, or a deterministic analysis system, wherein the model architecture comprises at least one of a neural network, a convolutional neural network ("CNN"), or a fully convolutional network ("FCN"), wherein the color vector is one of a fixed color vector or a learned color vector that is not based on the encoded first patch.

Optionally, the image of the virtual stain comprises one of a 3-channel image of the virtual stain, a RGB-transform image of the virtual stain, or a logarithmic transform image of the virtual stain.

Optionally, generating the predicted virtually stained image patch comprises adding the generated image of the virtual stain to the received first patch to produce the predicted virtually stained image patch.

Optionally, the first loss value comprises one of a pixel loss value between each pixel in the predicted virtually stained image patch and a corresponding pixel in the second patch or a generative adversarial network ("GAN") loss value between the predicted virtually stained image patch and the second patch, wherein the GAN loss value is generated based on one of a minimax GAN loss function, a non-saturating GAN loss function, a least squares GAN loss function, or a Wasserstein GAN loss function.

Optionally, training the AI system to update Model F comprises:

receiving, with the AI system, the first patch;

receiving, with the AI system, the second patch;

generating, with a second model of the AI system, an image of the virtual stain;

adding the generated image of the virtual stain to the received first patch to produce a predicted virtually stained image patch;

determining a first loss value between the predicted virtually stained image patch and the second patch;

calculating a loss value using a loss function, based on the first loss value between the predicted virtually stained image patch and the second patch; and updating, with the AI system, Model F to generate the third patch, by updating one or more parameters of Model F based on the calculated loss value.

Optionally, the second model comprises at least one of a convolutional neural network ("CNN"), a U-Net, an artificial neural network ("ANN"), a residual neural network ("ResNet"), an encode/decode CNN, an encode/decode U-Net, an encode/decode ANN, or an encode/decode ResNet.

Optionally, the method further comprises:

receiving, with the computing system, a fourth image, the fourth image comprising one of a fourth FOV of the first biological sample different from the first FOV and the second FOV or a fifth FOV of a second biological sample, wherein the second biological sample is different from the first biological sample; and; and identifying, using Model G*, second instances of features of interest in the second biological sample, based at least in part on the fourth image and based at least in part on training of Model G* using at least the third patch comprising the virtual stain of the first aligned image patches. Optionally, the method further comprises:

generating, using Model G*, a clinical score, based at least in part on the identified second instances of features of interest.

According to an aspect of some embodiments of the present invention there is provided a system, comprising:

a computing system, comprising:

at least one first processor; and a first non-transitory computer readable medium communicatively coupled to the at least one first processor, the first non-transitory computer readable medium having stored thereon computer software comprising a first set of instructions that, when executed by the at least one first processor, causes the computing system to:

receive a first image of a first biological sample, the first image comprising a first field of view ("FOV") of the first biological sample that has been stained with a first stain;

receive a second image of the first biological sample, the second image comprising a second FOV of the first biological sample that has been stained with at least a second stain;

align the first image with the second image to create first aligned images, by aligning one or more features of interest in the first biological sample as depicted in the first image with the same one or more features of interest in the first biological sample as depicted in the second image;

autonomously create first aligned image patches from the first aligned images, by extracting a portion of the first aligned images, the portion of the first aligned images comprising a first patch corresponding to the extracted portion of the first image and a second patch corresponding to the extracted portion of the second image;

train, using an artificial intelligence ("AI") system, a first AI model ("Model F") to generate a third patch comprising a virtual stain of the first aligned image patches, based at least in part on the first patch and the second patch, the virtual stain simulating staining by at least the second stain of features of interest in the first biological sample as shown in the second patch; and train, using the AI system, a second model ("Model G*") to identify or classify first instances of features of interest in the first biological sample, based at least in part on the third patch and based at least in part on results from an external instance classification process or a region of interest detection process.

Optionally, the computing system comprises one of a computing system disposed in a work environment, a remote computing system disposed external to the work environment and accessible over a network, a web server, a web browser, or a cloud computing system, wherein the work environment comprises at least one of a laboratory, a clinic, a medical facility, a research facility, a healthcare facility, or a room.

Optionally, the AI system comprises at least one of a machine learning system, a deep learning system, a neural network, a model architecture, a statistical model-based system, or a deterministic analysis system, wherein the model architecture comprises at least one of a neural network, a convolutional neural network ("CNN"), or a fully convolutional network ("FCN").

Optionally, the first biological sample comprises one of a human tissue sample, an animal tissue sample, a plant tissue sample, or an artificially produced tissue sample, wherein the features of interest comprise at least one of normal cells, abnormal cells, damaged cells, cancer cells, tumors, subcellular structures, or organ structures.

Optionally, the first image comprises highlighting of first features of interest in the first biological sample by the first stain that had been applied to the first biological sample, and wherein the third patch comprises one of highlighting of the first features of interest by the first stain and highlighting of second features of interest in the first biological sample by the virtual stain that simulates the second stain having been applied to the first biological sample or highlighting of the first features of interest by the first stain and highlighting of first features of interest by the virtual stain, the second features of interest being different from the first features of interest, wherein the second stain is one of the same as the first stain but used to stain the second features of interest or different from the first stain. Optionally, the first image comprises one of a first set of color or brightfield images, a first fluorescence image, a first phase image, or a first spectral image, wherein the first set of color or brightfield images comprises a first red-filtered ("R") image, a first green-filtered ("G") image, and a first blue-filtered ("B") image, wherein the first fluorescence image comprises at least one of a first autofluorescence image or a first labelled fluorescence image having one or more channels with different excitation or emission characteristics, wherein the first spectral image comprises at least one of a first Raman spectroscopy image, a first near infrared ("NIR") spectroscopy image, a first multispectral image, a first hyperspectral image, or a first full spectral image, wherein the second image comprises one of a second set of color or brightfield images, a second fluorescence image, a second phase image, or a second spectral image, wherein the second set of color or brightfield images comprises a second R image, a second G image, and a second B image, wherein the second fluorescence image comprises at least one of a second autofluorescence image or a second labelled fluorescence image having one or more channels with different excitation or emission characteristics, wherein the second spectral image comprises at least one of a second Raman spectroscopy image, a second NIR spectroscopy image, a second multispectral image, a second hyperspectral image, or a second full spectral image, wherein the third patch comprises one of a third set of color or brightfield images, a third fluorescence image, a third phase image, or a third spectral image, and wherein the third set of color or brightfield images comprises a third R image, a third G image, and a third B image, wherein the third fluorescence image comprises at least one of a third autofluorescence image or a third labelled fluorescence image having one or more channels with different excitation or emission characteristics, wherein the third spectral image comprises at least one of a third Raman spectroscopy image, a third NIR spectroscopy image, a third multispectral image, a third hyperspectral image, or a third full spectral image.

Optionally, training the AI system to update Model F comprises:

- receiving, with an encoder, the first patch;
- receiving the second patch;
- encoding, with the encoder, the received first patch;
- decoding, with the decoder, the encoded first patch;
- generating an intensity map based on the decoded first patch;
- simultaneously operating on the encoded first patch to generate a color vector;
- combining the generated intensity map with the generated color vector to generate an image of the virtual stain;
- adding the generated image of the virtual stain to the received first patch to produce a predicted virtually stained image patch;
- determining a first loss value between the predicted virtually stained image patch and the second patch;
- calculating a loss value using a loss function, based on the first loss value between the predicted virtually stained image patch and the second patch; and
- updating, with the AI system, Model F to generate the third patch, by updating one or more parameters of Model F based on the calculated loss value.

Optionally, the loss function comprises one of a mean squared error loss function, a mean squared logarithmic error loss function, a mean absolute error loss function, a Huber loss function, or a weighted sum of squared differences loss function.

Optionally, the first loss value comprises one of a pixel loss value between each pixel in the predicted virtually stained image patch and a corresponding pixel in the second patch or a generative adversarial network ("GAN") loss value between the predicted virtually stained image patch and the second patch, wherein the GAN loss value may be generated based on one of a minimax GAN loss function, a non-saturating GAN loss function, a least squares GAN loss function, or a Wasserstein GAN loss function.

Optionally, the first set of instructions, when executed by the at least one first processor, further causes the computing system to:

- receive a fourth image, the fourth image comprising one of a fourth FOV of the first biological sample different from the first FOV and the second FOV or a fifth FOV of a second biological sample, wherein the second biological sample is different from the first biological sample; and
- identify, using Model G*, second instances of features of interest in the second biological sample, based at least in part on the fourth image and based at least in part on training of Model G* using at least the third patch comprising the virtual stain of the first aligned image patches.

According to an aspect of some embodiments of the present invention there is provided a method, comprising:

- receiving, with a computing system, a first image of a first biological sample, the first image comprising a first field of view ("FOV") of the first biological sample; and
- identifying, using a first model ("Model G*") that is generated or updated by a trained artificial intelligence ("AI") system, first instances of features of interest in the first biological sample, based at least in part on the first image and based at least in part on training of Model G* using at least a first patch comprising a virtual stain of first aligned image patches, the first patch being generated by a second AI model (Model F) that is generated or updated by the trained AI system by using a second patch, wherein the first aligned image patches comprise an extracted portion of first aligned images, wherein the first aligned images comprise a second image and a third image that have been aligned, wherein the second image comprises a second FOV of a second biological sample that is different from the first biological sample that has been stained with a first stain, wherein the second patch comprises the extracted portion of the second image, wherein the third image comprises a third FOV of the second biological sample that has been stained with at least a second stain.

According to an aspect of some embodiments of the present invention there is provided a system, comprising:

- a computing system, comprising:
- at least one first processor; and
- a first non-transitory computer readable medium communicatively coupled to the at least one first processor, the first non-transitory computer readable medium having stored thereon computer software comprising a first set of instructions that, when executed by the at least one first processor, causes the computing system to:

receive a first image of a first biological sample, the first image comprising a first field of view ("FOV") of the first biological sample; and identify, using a first model ("Model G*") that is generated or updated by a trained artificial intelligence ("AI") system, first instances of features of interest in the first biological sample, based at least in part on the first image and based at least in part on training of Model G* using at least a first patch comprising a virtual stain of first aligned image patches, the first patch being generated by a second AI model (Model F) that is generated or updated by the trained AI system by using a second patch, wherein the first aligned image patches comprise an extracted portion of first aligned images, wherein the first aligned images comprise a second image and a third image that have been aligned, wherein the second image comprises a second FOV of a second biological sample that is different from the first biological sample that has been stained with a first stain, wherein the second patch comprises the extracted portion of the second image, wherein the third image comprises a third FOV of the second biological sample that has been stained with at least a second stain.

While certain features and aspects have been described with respect to exemplary embodiments, one skilled in the art will recognize that numerous modifications are possible. For example, the methods and processes described herein may be implemented using hardware components, software components, and/or any combination thereof. Further, while various methods and processes described herein may be described with respect to particular structural and/or functional components for ease of description, methods provided by various embodiments are not limited to any particular structural and/or functional architecture but instead can be implemented on any suitable hardware, firmware and/or software configuration. Similarly, while certain functionality is ascribed to certain system components, unless the context dictates otherwise, this functionality can be distributed among various other system components in accordance with the several embodiments.

Moreover, while the procedures of the methods and processes described herein are described in a particular order for ease of description, unless the context dictates otherwise, various procedures may be reordered, added, and/or omitted in accordance with various embodiments. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments are described with—or without—certain features for ease of description and to illustrate exemplary aspects of those embodiments, the various components and/or features described herein with respect to a particular embodiment can be substituted, added and/or subtracted from among other described embodiments, unless the context dictates otherwise. Consequently, although several exemplary embodiments are described above, it will be appreciated that the invention is intended to cover all modifications and equivalents within the scope of the following claims.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant machine learning models will be developed and the scope of the term machine learning model is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A computer-implemented method for training a ground truth generator machine learning model, comprising:

creating a ground truth multi-record training dataset wherein a record comprises:

a first image of a sample of tissue of a subject depicting a first group of biological objects, presenting at least one biomarker, a second image, comprising at least a portion of the same sample of tissue, wherein the second image comprises one or more biological objects in the first group of biological objects, sequentially stained with a stain configured to stain a second group of biological objects presenting at least one second biomarker, and ground truth labels indicating a respective biological object category, selected from a plurality of biological object categories, for a subgroup of biological objects in the first and second images;

optimizing the ground truth generator machine learning model based on the ground truth labels in the ground truth multi-record training dataset, for automatically generating ground truth labels for biological objects depicted in an input set of images of a first type corresponding to the first image;

feeding unlabeled sets of images of samples of tissue of a plurality of sample individuals into the ground truth generator machine learning model to obtain automatically generated ground truth labels, wherein the unlabeled sets of images depict biological objects respectively presenting the at least one first biomarker and at least one second biomarker; and creating a synthetic multi-record training dataset, wherein a synthetic record comprises images depicting the at least one first biomarker, labelled with the automatically generated ground truth labels obtained from the ground truth generator machine learning model:

wherein ground truth labels of biological objects presenting the at least one second biomarker depicted in one respective image of a respective set are mapped to corresponding non-labeled biological objects presenting the at least one first biomarker depicted in another respective image of the set, and wherein synthetic records of biological objects depicting the at least one first biomarker are labelled with ground truth labels mapped from biological objects depicting the at least one second biomarker.

2. The computer-implemented method of claim 1, wherein the first image comprises a brightfield image, and the second images comprises at least one of: (i) a fluorescent image with fluorescent markers indicating the at least one second biomarker, (ii) spectral imaging image indicating the at least one second biomarker, and (iii) a non-labelled image depicting the at least one second biomarker.

3. The computer-implemented method of claim 1, further comprising:

training a biological object machine learning model on the synthetic multi-record training dataset for generating an outcome of at least one of the plurality of biological object categories for respective target biological objects depicted in a target image depicting biological objects presenting at least one first biomarker.

4. The computer-implemented method of claim 3, further comprising:

training a diagnosis machine learning model on a biological object category multi-record training dataset comprising images depicting biological objects presenting at least one first biomarker, wherein biological objects depicted in the images are labelled with at least one of the plurality of biological object categories obtained as an outcome of the biological object machine learning model in response to input of the images, wherein images are labelled with ground truth labels indicative of a diagnosis.

5. The computer-implemented method of claim 1, wherein the biological objects comprise cells.

6. A computer-implemented method of generating ground truth images from a ground truth multi-record dataset comprising:

segmenting biological visual features of a first image of a first record using an automated segmentation process;

mapping the segmentation of the features of the first image to a second image of the first record;

for a respective segmentation of the second image:

computing intensity values of pixels within and/or in proximity to a surrounding of the respective segmentation indicating a visual depiction of at least one biomarker in the second image; and classifying the respective segmentation with one or more ground truth labels by mapping the computed intensity value using a set of rules to a classification category;

wherein the ground truth multi-record dataset comprises multiple records, and wherein a second record comprises:

a first image of a sample depicting a first group of cells, a second image of the same sample comprising the same group of cells, sequentially stained with a stain configured to stain a group of cells presenting at least one biomarker, and one or more ground truth labels indicating a respective category for at least one sub-group of cells in the second images.

7. A computer-implemented method of automatically generating ground truth labels for biological objects, comprising:

feeding unlabeled sets of images of samples of tissue of a plurality of sample individuals into a ground truth generator machine learning model, wherein the unlabeled sets of images depict biological objects respectively presenting at least one first biomarker and at least one second biomarker different than the at least one first biomarker; and obtaining automatically generated ground truth labels as an outcome of the ground truth generator machine learning model, wherein the ground truth generator machine learning model is trained on a ground truth multi-record training dataset wherein a record comprises:

a first image of a sample of tissue of a subject depicting a first group of biological objects presenting at least one first biomarker, a second image, comprising at least a portion of the same sample of tissue comprising one or more biological objects in the first group of biological objects, sequentially stained with a stain configured to stain a second group of biological objects presenting at least one second biomarker different from the at least one first biomarker, and ground truth labels indicating a respective biological object category for at least one sub-group of biological objects in the first and second images.

8. The computer-implemented method of claim 7, wherein in response to receiving a respective image of a respective sample of tissue of a respective sample individual depicting the first group of biological objects presenting the at least one first biomarker, the respective image is fed into a virtual stainer machine learning model; and obtaining as an outcome of the virtual stainer machine learning model at least one of: (i) a synthetic image used as a second image of the unlabeled sets of images, and (ii) a synthetic image used as the second image of the sample of the record of the ground truth multi-record training dataset, wherein the virtual stainer machine learning model is trained on a virtual imaging multi-record, wherein a record comprises a first image of a sample of tissue of a subject depicting a first group of biological objects presenting the at the least one first biomarker, and a ground truth indicated by a corresponding second image of the same sample of tissue depicting a second group of biological objects presenting the at least one second biomarker.

9. The computer-implemented method of claim 7, further comprising feeding a target image depicting a plurality of biological objects presenting the at least one first biomarker into a biological object machine learning model; and obtaining at least one of the plurality of biological object categories for respective target biological objects depicted in the target image as an outcome of the biological object machine learning model, wherein the biological object machine learning model is trained on a synthetic multi-record training dataset, wherein a synthetic record comprises images depicting the at least one first biomarker and excludes images depicting the at least one second biomarker, labelled with the automatically generated ground truth labels obtained from the ground truth generator machine learning model.

10. The computer-implemented method of claim 7, wherein the biological objects comprise cells, wherein the first biomarker comprises PD-L1 and the second biomarker comprises a biomarker expressed by at least one type of mammalian immune cell, and the ground truth labels are cell-level annotations indicating immune cell type.

11. The computer-implemented method of claim 7, wherein the biological objects comprise cells, wherein the ground truth labels comprise cell-level annotations for biological objects in the first and second images.

12. The computer-implemented method of claim 6, wherein the biomarker in the second image is P40.

* * * * *